US012723039B2

(12) United States Patent
Lazar et al.

(10) Patent No.: US 12,723,039 B2
(45) Date of Patent: Sep. 1, 2026

(54) SMALL MOLECULE INHIBITORS OF SLC15A4 WITH ANTI-INFLAMMATORY ACTIVITY

(71) Applicant: THE SCRIPPS RESEARCH INSTITUTE, La Jolla, CA (US)

(72) Inventors: Daniel Lazar, San Diego, CA (US); Appaso Jadhav, Jupiter, FL (US); Christopher George Parker, Palm Beach Gardens, FL (US); John Ross Teijaro, San Diego, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 904 days.

(21) Appl. No.: 17/802,628

(22) PCT Filed: Feb. 26, 2021

(86) PCT No.: PCT/US2021/019942
§ 371 (c)(1),
(2) Date: Aug. 26, 2022

(87) PCT Pub. No.: WO2021/174023
PCT Pub. Date: Sep. 2, 2021

(65) Prior Publication Data

US 2023/0109505 A1 Apr. 6, 2023

Related U.S. Application Data

(60) Provisional application No. 62/981,907, filed on Feb. 26, 2020.

(51) Int. Cl.
*C07D 403/12* (2006.01)
*C07D 209/08* (2006.01)
(Continued)

(52) U.S. Cl.
CPC ......... *C07D 403/12* (2013.01); *C07D 209/08* (2013.01); *C07D 209/86* (2013.01); *C07D 235/30* (2013.01); *C07D 401/12* (2013.01); *C07D 401/14* (2013.01); *C07D 403/06* (2013.01); *C07D 403/14* (2013.01);
(Continued)

(58) Field of Classification Search
CPC .. C07D 403/12; C07D 401/12; C07D 471/04; A61K 31/4184; A61K 31/428; A61K 31/437; A61P 25/00
See application file for complete search history.

(56) References Cited

FOREIGN PATENT DOCUMENTS

| | | | |
|---|---|---|---|
| EP | 3072891 | A1 | 9/2016 |
| WO | 2009126635 | A1 | 10/2009 |

(Continued)

OTHER PUBLICATIONS

Nawrocka et al., "Synthesis and antiproliferative activity in vitro of 2-aminobenzimidazole derivatives" IL Farmaco 59 (2004) 83-91 (Year: 2004).*

(Continued)

*Primary Examiner* — Savitha M Rao
*Assistant Examiner* — Elena V Vishnyakova
(74) *Attorney, Agent, or Firm* — Viksnins Harris Padys Malen LLP

(57) ABSTRACT

Disclosed are small molecule inhibitors of SLC15A4, and methods of using them to treat pDC-mediated diseases and conditions.

40 Claims, 84 Drawing Sheets

A

(51) Int. Cl.

| | |
|---|---|
| ***C07D 209/86*** | (2006.01) |
| ***C07D 235/30*** | (2006.01) |
| ***C07D 401/12*** | (2006.01) |
| ***C07D 401/14*** | (2006.01) |
| ***C07D 403/06*** | (2006.01) |
| ***C07D 403/14*** | (2006.01) |
| ***C07D 405/12*** | (2006.01) |
| ***C07D 405/14*** | (2006.01) |
| ***C07D 413/14*** | (2006.01) |
| ***C07D 417/12*** | (2006.01) |
| ***C07D 471/04*** | (2006.01) |

(52) U.S. Cl.

CPC ......... *C07D 405/12* (2013.01); *C07D 405/14* (2013.01); *C07D 413/14* (2013.01); *C07D 417/12* (2013.01); *C07D 471/04* (2013.01)

(56) References Cited

FOREIGN PATENT DOCUMENTS

| | | | | |
|---|---|---|---|---|
| WO | 2012164085 A1 | | 12/2012 | |
| WO | 2016029077 A1 | | 2/2016 | |
| WO | WO-2016016421 A1 | * | 2/2016 | .............. A61P 37/06 |
| WO | 2019028308 A1 | | 2/2019 | |
| WO | 2019215470 A1 | | 11/2019 | |

OTHER PUBLICATIONS

Bansal, et al., “2-Aminobenzimidazole conjugates of NSAIDS: novel compounds with immunomodulatory, anti-inflammatory and antioxidant actions”, Medicinal Chemistry Research 24(3), 1170-1179 (2014).

Nawrocka, et al., “Synthesis and antiproliferative activity in vitro of 2-aminobenzimidazole derivatives”, Il Farmaco 59(2), 83-91 (2004).

Patent Cooperation Treaty, International Search Report and Written Opinion for PCT/US2021/019942, 11 pages, dated Jun. 4, 2021.

Reizis, et al., “Plasmacytoid Dendritic Cells: Recent Progress and Open Questions”, Annual Review of Immunology 29 (1), 163-183 (2011).

CAS Registry, RN 331971-13-2, 1 page (2001).

CAS Registry, RN 2335568-22-2, 21 pages (2019).

Horgan, et al., “Hypotensive Activity of 3-Alkyl-2-iminobenzothiazolines”, Journal of Medicinal Chemistry 18(3), 315-318 (1975).

Mendez-Cuesta, et al., “Homology modeling, docking and molecular dynamics of the Leishmania mexicana arginase: A description of the catalytic site useful for drug design”, Journal of Molecular Graphics and Modelling 38, 50-59 (2012).

Zhukovskaya, et al., “1-Substituted 2-Benzylaminobenzimidazoles With Phenyl Methoxyles: Synthesis, Computer Prediction, and Pharmacological Activity”, Pharmaceutical Chemistry Journal 49 (11), 735-742 (2016).

* cited by examiner

B

C

FFF3
*fragment lead*

CP22
*active*

CP26
*inactive*

Example SLC15A4 binding probes

'probe'

'competitor'

1

2

3

4

Lead SLC15A4 Chemical Probes

Active Probe (5)
Inactive Competitor (5-comp)

Inactive Probe (6)
Inactive Competitor (6-comp)

16 17

18 19 20

7 8 9 10 11 12 13 14 15

21 22 24

$-25 \leq A < 10$; $10 \leq B < 25$; $25 \leq C < 50$; $50 \leq D$

| ID | % IFNα ±SD suppression at **10 μM** in human pDCs (% IFNα ±SD in mouse pDCs) | % IFNα ±SD at **1 μM** in human pDCs | % transport inhibition ±SD s at **10 μM** |
|---|---|---|---|
| **AJ2-1** | C | | A |
| **AJ2-2** | A | | A |
| **AJ2-3** | D | D | D |
| **AJ2-4** | C | | C |
| **AJ2-5** | C | | A |
| **AJ2-6** | A | | A |
| **AJ2-7** | B | | A |
| **AJ2-8** | C | | A |
| **AJ2-9** | A | | A |
| **AJ2-10** | A | | A |
| **AJ2-11** | A | | A |
| **AJ2-12** | D | | B |
| **AJ2-13** | A | | A |
| **AJ2-14** | C | | B |
| **AJ2-15** | D | | C |
| **AJ2-16** | D | | |
| **AJ2-17** | D | | |
| **AJ2-18** | C | | |

Fig. 7

| | | | |
|---|---|---|---|
| AJ2-19 | D | | |
| AJ2-20 | D | | |
| AJ2-21 | D | | |
| AJ2-22 | D | | |
| AJ2-23 | D | | |
| AJ2-24 | D | | |
| AJ2-25 | D | | |
| AJ2-26 | D | | |
| AJ2-27 | C | | |
| AJ2-28 | | D | |
| AJ2-28A | | | |
| AJ2-29 | | D | |
| AJ2-30 | | D | |
| AJ2-31 | D | D | |
| AJ2-32 | D | D | |
| AJ2-33 | C | D | |
| AJ2-34 | | | |
| AJ2-3A | D | D | |
| AJ2-17A | A | | |
| AJ2-25A | B | | |
| AJ2-CP53 | D | | |

Fig. 7 (CONT.)

| Compound # | IFNalpha |
|---|---|
| AJ2-1 |  |
| AJ2-1A |  |

| | |
|---|---|
| AJ2-2 |  |
| AJ2-3 |  |

AJ2-4

AJ2-5

AJ2-6

AJ2-8

| | |
|---|---|
| AJ2-9 |  |
| AJ2-10 |  |

| | |
|---|---|
| AJ2-11 |  |
| AJ2-12 |  |

| | |
|---|---|
| AJ2-13 |   |
| AJ2-14 |   |

AJ2-15

AJ2-16

| | |
|---|---|
| AJ2-17 |  |
| AJ2-17A |  |

| | |
|---|---|
| AJ2-19 |  |
| AJ2-21 |  |

| | |
|---|---|
| AJ2-25A |  |
| AJ2-26 |  |

| | |
|---|---|
| AJ2-27 |  |
| AJ2-28 |  |

| | |
|---|---|
| AJ2-28A |   |
| AJ2-29 |   |

AJ2-30

AJ2-32

AJ2-38

AJ2-39

AJ2-46

AJ2-47

AJ2-64

AJ2-65

| | |
|---|---|
| AJ2-66 |  |
| AJ2-67 |  |

| | |
|---|---|
| AJ2-68 |  |
| AJ2-69 |  |

| | |
|---|---|
| AJ2-70 |  |
| AJ2-71 |  |

| | |
|---|---|
| AJ2-72 |  |
| AJ2-73 |  |

| | |
|---|---|
| AJ2-74 |  |
| AJ2-75 |  |

| | |
|---|---|
| AJ2-76 |  |
| AJ2-77 |  |

| | |
|---|---|
| AJ2-78 |  |
| AJ2-79 |  |

| | |
|---|---|
| AJ2-80 |  |
| AJ2-81 |  |

| | |
|---|---|
| AJ2-82 |   |
| AJ2-83 |   |

| | |
|---|---|
| AJ2-84 |  |
| AJ2-85 |  |

*Primary human macrophages (derived from CD14+ monocytes)*

LPS simulated (TLR4)

*primary mouse B cells

PRELIMINARY PK PROFILE

| | | | |
|---|---|---|---|
| 5 mg/kg | AJ2-3A | AJ2-30 | AJ2-22 |
| $T_{1/2}$(hr) | 1.27 | 2.55 | 1.3 |
| $C_{MAX}$ (μM) | 1.58 | 1.73 | 1.82 |
| AUC (μM/hr) | 3.13 | 2.48 | 2.84 |
| | | | |
| 30 mg/kg, 5D | AJ2-3A | AJ2-30 | VEHICLE |
| ALBUMIN (g/dL) | 4.0 | 3.7 | 4.2 |
| ALK. PHOSPHATASE (U/L) | 90 | 89 | 57 |
| AMYLASE (U/L) | 756 | 1006 | 932 |
| ALA. AMINOTRANSFERASE (U/L) | 41 | 50 | 33 |
| BLOOD UREA NITROGEN (mg/dL) | 17 | 19 | 23 |
| BILIRUBIN (mg/dL) | 0.2 | 0.1 | 0.2 |
| CALCIUM (mg/dL) | 10.4 | 10.2 | 10.1 |
| PHOSPHOROUS (mg/dL) | 8.0 | 8.7 | 7.5 |
| GLUCOSE (mg/dL) | 191 | 184 | 217 |
| ELECTROLYTES (Na/K, mmol/L) | 135 | 134 | 152 |
| CREATININE (mg/dL) | 0.3 | 0.43 | 0.3 |
| TOTAL PROTEIN (g/dL) | 5.9 | 5.6 | 5.7 |
| GLOBULIN (g/dL) | 1.9 | 1.9 | 1.5 |

SMALL MOLECULE INHIBITORS OF SLC15A4 WITH ANTI-INFLAMMATORY ACTIVITY

CROSS REFERENCE TO RELATED APPLICATION

This application claims priority to U.S. provisional patent application No. 62/981,907, which was filed on Feb. 26, 2020, and which is hereby incorporated by reference in its entirety.

TECHNICAL FIELD

This disclosure relates to novel chemical compounds and methods useful for inhibiting SLC15A4.

BACKGROUND

The recognition of infectious pathogens is dependent on a series of germline-encoded immune sensors known as pattern receptors (TLRs) and NOD-like receptors (NLRs). TLRs are membrane sensors that scan the extracellular environment for microbial PAMPs while NLRs monitor the cytosolic environment. Viral and bacterial nucleic acids are prominent PAMPs recognized by several TLRs, including TLR3, TLR7, TLR8 and TLR9. Ligand binding to these sensors results in singling events which lead to the expression of some immune response genes, including inflammatory cytokines, stimulatory immune cytokines, chemokines, and costimulatory molecules that augment the killing of pathogens[1,2]. However, inappropriate recognition of host-nucleic acids can lead to autoimmune or autoinflammatory conditions[3-6]. Autoimmunity emerges by several coincident mechanisms that relate to the presence of auto-reactive immune cell subsets and loss of immunological tolerance. Loss of tolerance during central and peripheral differentiation of the adaptive immune response may lead to uncontrolled activation of self-reactive B and T cells which induce autoimmunity assisted by innate immune cells. TLR signaling plays an essential role in the activation of the adaptive immune system by inducing the production of pro-inflammatory cytokines and the continuous activation or dysregulation of TLR signaling directly contributes to the pathogenesis of autoimmunity[7]. A critical finding has been that the activation of endolysosomal nucleic acid sensing TLRs and the production of type I interferons (IFN-I), particularly by the APC class plasmacytoid dendritic cells (pDCs), are central driving pathogenic events[8].

pDCs are a specialized dendritic cell subset of recirculating cells that act as early sentinels in the surveillance of pathogens. pDCs produce ~1000 times more type 1 IFN (IFN-I) than any other cell types, in response to recognition of microbial nucleic acids as well as with endogenous nucleic acids[9, 10] by TLR7 and TLR9 (TLR7/9). TLR7/9 activation in pDCs can also induce other cytokines (IL-12. IL-6. TNFa) and inflammatory chemokines[11]. There is evidence that pDCs also activate B cells, act as APCs, and promote immunoregulation and tolerance[12-15] Given their central role in inflammation, it is perhaps not surprising that pDCs are causal effectors in the pathogenesis of multiple autoimmune disorders, including lupus and psoriasis. One of the strongest links between pDCs and autoimmune disease is during the systemic autoimmune disease (SLE)[8]. In most mouse models, lupus is dependent on IFN-I and genetic deletion or neutralization of IFN-I signaling can prevent or ameliorate disease[7]. Moreover, about 70% of SLE patients exhibit an elevated IFN-I signature[16] and clinical trials with IFN-I receptor neutralizing antibodies are currently being tested and have produced promising results in lupus patients in the clinic. pDCs have also been detected in the cerebrospinal fluid of multiple sclerosis (MS) patients[17] and accumulate in demyelinated lesions of inflamed MS brains[18].

Small molecule immune modulatory drugs have been developed to control detrimental immune responses during inflammation, transplantation and autoimmune conditions. Corticosteroids, calcineurin inhibitors, non-steroidal anti-inflammatory drugs (NSAIDs), mTOR inhibitors, and kinase inhibitors have been used to treat autoimmune conditions and improve transplantation efficiency. More recently, therapies like Gilenya and Tecfidera have shown efficacy in alleviating disease progression and symptoms in multiple sclerosis patients. However, most of these treatments are general modulators of inflammation or broad immunosuppressants and can engage signaling pathways common to nearly all cell types, resulting in unwanted side effects and limiting their usage[19]. Monoclonal antibody (mAb) therapies targeting specific immune targets have been developed (e.g. checkpoint inhibitors (anti-CTLA-4), anti-TNF) with some success, however they are often effective only for a fraction of patients and severe immune-related adverse events (irAEs) are often observed[19, 20] There currently are no available therapies targeting pDC mediated production of IFN-I, the central driver to numerous autoimmune conditions[21]. Thus, there exists a currently unmet need for novel small-molecule therapies for the plethora pDC-mediated conditions.

SLC15A4 plays a central role in pDC-mediated inflammation and autoimmunity. The solute carrier gene family 15 member 4 (SLC15A4), also known as Proton/Histidine Transporter 1 (PHT1), is a 12-membrane spanning protein with gene expression mostly restricted to APCs, specifically pDCs and B cells[22-24]. SLC15A4 is a member of the SLC15 family, which includes the proton/histidine transporter SLC15A3 (PHT2), and the di/tripeptide transporters SLC15A1 (PEPT1) and SLC15A2 (PEPT2). Both SLC15A3 and SLC15A4 contain acidic dileucine motifs, mediating localization to endosome/lysosomes and are annotated to be di- or tri-peptide co-transporters[25]. Lysosomes and endosomes are acidic, suggesting that SLC15A3 and SLC15A4, which share 60% sequence identity, transport short peptides into the cytosol using the outward-directed proton gradient[25, 26]. However, the substrates of endolysosomal SLC15A3 and SLC15A4 are not well-established. Several studies have demonstrated SLC15A4 can transport bacterial-derived peptidoglycans, such as MDP and Tri-DAP, which are ligands of the immune sensors NOD1 and NOD2, resulting in their activation[22-30]. SLC15A4 has also been intimately linked to TLR7/9 mediated signaling and IFN-I production. Specifically, studies reveal that both in Slc15a4 loss of function mutant (called 'feeble') and knock out mice result in pDCs that are defective IFN-I as well as TNFa, IL-6 and IL-12 production upon TLR stimulation, but otherwise display normal development[31 29 30,32]. This defect is not due to impaired TLR ligand uptake or IFN-I secretion and impacts both TLR 7 and 9 signaling pathways. Critically, Slc15a4. Treble mice showed striking reductions in lupus manifestations and extended life-spans[32]. Although SLC15A3 and SLC15A4 are thought to have similar functions, the disease-reducing effect of SLC15A4 mutation and deletion implies that there are either significant functional differences between these two transporters, or expression of both is required to ensure optimal function. Additionally, genome-wide association studies (GWAS) have revealed that SLC15A4 (and not SLC15A3) is closely associated with inflammatory diseases such as systemic lupus erythematosus (SLE) and inflammatory bowel disease (IBD)[33,34]. However, the exact mechanism(s) by which SLC15A4 contributes to these processes remains to be defined. Nevertheless, the essential pathogenic role of the pDC/TLR/IFN-I axis and the autoimmune disease ameliorative effects SLC15A4 loss-of-function in mouse models studies establish SLC15A4 as a critical modulator of inflammation and provides a strong basis for the characterization of SLC15A4 and development of inhibitors.

SLC biology and chemical probe discovery. The solute-like carrier (SLC) family of proteins is the largest group of membrane transporters with 456 members distributed across 52 subfamilies. SLCs have not only been implicated in numerous disorders arising from inherited polymorphisms, but also have established roles in tumorigenesis, autoimmune disease, and metabolic disorders[35-37]. Despite their importance, a large fraction (>30%) of SLCs remain poorly or completely uncharacterized and the vast majority (>80%) lack chemical probes[38]. One of the most significant obstacles is their complex integral membrane topography, which necessitates an intact membrane to maintain native functional characteristics. Difficulties in the expression and purification of SLCs in native state limits the use of traditional high-throughput screening (HTS) approaches and common in vitro biochemical investigations to annotate substrate scope, measure transport rates, and examine the effects of various perturbagens (e.g. mutations, inhibitors) on transport[38]. Due to inherent technical challenges, there are only 10 human SLCs with structures and few exist in multiple conformations or with substrates or drugs bound, limiting any potential for structure-based drug design[39]. Cell- and animal-based models for SLC investigations can similarly be challenging, as genetic perturbations can be complicated by overlapping specificities, compensatory mechanisms, and toxicity, limiting studies to only a subset of SLCs and sometimes obscuring the relative contribution of a transporter to the studied function or phenotype[35, 36, 40,41]. Considering these challenges, new approaches are desperately needed to investigate SLC biology and to develop useful SLC-targeting chemical probes.

Previous studies have established that SLC15A4 has a unique and critical role in the production of IFN-I and other inflammatory cytokines in pDCs as well as in the pathogenesis of autoimmune conditions, elevating SLC15A4 as a potential therapeutic target for such disorders. However, SLC15A4 heretofore remains undrugged and no inhibitors have been disclosed. Our application not only describes an enabling chemical proteomic strategy to deconvolute the mechanism by which SLC15A4 exerts control over TLR signaling but also assess the therapeutic potential of SLC15A4 for the treatment of pDC-mediated conditions.

There are no clinically approved drugs specifically targeting pDC's and their production of IFN-I and nucleotide-binding TLR signaling, central factors in the pathogenesis of numerous autoimmune conditions, such as Lupus, Crohn's disease, irritable bowl syndrome (IBS), type I diabetes, psoriasis and potentially even MS. Critically, SLC15A4 is primarily expressed in antigen presenting cells that directly contribute to the pathogenesis of autoimmune conditions, specifically pDCs, B-cells and macrophages, making it a highly relevant therapeutic target for the development of compounds to selectively suppress inflammation.

SUMMARY

Applicants have discovered novel SLC154A inhibitor compounds and evaluated the possession, performance and utility of representative examples of such compounds, both for biochemical potency (e.g., evaluating % IFNα±SD suppression in human pDCs and % transport inhibition)

In various embodiments, the disclosure relates to a compound of Formula (I) or (II):

(I)

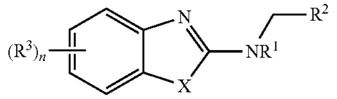

(II)

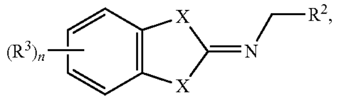

wherein

X is $NR^4$ or S;

$R^1$ is H or —C(O)—$C_{1-10}$alkyl;

$R^2$ is heterocyclyl or aryl;

$R^3$ is halogen, —$CHF_2$, or —$CF_3$;

$R^4$ is H, —$C_{1-10}$alkyl, —C(O)—$C_{1-10}$alkyl, —C(O)—$C_{3-10}$cycloalkyl, —$S(O)_2$—$C_{1-10}$alkyl, or

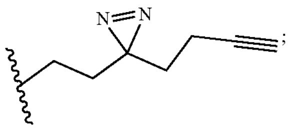 [SMILES: *CCC1(CCC#C)N=N1]

and n is 0, 1, 2, 3, or 4;

or a pharmaceutically acceptable salt thereof.

In various embodiments, the disclosure relates to a compound of FIG. 15.

In various embodiments, the disclosure relates to a method of treating a pDC. B cells, macrophages or monocytes-mediated condition.

Figure 1:
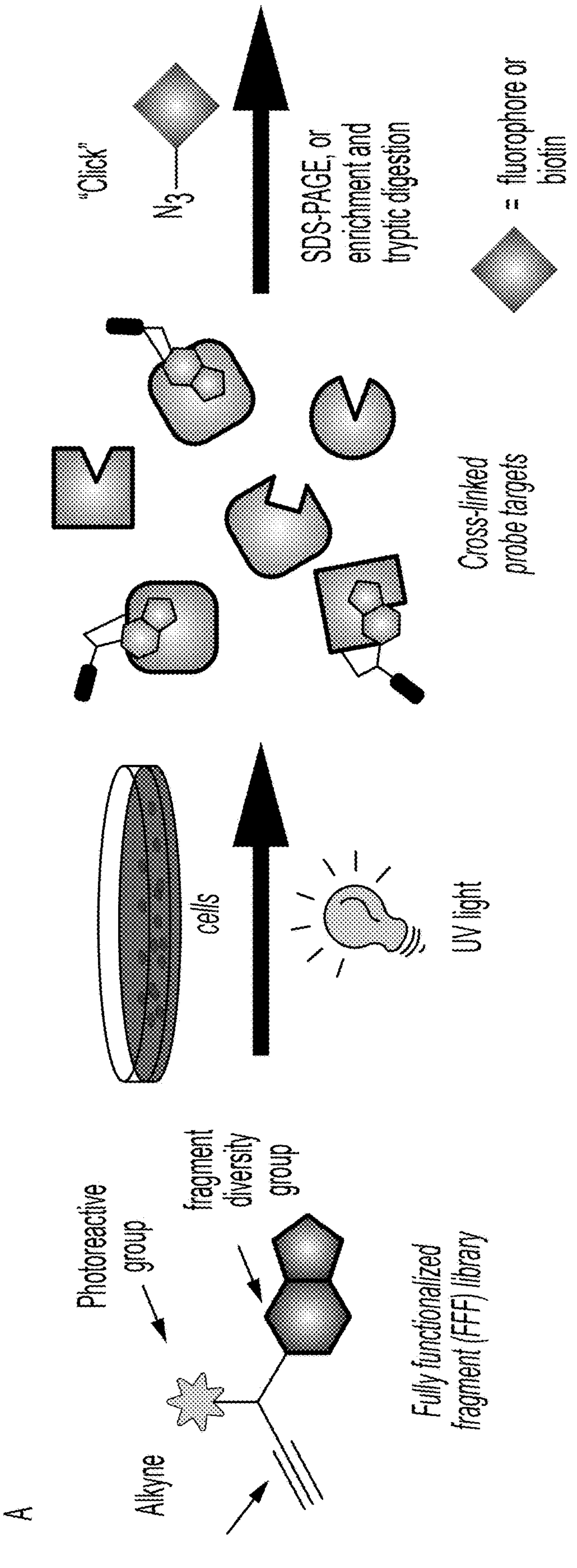
FIGS. 1A-1C represent the Fragment-based Ligandability Mapping in Cells (FbLMiC). Overview of method and specialized chemical libraries. (A) Fully functionalized fragment (FFF) probes are composed of a drug-like fragment as well as a retrieval tag, which enables the covalent capture of fragment-bound protein targets directly in cells upon UV irradiation. Fragment targets, as well as the site of fragment interaction, can be identified and quantified by mass spectrometry- and gel-based methods. (B) General structure of FFF library showing the constant affinity tag region (red), containing photoreactive (diazirine) and latent affinity (alkyne) groups, and the variable region (blue), containing fragment recognition elements for binding to proteins. Examples of fragments shown. (C) Subset of proteins that FFF liganding provided first evidence of druggability (non-Drugbank) and functional classification against established druggable proteins (Drugbank). (46,47)
Figure 1:
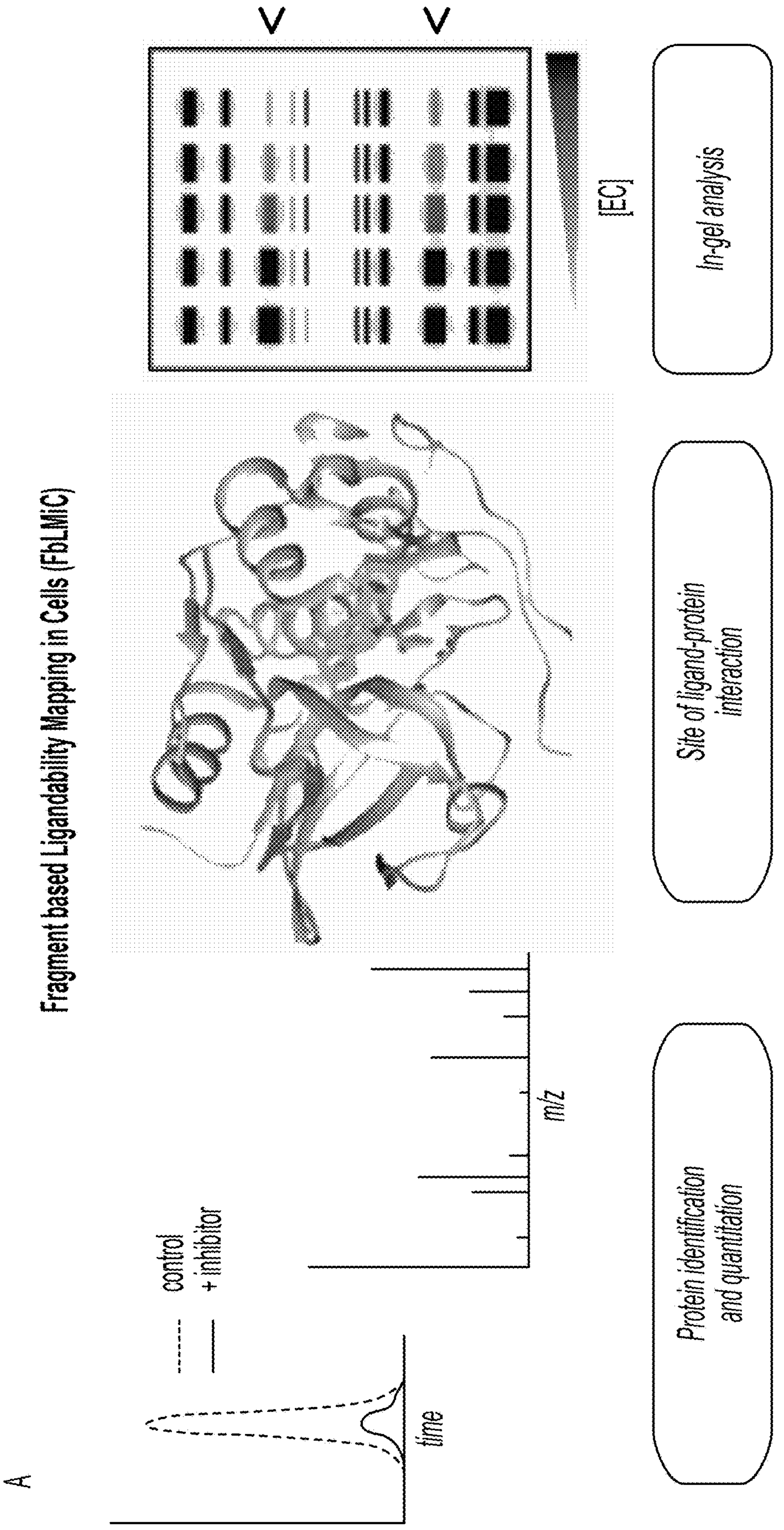
Figure 1:
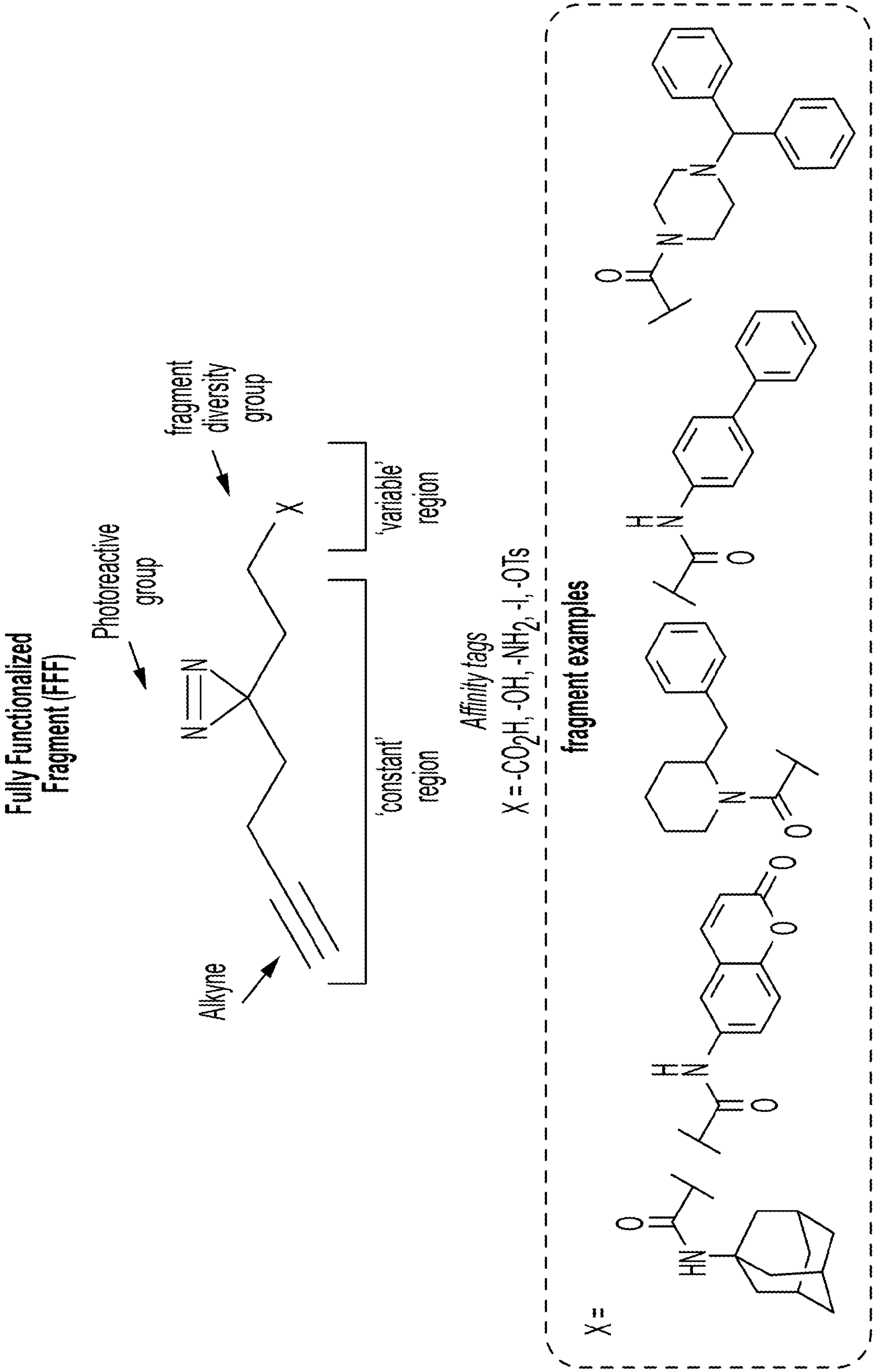
Figure 1:
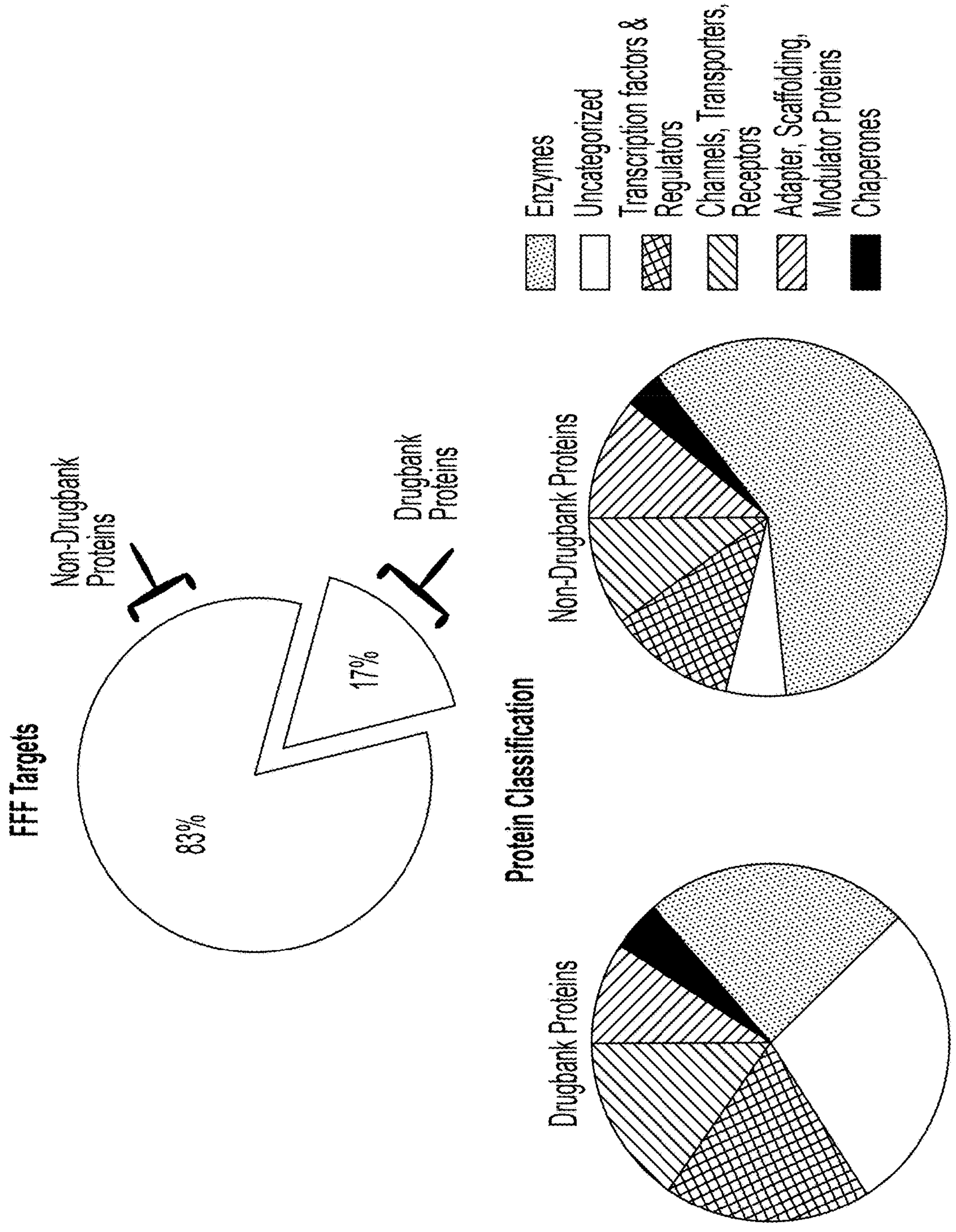

and show chemotype selectivity (e.g. not enriched by all FFFs). X-axis displays SLC subfamily and y-axis displays fraction of SLC subfamily considered to be FFF targets. (B) Structures of FFF3, fragment-based inhibitor (CP22), and control compound (CP26) for previously published (46) functional investigations of SLC25A20. (C) FFF3 probe labeling site mapped onto homolog SLC25A20 structure (brown). Example MS1 chromatogram shown for probe-labeled tryptic peptide shown in blue. (D) CP22 increase long chain acylcarnitine content in HSC5 cells. Data=avg±SD; p<0.01, *p<0.001, and ****p<0.0001 for treated groups; n=3-5.

FIGS. 3A-3D represent chemical proteomic development of SLC15A4 chemical probes. (A) Structures of FFF probes, identified to engage SLC15A4 in proteomics experiments (see text for experimental description). All probes were examined for their ability to suppress IFN-I production in human pDCs, 5, showed the highest activity. Structurally similar 6 was not found to engage SLC15A4 or suppress IFN-1 production. (B) Gel-based competition readouts showing interactions of 5 being competed with excess 5-comp in human PBMCs. (C) Isotopic reductive demethylation heatmap showing 5-enriched proteins (20 mM) competed by excess 5-comp or 6-comp (80 mM) in human PBMCs. Inset shows identities of top 15 competed targets. (D) Example MS1 of SLC15A4 tryptic peptide from competition experiments.

FIGS. 4A-4D show SLC15A4 chemical probes suppress inflammatory cytokine (IFN-I and IL-6) in primary mouse and human pDCs. Suppression of IFN-I production in isolated human (A and B) and mouse (C) pDCs. (D) Suppression of IL-6 in primary mouse pDCs. Avg±SD (n=3).

Figure 5A:
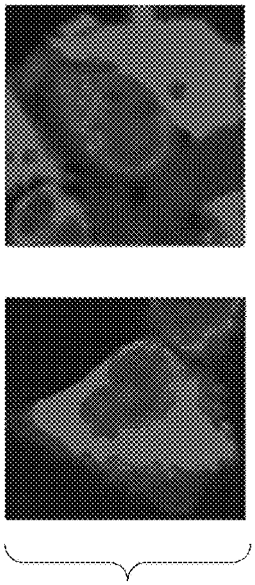
Figure 5B:
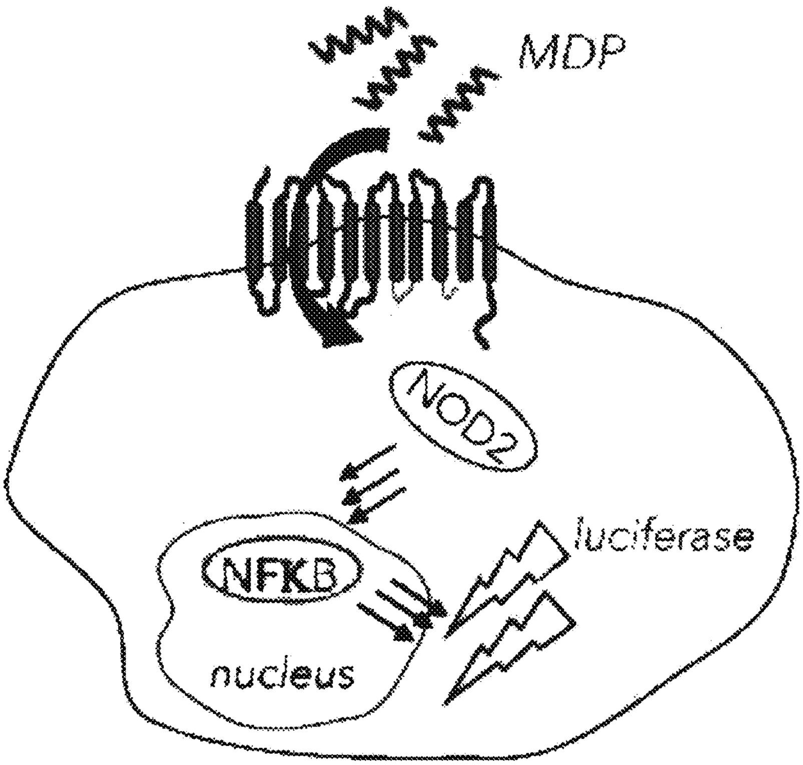
Figure 5C:
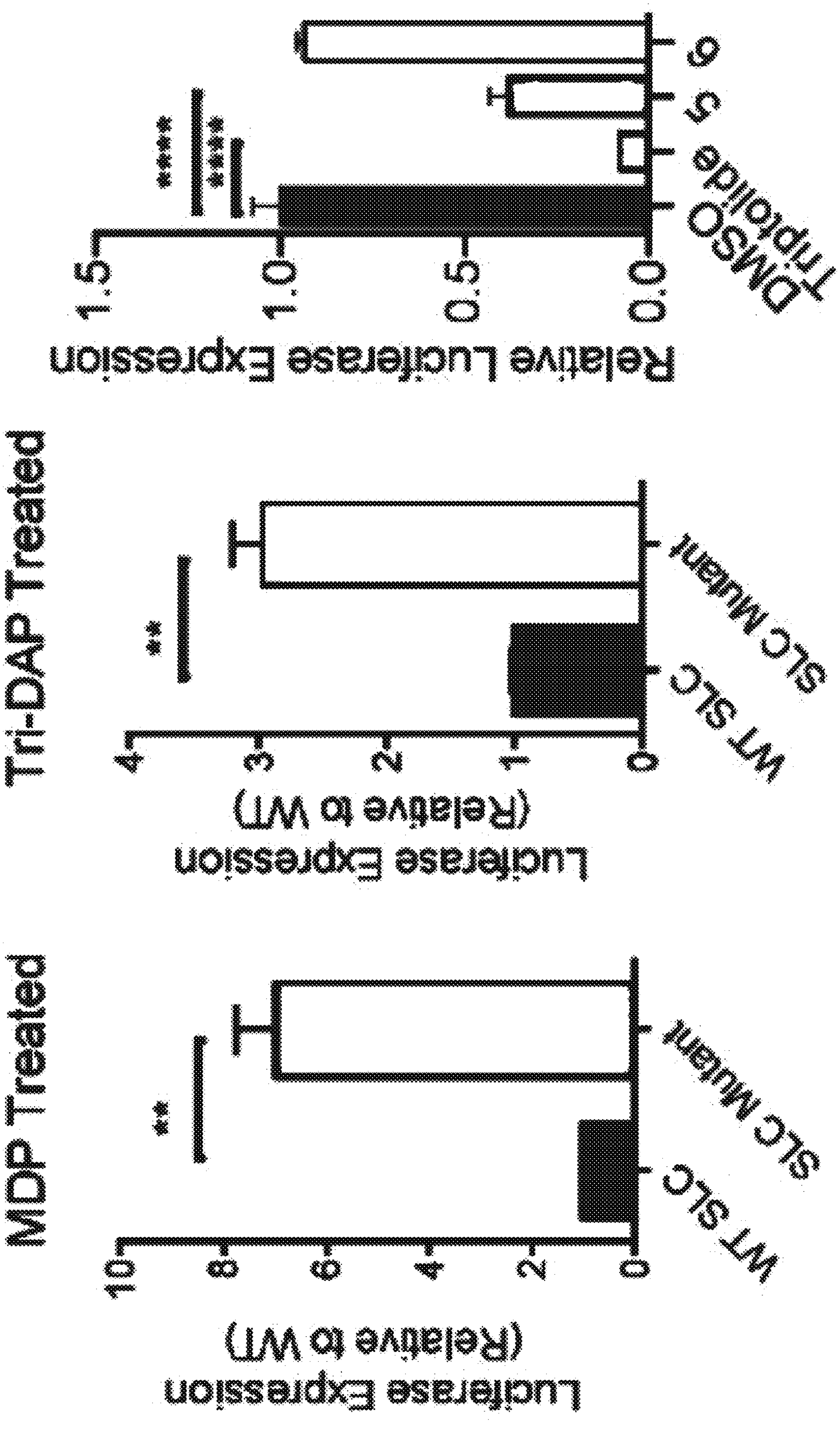

FIGS. 5A-5C represent the development of SLC15A4 transport reporter assay. (A) Fluorescence micrographs of A549 cell stable transfected with SLC15A4-mCherry WT (top) and mutant (L14A, L15A, L318A, V319A, bottom). SLC15A4 mutant expression localizes to cell membrane (B) Schematic of SLC15A4 NFkB transporter assay ran in 96-well format. (C) SLC15A4 mutant, but not WT, produce luciferase signal upon treatment of either MDP or Tri-DAP. Luciferase expression is suppressed in the presence of triptolide (NFkB inhibitor) and 5, but not 6. Avg±SD (n=3).

FIGS. 6A-6E represent SAR studies of SLC15A4 inhibitors and functional evaluation. (A) Structure of 5-comp and two general synthetic routes for SAR studies. (B) Structures of 5-comp analogs. (C) Representative cytotoxicity profile of isolated human pDCs treated with 10 mM of each compound after 24 hrs. Read out by Cell Titer Glo. (D) Correlation plot of IFN-I suppression (x-axis) vs transport inhibition (y-axis) for each compound at 10 mM. (E) Dose-dependent suppression in primary human pDCs with lead analog 8. Avg±SD (n=3).

FIG. 7 is a table summarizing IFNα suppression in human pDCs and transport inhibition.

Figure 8:
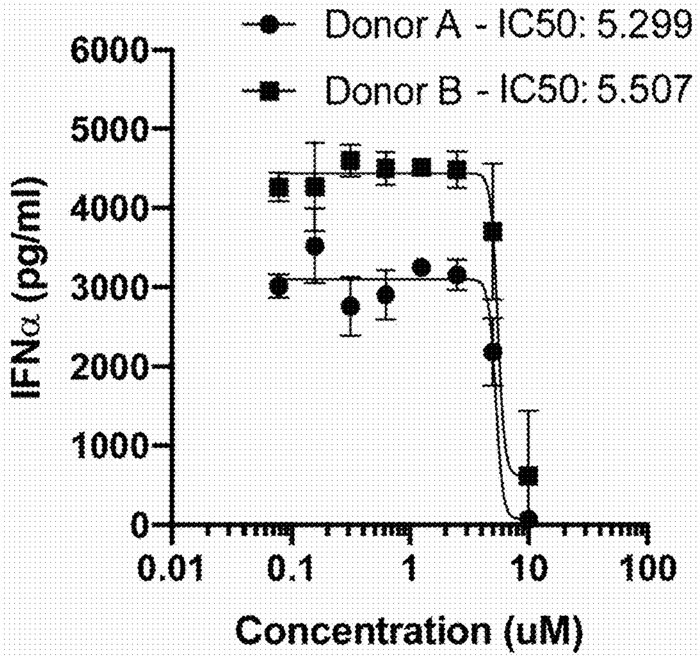
Figure 8:
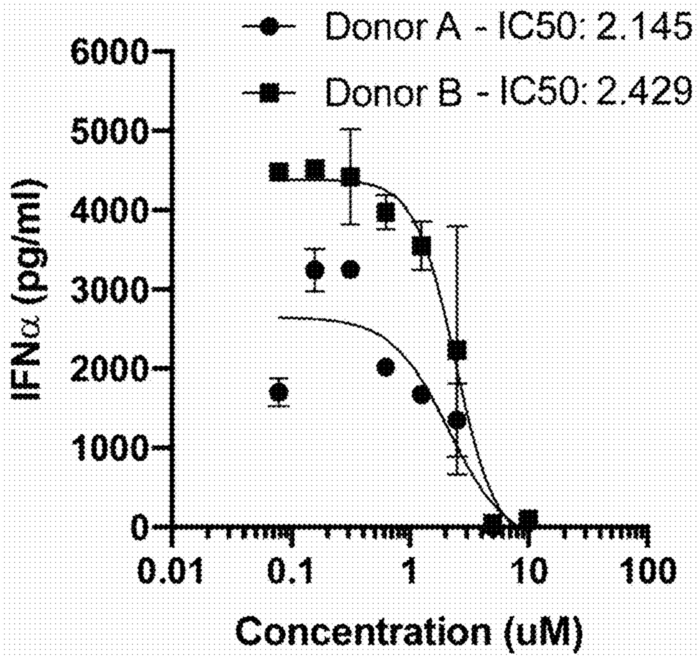
Figure 8:
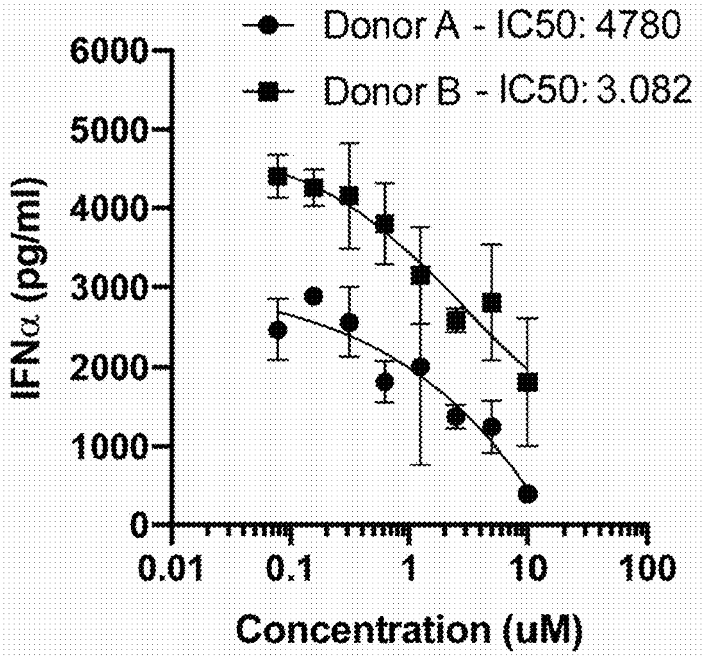
Figure 8:
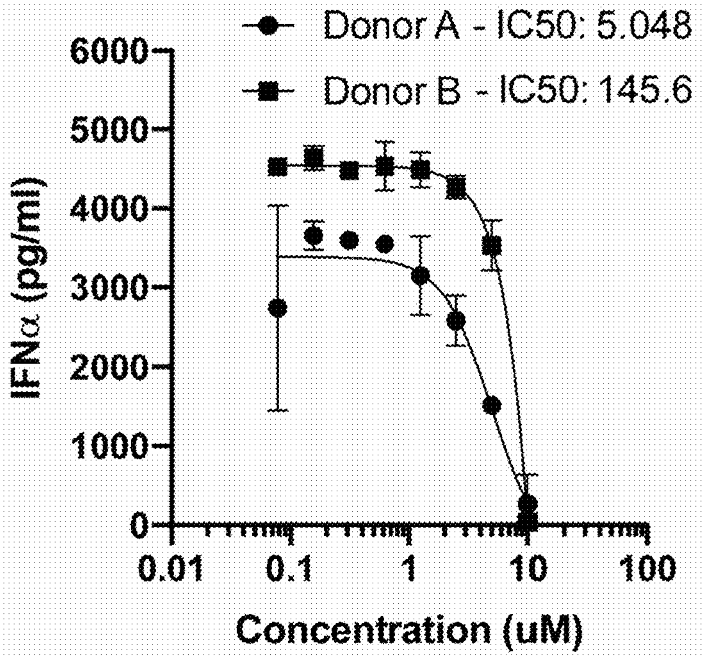
Figure 8:
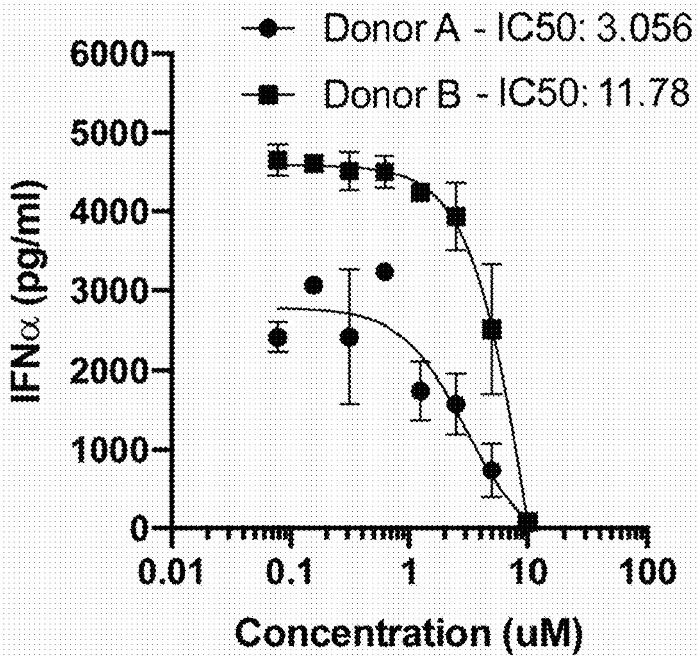
Figure 8:
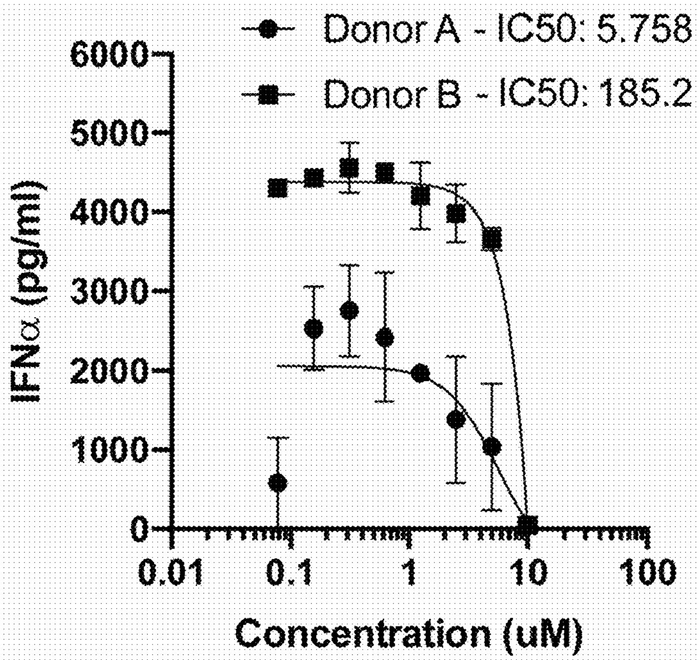
Figure 8:
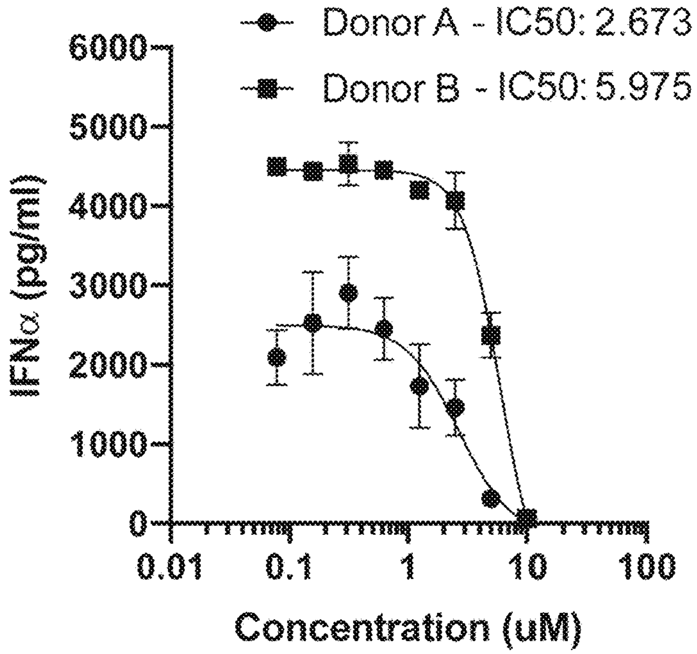
Figure 8:
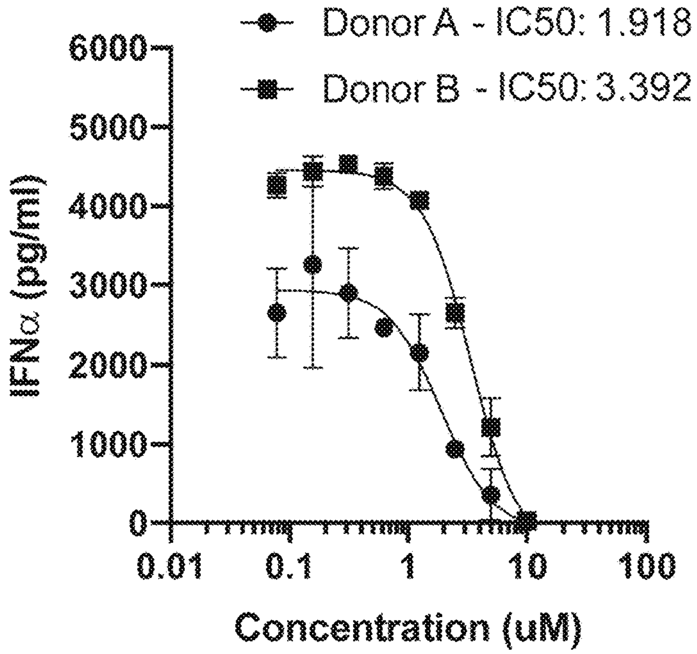
Figure 8:
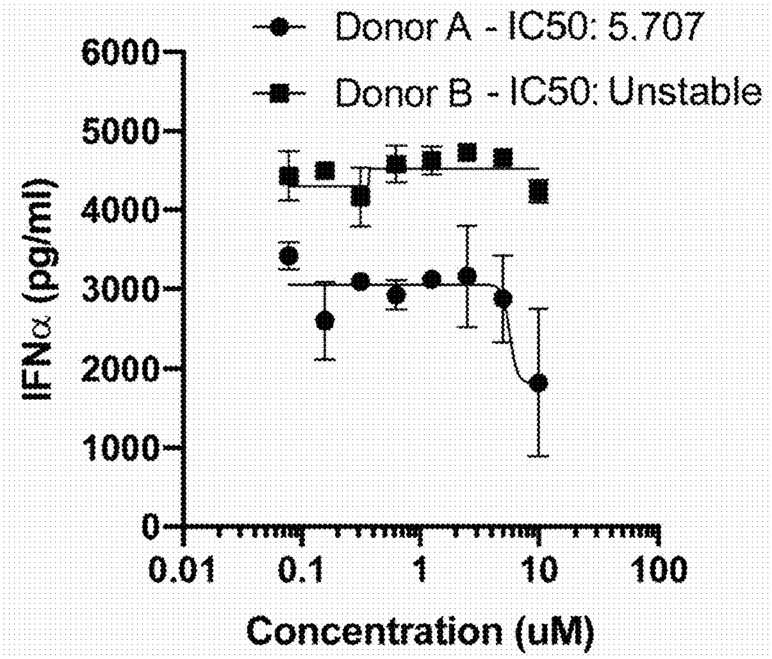
Figure 8:
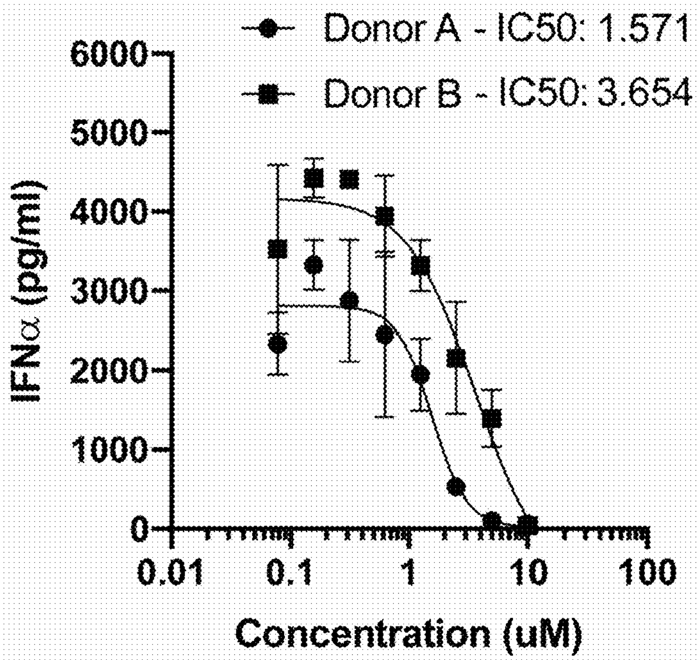
Figure 8:
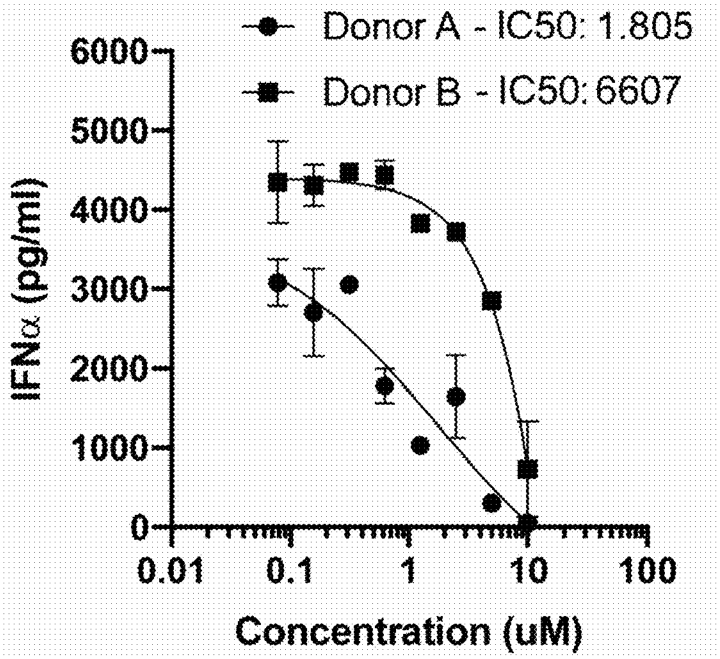
Figure 8:
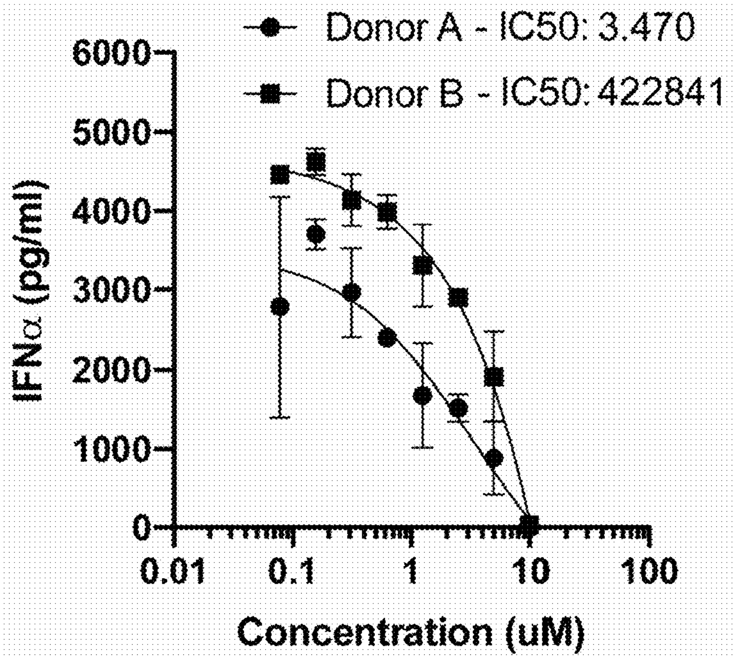
Figure 8:
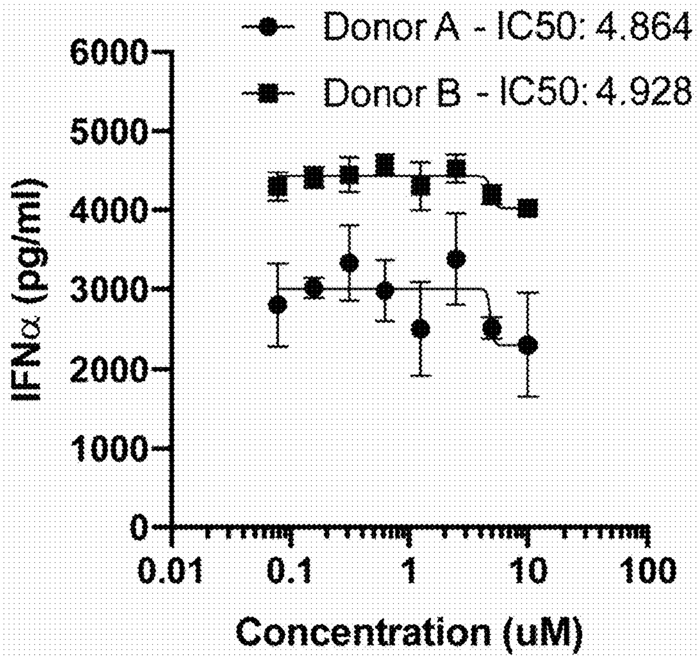
Figure 8:
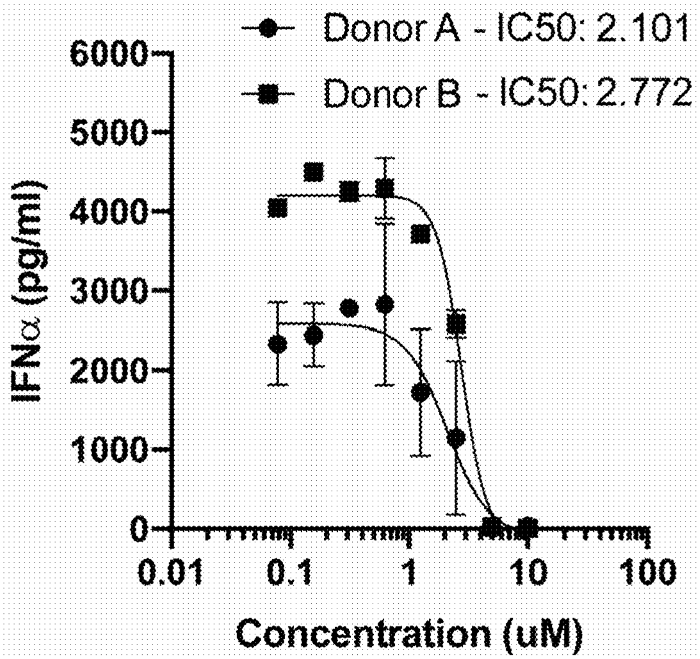
Figure 8:
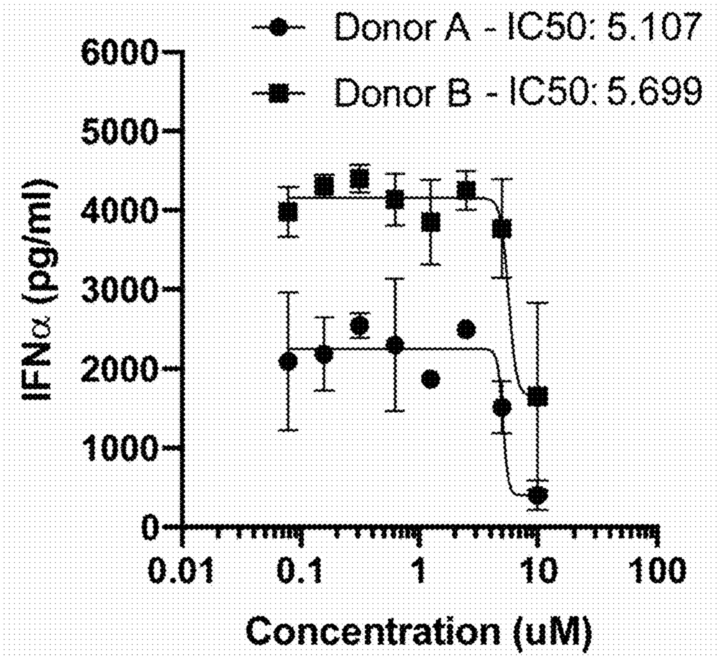
Figure 8:
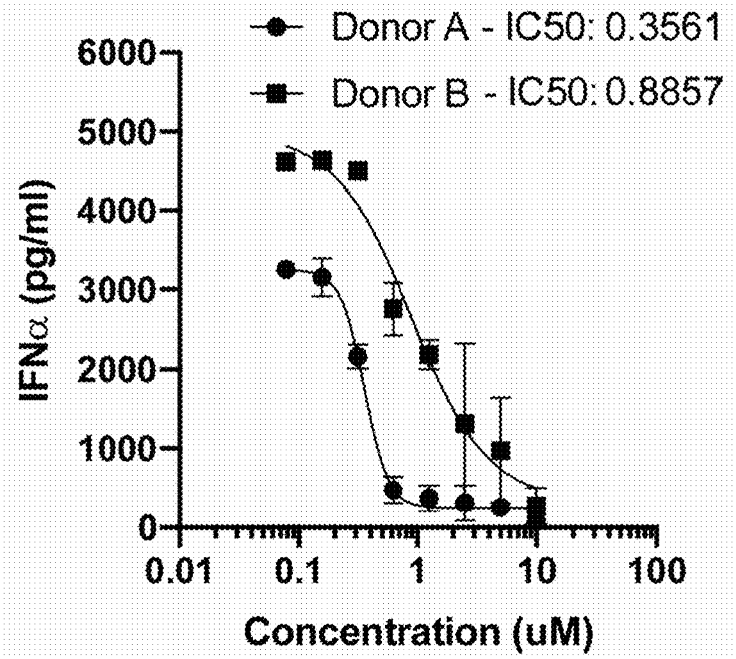
Figure 8:
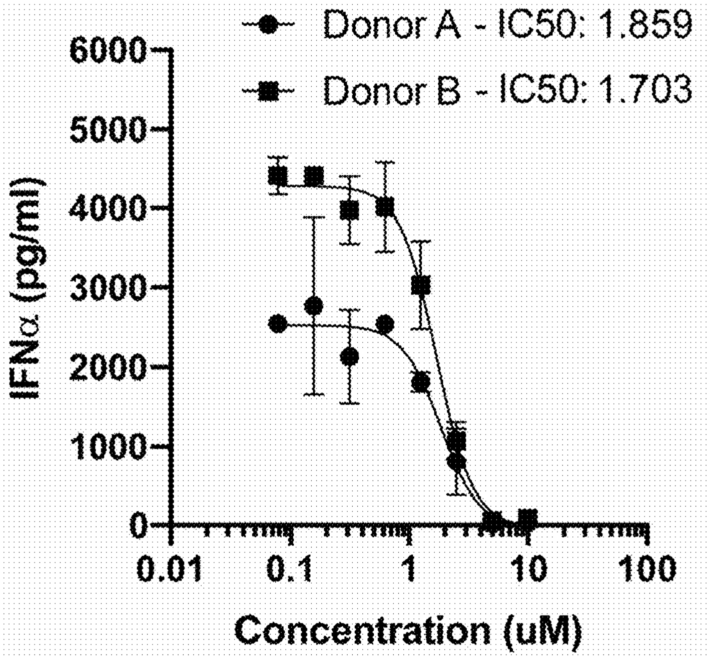
Figure 8:
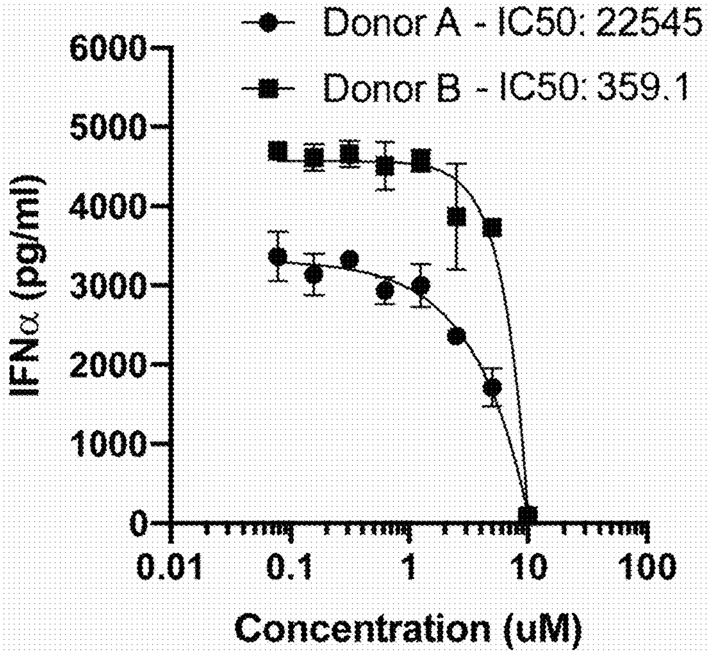
Figure 8:
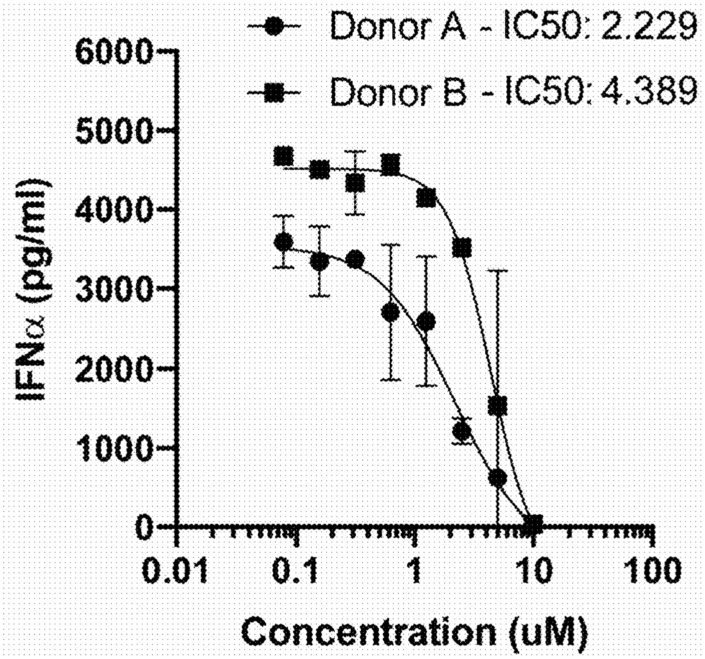
Figure 8:
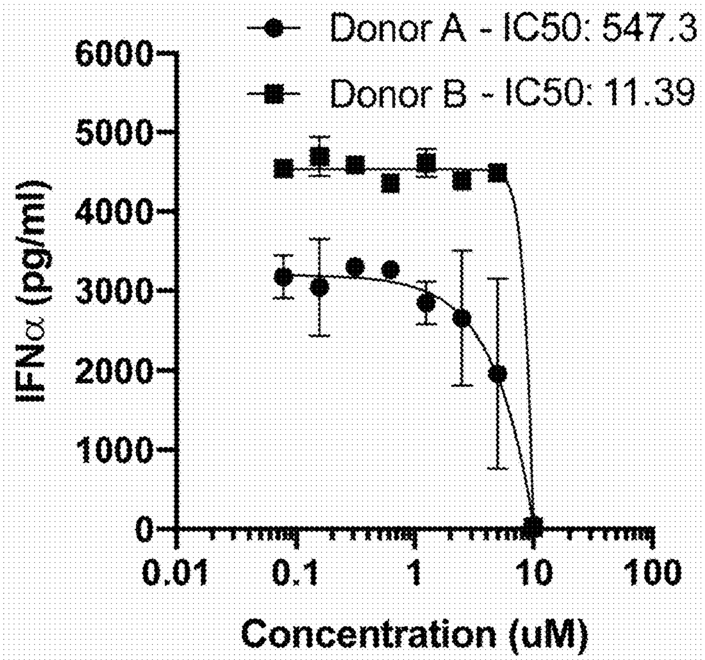
Figure 8:
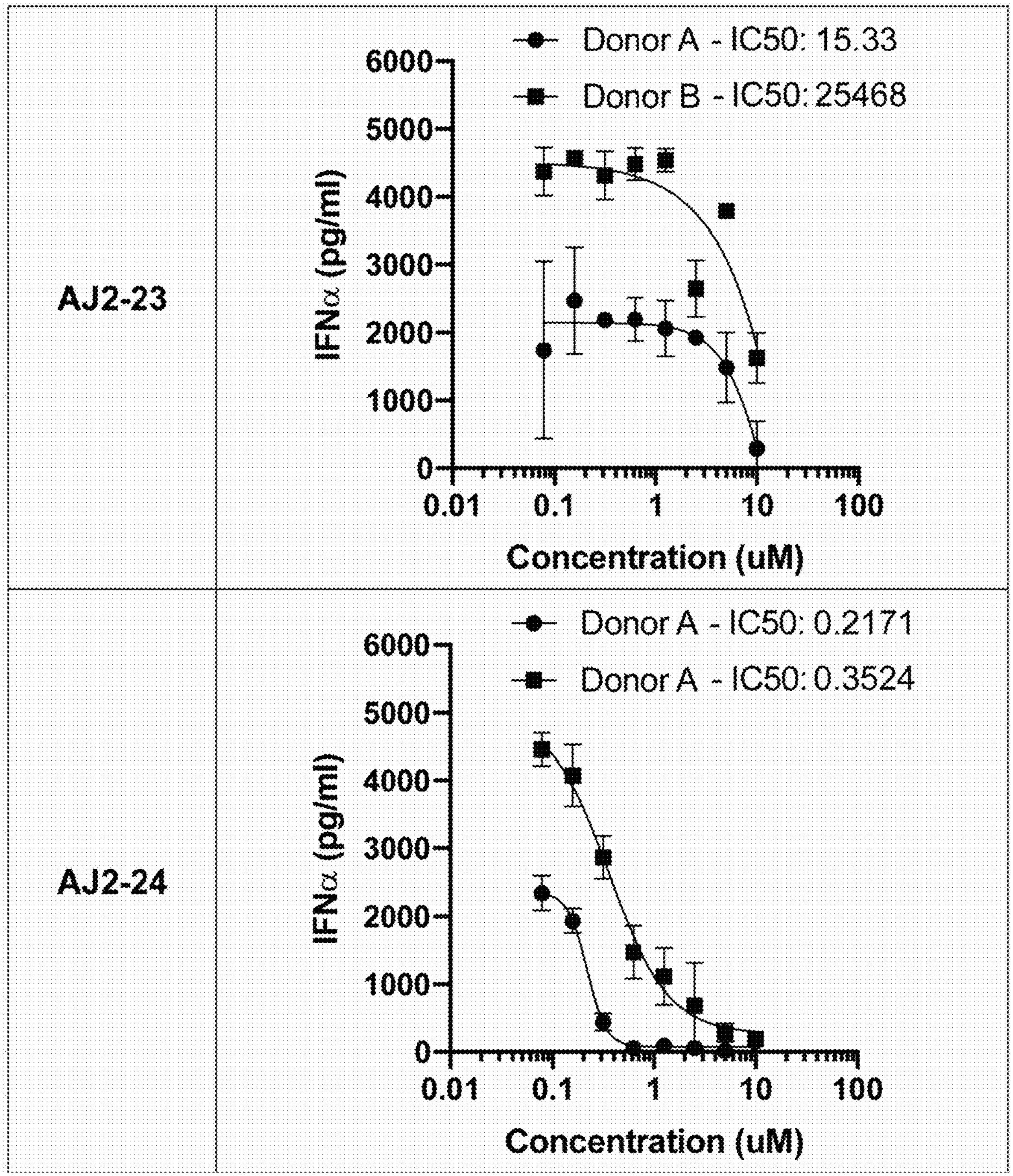
Figure 8:
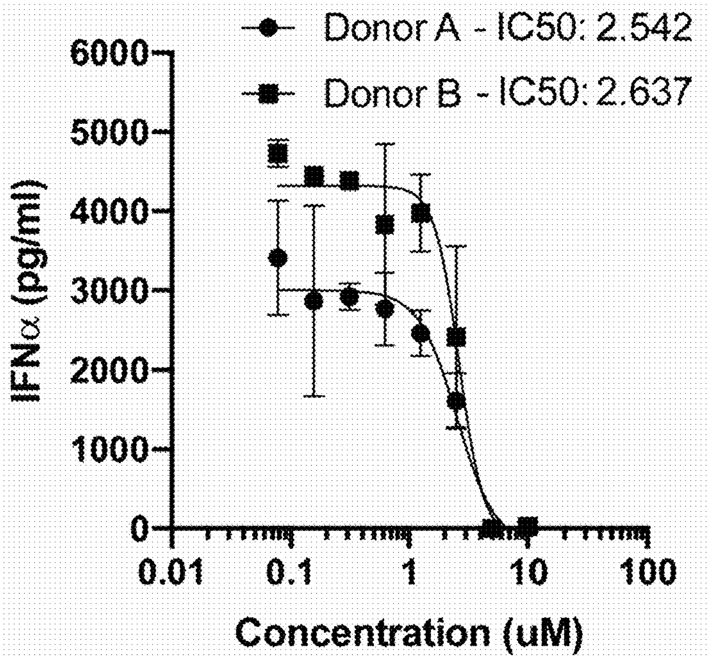
Figure 8:
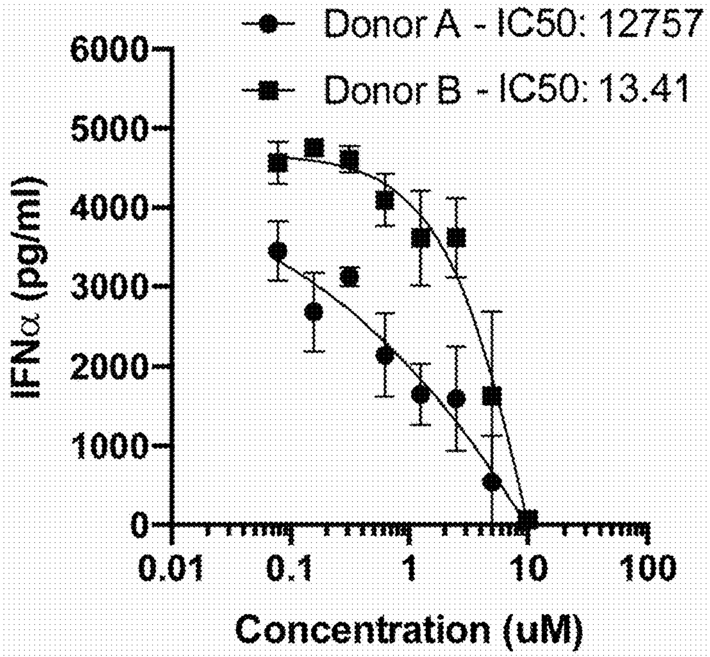
Figure 8:
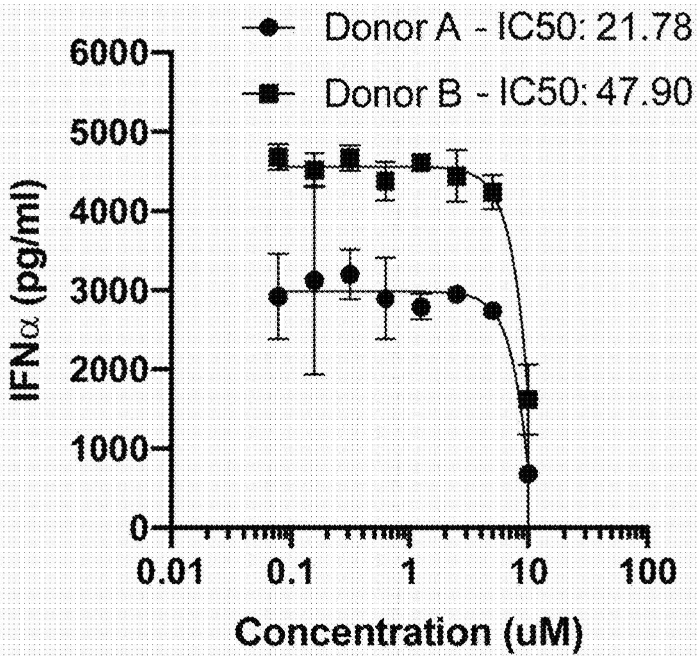
Figure 8:
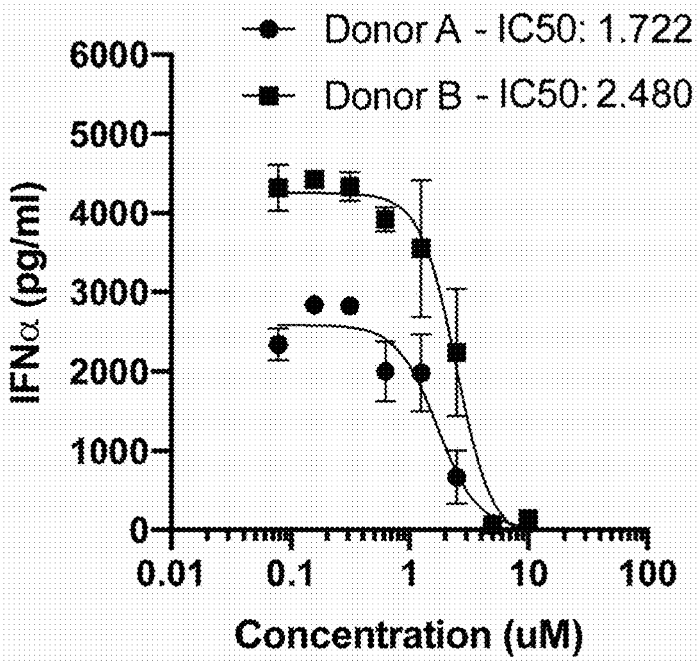
Figure 8:
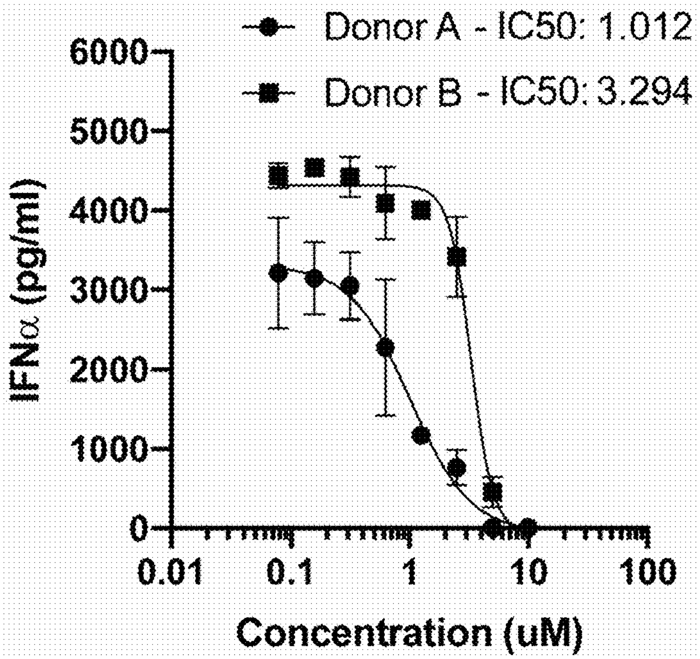
Figure 8:
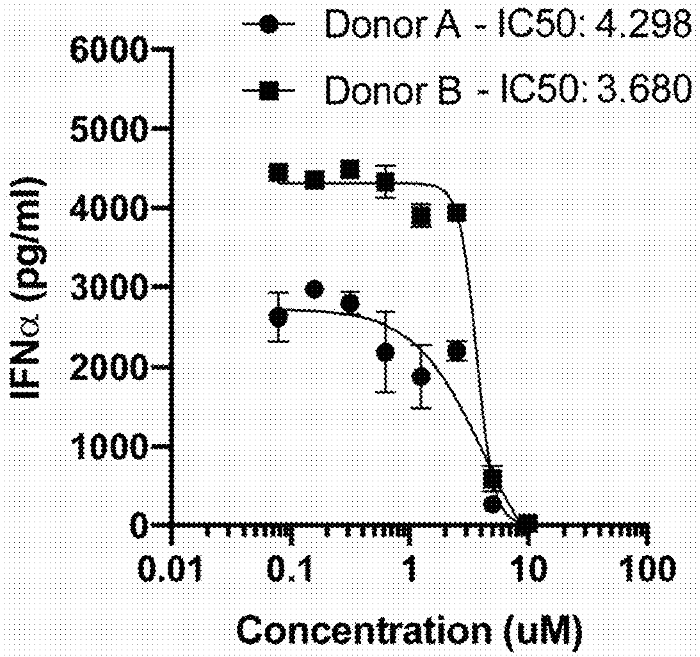
Figure 8:
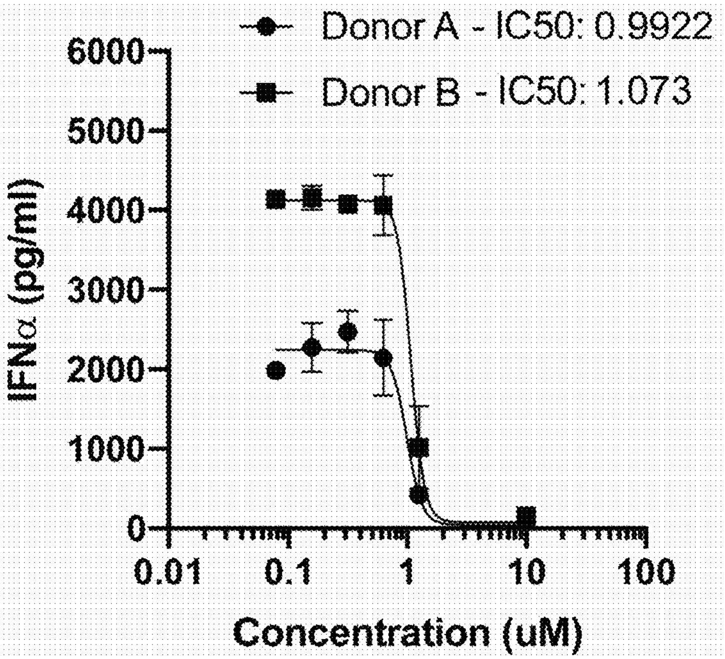
Figure 8:
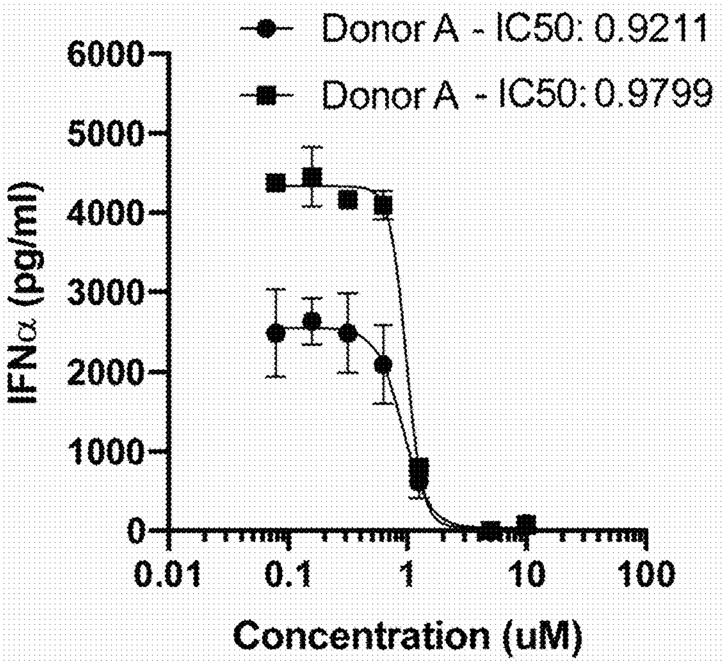
Figure 8:
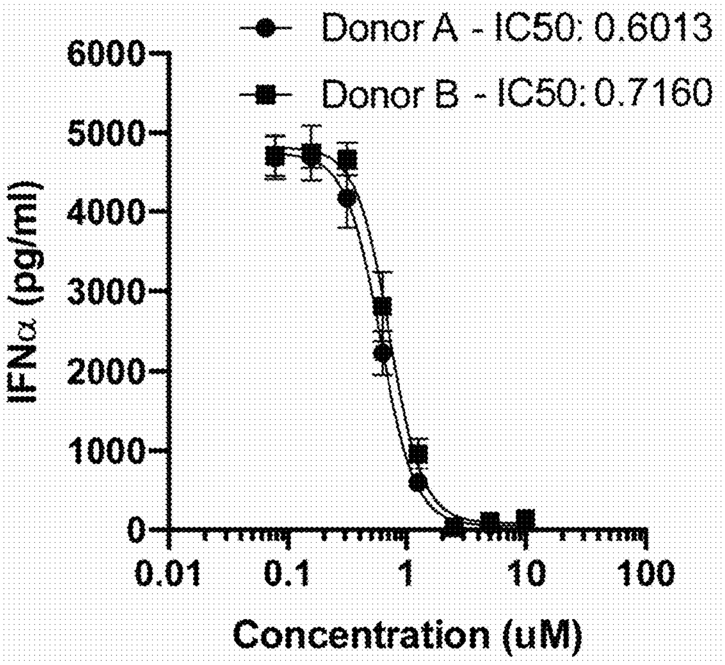
Figure 8:
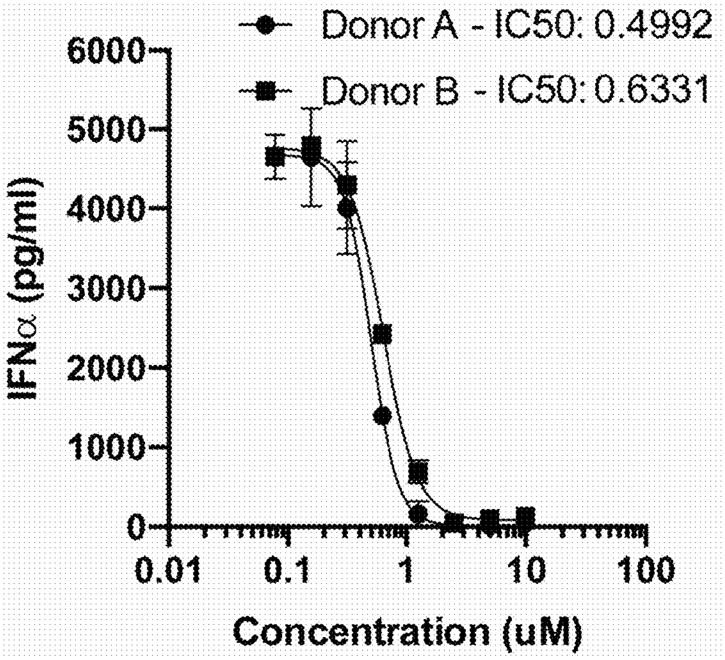
Figure 8:
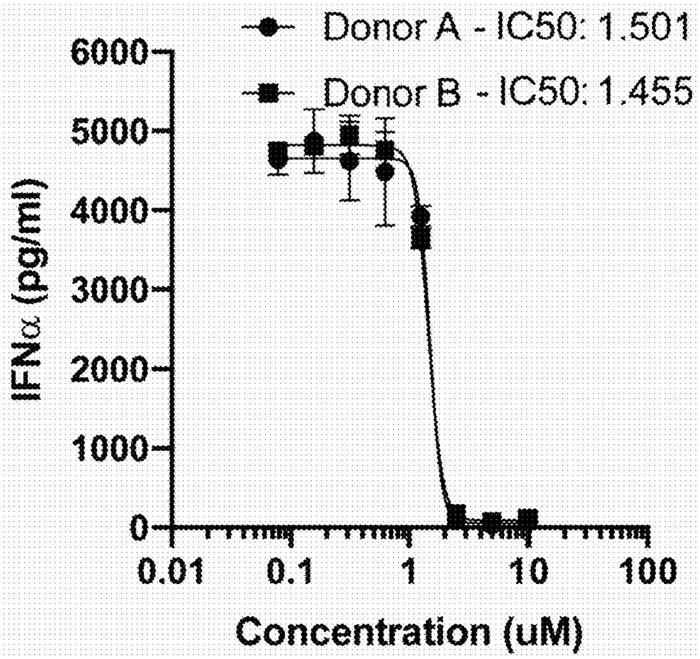
Figure 8:
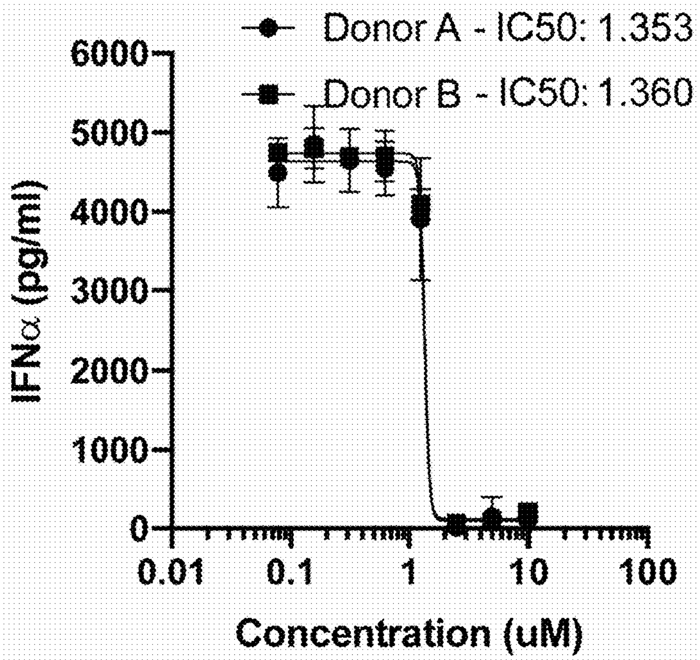
Figure 8:
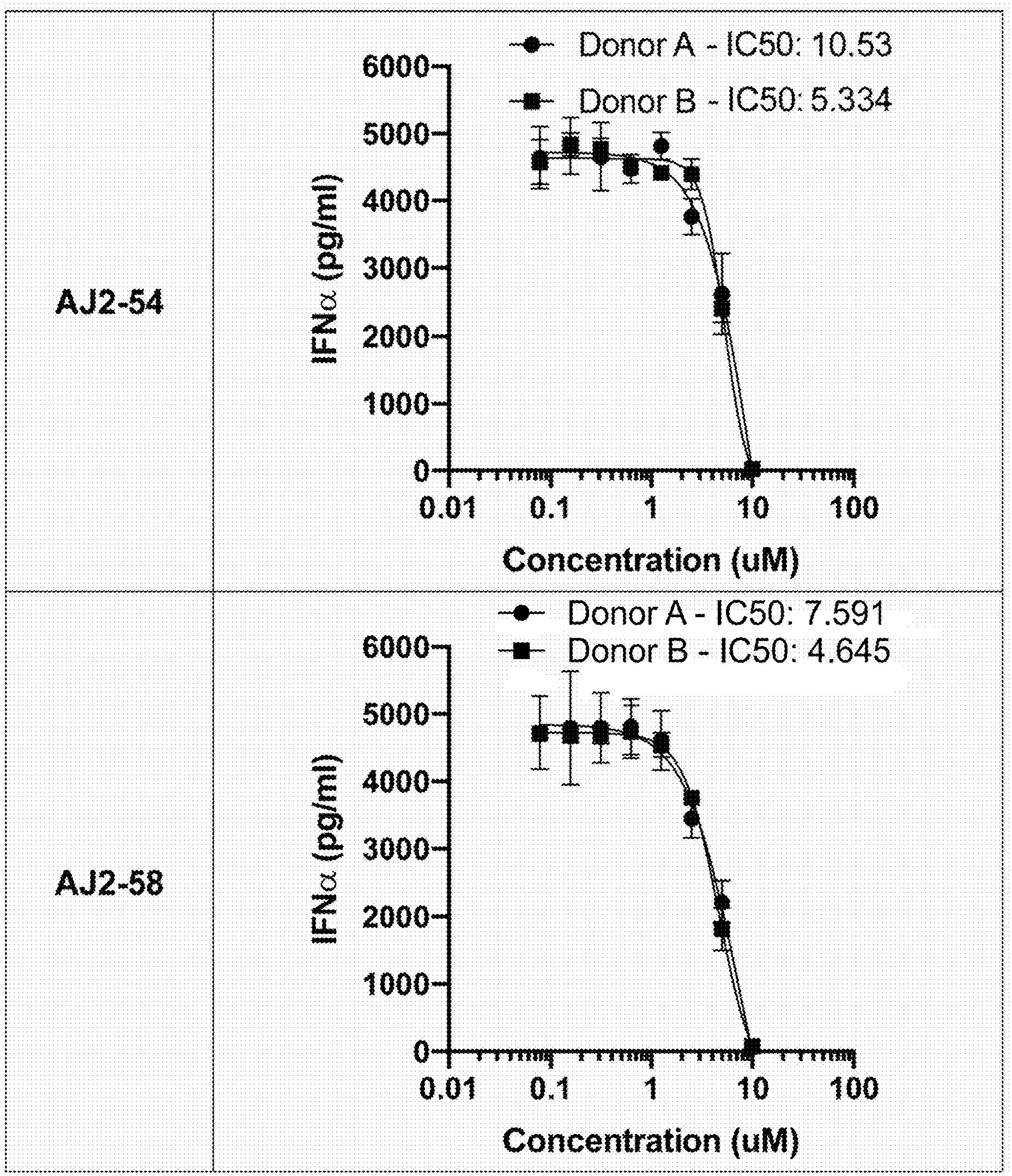
Figure 8:
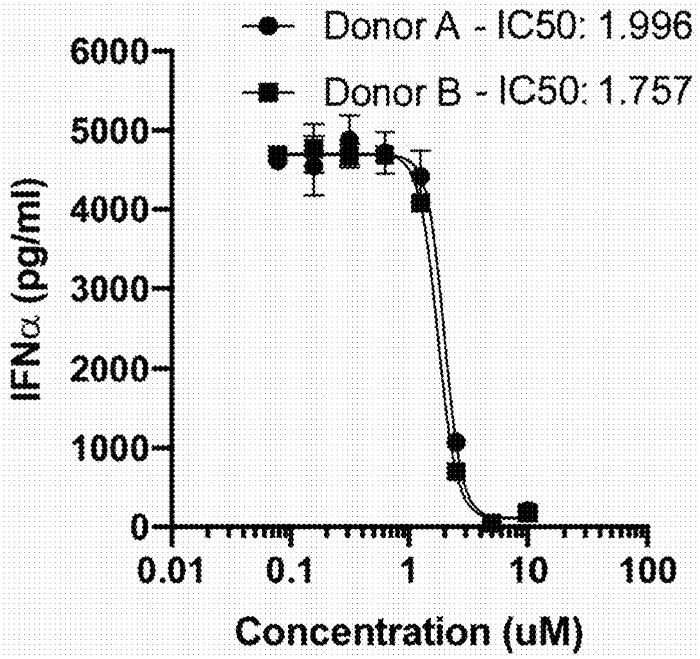
Figure 8:
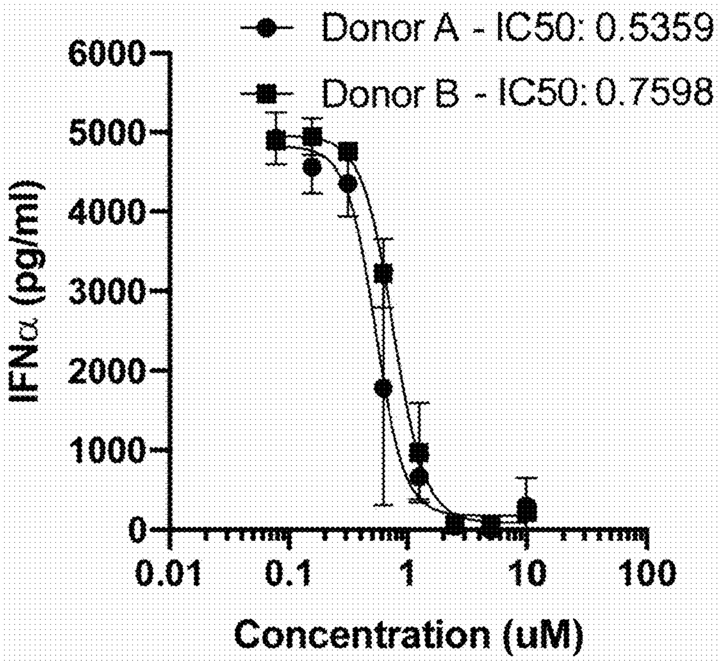
Figure 8:
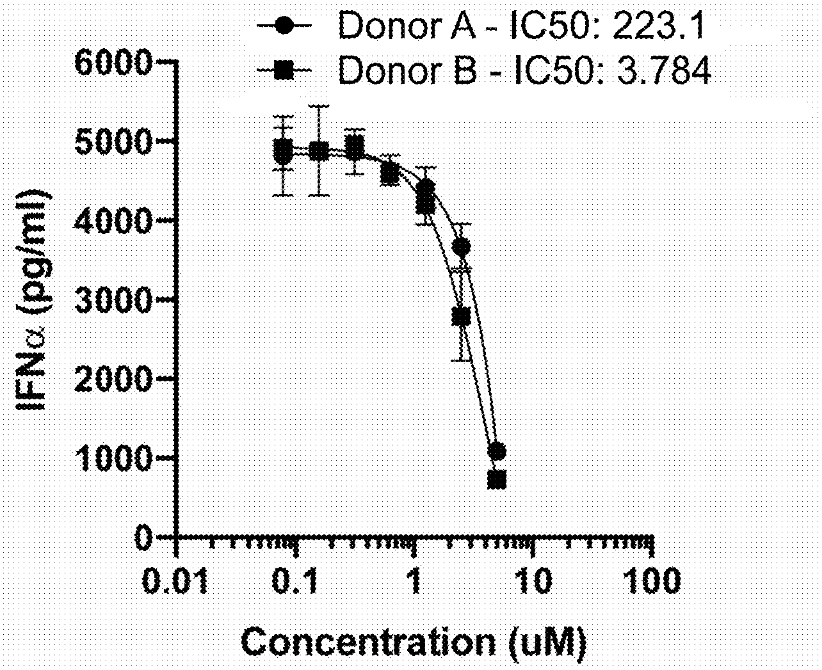
Figure 8:
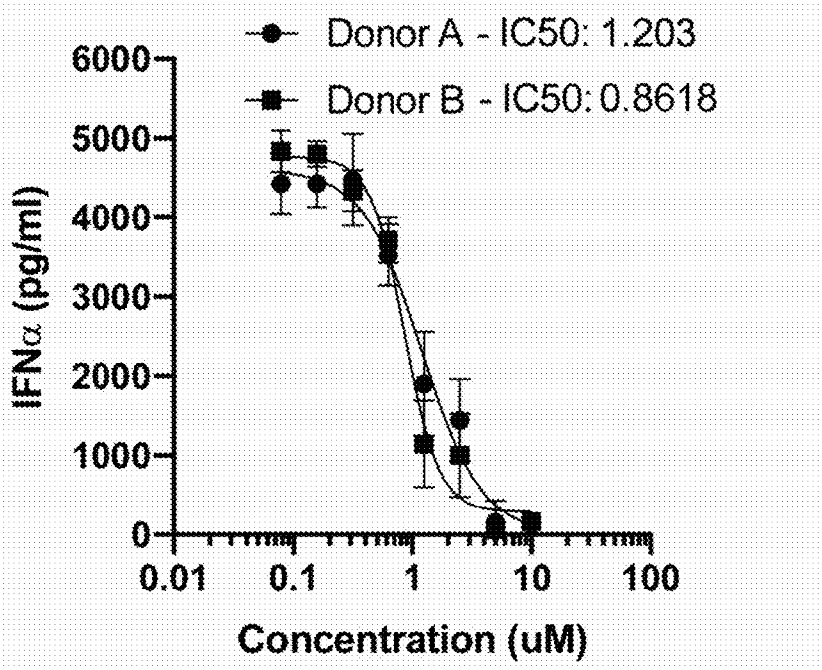
Figure 8:
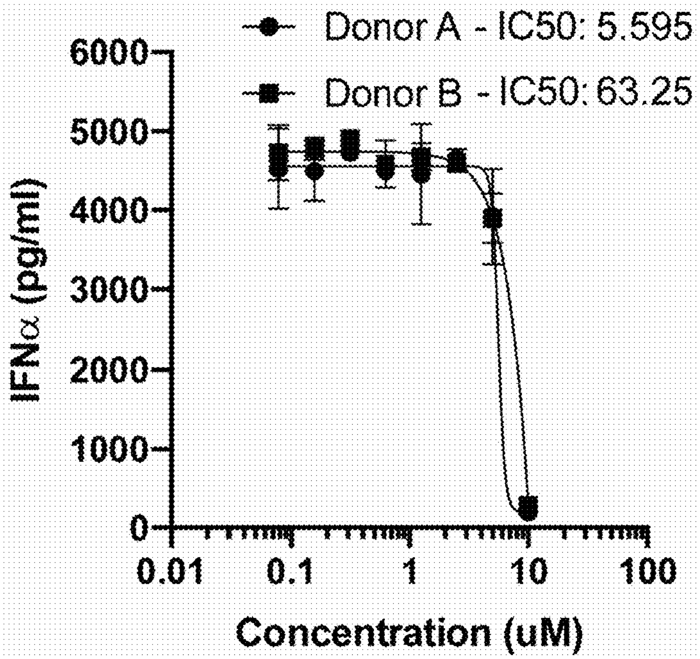
Figure 8:
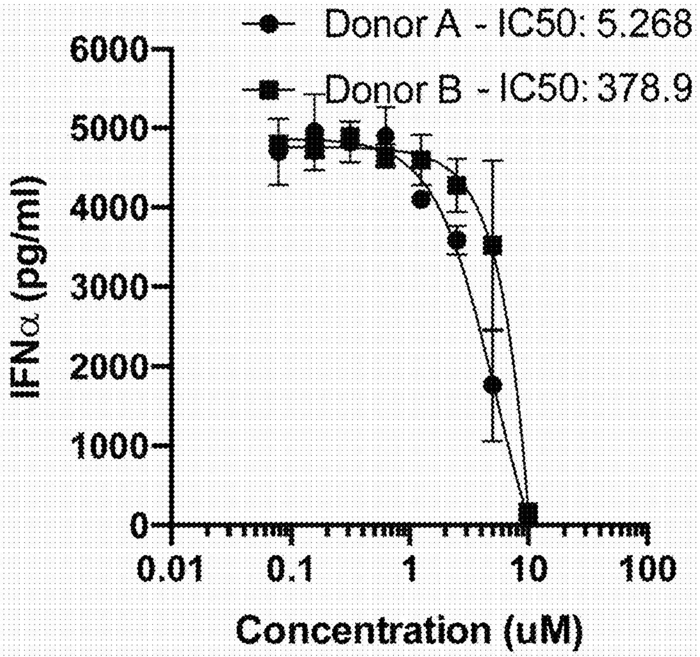
Figure 8:
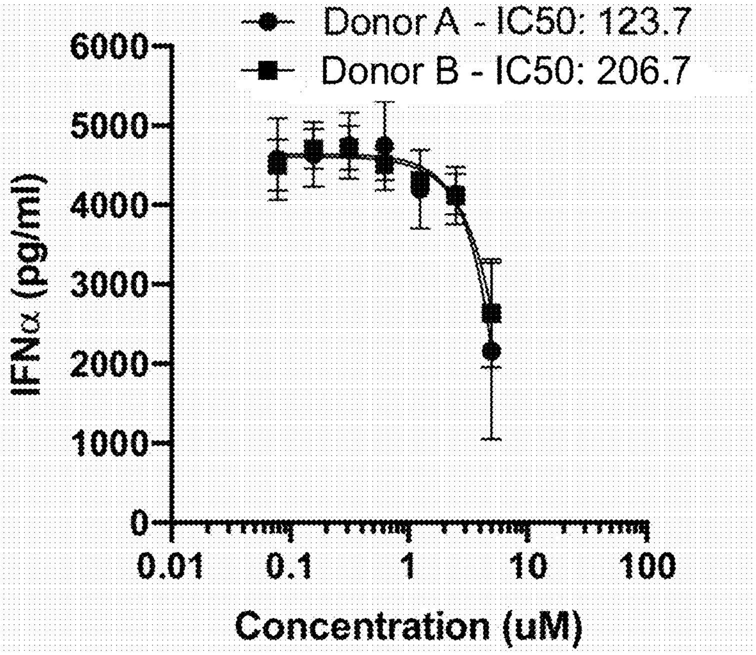
Figure 8:
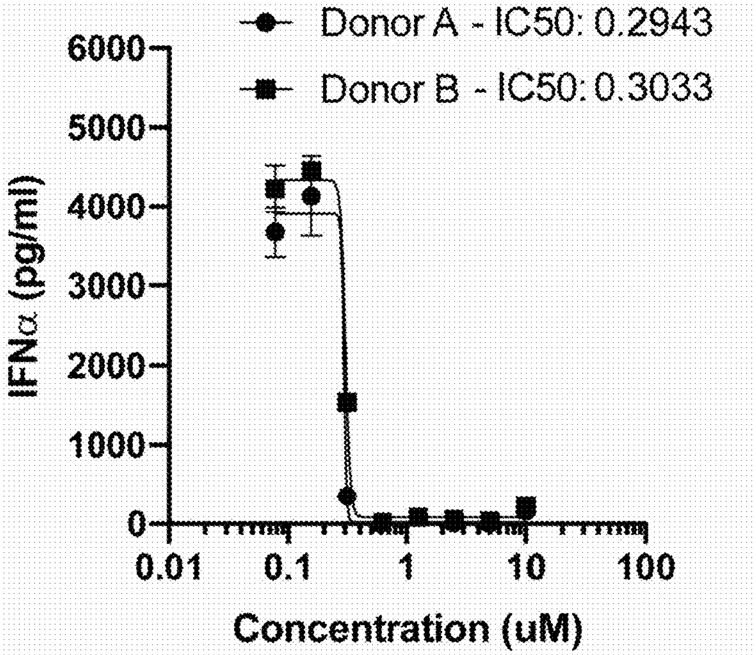
Figure 8:
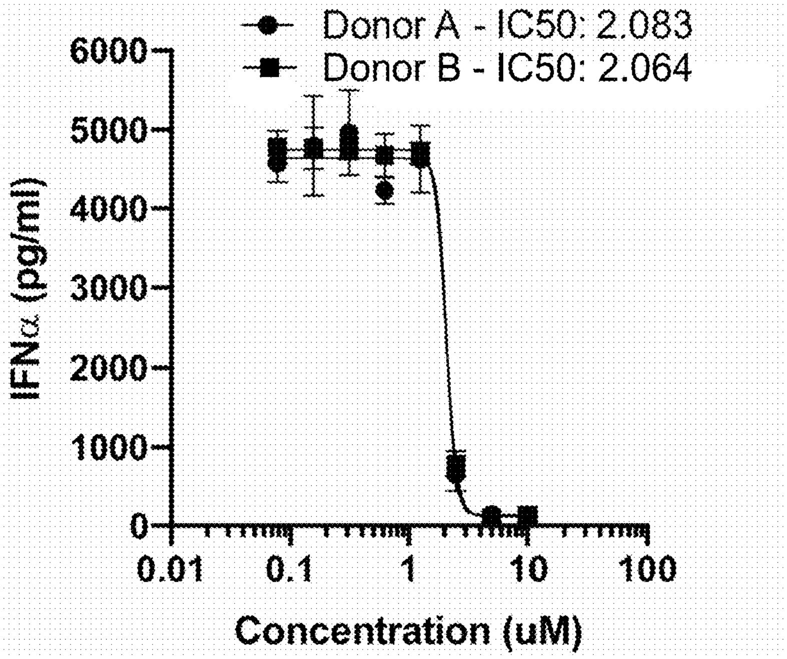
Figure 8:
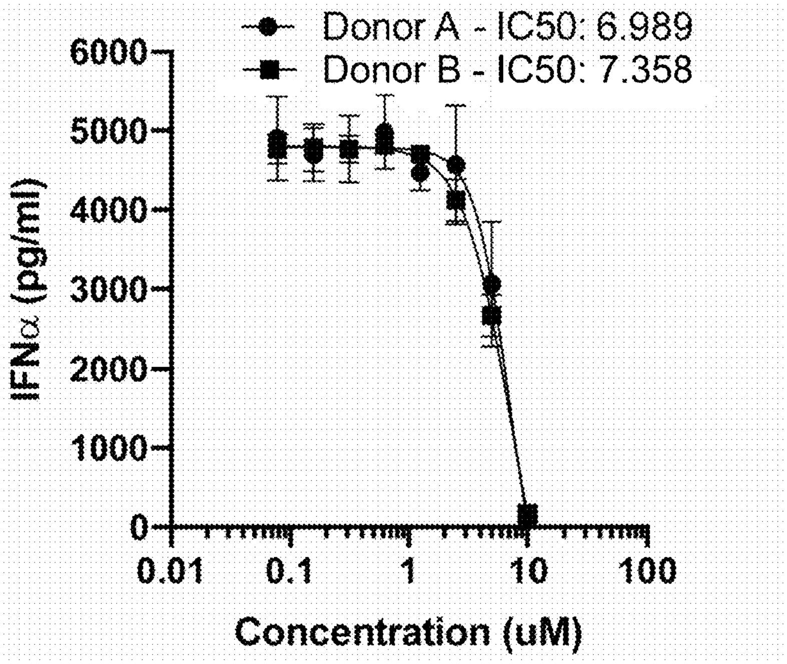
Figure 8:
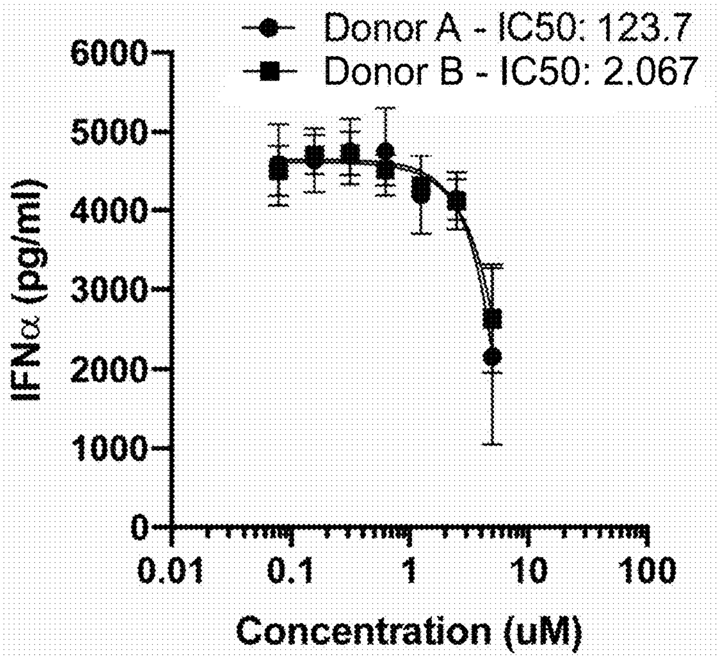
Figure 8:
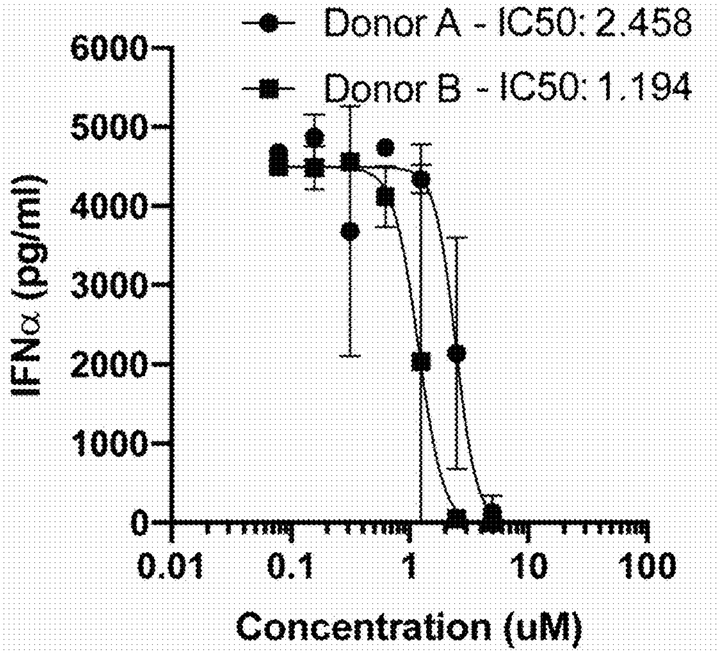
Figure 8:
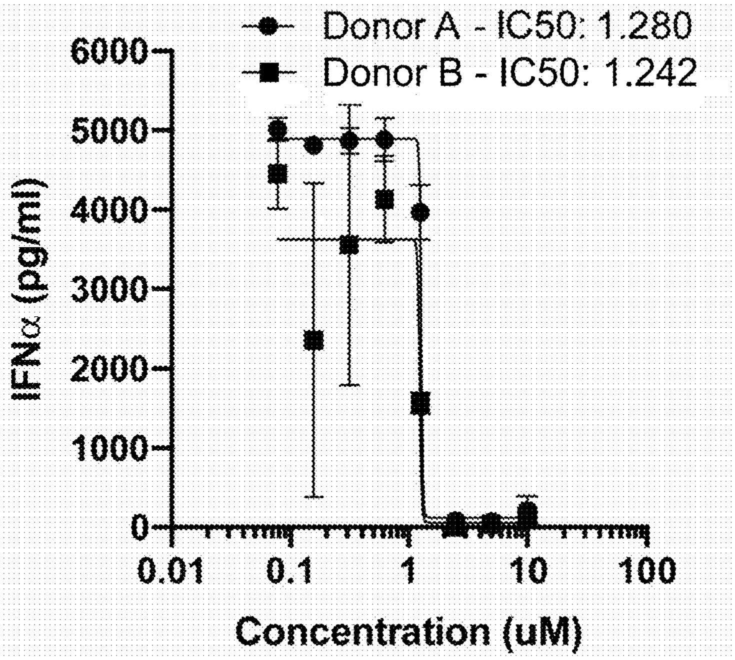
Figure 8:
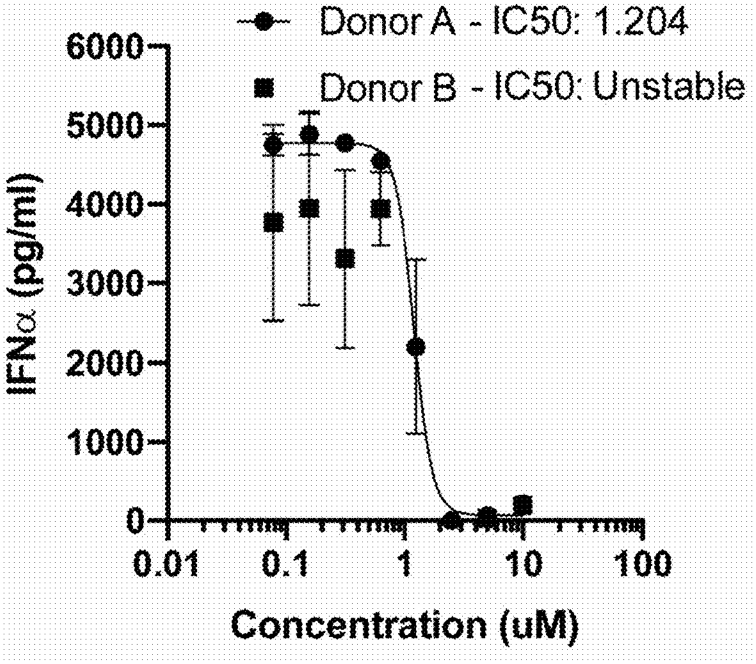
Figure 8:
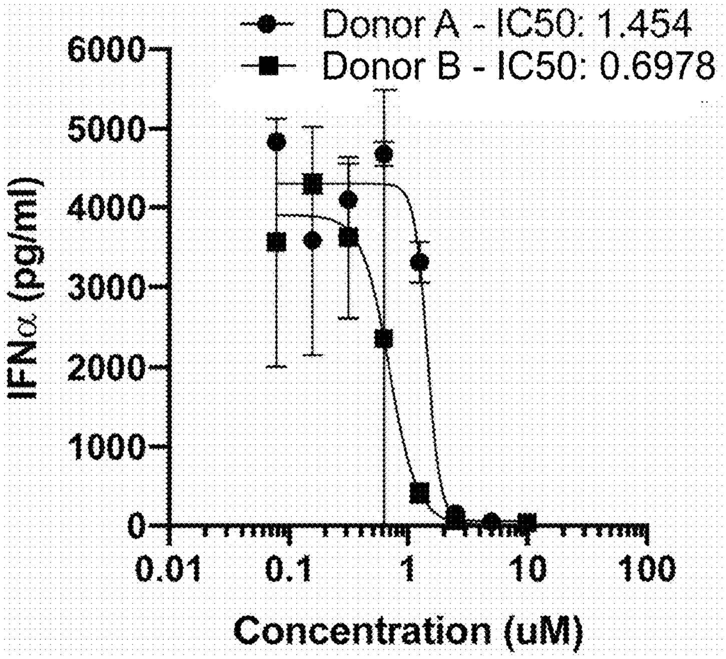
Figure 8:
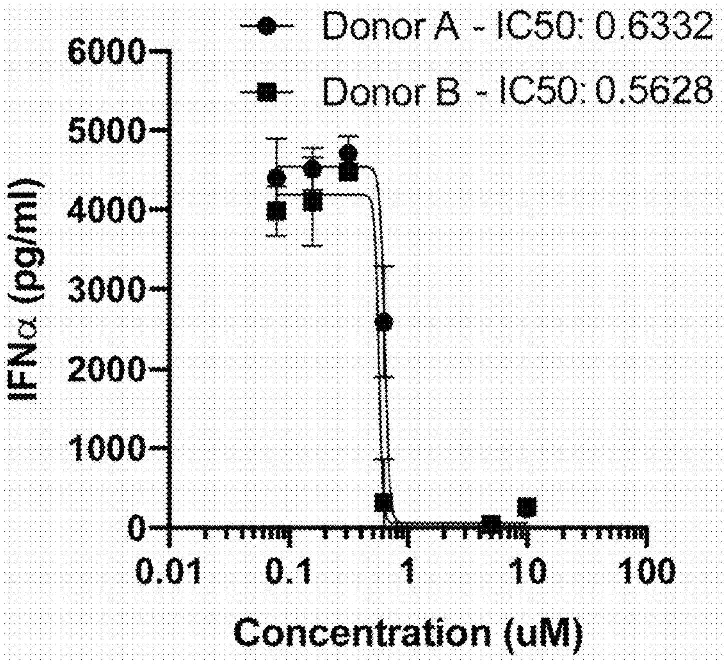
Figure 8:
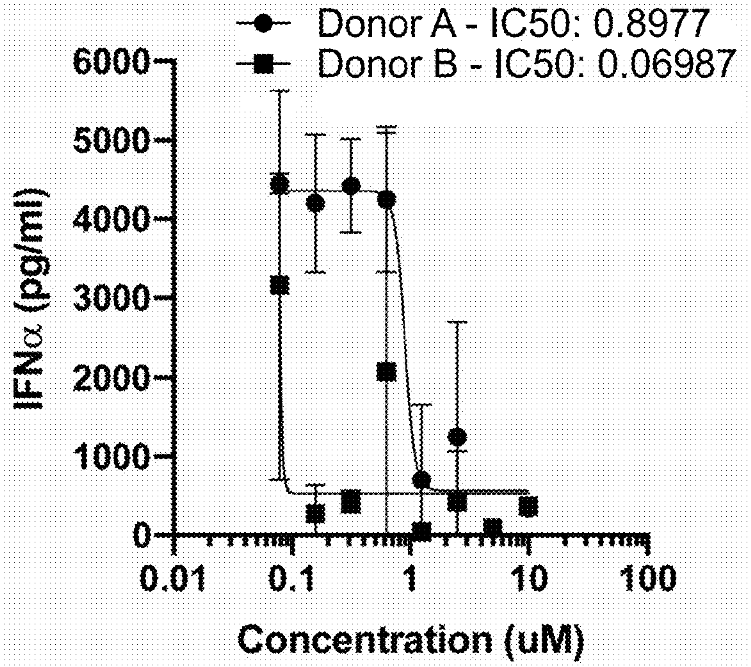
Figure 8:
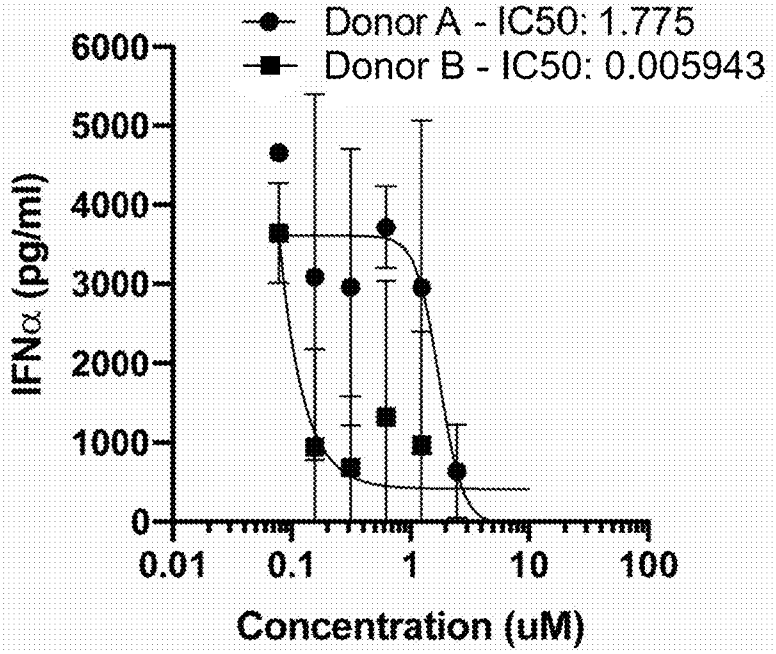
Figure 8:
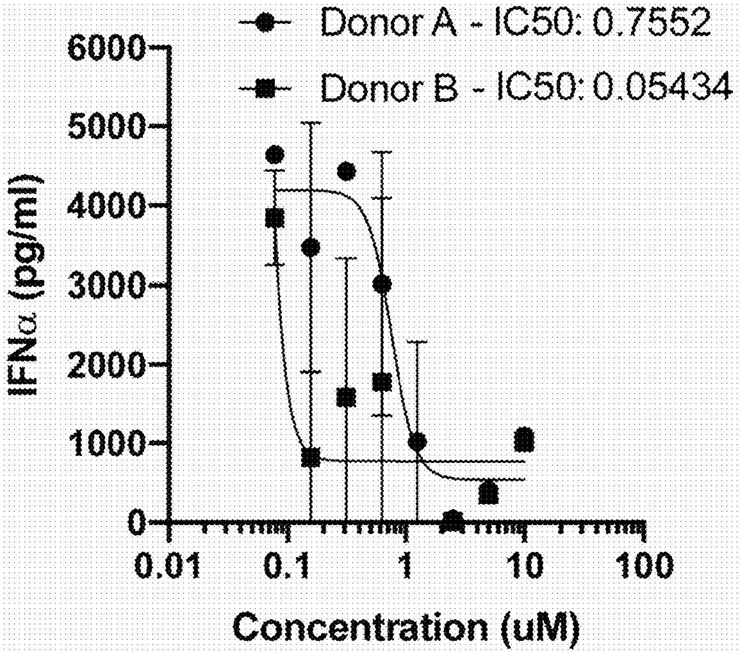
Figure 8:
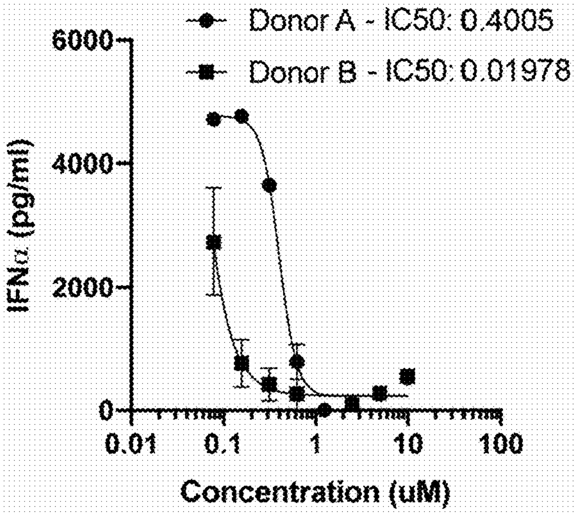
Figure 8:
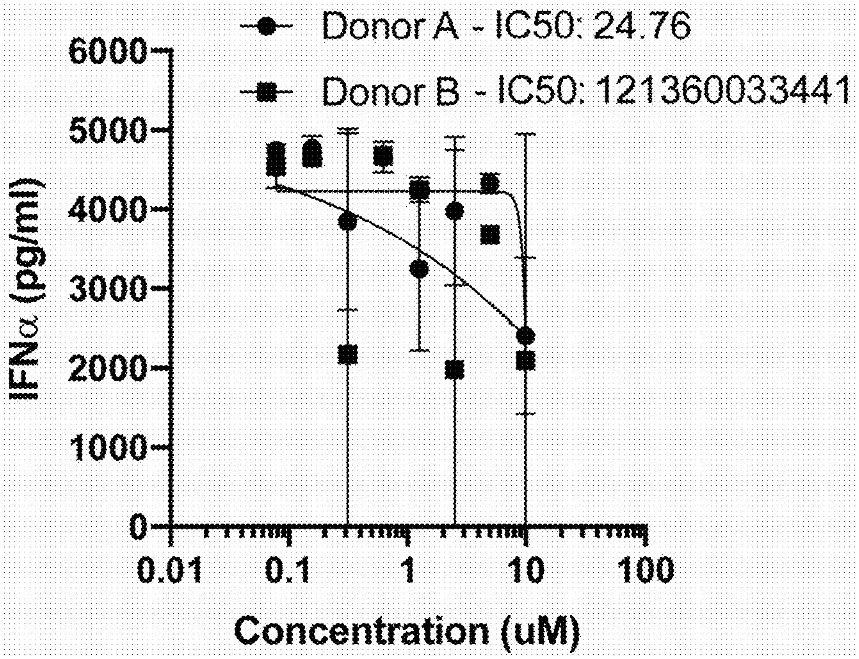
Figure 8:
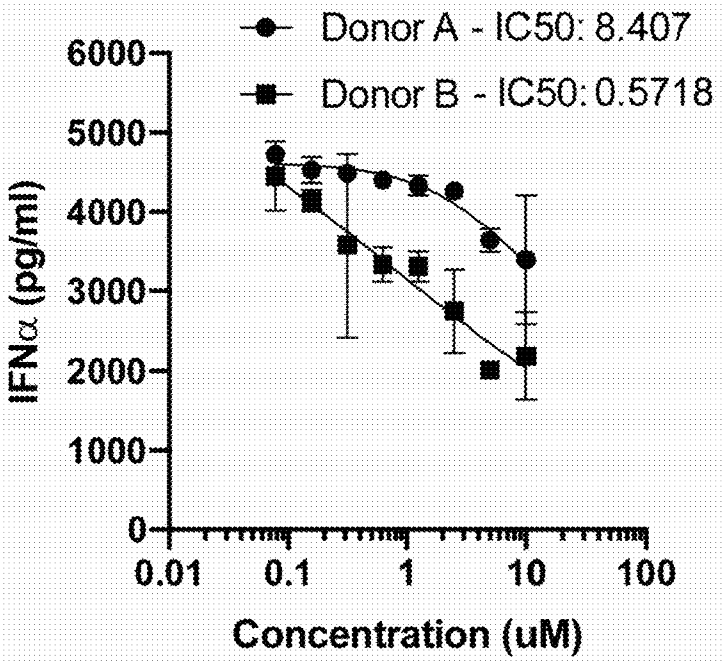
Figure 8:
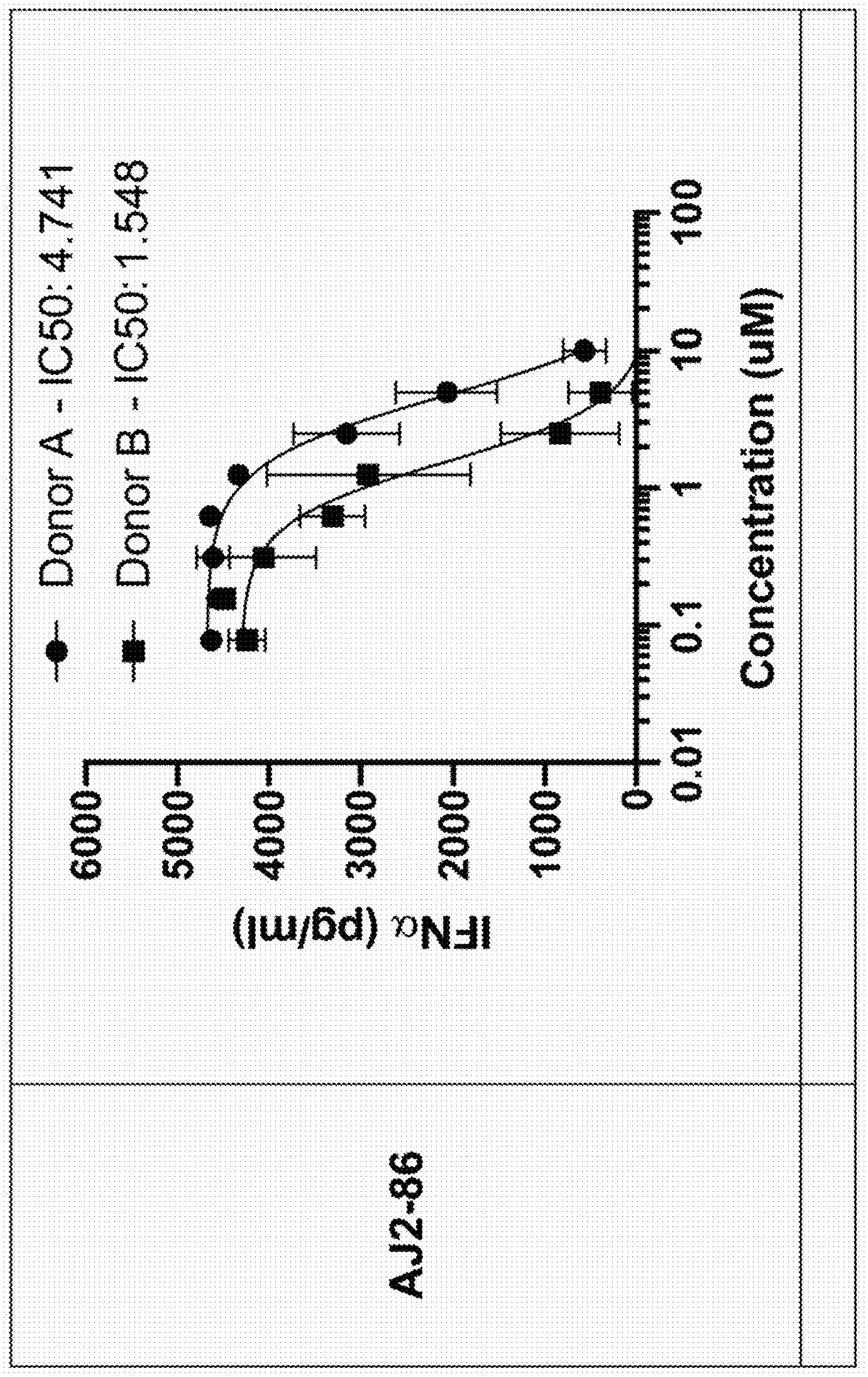
Figure 8:
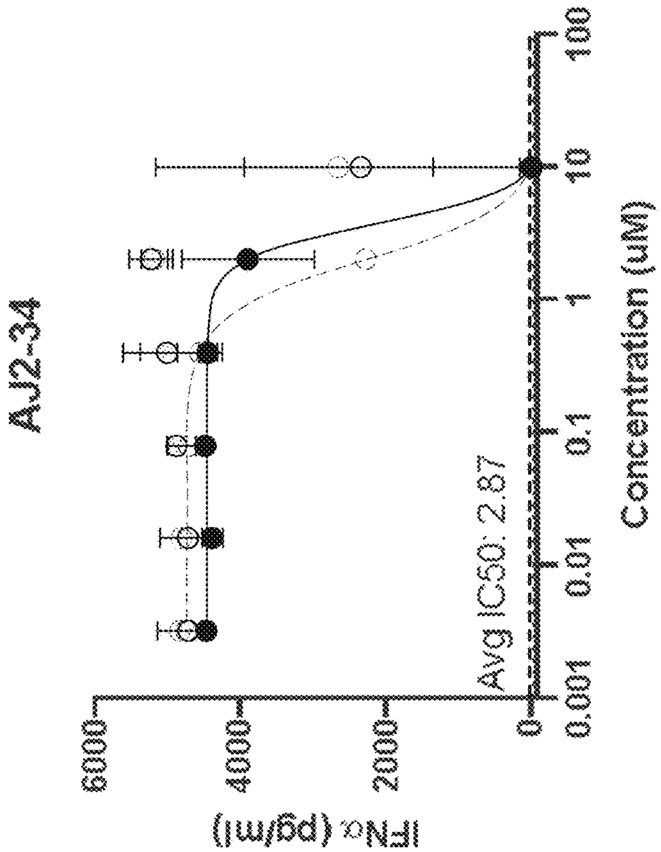
Figure 8:
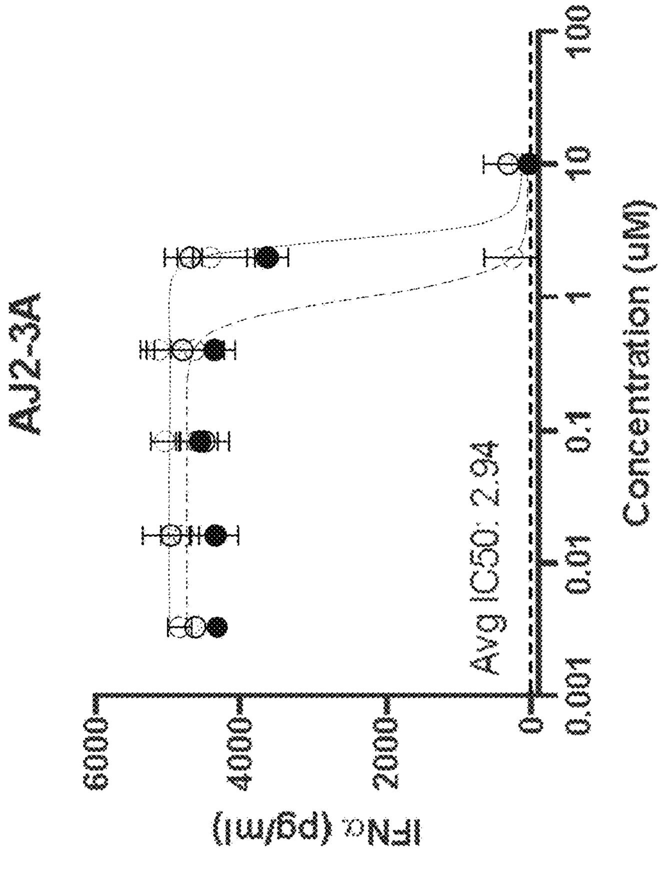
Figure 8:
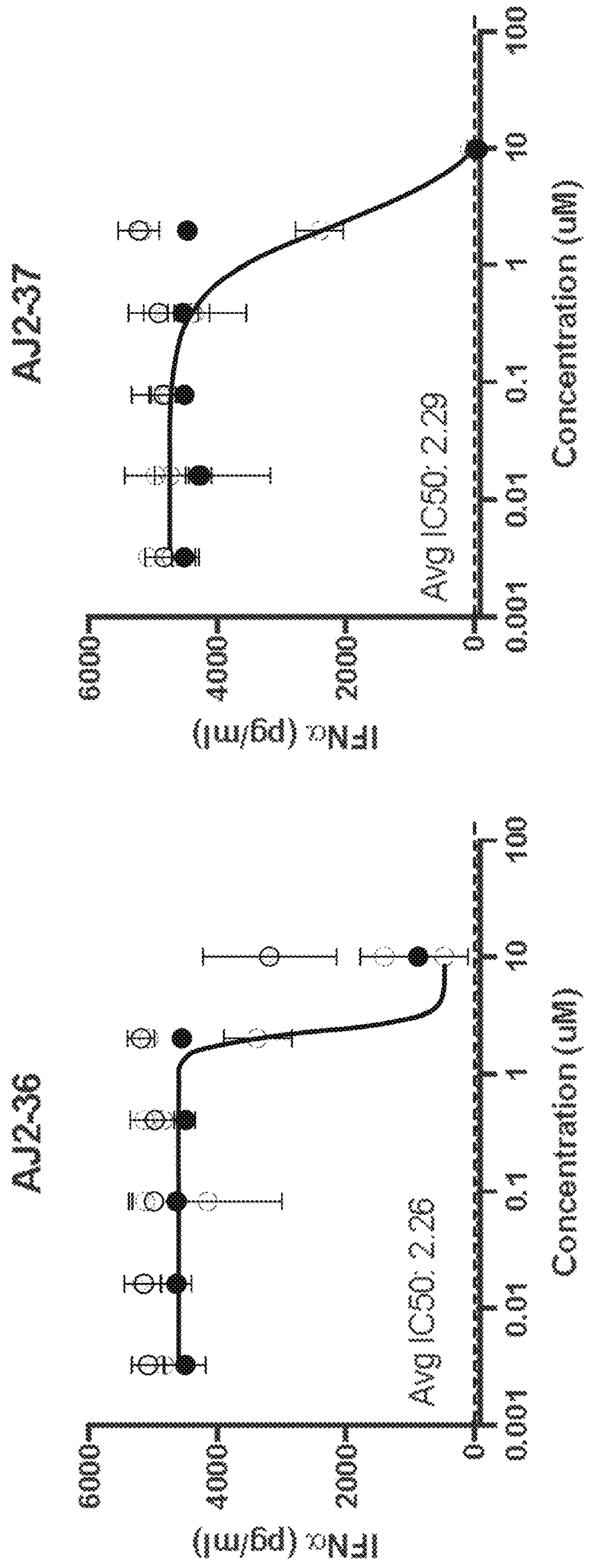
Figure 8:
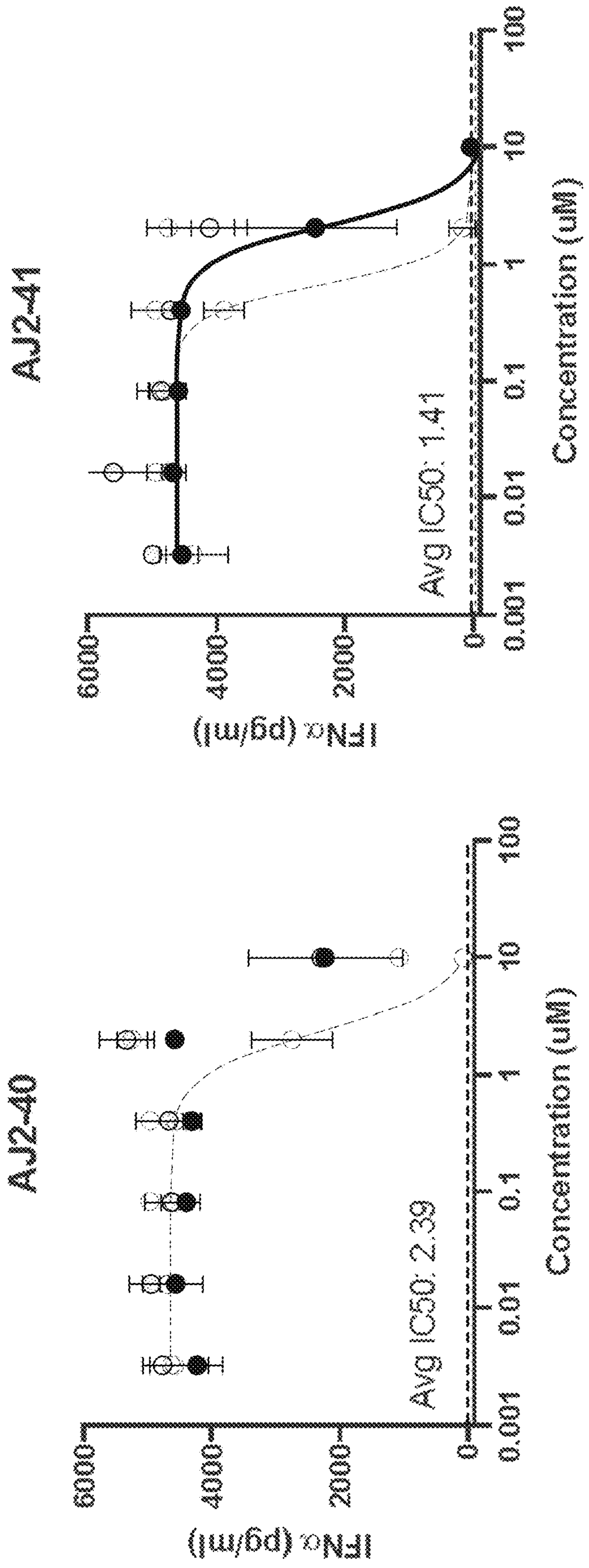
Figure 8:
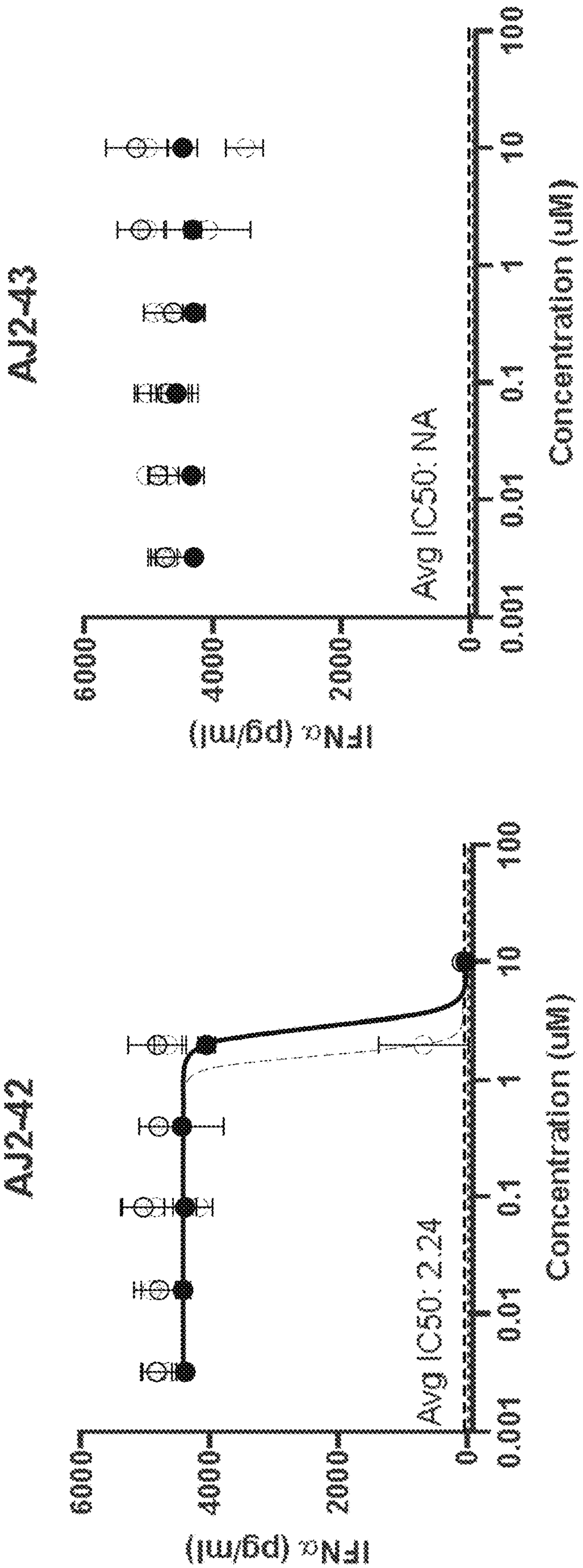
Figure 8:
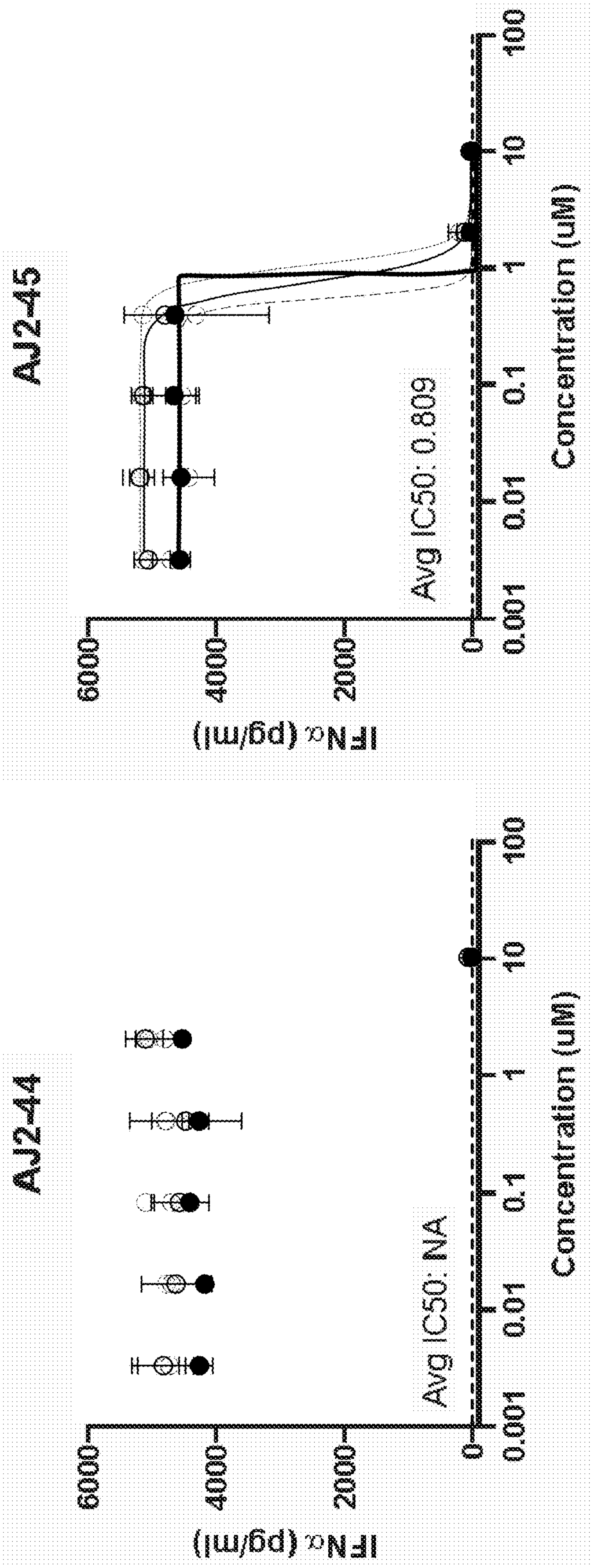
Figure 8:
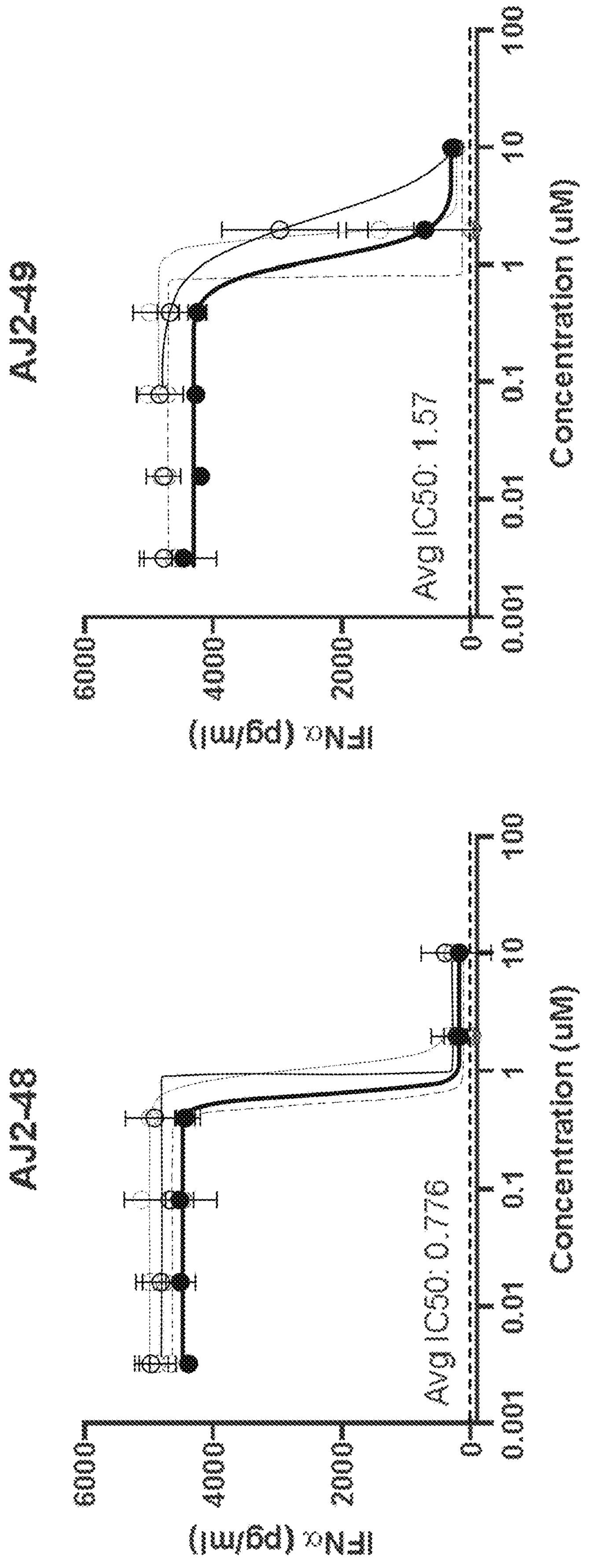
Figure 8:
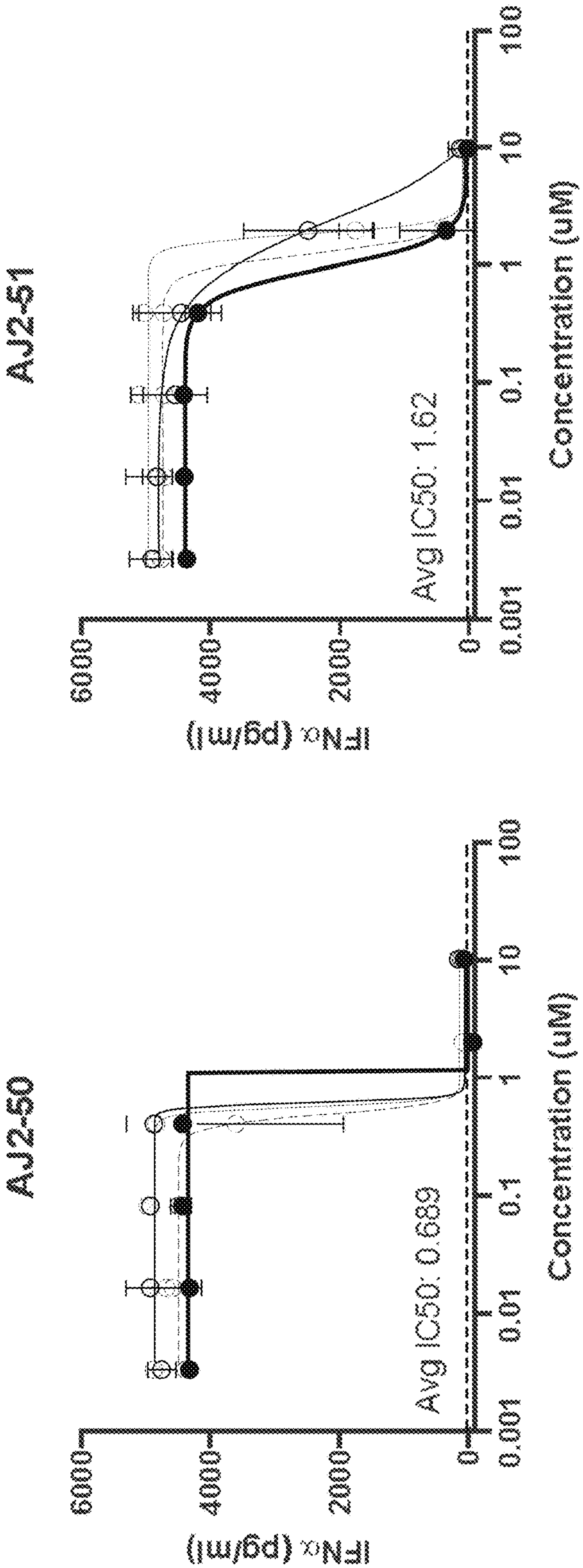
Figure 8:
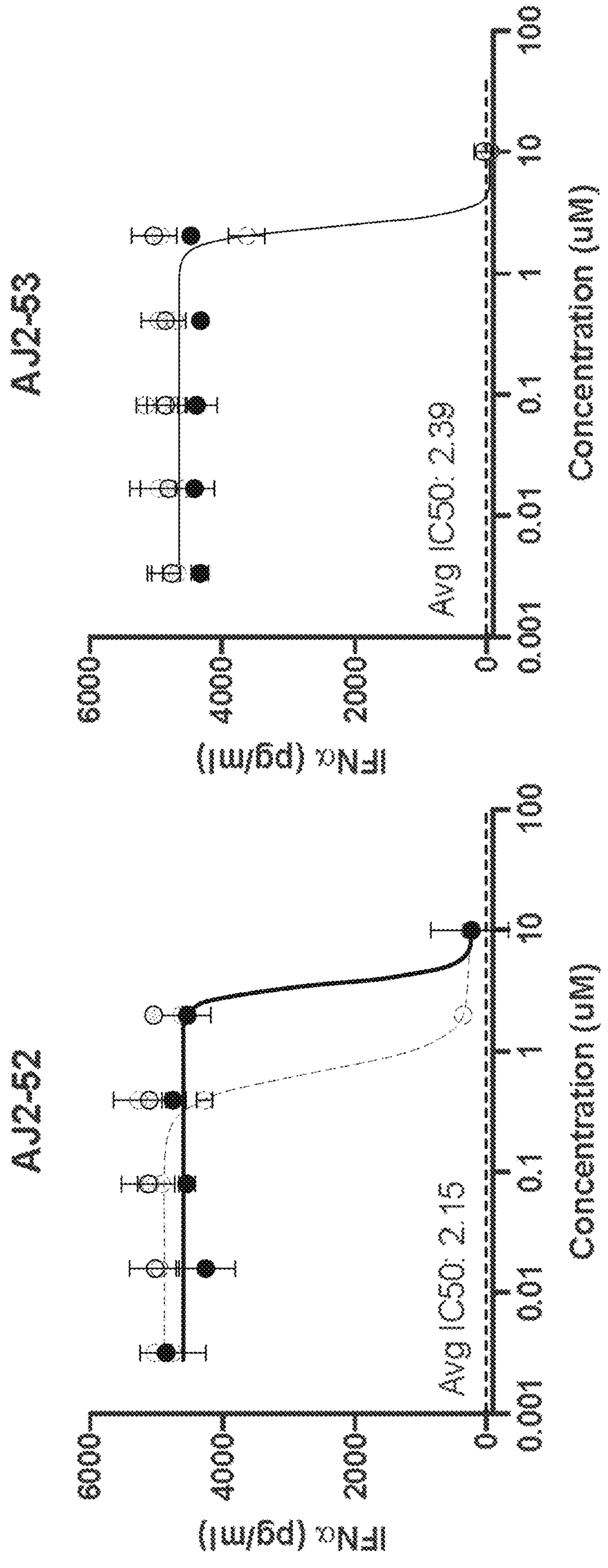
Figure 8:
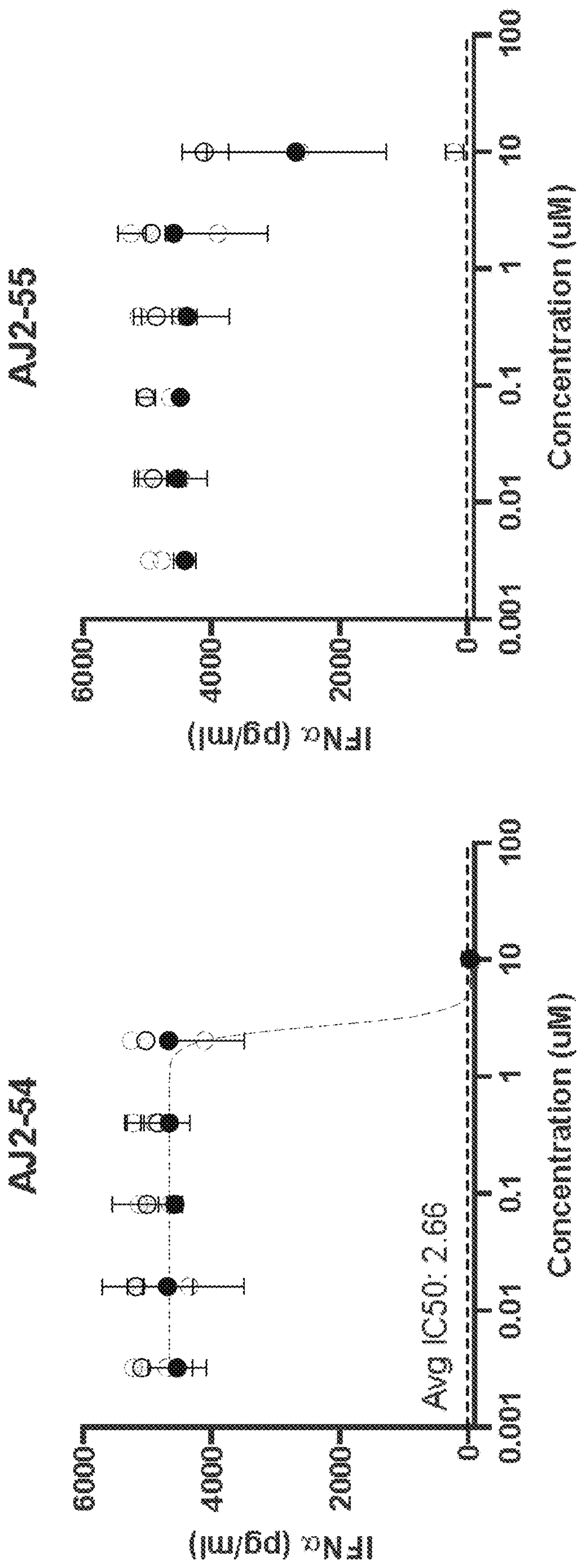
Figure 8:
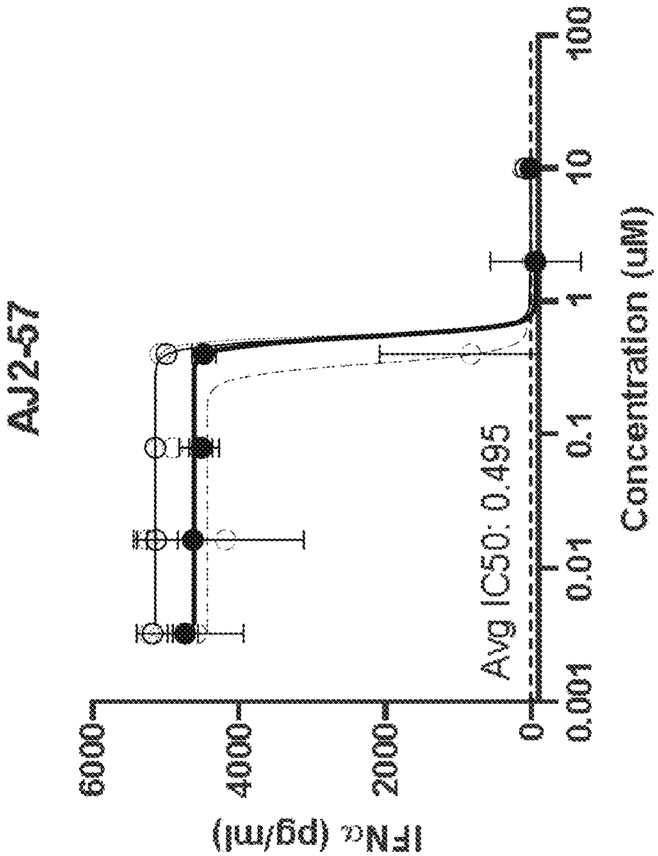
Figure 8:
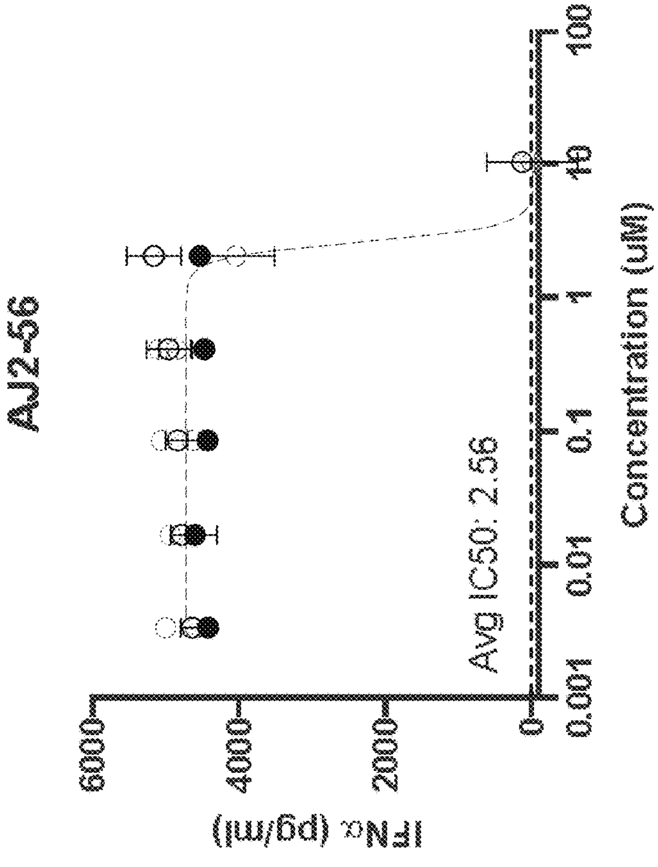
Figure 8:
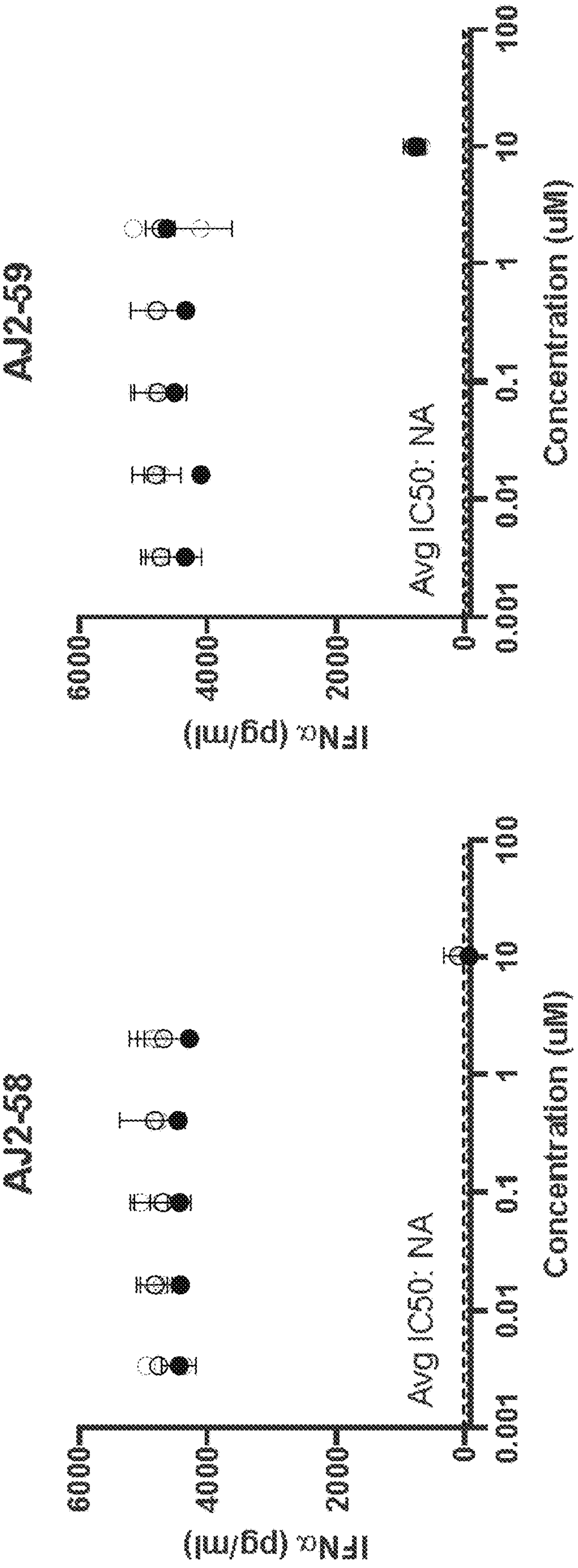
Figure 8:
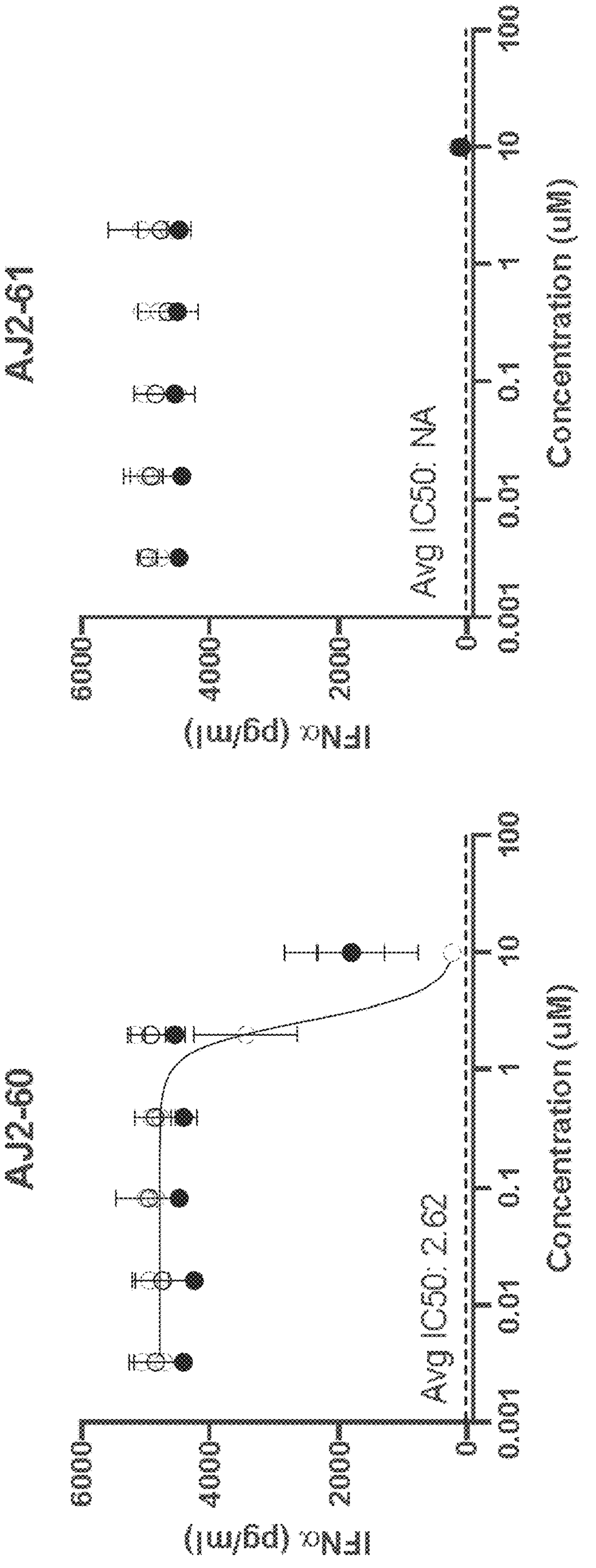
Figure 8:
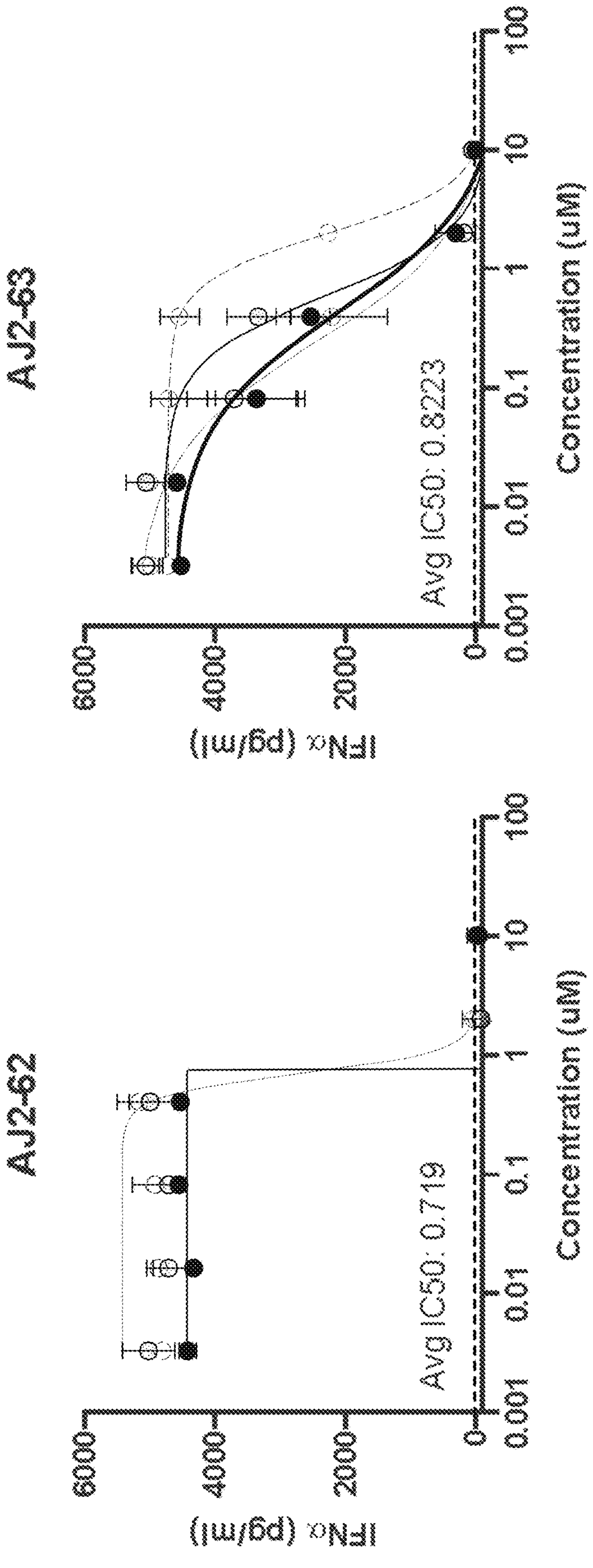

FIG. 8 is a table of IC50 of SLC15A4 inhibitors.

Figure 9:
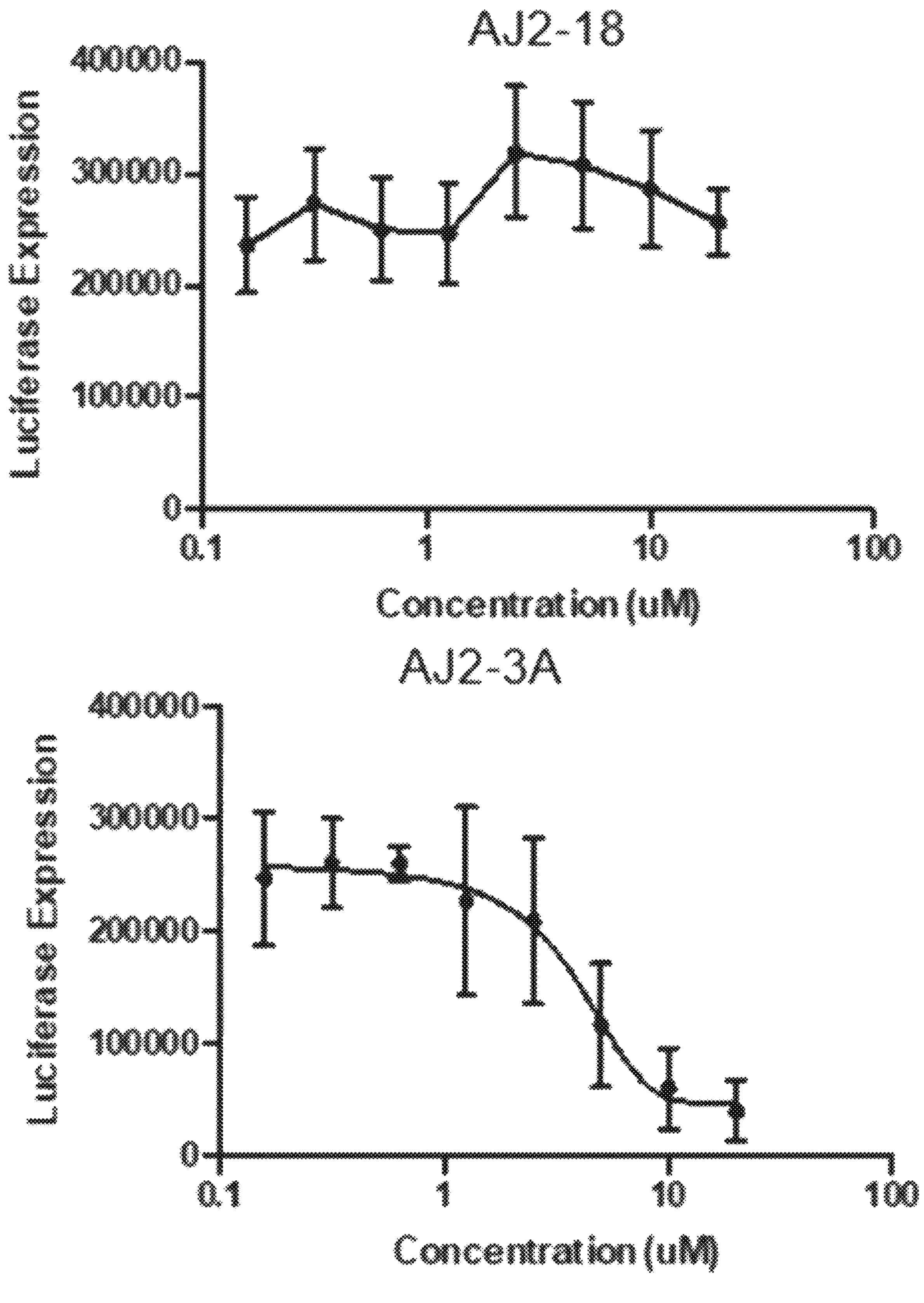
Figure 9:
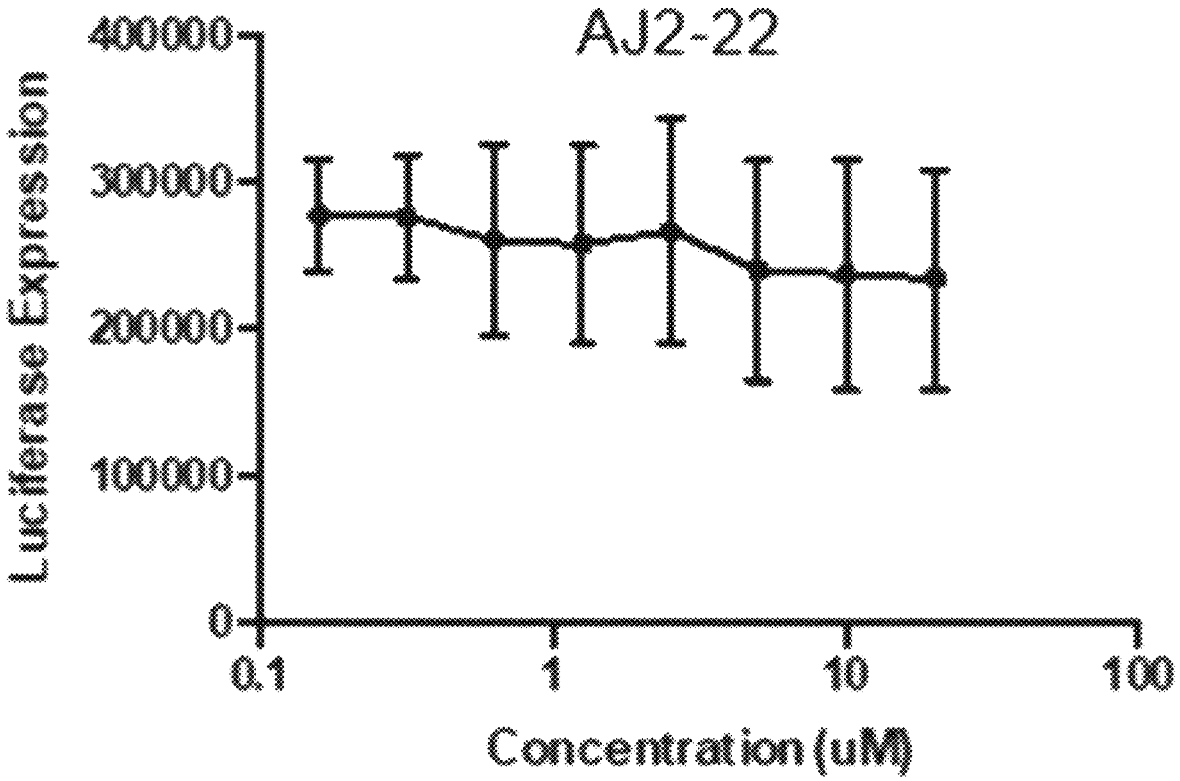
Figure 9:
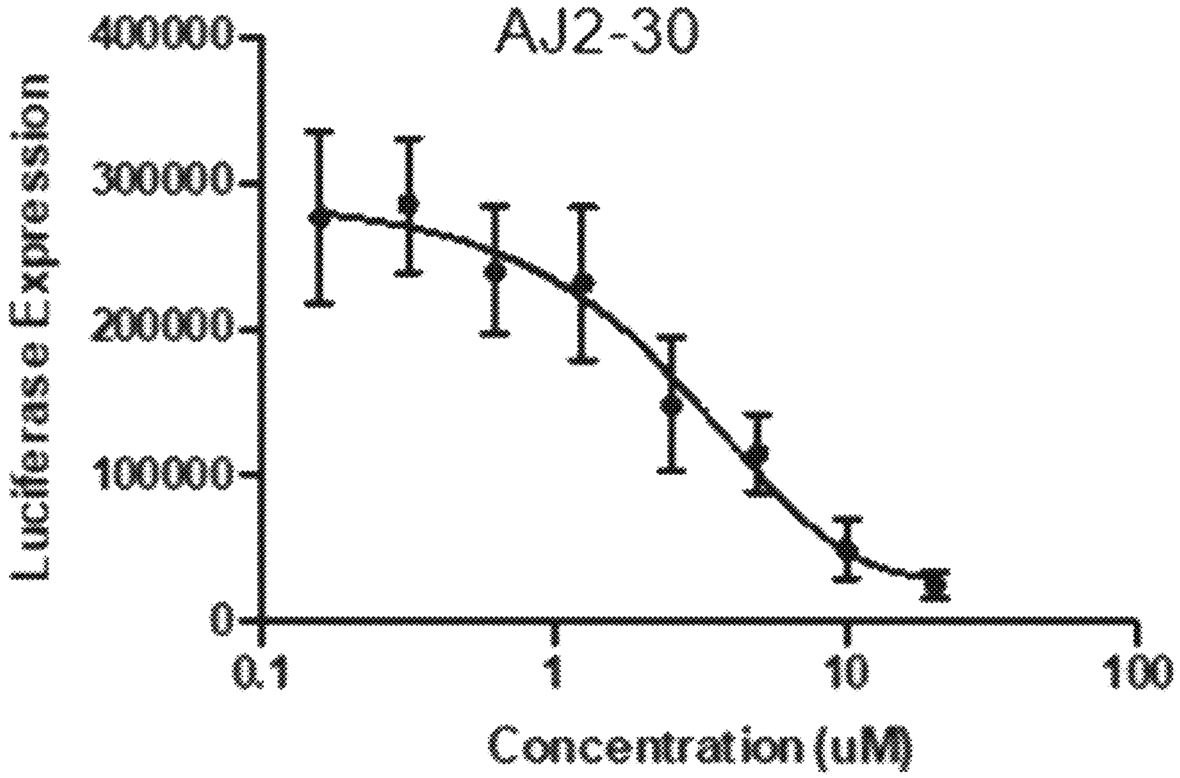

FIG. 9 is a series of graphic showing SLC15A4 inhibitors block MDP transport in a dose-dependent fashion with AJ2-3A and AJ2-30 being active and AJ2-18 and AJ2-22 being inactive controls.

Figure 10:
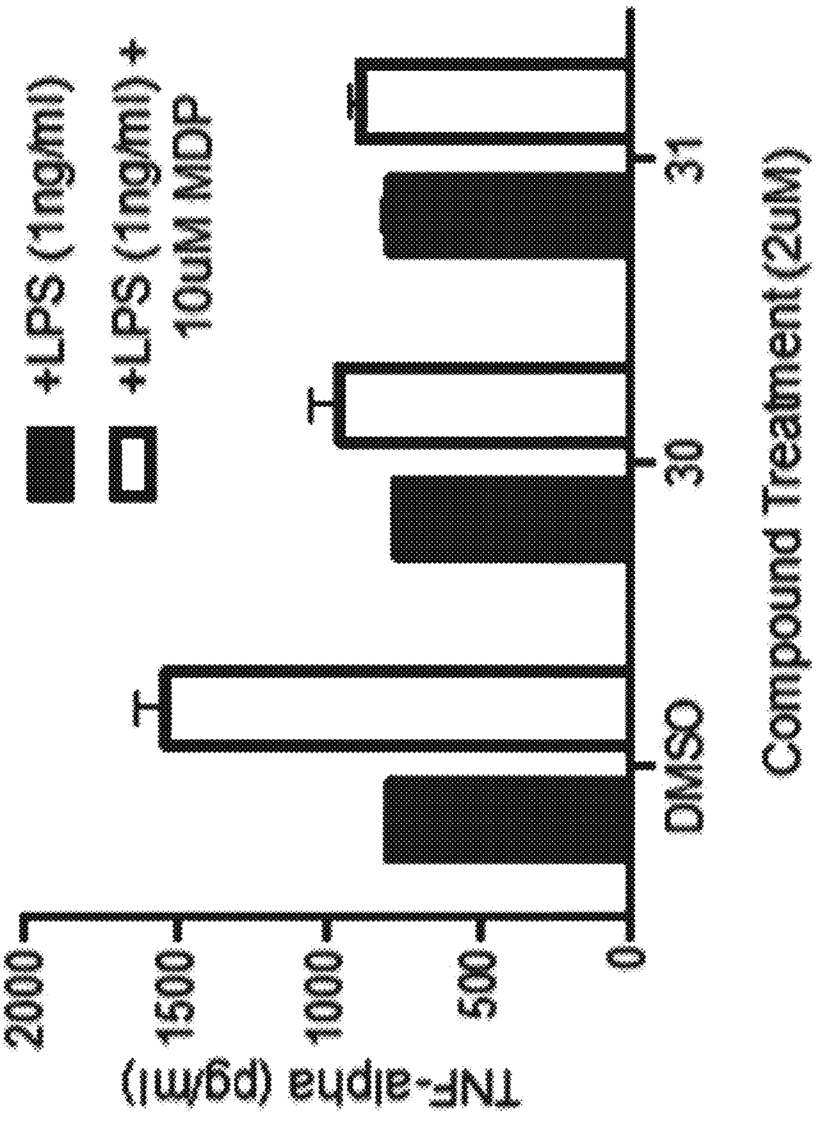

FIG. 10 shows compounds that engage SLC15A4 block endogenous NOD signaling in THP cells.

Figure 11:
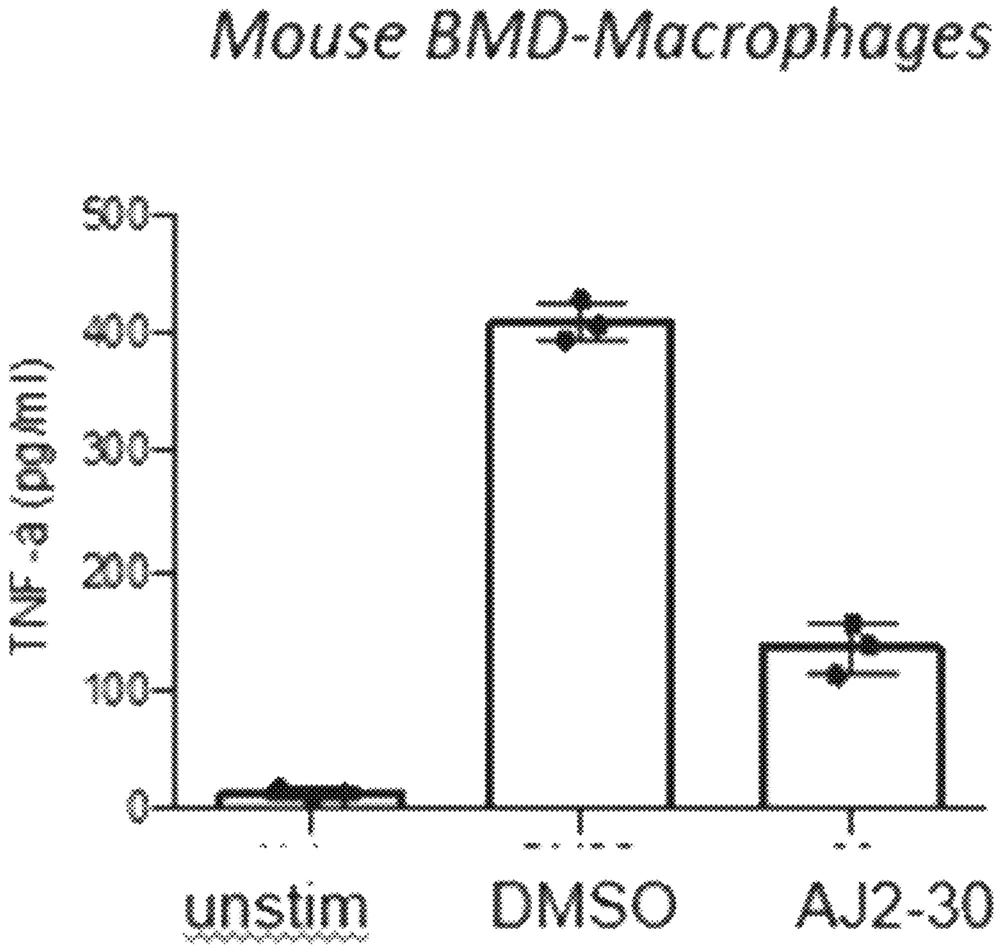
Figure 11:
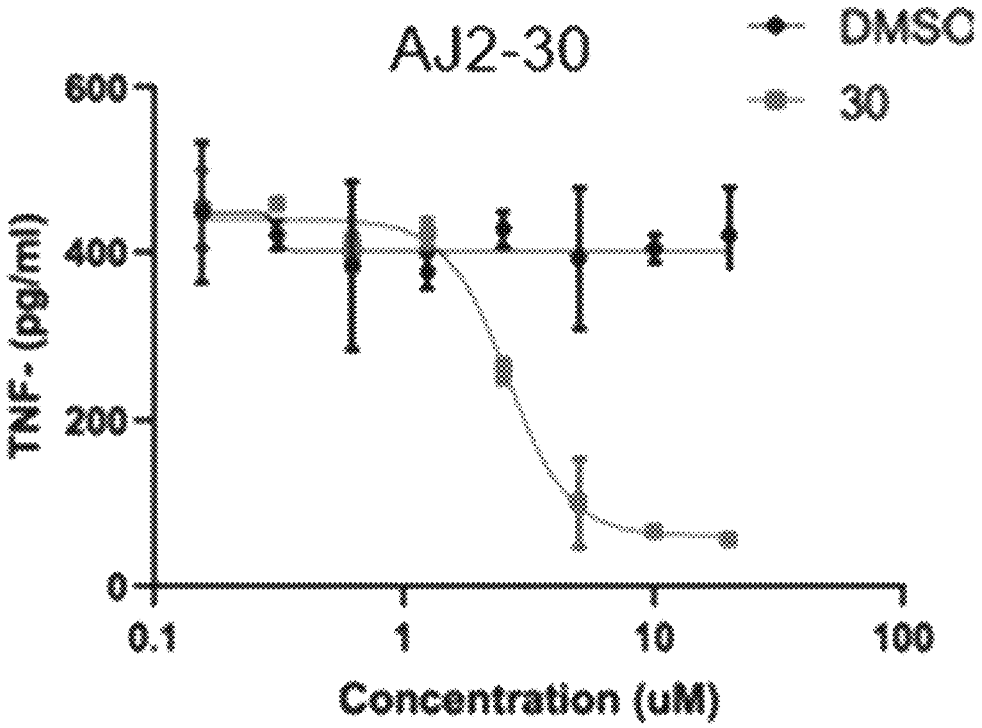
Figure 11:
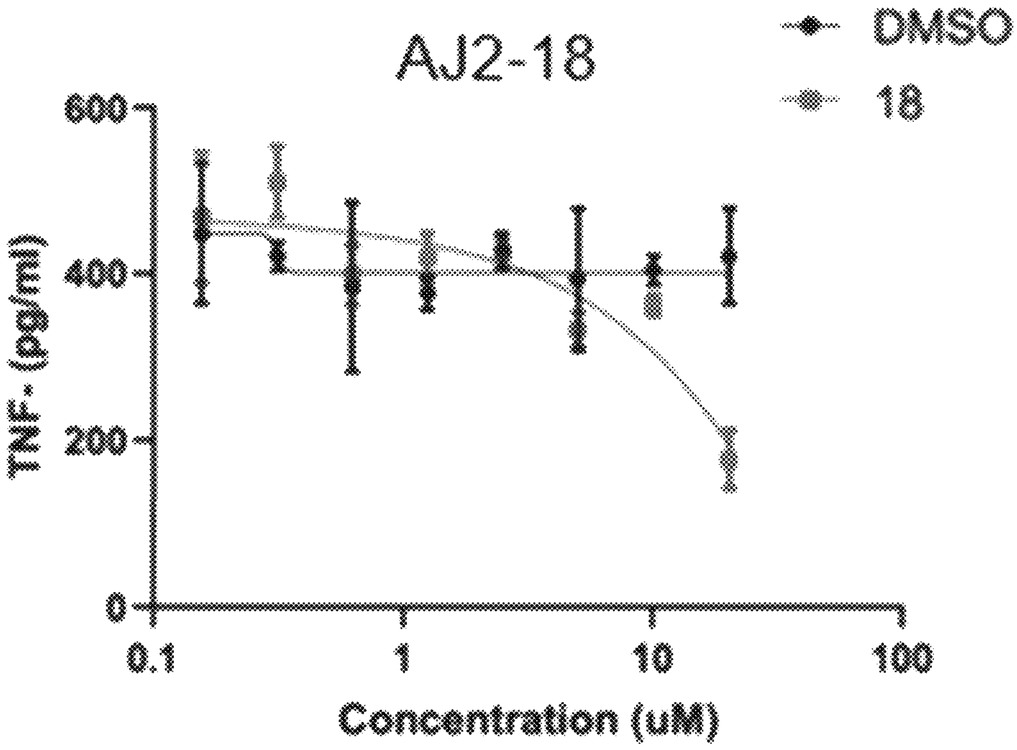

FIG. 11 shows compounds that engage SLC15A4 block endogenous NOD signaling in human and mouse macrophages with AJ2-30 being active and AJ2-18 being an in active control.

Figure 12:
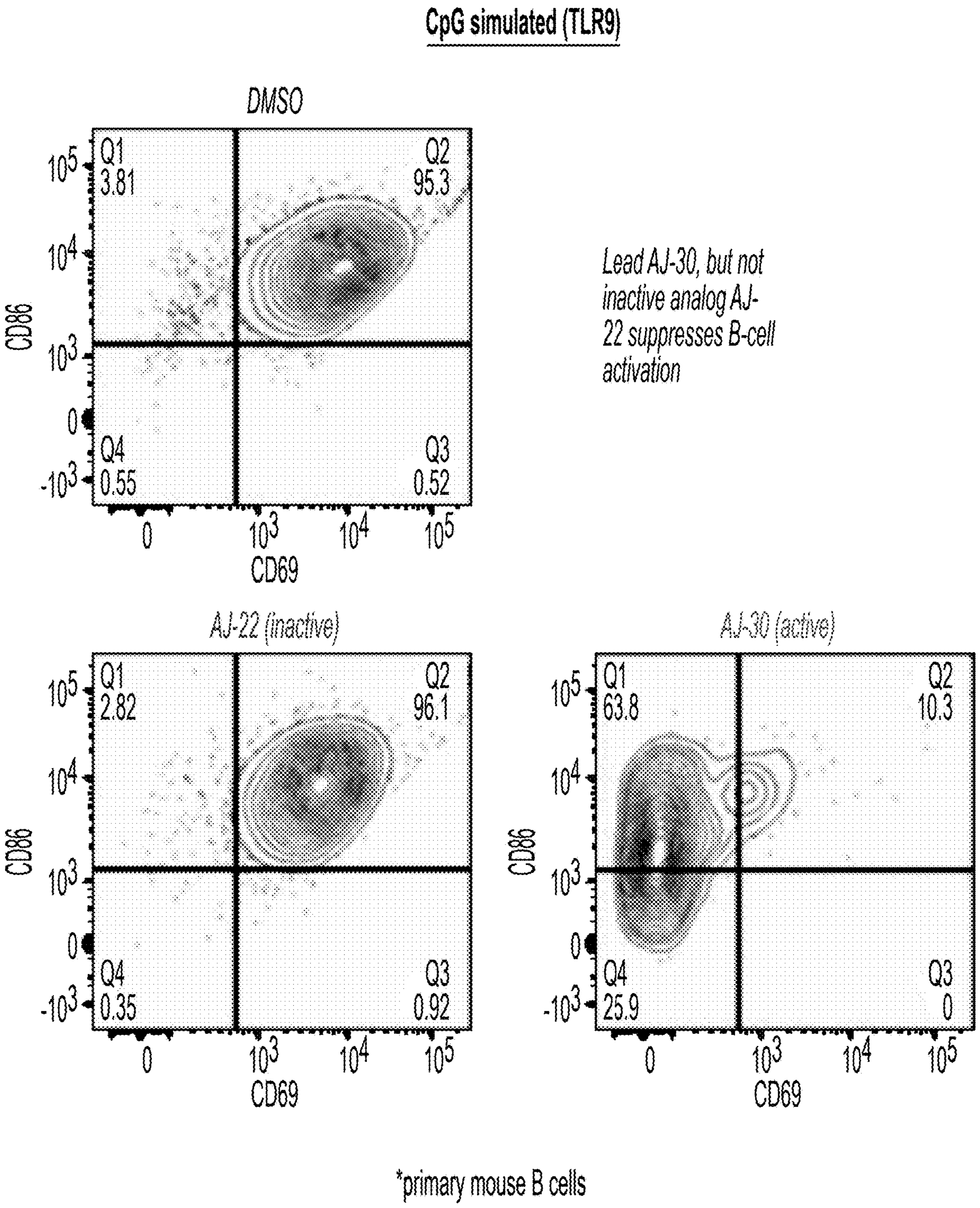
Figure 12:
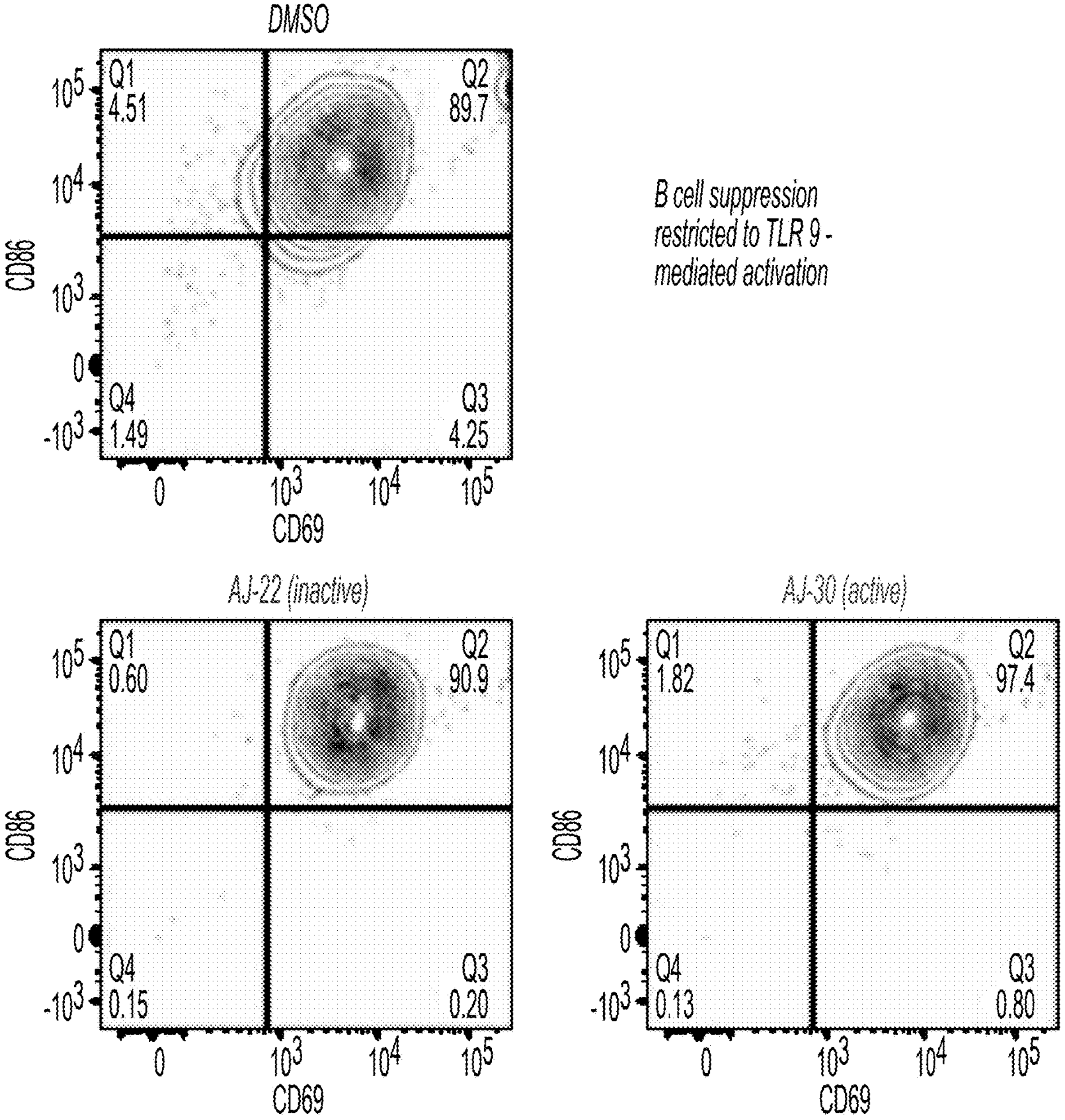

FIG. 12 shows SLC15A4 inhibitors suppress TLR9-mediated B cell activation.

Figure 13:
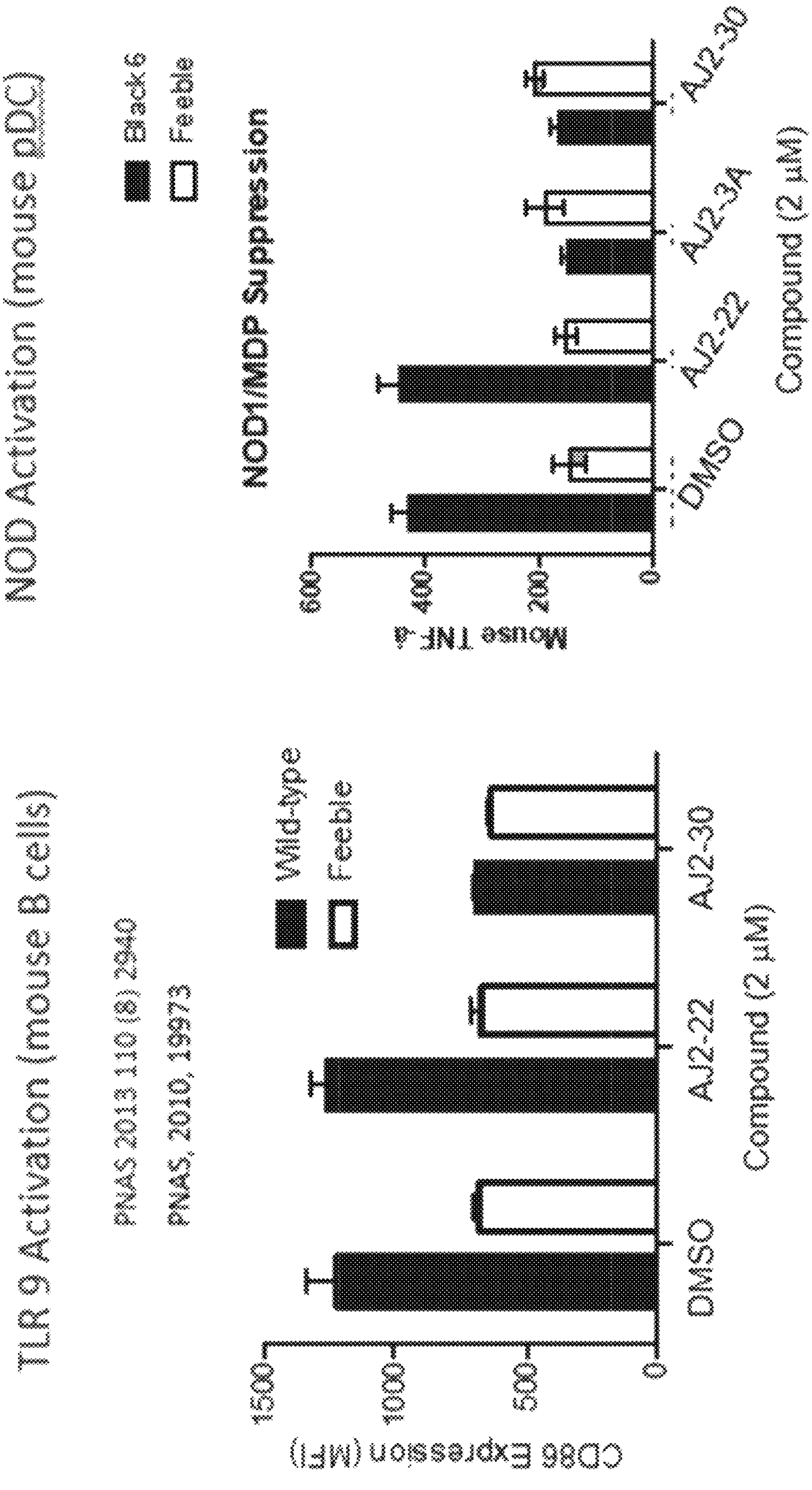

FIG. 13 shows SLC15A4 inhibitors are inactive in immune cells from SLC15A4 feeble mice AJ2-3A and AJ2-30 being active and AJ2-18 and AJ2-22 being inactive controls.

Figure 14:
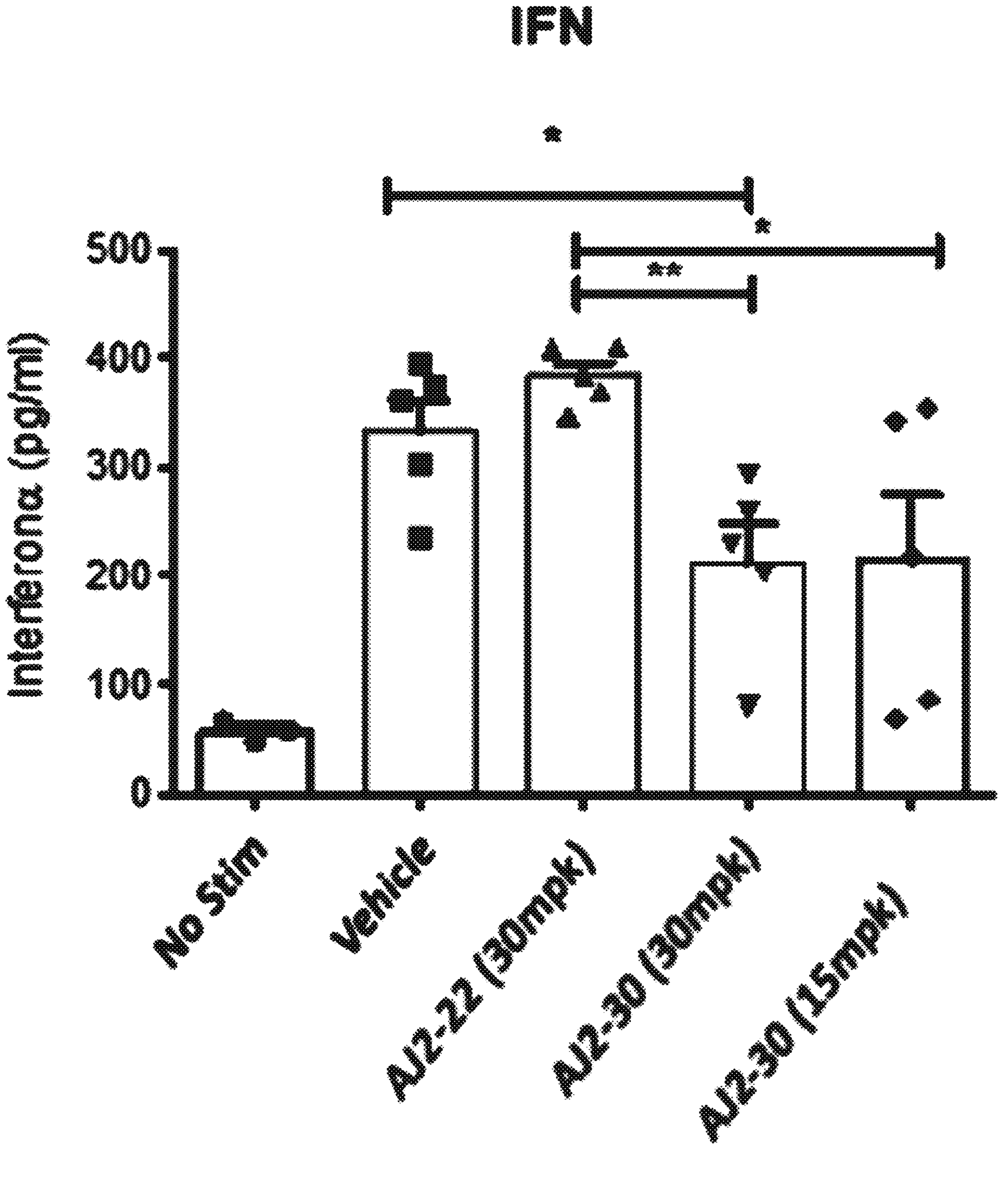
Figure 14:
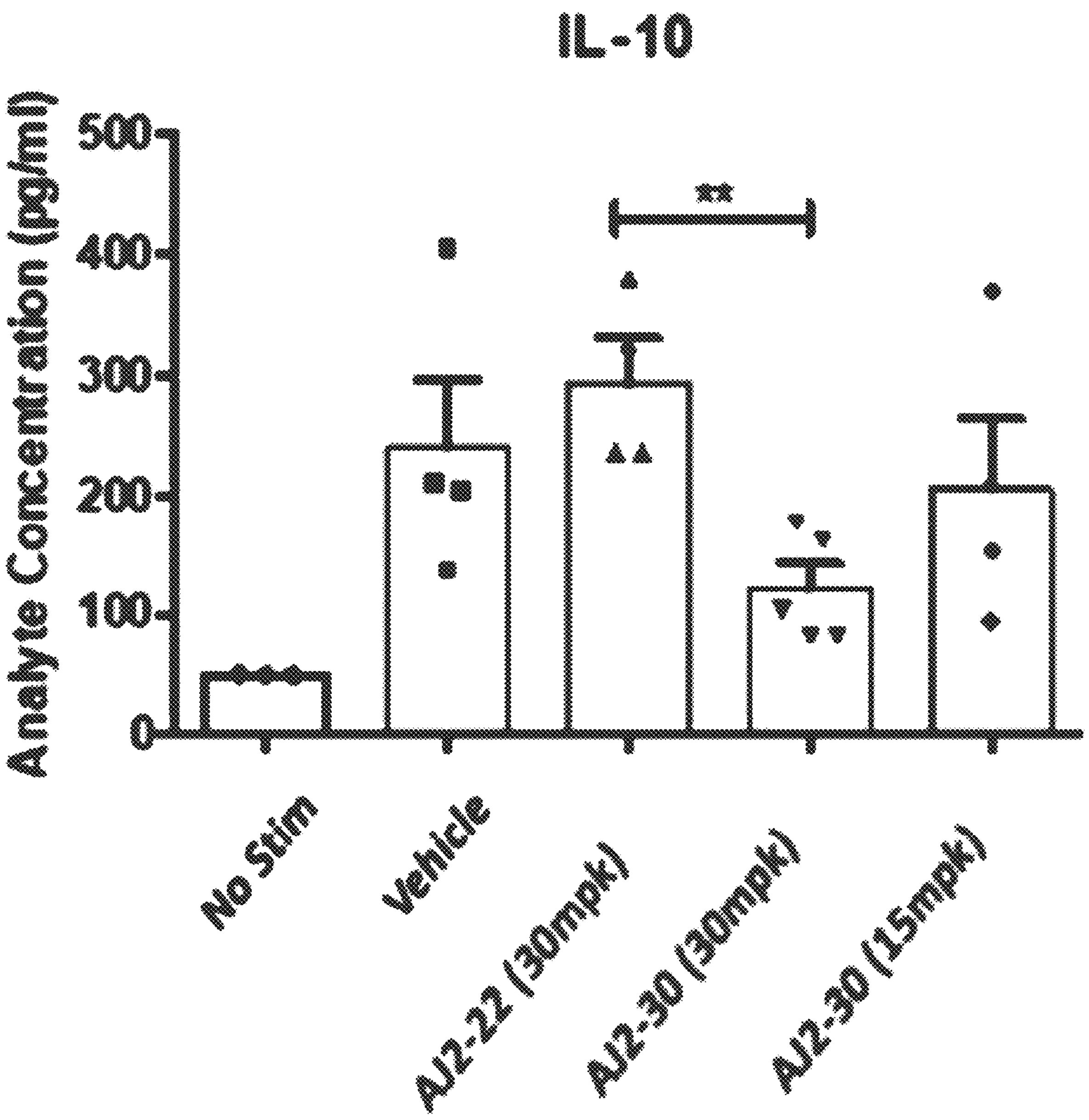

FIG. 14 shows SLC15A4 inhibitors in vivo efficacy in simple models of inflammation. Mice were co-injected with compounds (or vehicle) and CpG (TLR9); serum drawn after 6 hr, cytokines measured (single dose); with AJ2-3 and AJ2-30 being active and AJ2-22 being an inactive control.

Figure 15:
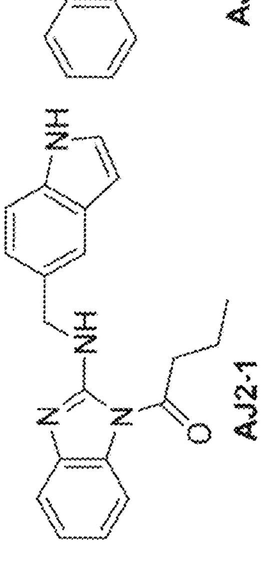
Figure 15:
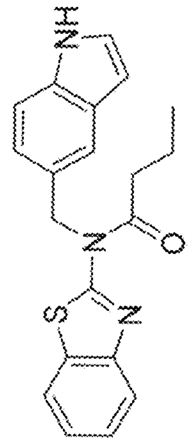
Figure 15:
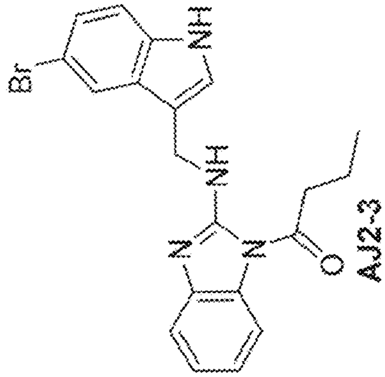
Figure 15:
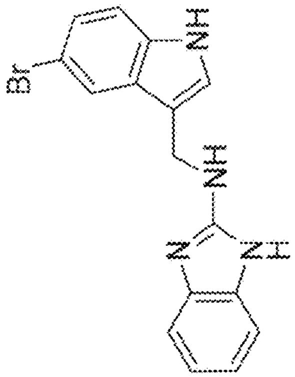
Figure 15:
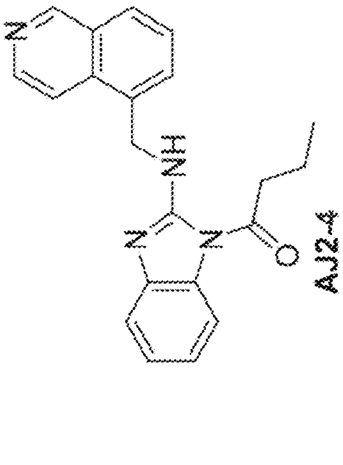
Figure 15:
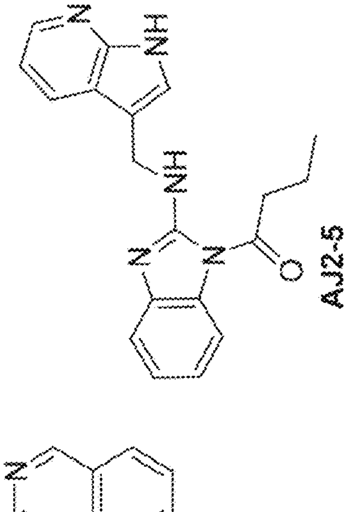
Figure 15:
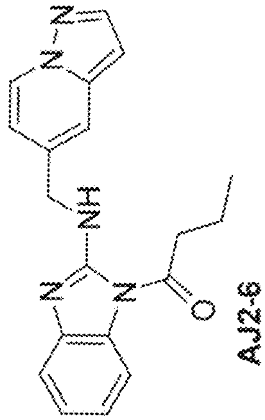
Figure 15:
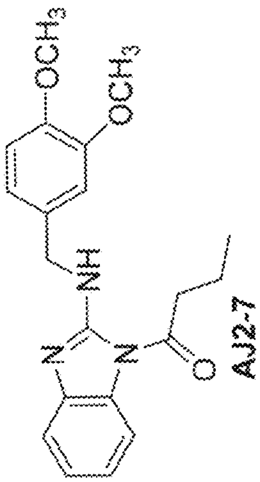
Figure 15:
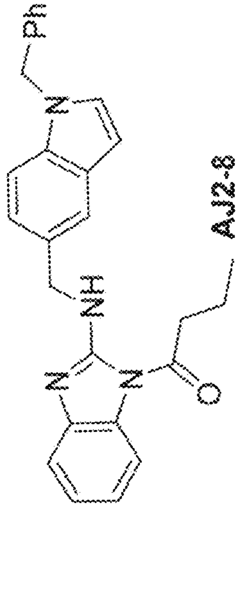
Figure 15:
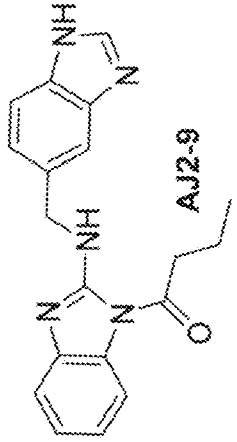
Figure 15:
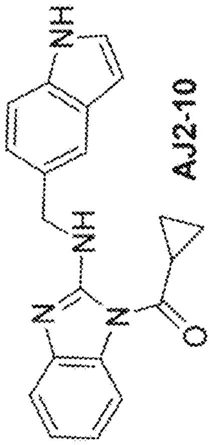
Figure 15:
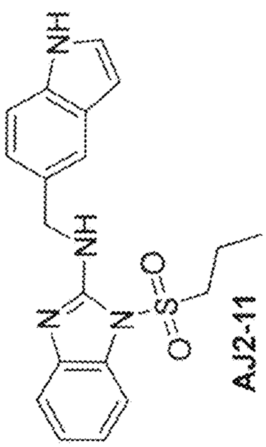
Figure 15:
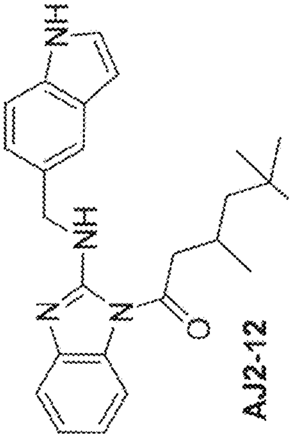
Figure 15:
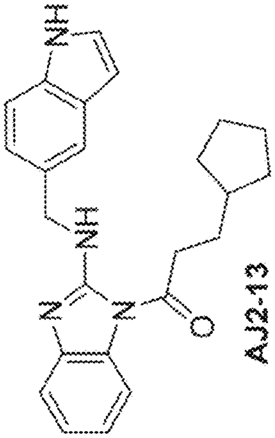
Figure 15:
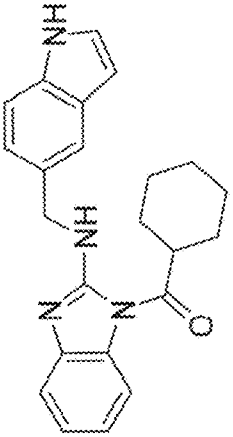
Figure 15:
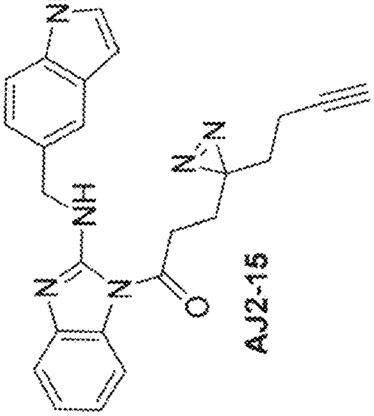
Figure 15:
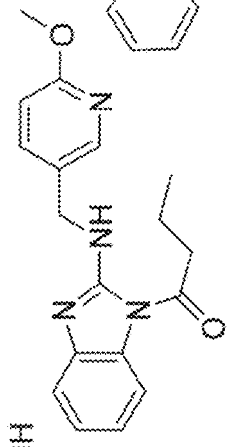
Figure 15:
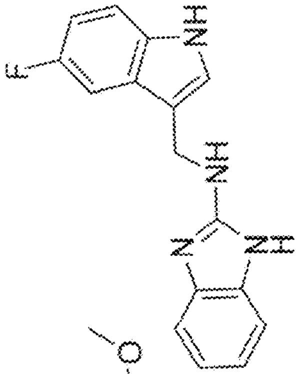
Figure 15:
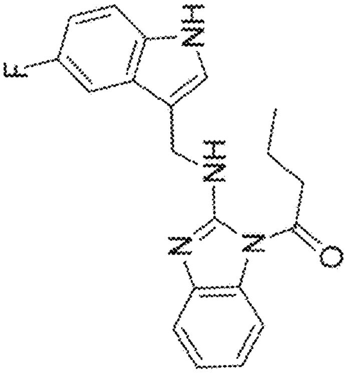
Figure 15:
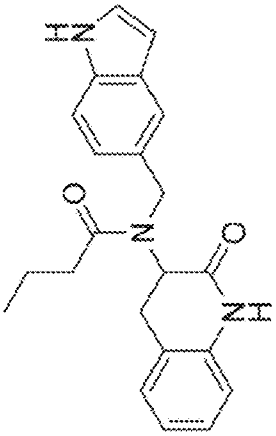
Figure 15:
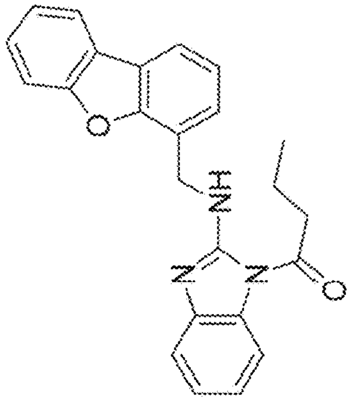
Figure 15:
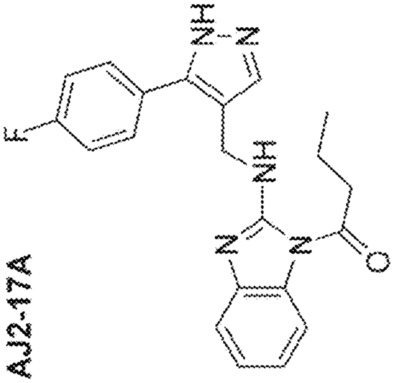
Figure 15:
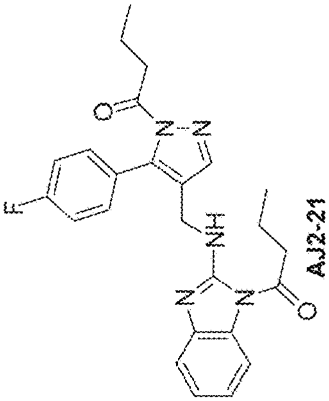
Figure 15:
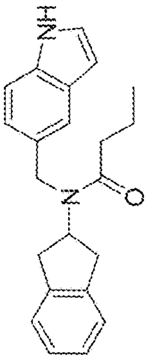
Figure 15:
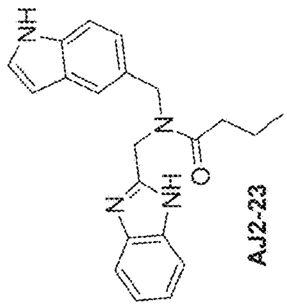
Figure 15:
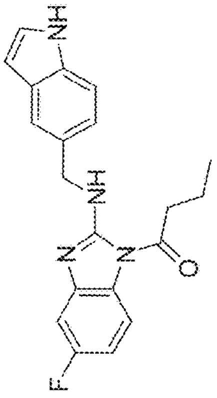
Figure 15:
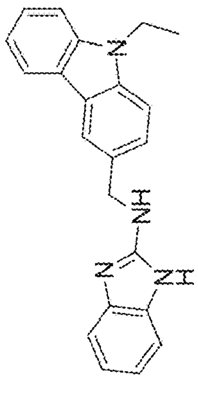
Figure 15:
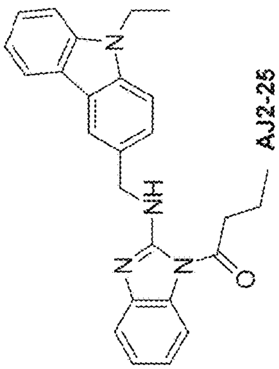
Figure 15:
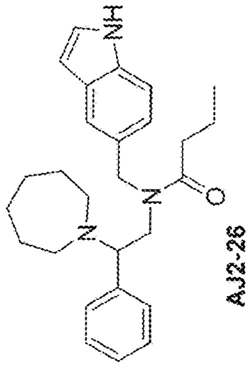
Figure 15:
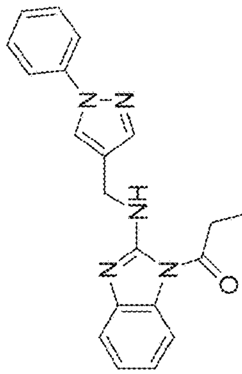
Figure 15:
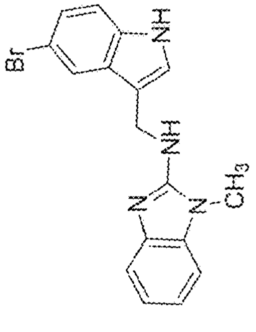
Figure 15:
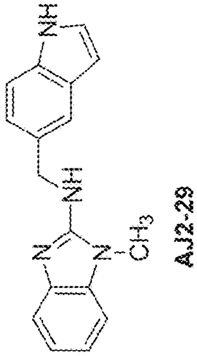
Figure 15:
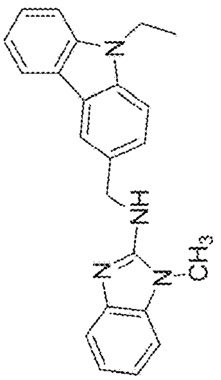
Figure 15:
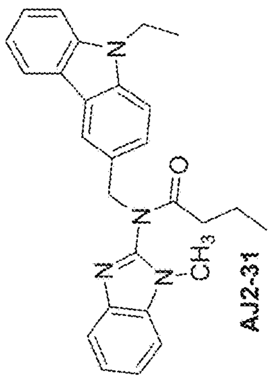
Figure 15:
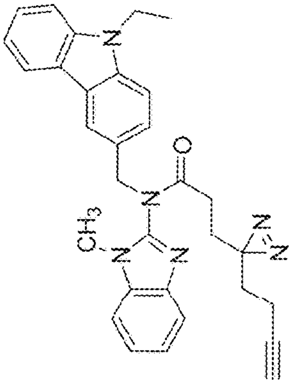
Figure 15:
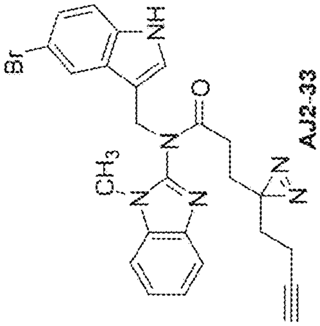
Figure 15:
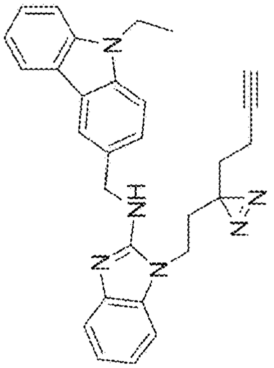
Figure 15:
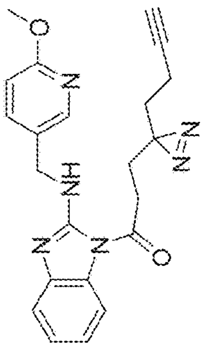
Figure 15:
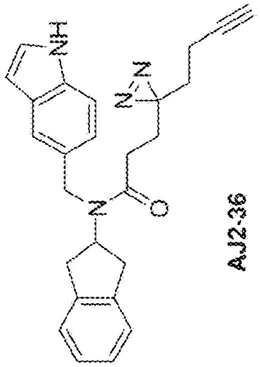
Figure 15:
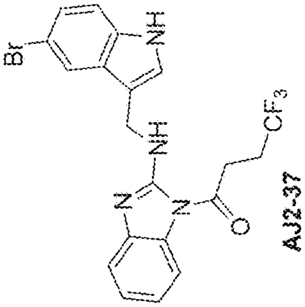
Figure 15:
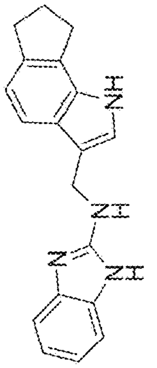
Figure 15:
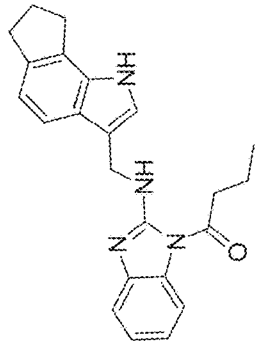
Figure 15:
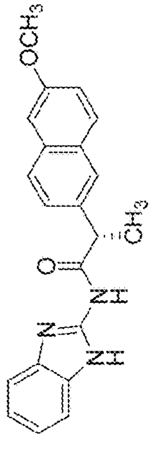
Figure 15:
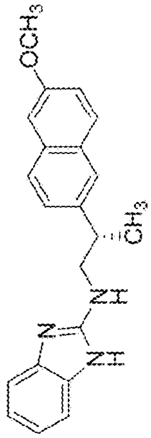
Figure 15:
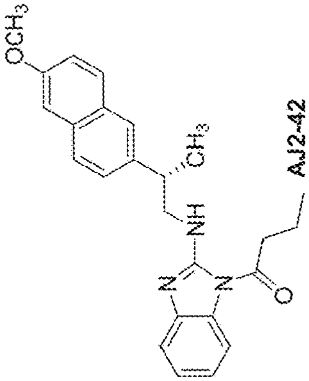
Figure 15:
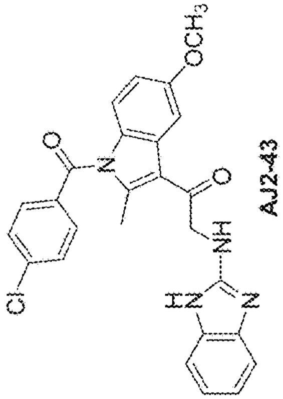
Figure 15:
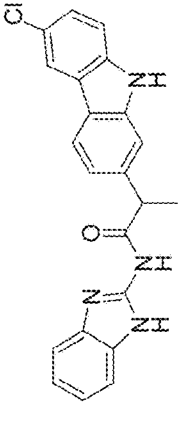
Figure 15:
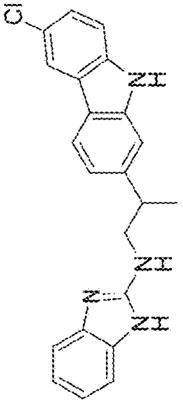
Figure 15:
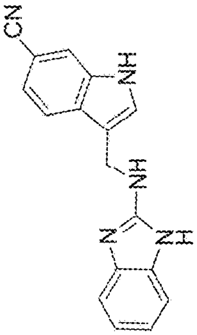
Figure 15:
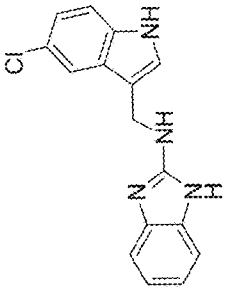
Figure 15:
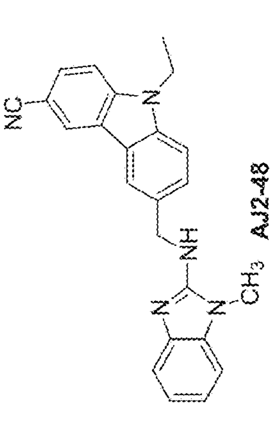
Figure 15:
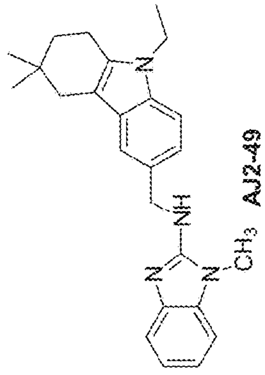
Figure 15:
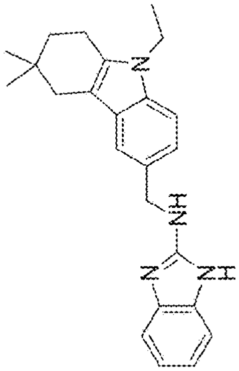
Figure 15:
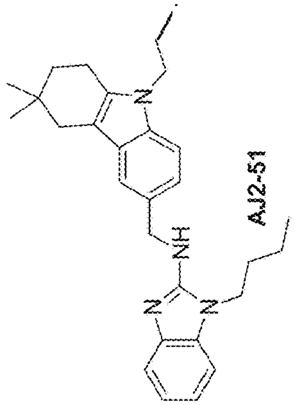
Figure 15:
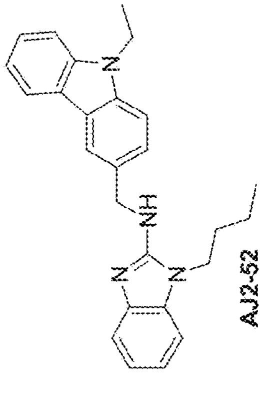
Figure 15:
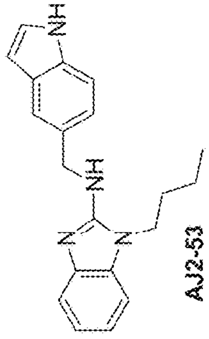
Figure 15:
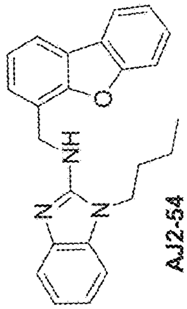
Figure 15:
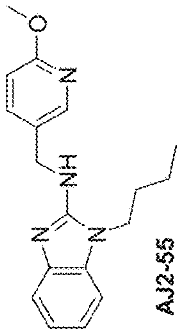
Figure 15:
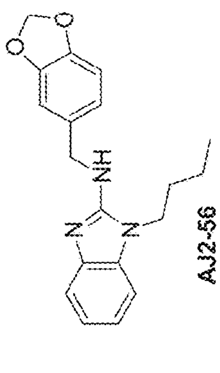
Figure 15:
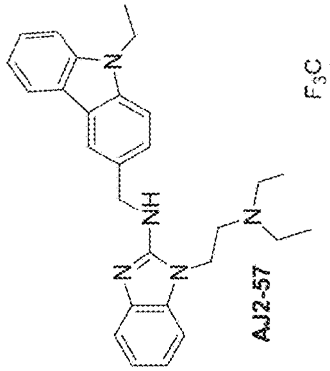
Figure 15:
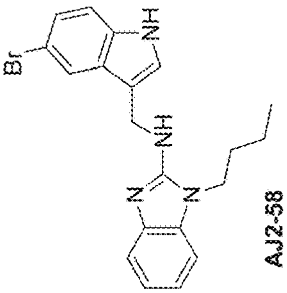
Figure 15:
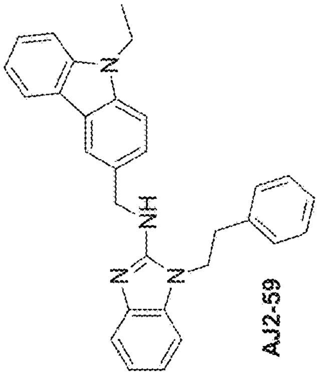
Figure 15:
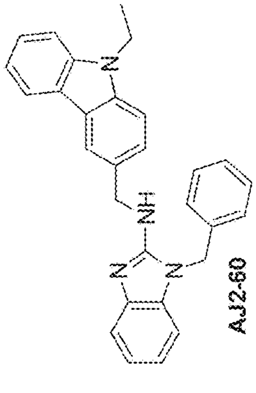
Figure 15:
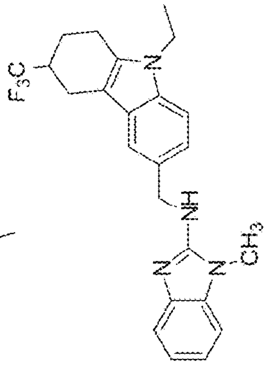
Figure 15:
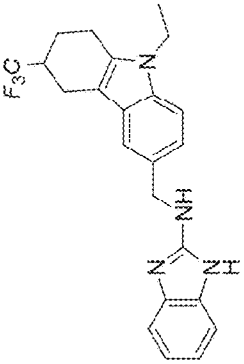
Figure 15:
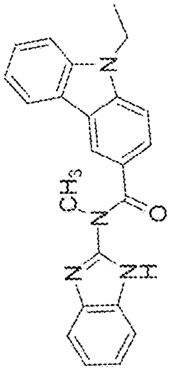
Figure 15:
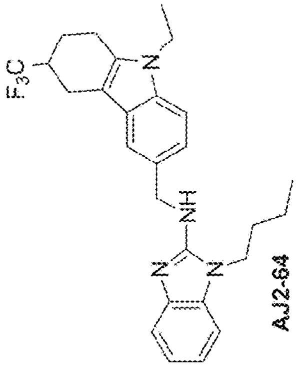
Figure 15:
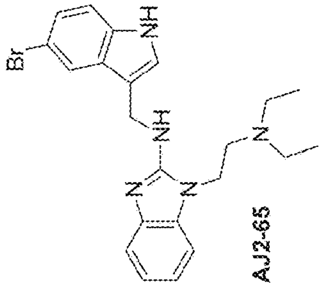
Figure 15:
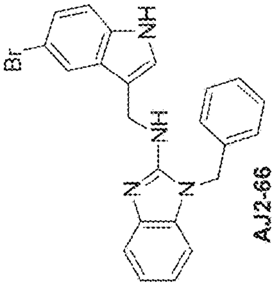
Figure 15:
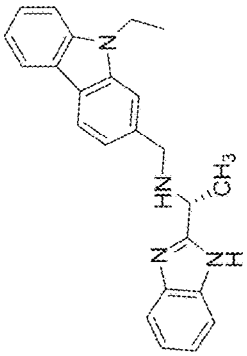
Figure 15:
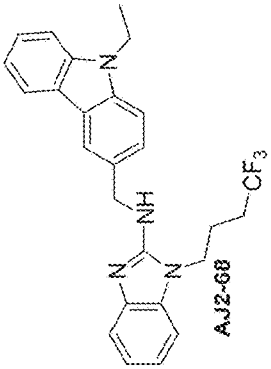
Figure 15:
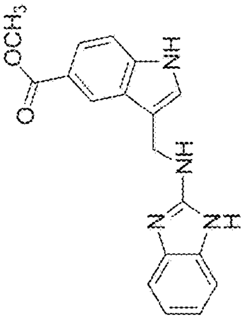
Figure 15:
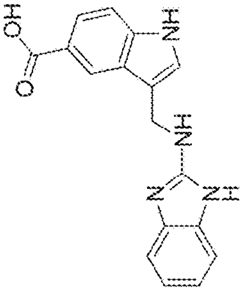
Figure 15:
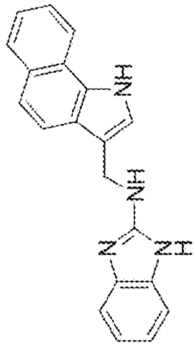
Figure 15:
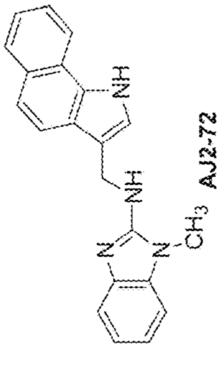
Figure 15:
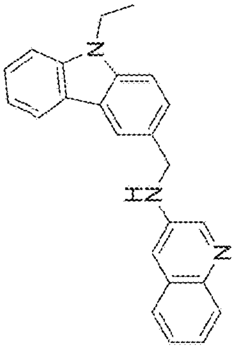
Figure 15:
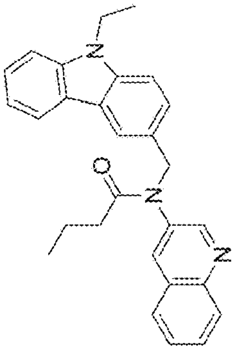
Figure 15:
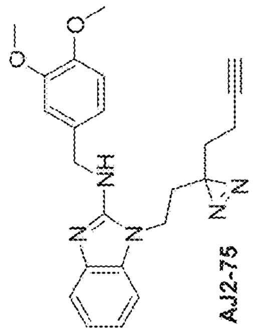
Figure 15:
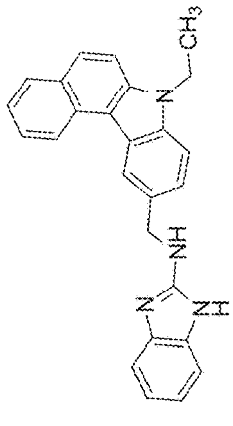
Figure 15:
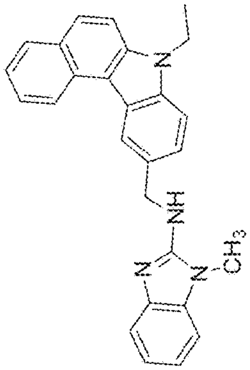
Figure 15:
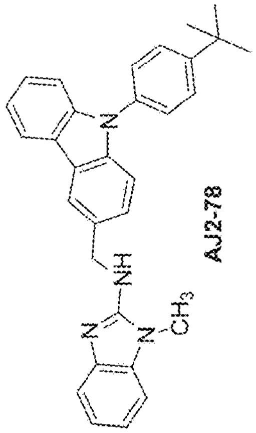
Figure 15:
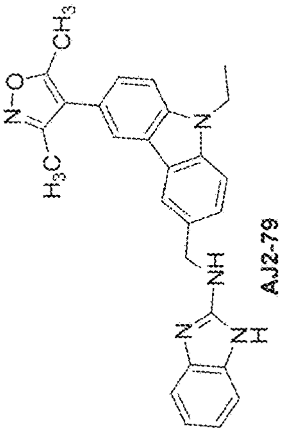
Figure 15:
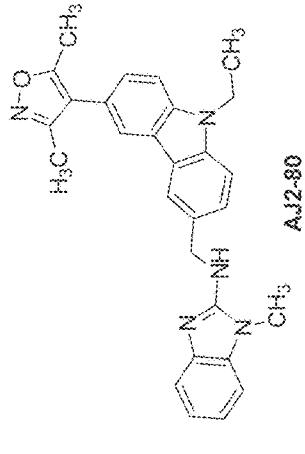
Figure 15:
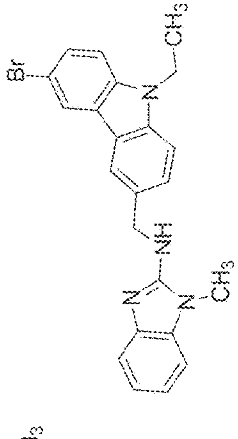
Figure 15:
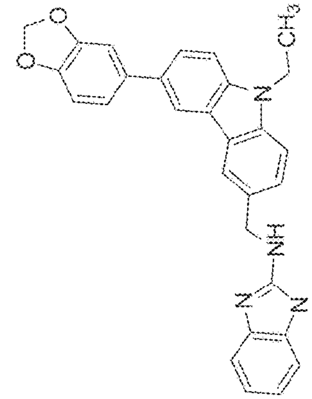
Figure 15:
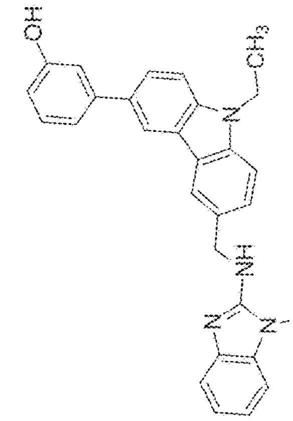
Figure 15:
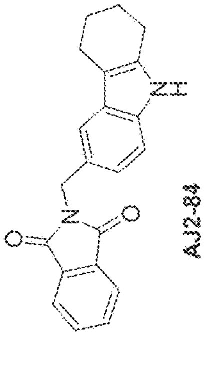
Figure 15:
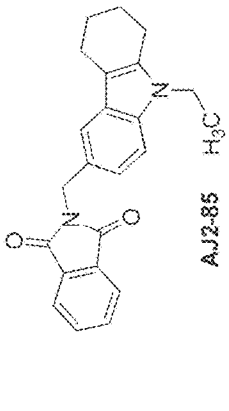
Figure 15:
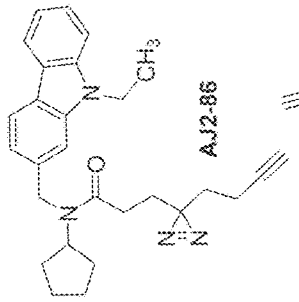
Figure 15:
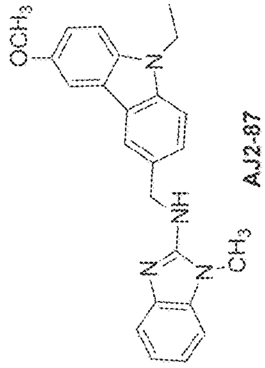
Figure 15:
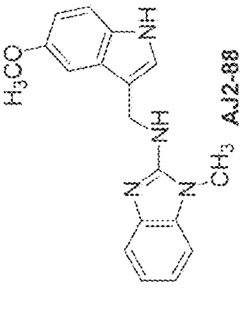
Figure 15:
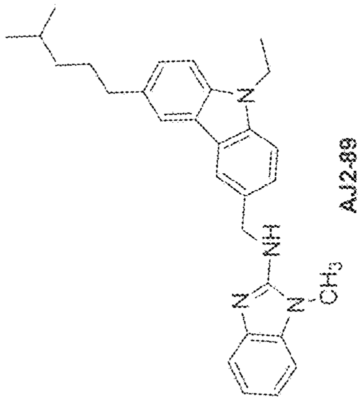
Figure 15:
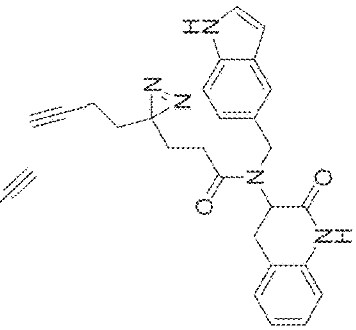
Figure 15:
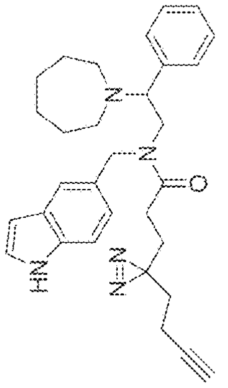
Figure 15:
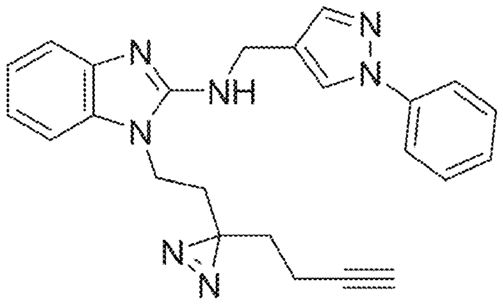
Figure 15:
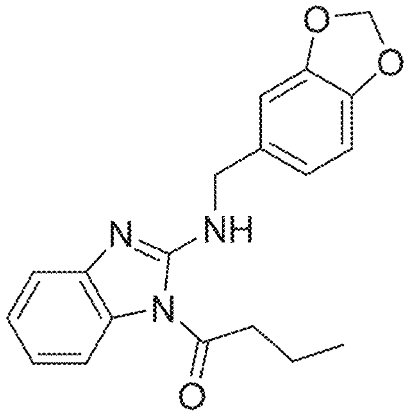

FIG. 15 is the structure of SLC15A4 inhibitor AJ2-1 to AJ2-92 and AJ2-CP53.

DETAILED DESCRIPTION

In various embodiments, the disclosure relates to compounds that inhibit SLC15A4. In various embodiments, the compounds are selective for SLC15A4.

The compounds are useful for the treatment of pDC, B cells, macrophages or monocytes-mediated condition.

Definitions

For convenience, before further description of the present disclosure, certain teens employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

In order for the present disclosure to be more readily understood, certain terms and phrases are defined below and throughout the specification.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one. B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Various compounds contained in compositions of the present disclosure may exist in particular geometric or stereoisomeric forms. In addition, polymers of the present disclosure may also be optically active. The present disclosure contemplates all such compounds, including cis- and trans-isomers, R- and S-enantiomers, diastereomers, (D)-isomers, (L)-isomers, the racemic mixtures thereof, and other mixtures thereof, as falling within the scope of the disclosure. Additional asymmetric carbon atoms may be present in a substituent such as an alkyl group. All such isomers, as well as mixtures thereof, are intended to be included in this disclosure.

If, for instance, a particular enantiomer of compound of the present disclosure is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Structures depicted herein are also meant to include compounds that differ only in the presence of one or more isotopically enriched atoms. For example, compounds produced by the replacement of a hydrogen with deuterium or tritium, or of a carbon with a $^{13}$C- or $^{13}$C-enriched carbon are within the scope of this disclosure.

The term "prodrug" as used herein encompasses compounds that, under physiological conditions, are converted into therapeutically active agents. A common method for making a prodrug is to include selected moieties that are hydrolyzed under physiological conditions to reveal the desired molecule. In other embodiments, the prodrug is converted by an enzymatic activity of the host animal.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ or portion of the body, to another organ or portion of the body. Each carrier must be "acceptable" in the sense of being compatible with the other ingredients of the formulation, not injurious to the patient, and substantially non-pyrogenic. Some examples of materials which can serve as pharmaceutically acceptable carriers include: (1) sugars, such as lactose, glucose, and sucrose; (2) starches, such as corn starch and potato starch; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In various embodiments, pharmaceutical compositions of the present disclosure are non-pyrogenic, i.e., do not induce significant temperature elevations when administered to a patient.

The term "pharmaceutically acceptable salts" refers to the relatively non-toxic, inorganic and organic acid addition salts of the compound(s). These salts can be prepared in situ during the final isolation and purification of the compound(s), or by separately reacting a purified compound(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts, and the like. (See, for example. Berge et al. (1977) "Pharmaceutical Salts", *J. Pharm. Sci.* 66:1-19.)

In other cases, the compounds useful in the methods of the present disclosure may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of a compound(s). These salts can likewise be prepared in situ during the final isolation and purification of the compound(s), or by separately reacting the purified compound(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

A "therapeutically effective amount" (or "effective amount") of a compound with respect to use in treatment, refers to an amount of the compound in a preparation which, when administered as part of a desired dosage regimen (to a mammal, e.g. a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic. (i.e., it is intended to diminish, ameliorate, or stabilize the existing unwanted condition or side effects thereof).

The term "patient" or 'subject" refers to a mammal in need of a particular treatment. In various embodiments, a patient or subject is a primate, canine, feline, or equine. In various embodiments, a patient or subject is a human.

An aliphatic chain comprises the classes of alkyl, alkenyl and alkynyl defined below. A straight aliphatic chain is limited to unbranched carbon chain moieties. As used herein, the term "aliphatic group" refers to a straight chain, branched-chain, or cyclic aliphatic hydrocarbon group and includes saturated and unsaturated aliphatic groups, such as an alkyl group, an alkenyl group, or an alkynyl group.

"Alkyl" refers to a fully saturated cyclic or acyclic, branched or unbranched carbon chain moiety having the number of carbon atoms specified, or up to 30 carbon atoms if no specification is made. For example, alkyl of 1 to 8 carbon atoms refers to moieties such as methyl, ethyl, propyl, butyl, pentyl, hexyl, heptyl, and octyl, and those moieties which are positional isomers of these moieties. Alkyl of 10 to 30 carbon atoms includes decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl. In various embodiments, a straight chain or branched chain alkyl has 30 or fewer carbon atoms in its backbone (e.g., $C_1$-$C_{30}$ for straight chains, $C_3$-$C_{30}$ for branched chains), or 20 or fewer. Alkyl groups may be substituted or unsubstituted.

As used herein, the term "alkylene" refers to an alkyl group having the specified number of carbons, for example from 2 to 12 carbon atoms, that contains two points of attachment to the rest of the compound on its longest carbon chain. Non-limiting examples of alkylene groups include methylene $-(CH_2)-$, ethylene $-(CH_2CH_2)-$, n-propylene $-(CH_2CH_2CH_2)-$, isopropylene $-(CH_2CH(CH_3))-$, and the like. Alkylene groups can be cyclic or acyclic, branched or unbranched carbon chain moiety, and may be optionally substituted with one or more substituents.

"Cycloalkyl" means mono- or bicyclic or bridged or spirocyclic, or polycyclic saturated carbocyclic rings, each having from 3 to 12 carbon atoms. Likewise, some cycloalkyls have from 3-10 carbon atoms in their ring structure, and some have 3-6 carbons in the ring structure. Cycloalkyl groups may be substituted or unsubstituted.

Unless the number of carbons is otherwise specified, "lower alkyl," as used herein, means an alkyl group, as defined above, but having from one to ten carbons, from one to six carbon atoms in its backbone structure such as methyl, ethyl, n-propyl, isopropyl, n-butyl, isobutyl, sec-butyl, and tert-butyl. Likewise, "lower alkenyl" and "lower alkynyl" have similar chain lengths. Throughout the application, alkyl groups can be lower alkyls. In various embodiments, a substituent designated herein as alkyl is a lower alkyl.

"Alkenyl" refers to any cyclic or acyclic, branched or unbranched unsaturated carbon chain moiety having the number of carbon atoms specified, or up to 26 carbon atoms if no limitation on the number of carbon atoms is specified; and having one or more double bonds in the moiety. Alkenyl of 6 to 26 carbon atoms is exemplified by hexenyl, heptenyl, octenyl, nonenyl, decenyl, undecenyl, dodenyl, tridecenyl, tetradecenyl, pentadecenyl, hexadecenyl, heptadecenyl, octadecenyl, nonadecenyl, eicosenyl, heneicosoenyl, docosenyl, tricosenyl, and tetracosenyl, in their various isomeric forms, where the unsaturated bond(s) can be located anywhere in the moiety and can have either the (Z) or the (E) configuration about the double bond(s).

"Alkynyl" refers to hydrocarbyl moieties of the scope of alkenyl, but having one or more triple bonds in the moiety.

The term "alkylthio" refers to an alkyl group, as defined above, having a sulfur moiety attached thereto. In various embodiments, the "alkylthio" moiety is represented by one of —(S)-alkyl, —(S)-alkenyl, —(S)-alkynyl, and —(S)—$(CH_2)_m$—$R^1$, wherein m and $R^1$ are defined below. Representative alkylthio groups include methylthio, ethylthio, and the like. The terms "alkoxyl" or "alkoxy" as used herein refers to an alkyl group, as defined below, having an oxygen moiety attached thereto. Representative alkoxyl groups include methoxy, ethoxy, propoxy, tert-butoxy, and the like. An "ether" is two hydrocarbons covalently linked by an oxygen. Accordingly, the substituent of an alkyl that renders that alkyl an ether is or resembles an alkoxyl, such as can be represented by one of —O-alkyl, —O— alkenyl, —O-alkynyl, —O—$(CH_2)_m$—$R_{10}$, where m and $R_{10}$ are described below.

The terms "amine" and "amino" are art-recognized and refer to both unsubstituted and substituted amines, e.g., a moiety that can be represented by the formulae:

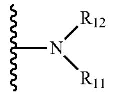
or
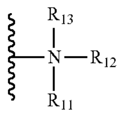

wherein $R_{11}$, $R_{12}$ and $R_{13}$ each independently represent a hydrogen, an alkyl, an alkenyl, —$(CH_2)_m$—$R_{10}$, or $R_{11}$ and $R_{12}$ taken together with the N atom to which they are attached complete a heterocycle having from 4 to 8 atoms in the ring structure; $R_{10}$ represents an alkenyl, aryl, cycloalkyl, a cycloalkenyl, a heterocyclyl, or a polycyclyl; and m is zero or an integer in the range of 1 to 8. In various embodiments, only one of $R_{11}$ or $R_{12}$ can be a carbonyl, e.g., $R_{11}$, $R_{12}$, and the nitrogen together do not form an imide. In even more various embodiments, $R_{11}$ and $R_{12}$ (and optionally $R_{13}$) each independently represent a hydrogen, an alkyl, an alkenyl, or $-(CH_2)_m-R_{10}$. Thus, the teen "alkylamine" as used herein means an amine group, as defined above, having a substituted or unsubstituted alkyl attached thereto, i.e., at least one of $R_{11}$ and $R_{12}$ is an alkyl group. In various embodiments, an amino group or an alkylamine is basic, meaning it has a conjugate acid with a $pK_a$>7.00, i.e., the protonated forms of these functional groups have $pK_a$s relative to water above about 7.00.

The term "amide", as used herein, refers to a group

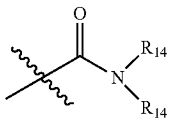

wherein each $R_{14}$ independently represent a hydrogen or hydrocarbyl group, or two $R_{14}$ are taken together with the N atom to which they are attached complete a heterocycle having from 4 to 8 atoms in the ring structure.

The term "aryl" as used herein includes 3- to 12-membered substituted or unsubstituted single-ring aromatic groups in which each atom of the ring is carbon (i.e., carbocyclic aryl) or where one or more atoms are heteroatoms (i.e., heteroaryl). Aryl groups include 5- to 12-membered rings, 6- to 10-membered rings The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Carboycyclic aryl groups include benzene, naphthalene, phenanthrene, phenol, aniline, and the like. Heteroaryl groups include substituted or unsubstituted aromatic 3- to 12-membered ring structures, 5- to 12-membered rings, 5- to 10-membered rings, whose ring structures include one to four heteroatoms. Heteroaryl groups include, for example, pyrrole, furan, thiophene, imidazole, oxazole, thiazole, triazole, pyrazole, pyridine, pyrazine, pyridazine and pyrimidine, and the like. Aryl and heteroaryl can be monocyclic, bicyclic, or polycyclic. Each instance of an aryl group may be independently optionally substituted, i.e., unsubstituted (an "unsubstituted aryl") or substituted (a "substituted aryl") with one or more substituents; e.g., for instance from 1 to 5 substituents, 1 to 4 substituents, 1 to 3 substituents, 1 to 2 substituents or just 1 substituent. The aromatic ring may be substituted at one or more ring positions with one or more substituents, such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. For example, in various embodiments, the aryl group can be an unsubstituted $C_5$-$C_{12}$ aryl and in various embodiments, the aryl group can be a substituted $C_5$-$C_{10}$ aryl.

The term "halo", "halide", or "halogen" as used herein means halogen and includes, for example, and without being limited thereto, fluoro, chloro, bromo, iodo and the like, in both radioactive and non-radioactive forms. In various embodiment, halo is selected from the group consisting of fluoro, chloro and bromo.

The terms "heterocyclyl" or "heterocyclic group" refer to 3- to 12-membered ring structures, 5- to 12-membered rings, 5- to 10-membered rings, whose ring structures include one to four heteroatoms. Heterocycles can be monocyclic, bicyclic, spirocyclic, or polycyclic. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, sulfamoyl, sulfinyl, ether, alkylthio, sulfonyl, ketone, aldehyde, ester, a heterocyclyl, an aromatic or heteroaromatic moiety, $-CF_3$, $-CN$, and the like.

The term "carbonyl" is art-recognized and includes such moieties as can be represented by the formula.

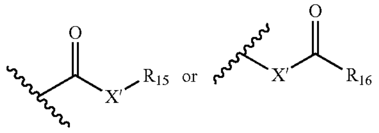

wherein X' is a bond or represents an oxygen or a sulfur, and $R^{15}$ represents a hydrogen, an alkyl, an alkenyl, $-(CH_2)_m-R_{10}$ or a pharmaceutically acceptable salt. Rib represents a hydrogen, an alkyl, an alkenyl or $-(CH_2)_m-R_{10}$, where m and $R_{10}$ are as defined above. Where X' is an oxygen and $R_{15}$ or $R_{16}$ is not hydrogen, the formula represents an "ester." Where X' is an oxygen, and $R_{15}$ is as defined above, the moiety is referred to herein as a carboxyl group, and particularly when $R_{15}$ is a hydrogen, the formula represents a "carboxylic acid". Where X' is an oxygen, and $R_{16}$ is a hydrogen, the formula represents a "formate." In general, where the oxygen atom of the above formula is replaced by a sulfur, the formula represents a "thiocarbonyl" group. Where X' is a sulfur and $R_{15}$ or $R_{16}$ is not hydrogen, the formula represents a "thioester" group. Where X' is a sulfur and $R_{15}$ is a hydrogen, the formula represents a "thiocarboxylic acid" group. Where X' is a sulfur and $R_{16}$ is a hydrogen, the formula represents a "thioformate" group. On the other hand, where X' is a bond, and $R_{15}$ is not hydrogen, the above formula represents a "ketone" group. Where X' is a bond, and $R_{15}$ is a hydrogen, the above formula represents an "aldehyde" group.

As used herein, the term "nitro" means $-NO_2$; the term "halogen" designates $-F$, $-Cl$, $-Br$, or $-I$; the term "sulfhydryl" means $-SH$; the term "hydroxyl" means $-OH$; the term "sulfonyl" means $-SO_2-$; the term "azido" means $-N_3$; the term "cyano" means $-CN$; the term "isocyanato" means $-NCO$; the term "thiocyanato"

means —SCN; the term "isothiocyanato" means —NCS; and the term "cyanato" means —OCN.

As used herein, the definition of each expression, e.g., alkyl, m, n, etc., when it occurs more than once in any structure, is intended to be independent of its definition elsewhere in the same structure.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In various embodiments, the substituents on substituted alkyls are selected from $C_{1-6}$ alkyl, $C_{3-6}$ cycloalkyl, halogen, carbonyl, cyano, or hydroxyl. In more various embodiments, the substituents on substituted alkyls are selected from fluoro, carbonyl, cyano, or hydroxyl. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

For purposes of this disclosure, the chemical elements are identified in accordance with the Periodic Table of the Elements, CAS version. Handbook of Chemistry and Physics, 67th Ed., 1986-87, inside cover.

Exemplary Compounds of the Disclosure

In various embodiments, the disclosure relates to a compound of Formula (I) or (II):

(II)

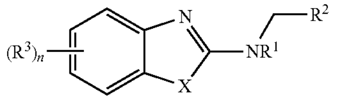

(II)

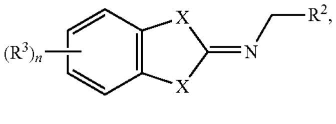

wherein

X is $NR^4$ or S;

$R^1$ is H or —C(O)—$C_{1-10}$alkyl;

$R^2$ is heterocyclyl or aryl;

$R^3$ is halogen, —$CHF_2$, or —$CF_3$;

$R^4$ is H, —$C_{1-10}$alkyl, —C(O)—$C_{1-10}$alkyl, —C(O)—$C_{3-10}$cycloalkyl, —$S(O)_2$—$C_{1-10}$alkyl, or

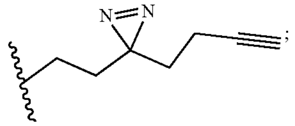 [SMILES: *CCC1(CCC#C)N=N1]

and n is 0, 1, 2, 3, or 4;

or a pharmaceutically acceptable salt thereof.

In some embodiments, the compound is a compound of Formula (I). In some embodiments, the compound is a compound of Formula (II).

In some embodiments. $R^1$ is H. In some embodiments. $R^1$ is —C(O)—$C_{1-10}$alkyl. In some embodiments, $R^1$ is —C(O)—$C_1H_3$. In some embodiments, $R^1$ is —C(O)—$C_2H_5$. In some embodiments, $R^1$ is —C(O)—$C_3H_7$. In some embodiments, $R^1$ is —C(O)—$C_4H_9$.

In some embodiments, $R^2$ is unsubstituted heterocyclyl. In some embodiments, $R^2$ is substituted heterocyclyl. In some embodiments, the heterocyclyl is monocyclic. In some embodiments, the heterocyclyl is bicyclic. In some embodiments, the heterocyclyl is tricyclic. In some embodiments, the heterocyclyl is aromatic. In some embodiments, the heterocyclyl is non-aromatic. In some embodiments, $R^2$ is unsubstituted aryl. In some embodiments, $R^2$ is substituted aryl.

In some embodiment, $R^2$ is substituted with at least one substituent selected from halogen, alkyl, aralkyl, alkenyl, alkynyl, cycloalkyl, hydroxyl, amino, nitro, sulfhydryl, imino, amido, sulfamoyl, sulfinyl, alkylthio, sulfonyl, ketone, a heterocyclyl, an aromatic or heteroaromatic moiety, —$CHF_2$—$CF_3$, —CN. If $R^2$ is substituted with two or more substituents, the substituents can be the same or different.

In some embodiments, $R^2$ is selected from the group consisting of:

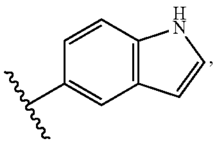,
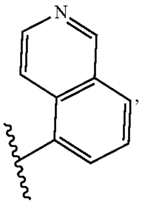,
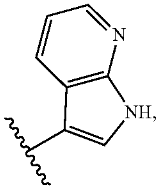

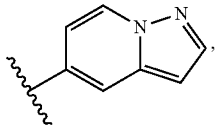,
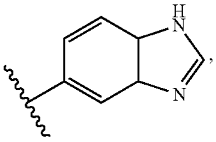, and

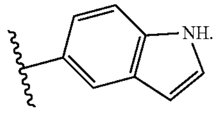

In some embodiments, $R^2$ is:

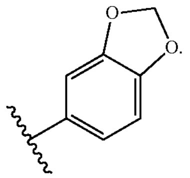 [SMILES: *c1ccc2c(c1)OCO2]

In some embodiments, $R^2$ is:

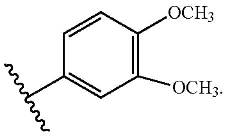 [SMILES: *c1ccc(OC)c(OC)c1]

In some embodiments. $R^2$ is

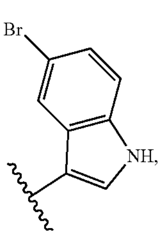

or

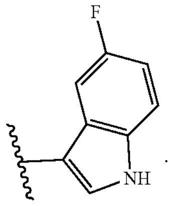

In some embodiments, $R^2$ is

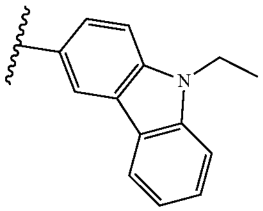

, or

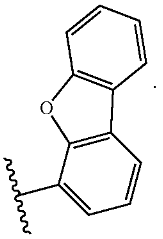

In some embodiments. $R^2$ is selected from the group consisting of

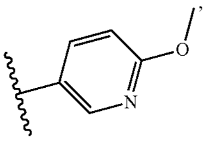

,

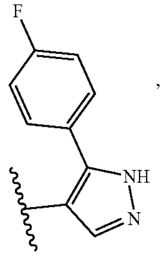

,

-continued

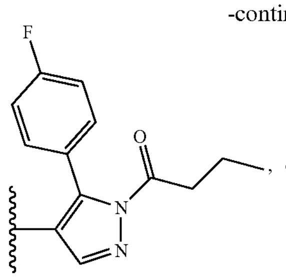

, or

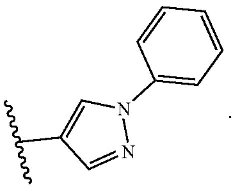

In some embodiments, $R^3$ is F. In some embodiments, $R^3$ is Cl. In some embodiments, $R^3$ is Br. In some embodiments, $R^3$ is —$CHF_2$. In some embodiments, $R^3$ is —$CF_3$ In some embodiments, $R^4$ is H. In some embodiments, $R^4$ is —$C_{1-10}$alkyl. In some embodiments, $R^4$ is methyl, ethyl, i-propyl, n-propyl, t-butyl, i-butyl, or n-butyl. In some embodiments, $R^4$ is methyl.

In some embodiments, $R^4$ is —C(O)—$C_{1-10}$alkyl. In some embodiments, $R^4$ is —C(O)— methyl, —C(O)-ethyl, —C(O)-i-propyl, —C(O)-n-propyl, —C(O)-t-butyl, —C(O)-i-butyl, or —C(O)-n-butyl. In some embodiments, $R^4$ is —C(O)—$C_{5-10}$alkyl.

In some embodiments, $R^4$ is

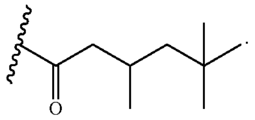 [SMILES: *C(=O)CC(C)CC(C)(C)C]

In some embodiments, $R^4$ is —C(O)—$C_3H_7$.

In some embodiments, $R^4$ is —C(O)—$C_{3-10}$cycloalkyl. In some embodiments, $R^4$ is —C(O)-cyclopropyl. In some embodiments, $R^4$ is —C(O)-cyclohexyl.

In some embodiments, wherein $R^4$ is —$S(O)_2$—$C_{1-10}$alkyl. In some embodiments, $R^4$ is $S(O)_2$-methyl, —$S(O)_2$-ethyl, —$S(O)_2$-i-propyl, —$S(O)_2$-n-propyl, —$S(O)_2$-n-butyl, —$S(O)_2$-i-butyl, or —$S(O)_2$-n-butyl. In some embodiments, $R^4$ is —$S(O)_2$—$C_{5-10}$alkyl.

In some embodiments, $R^4$ is —$S(O)_2$—$C_3H_7$.

In some embodiments, $R^4$ is

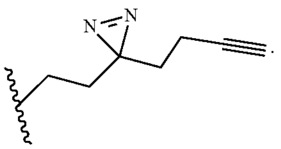 [SMILES: *CCC1(CCC#C)N=N1]

In some embodiments, n is 0. In some embodiments, n is 1. In some embodiments, n is 2. In some embodiments, is 3. In some embodiments, n is 4.

In some embodiments, the compound of formula (I) is selected from the group consisting of:

-continued
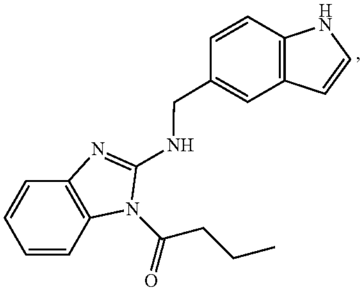,
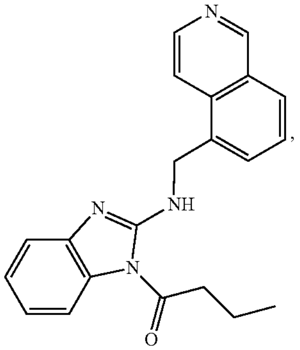,
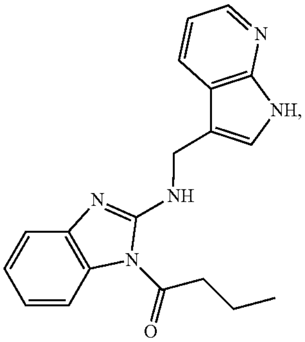,
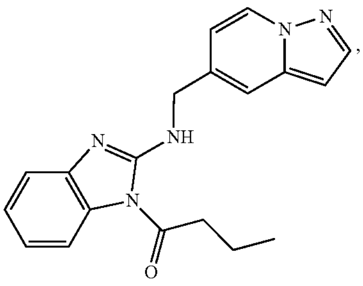,
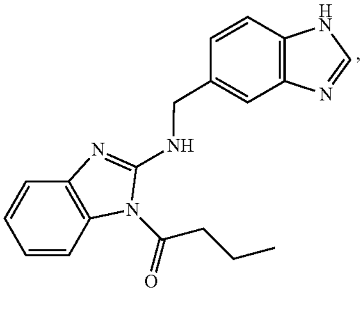,
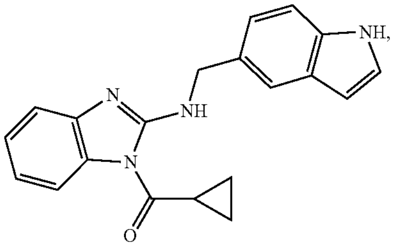,
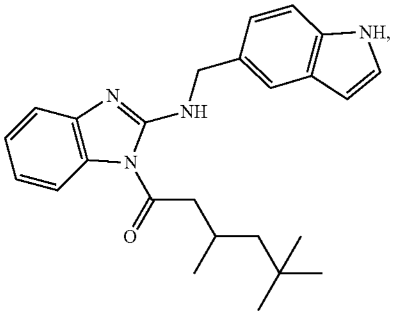,
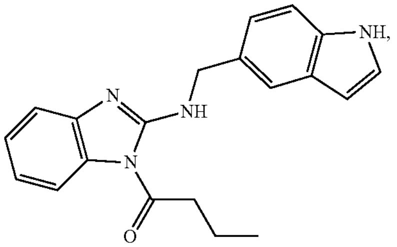,
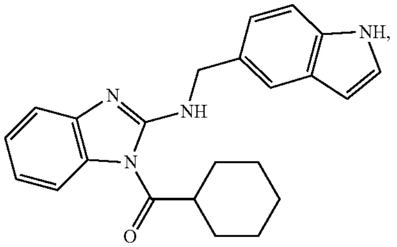,
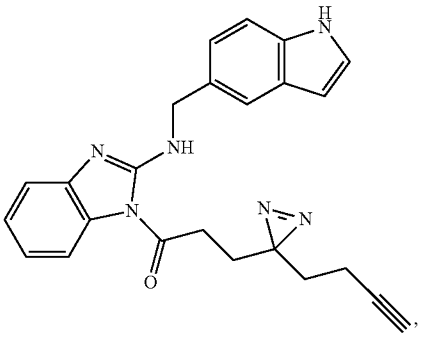,
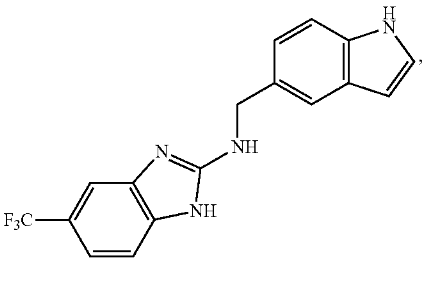, and -continued
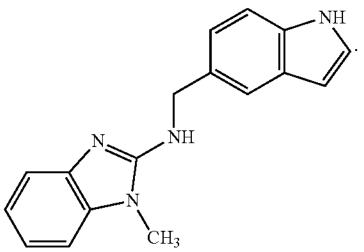
In some embodiments, the compound of formula (I) is
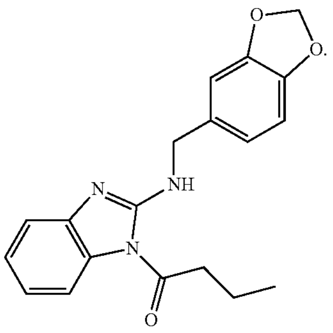 [SMILES: CCCC(=O)n1c(NCc2ccc3c(c2)OCO3)nc2ccccc21]
In some embodiments, the compound of formula (I) is selected from the group consisting of:
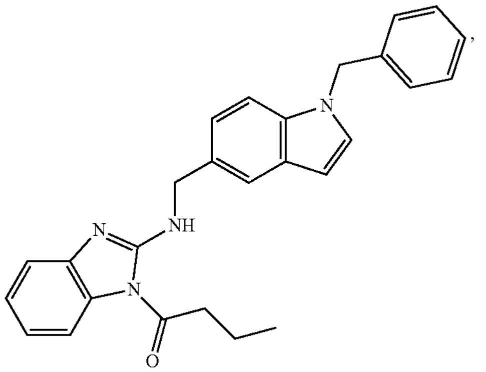
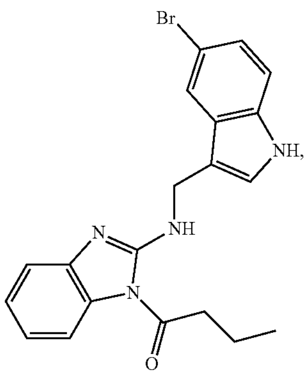
-continued
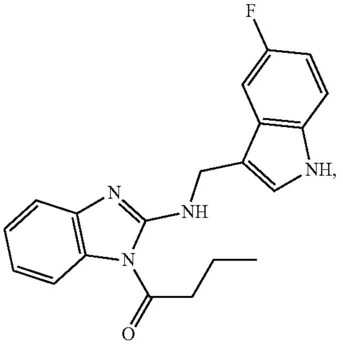
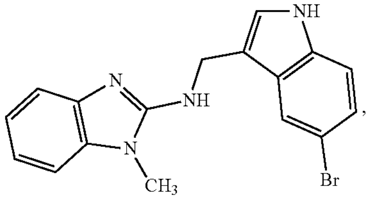
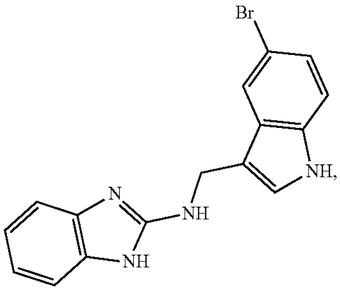
and
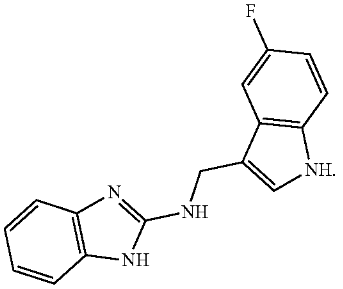
In some embodiments, the compound of Formula (I) is:
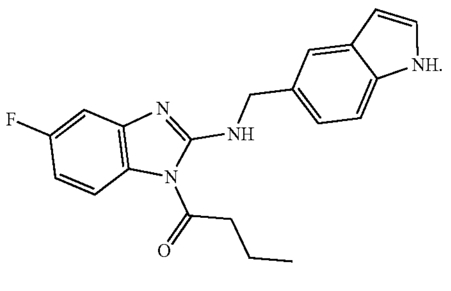 [SMILES: CCCC(=O)n1c(NCc2ccc3[nH]ccc3c2)nc2cc(F)ccc21]
In some embodiments, the compound of formula (II) is selected from is selected from the group consisting of:

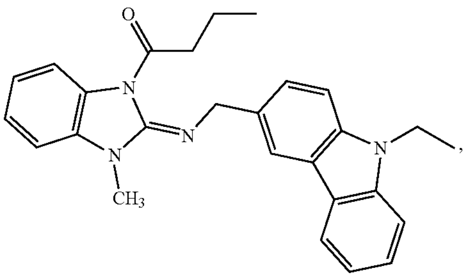
,
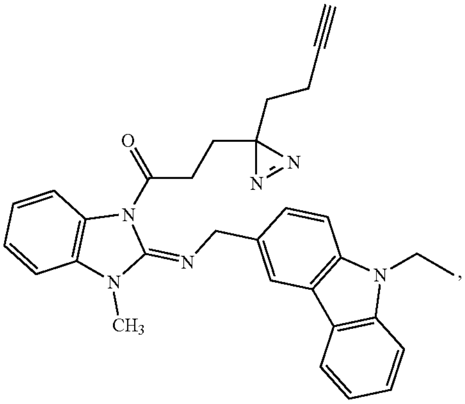
, and
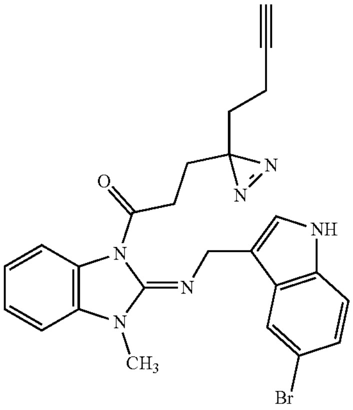
.
In some embodiments, the compound of Formula (I) is selected from
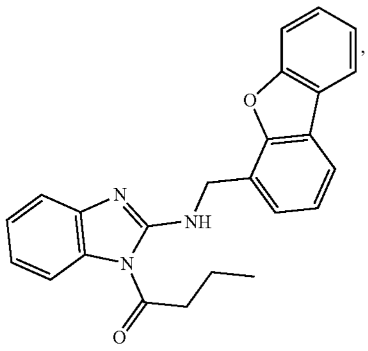
,
-continued
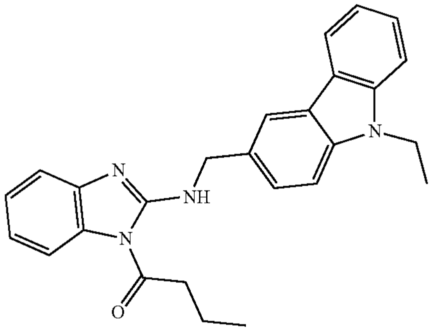
,
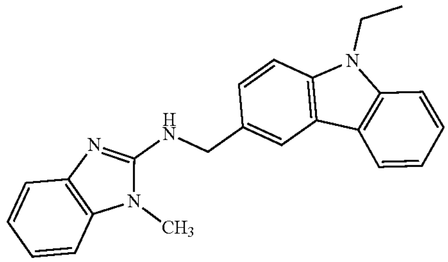
,
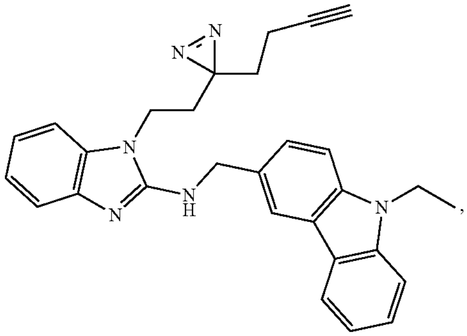
, and
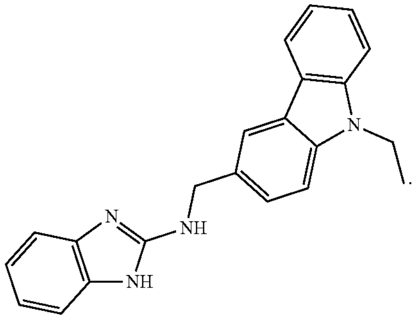
.
In some embodiments, compound of Formula (I) is selected from the group consisting of:
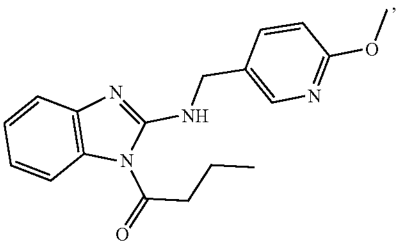
, -continued

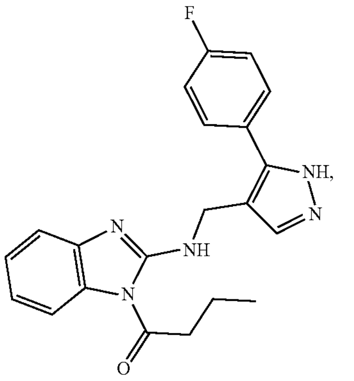

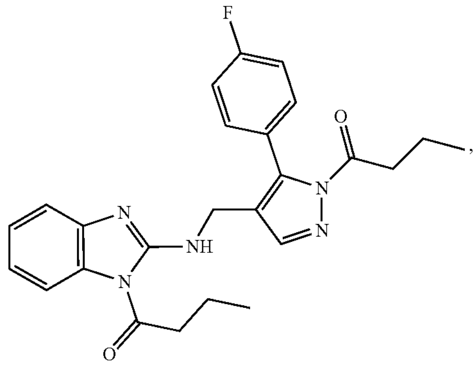

, and

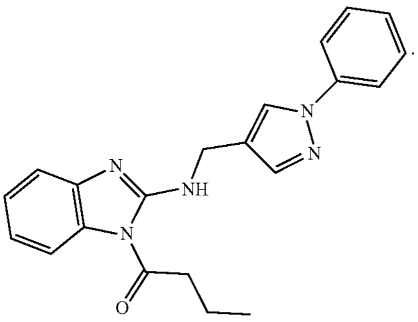

In some embodiments, the compound of Formula (I) is:

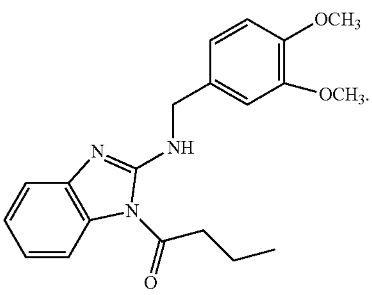 [SMILES: CCCC(=O)n1c(NCc2ccc(OC)c(OC)c2)nc2ccccc21]

In some embodiments, the compound of Formula (I) is

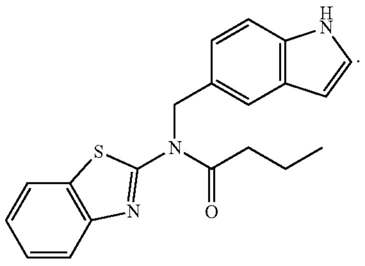 [SMILES: CCCC(=O)N(Cc1ccc2[nH]ccc2c1)c1nc2ccccc2s1]

In some embodiments, the compound of Formula (I) is

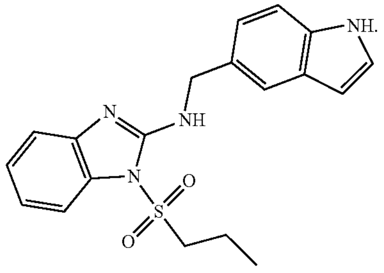 [SMILES: CCCS(=O)(=O)n1c(NCc2ccc3[nH]ccc3c2)nc2ccccc21]

Exemplary Pharmaceutical Compositions

In various embodiments, the disclosure relates to a pharmaceutical composition comprising any one of the compounds disclosed herein and a pharmaceutically acceptable carrier.

Patients, including but not limited to humans, can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

The concentration of active compound in the drug composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient can be administered at once or can be divided into a number of smaller doses to be administered at varying intervals of time.

In various embodiments, the mode of administration of the active compound is oral. Oral compositions will generally include an inert diluent or an edible carrier. They can be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, unit dosage forms can contain various other materials that modify the physical form of the dosage unit, for example, coatings of sugar, shellac, or other enteric agents.

The compound can be administered as a component of an elixir, suspension, syrup, wafer, chewing gum or the like. A syrup can contain, in addition to the active compound(s), sucrose or sweetener as a sweetening agent and various preservatives, dyes and colorings and flavors.

The compound or a pharmaceutically acceptable prodrug or salts thereof can also be mixed with other active materials that do not impair the desired action, or with materials that supplement the desired action, such as antibiotics, antifungals, anti-inflammatories or other antivirals, including but not limited to nucleoside compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents, such as ethylenediaminetetraacetic acid; buffers, such as acetates, citrates or phosphates, and agents for the adjustment of tonicity, such as sodium chloride or dextrose. The parental preparation can be enclosed in ampoules, disposable syringes or multiple dose vials made of glass or plastic.

If administered intravenously, carriers include physiological saline and phosphate buffered saline (PBS).

In various embodiments, the active compounds are prepared with carriers that will protect the compound against rapid elimination from the body, such as a controlled release formulation, including but not limited to implants and microencapsulated delivery systems. Biodegradable, biocompatible polymers can be used, such as ethylene vinyl acetate, polyanhydrides, polyglycolic acid, collagen, polyorthoesters and polylactic acid. For example, enterically coated compounds can be used to protect cleavage by stomach acid. Methods for preparation of such formulations will be apparent to those skilled in the art. Suitable materials can also be obtained commercially.

Liposomal suspensions (including but not limited to liposomes targeted to infected cells with monoclonal antibodies to viral antigens) are also pharmaceutically acceptable carriers. These can be prepared according to methods known to those skilled in the art, for example, as described in U.S. Pat. No. 4,522,811 (incorporated by reference). For example, liposome formulations can be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension.

Exemplary Methods of the Disclosure

In various embodiments, the disclosure relates to a method of treating a pDC, B cells, macrophages or monocytes-mediated disease or condition comprising the step of: administering to a subject in need thereof a therapeutically effective amount of any one of the aforementioned compounds. In some embodiments, the pDC-mediated disease is Lupus. Crohn's disease, irritable bowl syndrome (IBS), type I diabetes, dermatomyositis, Sjogren's Syndrome, psoriasis or any type 1 interferon drive interferonopathy. In some embodiments, the pDC-mediated disease is multiple sclerosis (MS).

EXAMPLES

The disclosure now being generally described will be more readily understood by reference to the following examples, which are included merely for purposes of illustration of aspects and embodiments of the present disclosure, and are not intended to limit the disclosure.

Figure 6A:
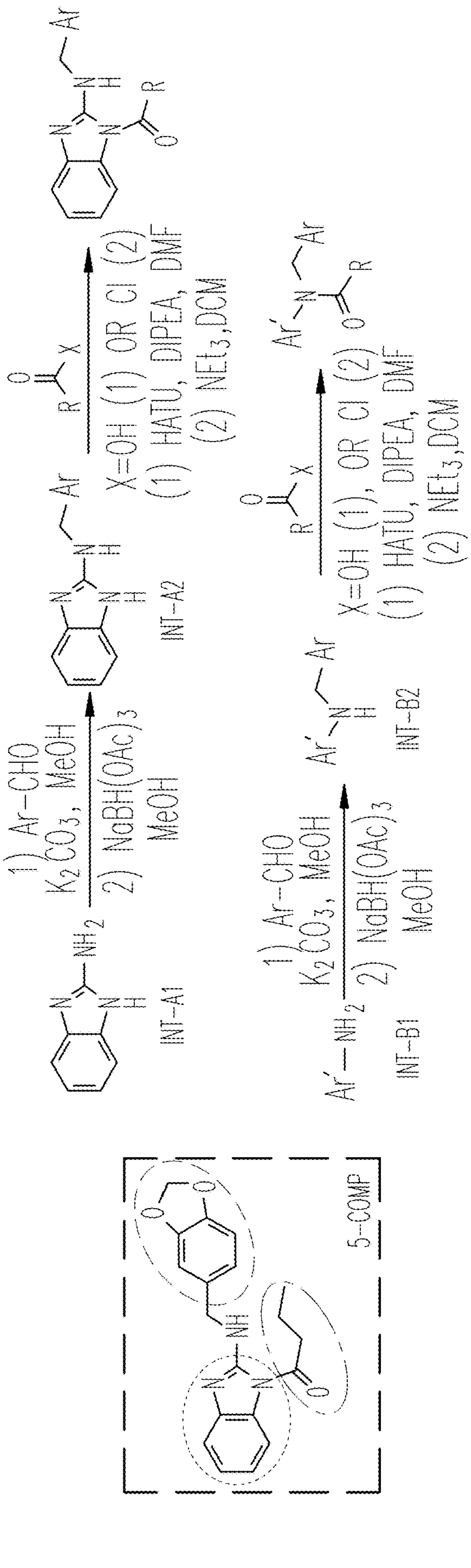
Figure 6B:
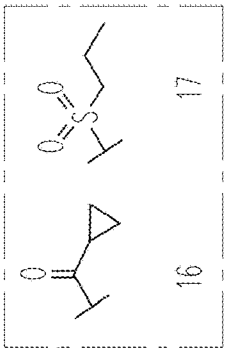
Figure 6B:
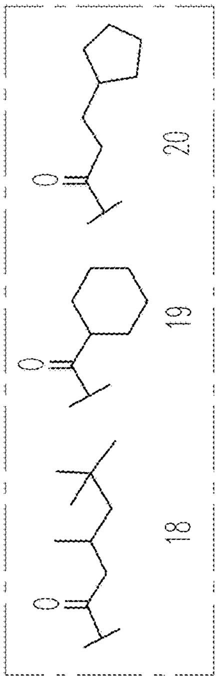
Figure 6B:
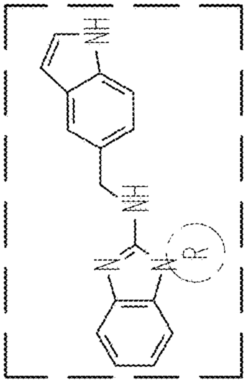
Figure 6B:
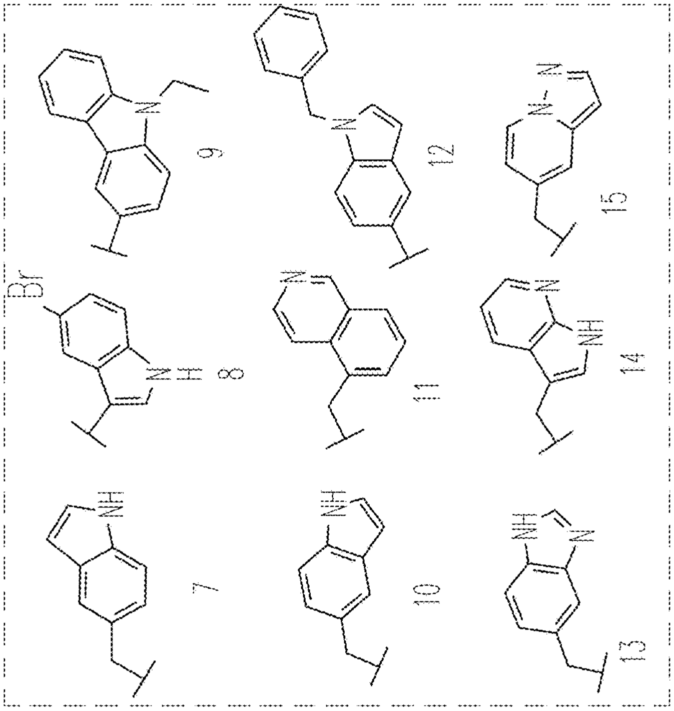
Figure 6B:
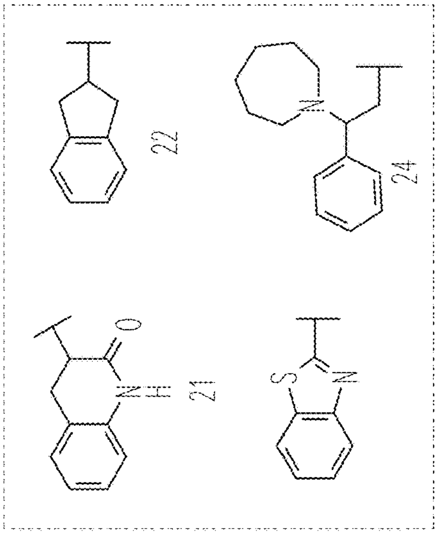
Figure 6B:
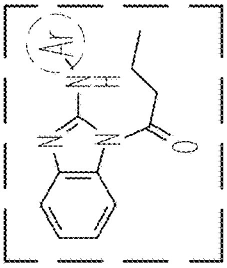
Figure 6B:
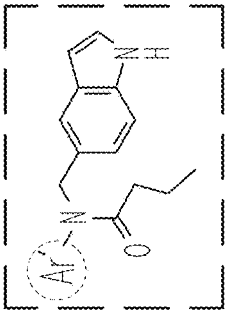
Figure 6C:
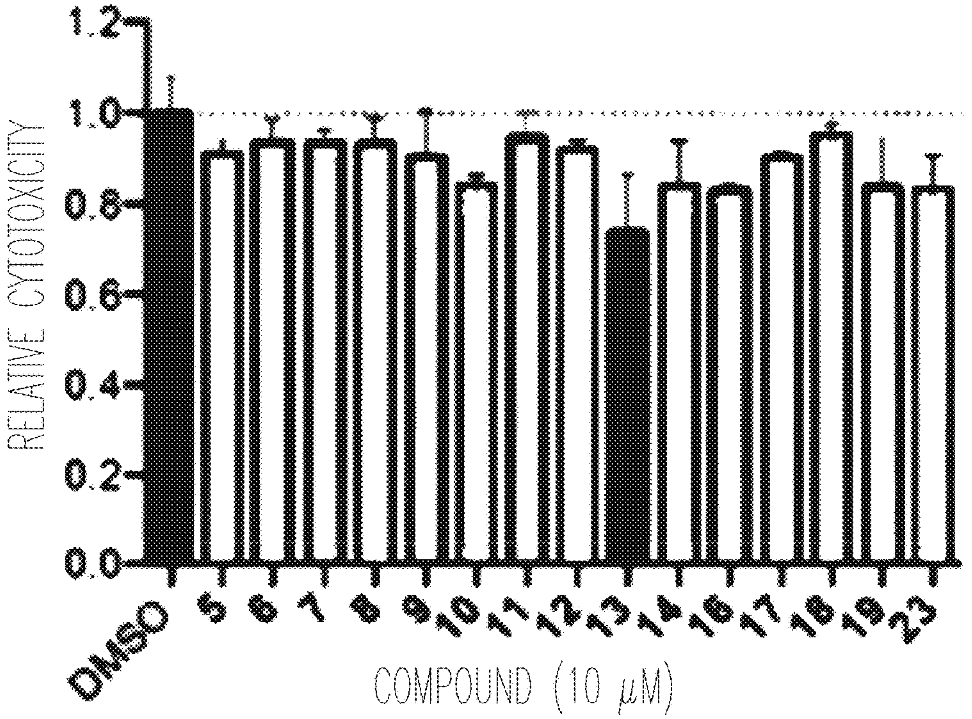

Example 1. General Schemes and Procedures for the Preparation of Compounds of the Disclosure Synthesis of various compounds are illustrated in FIG. 6A.

Example 2. Representative Preparation of Compounds of the Disclosure (A) Chemistry Material Chemicals and reagents were purchased from commercial vendors, including Sigma-Aldrich, Fisher Scientific, Combi-Blocks, MedChemExpress, Alfa Aesar and AstaTech, and were used as received without further purification, unless otherwise noted. Anhydrous solvents were purchased from Sigma-Aldrich in Sure/Seal™ formulations. All reactions were monitored by thin-layer chromatography (TLC, Merck silica gel 60 F-254 plates). The plates were stained either with p-anisaldehyde (2.5% p-anisaldehyde, 1% AcOH, 3.5% $H_2SO_4$ (conc.) in 95% EtOH), ninhydrin (0.3% ninhydrin (w/v), 97:3 EtOH—AcOH), KMnO4 (1.5 g of $KMnO_4$, 10 g $K_2CO_3$, and 1.25 mL 10% NaOH in 200 mL water), iodine or directly visualized with UV light. Reaction purification was carried out using Flash chromatography (230-400 mesh silica gel), Biotage® or preparative thin layer chromatography (pTLC, Analtech, 500-2000 μm thickness). NMR spectra were recorded on Bruker DPX-400 or Bruker AV-600 spectrometers in the indicated solvent. Multiplicities are reported with the following abbreviations: s singlet; d doublet; t triplet; q quartet; p pentet; m multiplet; br broad; dd doublet of doublets; dt doublet of triplets; td triplet of doublets; Chemical shifts are reported in ppm relative to the residual solvent peak and J values are reported in Hz. Mass spectrometry data were collected on an Agilent 6120 single-quadrupole LC/MS instrument (ESI, low resolution).

(B) Compound Synthesis and Characterization Data:

a) General synthetic Scheme 1

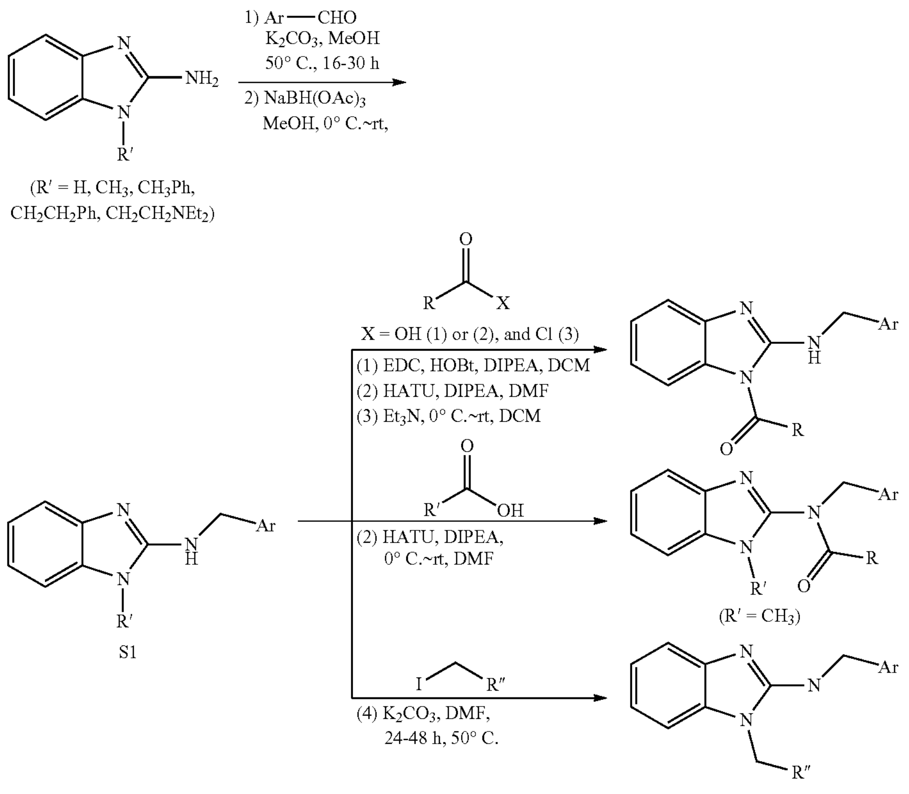

General Procedure 1: Coupling Procedure for the Synthesis of Benzo[d]Imidazole Amine Intermediate (S1)

To a dried round bottom flask containing solution of commercially available 2-aminobenzimidazole derivatives (1.0 eq.) and corresponding aldehyde (1.0 eq.) in dry methanol, $K_2CO_3$ (3.0 eq.) was added and the reaction mixture was heated at 50° C. for 16 to 30 hr. The solvent was filtered to remove the excess potassium carbonate and sodium triacetoxyborohydride (1.5 eq.) was added at 0° C. to the solution and resulting mixture was stirred for 3-5 hours at room temperature. After completion (monitored by TLC) the solvent was removed by rotary evaporation, crude mixture were diluted with water and washed with saturated aqueous $NaHCO_3$ solution extracted in ethyl acetate, the combined extract were dried over $Na_2SO_4$, filtered and concentrated in vacuum, purified by column on biotage to give corresponding amine (S1).

General Procedure 2: Coupling of Amine Intermediate (S1) with Acid

To a vial containing corresponding amine intermediate (S1, 1 eq.) in DCM (60 mM relative to S1), commercially available butyric acid or 3-(3-(but-3-yn-1-yl)-3H-diazirin-3-yl)propanoic acid (1.1 eq.), DIPEA (3.0 eq.), EDC-HCl (1.5 eq.) and HOBt (1.5 eq.) were added. Reaction mixtures were stirred at room temperature for 4 hr to overnight when TLC indicated reaction completed. The crude mixture was diluted with DCM and washed first with saturated aqueous $NH_4Cl$ and saturated aqueous $NaHCO_3$ then dried over anhydrous $Na_2SO_4$ and volatiles removed by rotary evaporation. Crude products were purified by PTLC or flash column chromatography to give the corresponding product.

General Procedure 3: Coupling of Amine Intermediate (S1) with Acid

To a solution of corresponding butyric acid or 3-(3-(but-3-yn-1-yl)-3H-diazirin-3-yl)propanoic acid in DMF (60 mM relative to S1), HATU (1.1 eq.) and DIPEA (3.0 eq.) were added at 0° C. and resulting mixture was stirred for 5 minutes then corresponding amine intermediate (S1) was added and resulting mixture was stirred at room temperature until amine was fully consumed, as indicated by TLC. The crude mixture was diluted with cold water and extracted in ethyl acetate then dried over anhydrous $Na_2SO_4$ and volatiles removed by rotary evaporation. Crude products were purified by PTLC or flash column chromatography to give the corresponding product.

General Procedure 4: Coupling Procedure for Synthesis of Amide with Acid Chloride To a solution of corresponding amine (S1, 1.0 equiv) in DCM (0.1 M), added triethylamine (1.1 eq.) followed by the slow addition of corresponding acid chloride (1.0 eq.) at 0° C., and resulting mixture was allowed to stir at room temperature until amine was fully consumed, as indicated by TLC. The crude mixture was diluted with DCM, washed first with saturated aqueous $NH_4Cl$ and saturated aqueous $NaHCO_3$, then dried over anhydrous $Na_2SO_4$ and volatiles removed by rotary evaporation. Crude products were purified by PTLC or Biotage® to obtain the corresponding product.

General Procedure 5: Coupling Procedure for Synthesis of N-Alkyl Containing Molecules To a solution of corresponding amine (S1, 1.0 eq) in DMF (0.1 M), added dry $K_2CO_3$ (2.0 eq) followed by addition of corresponding alkyl iodide or 3-(but-3-yn-1-yl)-3-(2-iodoethyl)-3H-diazirine (2.0 eq) at room temperature, and resulting mixture was allowed to stir at 50° C. until amine was fully consumed typically 18-24 hr., as indicated by TLC. The crude mixture was diluted with cold water, and extracted with ethyl acetate, combined extract was dried over anhydrous $Na_2SO_4$ and volatiles removed by rotary evaporation. Crude products were purified by PTLC or flash column chromatography to obtain the corresponding product.

b) General synthetic scheme 2

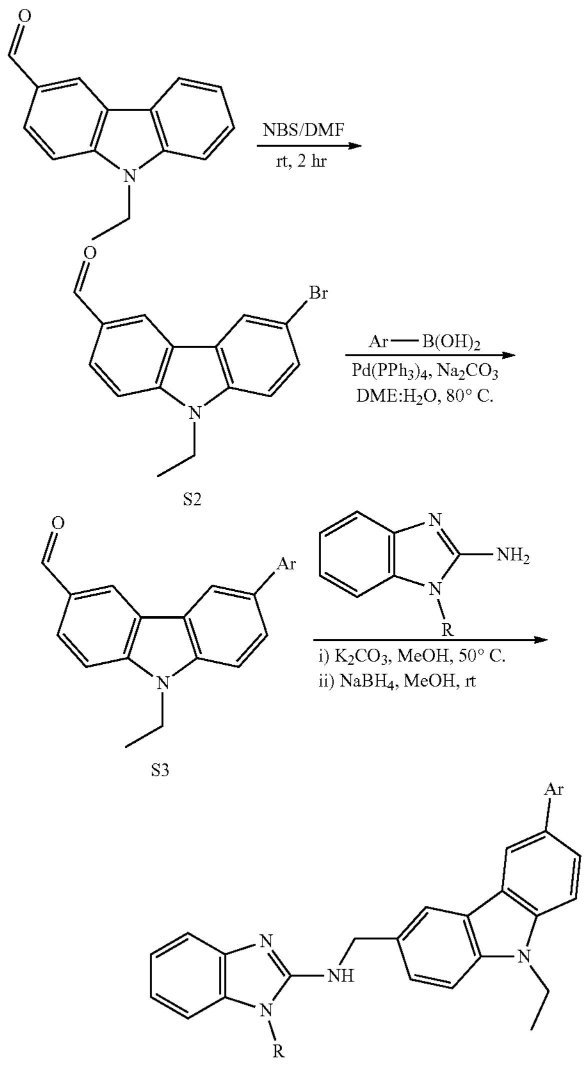

S2

S3

R = H, $CH_3$
AJ2-79, AJ2-80
AJ2-83 and AJ2-83

6-Bromo-9-ethylcarbazole-3-carbaldehyde (S2) 9-Ethylcarbazole-3-carbaldehyde (2 g, 8.95 mmol) was dissolved in DMF (15 mL) and the solution was cooled in an ice bath. A solution of N-bromosuccinimide (1.91 g, 10.74 mmol) in DMF (10 mL) was added dropwise over 10 minutes. The reaction mixture was allowed to stir for 2 hr at room temperature. Then, the mixture was poured into ice water, extracted with ethyl acetate, combined extract was dried over anhydrous $Na_2SO_4$ and volatiles removed by rotary evaporation. Crude products were purified by flash column chromatography to obtain the corresponding 6-bromo-9-ethylcarbazole-3-carbaldehyde product (S2).

General Procedure 6: Suzuki Coupling Procedure for Synthesis of (S3)

To a solution of 6-bromo-9-ethylcarbazole-3-carbaldehyde (0.822 mmol) and boronic acid (0.986 mmol) and potassium carbonate (0.246 mmol) in dimethoxyethane (9 mL) and water (3 mL) was degassed with bubbling argon over 5 minutes, followed by addition of tetrakis(triphenylphosphino)palladium (47 mg, 0.041 mmol). The resulting mixture was stirred at 80° C. for 6-8 hr. After cooling the reaction mixture was filter through celite, diluted with water, and extracted in ethyl acetate, combined extract was dried over anhydrous $Na_2SO_4$ and volatiles removed by rotary evaporation. Crude products were purified by flash column chromatography ethyl acetate/hexane to obtain the corresponding product (S3).

c) General synthetic scheme 3

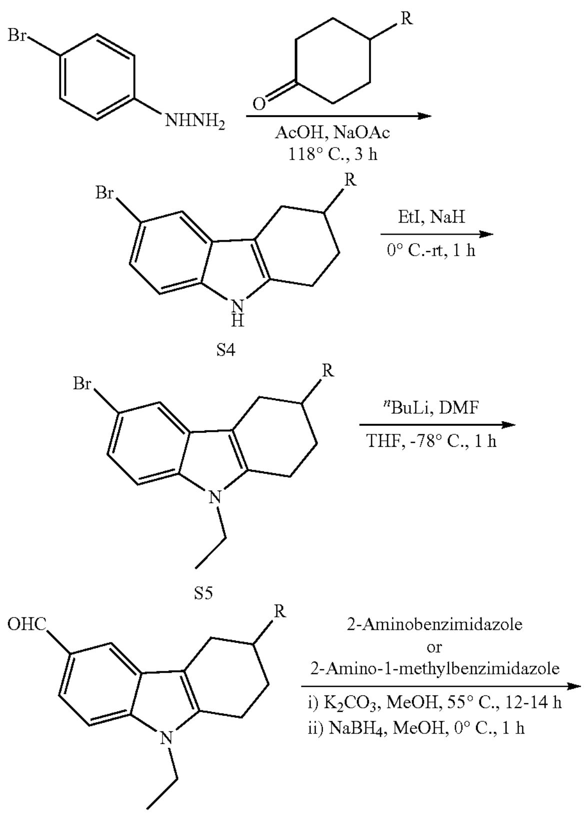

S4

S5

S6

-continued

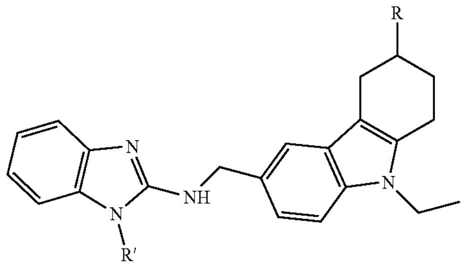

(R' = H, $CH_3$, R = $(CH_3)_2$, $CF_3$)
AJ2-49 to 51 and AJ2-61 & AJ2-62

Step 1; Synthesis of intermediate (S4): To a stirred solution of 4-bromophenylhydrazine (1.1 eq) in AcOH was added substituted cyclohexanone (1.1 eq), the reaction mixture was stirred at 118° C. for 3 h. After cooling the acetic acid was removed by rotary evaporation, the reaction mixture was diluted with water and saturated aqueous $NaHCO_3$ solution and extracted with ethyl acetate, combined extract was dried over anhydrous $Na_2SO_4$ and volatiles removed by rotary evaporation. Crude products were purified by flash column chromatography ethyl acetate/hexane to obtain the corresponding product (S4).

Step 2; Synthesis of intermediate (S5): To a stirred solution of (S4) (1 eq.) in DMF, a suspension of sodium hydride (1.1 eq.) (60% in mineral oil) was slowly added at 0° C., over 10 minutes, the resulting mixture was stirred for 15 minutes in cold ice bath, a solution of ethyl iodide (1.5 eq) was added dropwise over 5 minutes, the resulting mixture was allowed to stir for 1 hr at room temperature, the reaction mixture was diluted with water and extracted with ethyl acetate, combined extract was dried over anhydrous $Na_2SO_4$ and volatiles removed by rotary evaporation. Crude products were purified by flash column chromatography ethyl acetate/hexane to obtain the corresponding product (S5).

Step 3; Synthesis of intermediate (S6): n-Butyllithium (1.1 eq) was added to a stirred solution of (S5) (1 eq.) in THF, at −78° C. under argon atmosphere the resulting mixture was stirred for 20 minutes before adding the DMF (3 eq). The reaction mixture was allowed to stir for 2 hr at room temperature. Then, the mixture was poured into ice cold solution of ammonium chloride, extracted with ethyl acetate, combined extract was dried over anhydrous $Na_2SO_4$ and volatiles removed by rotary evaporation. Crude products were purified by flash column chromatography to obtain the corresponding aldehyde (S6).

d) General synthetic scheme 4

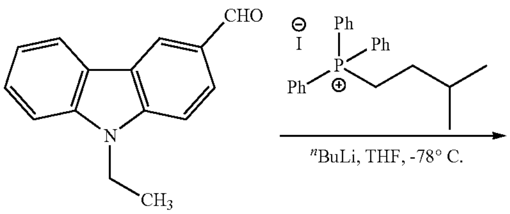

-continued

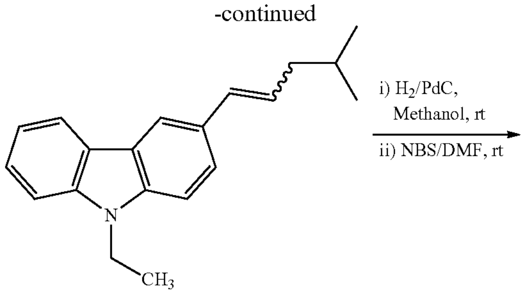

(S7)

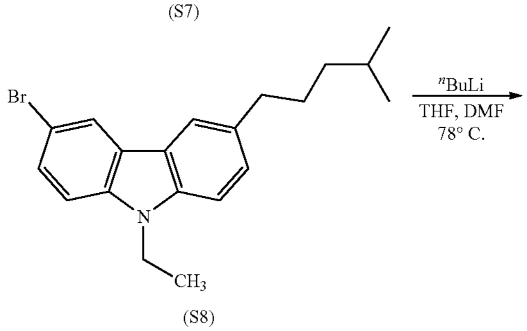

(S8)

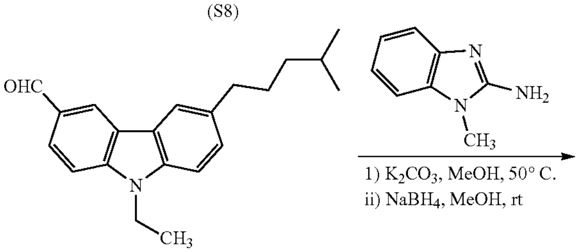

(S9)

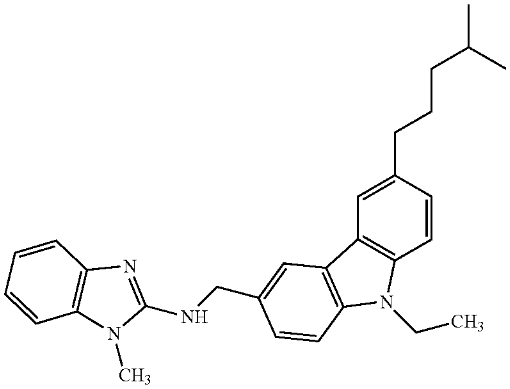

AJ2-89

Step 1; Synthesis of intermediate (S7): n-Butyllithium (1.1 eq) was added to a stirred solution of corresponding wittig salt (1.0 eq.) in THF at −78° C. under argon atmosphere the resulting mixture was stirred for 20 minutes before adding a solution of 9-Ethyl-3-carbazolecarboxaldehyde (1.0 eq) in THF. The reaction mixture was allowed to stir for 2 h at room temperature. The mixture was poured into ice cold solution of ammonium chloride, extracted with ethyl acetate, combined extract was dried over anhydrous $Na_2SO_4$ and volatiles removed by rotary evaporation. Crude products were purified by flash column chromatography to obtain the corresponding aldehyde (S7).

Step 2; Synthesis of intermediate (S8): To a solution of intermediate (S7) in methanol, 5% wt Pd/C was added and the resulting mixture was stirred in hydrogen environment for 8 h at room temperature. After completion the reaction mixture was filtered with short celite pad and washed with methanol, dried over rotary evaporation, and dissolved in DMF and a solution of N-bromosuccinimide (1.2 eq) in DMF was added dropwise over 10 minutes at 0° C. The reaction mixture was allowed to stir for 2 h at room temperature. The mixture was poured into ice water, extracted with ethyl acetate, combined extract was dried over anhydrous $Na_2SO_4$ and volatiles removed by rotary evaporation. Crude products were purified by flash column chromatography to obtain the corresponding bromo product (S8).

Step 3; Synthesis of intermediate (S9): n-Butyllithium (1.1 eq) was added to a stirred solution of (S8) (1.0 eq.) in THF, at −78° C. under argon atmosphere the resulting mixture was stirred for 20 minutes before adding the DMF (3.0 eq). The reaction mixture was allowed to stir for 2 hr at room temperature. Then, the mixture was poured into ice cold solution of ammonium chloride, extracted with ethyl acetate, combined extract was dried over anhydrous $Na_2SO_4$ and volatiles removed by rotary evaporation. Crude products were purified by flash column chromatography to obtain the corresponding aldehyde (S9).

AJ2-1

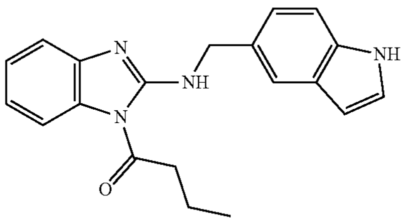

1-(2-(((1H-indol-5-yl)methyl)amino)-1H-benzo[d]imidazol-1-yl)butan-1-one (AJ2-1): Synthesized according to scheme 1 and following general procedure 4, purified by biotage (Hexane/EtOAc, 6:4) to afford AJ2-1 as an off white solid (17 mg, 62%). $^1H$ NMR (400 MHz, $CDCl_3$) δ 8.21 (s, 1H), 8.16 (s, 1H), 7.68 (dt, J=1.6, 0.8 Hz, 1H), 7.47 (dd, J=7.8, 1.2 Hz, 1H), 7.38 (ddd, J=8.4, 2.5, 1.7 Hz, 2H), 7.26-7.20 (m, 4H), 7.06 (ddd, J=8.6, 7.5, 1.3 Hz, 1H), 6.53-6.55 (m, 1H), 4.85 (d, J=5.2 Hz, 2H), 2.99 (t, J=7.2 Hz, 2H), 1.84 (p, J=7.3 Hz, 2H), 1.08 (t, J=7.4 Hz, 3H). LCMS calcd for $C_{20}H_{21}N_4O$, 333.2 (M+H$^+$), found: 333.2.

AJ2-2

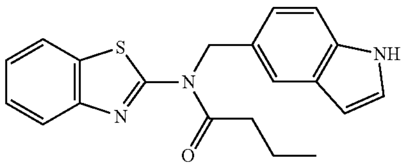

N-((1H-indol-5-yl)methyl)-N-(benzo[d]thiazol-2-yl)butyramide (AJ2-2): Synthesized according to scheme 1 and following general procedure 2, purified by PTLC (Hexane/EtOAc, 4:2) to afford AJ2-2 as brown solid (8 mg, 62%) $^1H$ NMR (400 MHz, $CDCl_3$) δ 8.17 (s, 1H), 7.84 (dt, J=7.7, 1.1 Hz, 1H), 7.79 (dt, J=8.2, 0.9 Hz, 1H), 7.48-7.45 (m, 1H), 7.40 (ddd, J=8.3, 7.2, 1.3 Hz, 1H), 7.36-7.27 (m, 2H), 7.20 (dd, J=3.2, 2.4 Hz, 1H), 7.09 (dd, J=8.5, 1.8 Hz, 1H), 6.48 (ddd, J=3.1, 2.0, 1.0 Hz, 1H), 5.74 (s, 2H), 2.62 (t, J=7.3 Hz, 2H), 1.72 (q, J=7.4 Hz, 2H), 0.92 (t, J=7.4 Hz, 3H). LCMS calcd for $C_{20}H_{20}N_3OS$ 350.1 (M+H$^+$), found: 350.0.

AJ2-3A

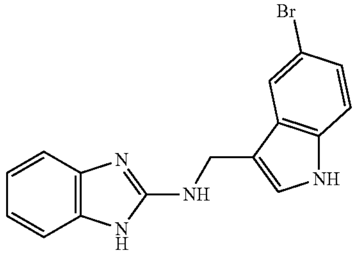

N-((5-bromo-1H-indol-3-yl)methyl)-1H-benzo[d]imidazol-2-amine (AJ2-3A): synthesized according to scheme 1, purified by biotage (Hexane/EtOAc, 3:7) to afford AJ2-3A as light brown solid (160 mg, 64%); $^1H$ NMR (400 MHz, $CD_3OD$) δ 7.74 (s, 1H), 7.28 (s, 1H), 7.23 (dd, J=8.6, 0.6 Hz, 1H), 7.20-7.12 (m, 3H), 6.94 (dd, J=5.8, 3.2 Hz, 2H), 4.64 (d, J=0.8 Hz, 2H). LCMS calcd for $C_{16}H_{14}BrN_4$ 341.0 (M+H$^+$), found: 340.9.

AJ2-3

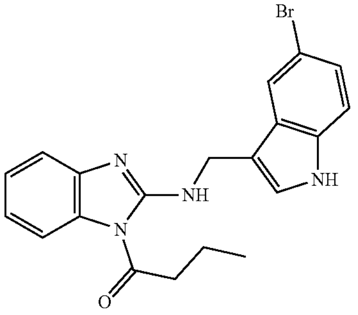

1-(2-(((5-bromo-1H-indol-3-yl)methyl)amino)-1H-benzo[d]imidazol-1-yl)butan-1-one (AJ2-3): Synthesized according to scheme 1 and general procedure 4, purified by biotage (Hexane/EtOAc, 3:2) to afford AJ2-3 as brown solid (32 mg, 64%) $^1H$ NMR (400 MHz, $CDCl_3$) δ 8.19 (s, 1H), 8.03 (s, 1H), 7.84 (dd, J=1.7, 0.9 Hz, 1H), 7.49 (dd, J=7.9, 1.2 Hz, 1H), 7.40 (d, J=8.1 Hz, 1H), 7.32-7.27 (m, 3H), 7.25 (dd, J=1.8, 0.9 Hz, 1H), 7.08 (ddd, J=8.1, 7.5, 1.3 Hz, 1H), 4.88 (d, J=4.3 Hz, 2H), 2.99 (t, J=7.2 Hz, 2H), 1.84 (h, J=7.4 Hz, 2H), 1.08 (t, J=7.4 Hz, 3H). LCMS calcd for $C_{20}H_{20}BrN_4O$; 411.1 (M+H$^+$), found: 411.1.

AJ2-4

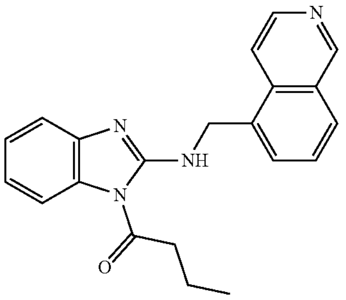

1-(2-((isoquinolin-5-ylmethyl)amino)-1H-benzo[d]imidazol-1-yl)butan-1-one (AJ2-4): Synthesized according to scheme 1 and general procedure 4, purified by biotage (Hexane/EtOAc, 3:2) to afford AJ2-4 as light brown solid (7 mg, 54%) $^1$H NMR (400 MHz, $CD_3OD$) δ 9.17 (s, 1H), 8.40 (d, J=6.1 Hz, 1H), 7.96 (dd, J=7.2, 4.6 Hz, 2H), 7.76 (dd, J=7.2, 1.2 Hz, 1H), 7.62-7.54 (m, 1H), 7.48 (d, J=8.2 Hz, 1H), 7.24-7.20 (m, 1H), 7.12 (td, J=7.7, 1.0 Hz, 1H), 7.07-6.99 (m, 1H), 5.09 (s, 2H), 3.00 (t, J=7.1 Hz, 2H), 1.73 (q, J=7.3 Hz, 2H), 0.98 (t, J=7.4 Hz, 3H). LCMS calcd for $C_{21}H_{21}N_4O$; 345.2 (M+H$^+$), found: 345.2.

AJ2-5

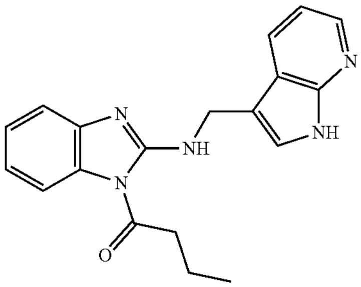

1-(2-(((1H-pyrrolo[2,3-b]pyridin-3-yl)methyl)amino)-1H-benzo[d]imidazol-1-yl)butan-1-one (AJ2-5): Synthesized according to scheme 1 and general procedure 4, purified by biotage (Hexane/EtOAc, 4:2) to afford AJ2-5 as brown solid (12 mg, 62%); $^1$H NMR (400 MHz, $CDCl_3$) δ 10.42 (s, 1H), 8.33 (dd, J=4.8, 1.5 Hz, 1H), 8.10 (t, J=5.2 Hz, 1H), 8.05 (dd, J=7.9, 1.5 Hz, 1H), 7.50 (dd, J=8.0, 1.3 Hz, 1H), 7.44-7.38 (m, 2H), 7.30-7.24 (m, 2H), 7.13-7.05 (m, 2H), 4.93 (dd, J=5.1, 0.8 Hz, 2H), 2.98 (t, J=7.2 Hz, 2H), 1.83 (q, J=7.3 Hz, 2H), 1.07 (t, J=7.4 Hz, 3H). LCMS calcd for $C_{19}H_{20}N_5O$; 334.1 (M+H$^+$), found: 334.1.

AJ2-6

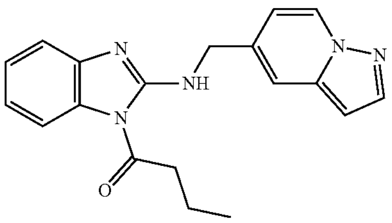

1-(2-((pyrazolo[1,5-a]pyridin-5-ylmethyl)amino)-1H-benzo[d]imidazol-1-yl)butan-1-one (AJ2-6): Synthesized according to scheme 1 and general procedure 4, purified by biotage (Hexane/EtOAc, 4:2) to afford AJ2-6 as a brown solid (6 mg, 52%) $^1$H NMR (400 MHz, $CDCl_3$) δ 8.45 (d, J=7.2 Hz, 1H), 8.34 (s, 1H), 7.95 (d, J=2.3 Hz, 1H), 7.55 (s, 1H), 7.45 (t, J=8.3 Hz, 2H), 7.29 (d, J=0.9 Hz, 2H), 7.16-7.06 (m, 1H), 6.82 (dd, J=7.2, 2.0 Hz, 1H), 6.49 (d, J=2.3 Hz, 1H), 4.83 (d, J=5.9 Hz, 2H), 3.06 (t, J=7.2 Hz, 2H), 1.92 (q, J=7.3 Hz, 2H), 1.14 (t, J=7.4 Hz, 3H). LCMS calcd for $C_{19}H_{20}N_5O$, 334.16 (M+H$^+$), found: 334.16.

AJ2-7

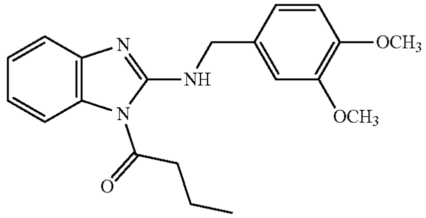

1-(2-((3,4-dimethoxybenzyl)amino)-1H-benzo[d]imidazol-1-yl)butan-1-one (AJ2-7): synthesized according to scheme 1 and general procedure 4, purified by biotage (Hexane/EtOAc, 3:2) to afford AJ2-7 as a brown solid (12 mg, 72%) $^1$H NMR (400 MHz, $CDCl_3$) δ 8.14 (t, J=5.5 Hz, 1H), 7.45 (ddd, J=7.9, 1.3, 0.5 Hz, 1H), 7.38 (dt, J=8.2, 0.8 Hz, 1H), 7.24 (dd, J=7.7, 1.0 Hz, 1H), 7.06 (ddd, J=8.2, 7.5, 1.3 Hz, 1H), 6.98-6.93 (m, 2H), 6.87-6.81 (m, 1H), 4.70 (d, J=5.4 Hz, 2H), 3.88 (s, 3H), 3.87 (s, 3H), 2.99 (t, J=7.2 Hz, 2H), 1.86 (q, J=7.3 Hz, 2H), 1.09 (t, J=7.4 Hz, 3H). LCMS calcd for $C_{20}H_{24}N_3O_3$; 354.2 (M+H$^+$), found: 354.2.

AJ2-8

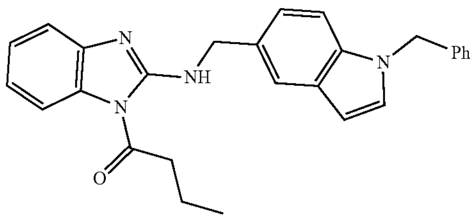

1-(2-(((1-benzyl-1H-indol-5-yl)methyl)amino)-1H-benzo[d]imidazol-1-yl)butan-1-one (AJ2-8): Synthesized according to scheme 1 and general procedure 4, purified by biotage (Hexane/EtOAc, 3:2) to afford AJ2-8 as an off white solid (14 mg, 74%)$^1$H NMR (400 MHz, $CDCl_3$) δ 8.13 (s, 1H), 7.71-7.65 (m, 1H), 7.46 (dd, J=7.9, 1.2 Hz, 1H), 7.38 (d, J=8.1 Hz, 1H), 7.33-7.27 (m, 3H), 7.25-7.23 (m, 2H), 7.15 (d, J=3.2 Hz, 1H), 7.10 (dd, J=4.5, 2.1 Hz, 1H), 7.09-7.02 (m, 2H), 6.53 (dd, J=3.1, 0.8 Hz, 1H), 5.32 (s, 2H), 4.84 (d, J=5.1 Hz, 2H), 2.98 (t, J=7.2 Hz, 2H), 1.84 (q, J=7.4 Hz, 2H), 1.08 (t, J=7.4 Hz, 3H). LCMS calcd for $C_{27}H_{27}N_4O$; 423.2 (M+H$^+$), found: 423.2.

AJ2-9

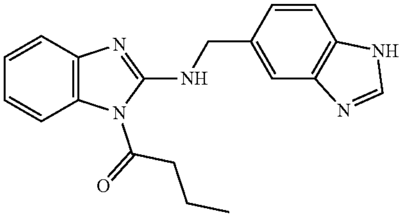

1-(2-(((1H-benzo[d]imidazol-5-yl)methyl)amino)-1H-benzo[d]imidazol-1-yl)butan-1-one (AJ2-9): Synthesized according to scheme 1 and general procedure 4, purified by PTLC (DCM/MeOH, 9:1) to afford AJ2-9 as off white solid (6 mg, 48%)$^1$H NMR (400 MHz, MeOD) δ 8.05 (s, 1H), 7.57 (d, J=1.5 Hz, 1H), 7.50 (d, J=8.3 Hz, 1H), 7.24 (dd, J=8.3, 1.7 Hz, 1H), 7.15-7.12 (m, 3H), 6.94 (dd, J=5.9, 3.1

Hz, 2H), 4.62 (s, 2H), 2.12 (t, J=7.4 Hz, 2H), 1.56-1.47 (m, 2H), 0.84 (t, J=7.4 Hz, 3H). LCMS calcd. for $C_{19}H_{20}N_5O$; 334.2 (M+H$^+$), found: 334.16.

AJ2-10

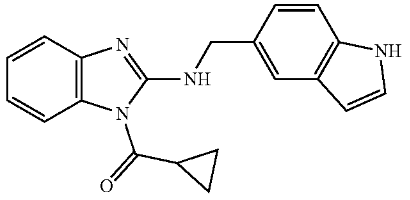

(2-(((1H-indol-5-yl)methyl)amino)-1H-benzo[d]imidazol-1-yl)(cyclopropyl)methanone (AJ2-10): Synthesized according to scheme 1 and general procedure 4, purified by PTLC (Hexane/Ethyl acetate 3:2) to afford AJ2-10 as off white solid (11 mg, 54%) $^1$H NMR (400 MHz, $CDCl_3$) δ 8.30 (s, 1H), 7.68 (t, J=5.2 Hz, 1H), 7.58 (s, 1H), 7.51 (d, J=8.1 Hz, 1H), 7.40 (d, J=7.9 Hz, 1H), 7.26 (d, J=8.4 Hz, 1H), 7.15 (dd, J=14.9, 2.5 Hz, 4H), 6.98 (t, J=7.8 Hz, 1H), 6.44 (d, J=3.2 Hz, 1H), 4.75 (d, J=4.6 Hz, 2H), 2.41 (tt, J=8.3, 4.6 Hz, 1H), 1.32-1.24 (m, 2H), 1.12 (dd, J=7.8, 3.4 Hz, 2H). $^{13}$C NMR (151 MHz, $CDCl_3$) δ 174.96, 154.41, 143.92, 135.36, 130.69, 129.28, 129.26, 128.07, 124.78, 124.73, 124.61, 122.32, 120.14, 117.07, 112.78, 111.36, 111.31, 102.62, 102.56, 47.56, 16.72, 10.26. LCMS calcd for $C_{20}H_{19}N_4O$; 331.1 (M+H$^+$), found: 331.1.

AJ2-11

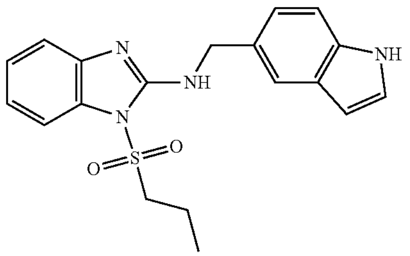

N-((1H-indol-5-yl)methyl)-1-(propylsulfonyl)-1H-benzo[d]imidazol-2-amine (AJ2-11): Synthesized according to scheme 1 and general procedure 4, purified by PTLC (Hexane/Ethyl acetate 3:2) to afford AJ2-11 as an off white solid (5 mg, 43%) $^1$H NMR (400 MHz, DMSO) δ 11.05 (s, 1H), 7.56 (d, J=1.6 Hz, 1H), 7.54-7.48 (m, 1H), 7.36 (d, J=8.3 Hz, 1H), 7.34-7.28 (m, 2H), 7.22-7.14 (m, 2H), 7.09 (t, J=5.9 Hz, 1H), 7.05 (td, J=7.7, 1.2 Hz, 1H), 6.39 (dd, J=2.0, 0.9 Hz, 1H), 4.69 (d, J=5.8 Hz, 2H), 3.65-3.56 (m, 2H), 1.60-1.48 (m, 2H), 0.82 (t, J=7.4 Hz, 3H). $^{13}$C NMR (151 MHz, DMSO) δ 152.60, 142.79, 135.63, 131.68, 129.76, 128.01, 126.12, 124.89, 121.49, 121.13, 119.41, 116.76, 112.22, 111.76, 101.42, 54.76, 47.20, 16.88, 12.49. LCMS calcd for $C_{19}H_{21}N_4O_2S$; 369.1 (M+H$^+$), found: 469.13.

AJ2-12

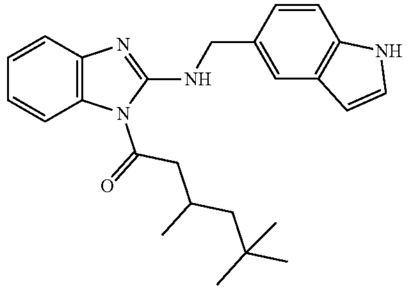

1-(2-(((1H-indol-5-yl)methyl)amino)-1H-benzo[d]imidazol-1-yl)-3,5,5-trimethylhexan-1-one (AJ2-12): Synthesized according to scheme 1 and general procedure 4, purified by PTLC (Hexane/Ethyl acetate 3:2) to afford AJ2-12 as an off white solid (6 mg, 45%)$^1$H NMR (400 MHz, $CDCl_3$) δ 8.38 (s, 1H), 8.19 (t, J=5.2 Hz, 1H), 7.68-7.64 (m, 1H), 7.46 (dd, J=7.9, 1.3 Hz, 1H), 7.40-7.33 (m, 2H), 7.25-7.19 (m, 3H), 7.11-7.00 (m, 2H), 6.52 (dd, J=2.0, 0.9 Hz, 1H), 4.84 (d, J=5.1 Hz, 2H), 3.00-2.94 (m, 1H), 2.89-2.84 (m, 1H), 2.38-2.26 (m, 2H), 1.38 (d, J=3.9 Hz, 1H), 1.10 (s, 3H), 1.01 (d, J=6.3 Hz, 1H), 0.93 (s, 9H).). LCMS calcd for $C_{25}H_{31}N_4O$, 403.2 (M+H$^+$), found: 403.2.

AJ2-13

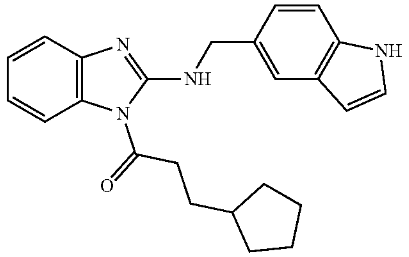

1-(2-(((1H-indol-5-yl)methyl)amino)-1H-benzo[d]imidazol-1-yl)-3-cyclopentylpropan-1-one (AJ2-13): Synthesized according to scheme 1 and general procedure 4, purified by PTLC (Hexane/Ethyl acetate 3:2) to afford AJ2-13 as off white solid (8 mg, 47%) $^1$H NMR (400 MHz, $CDCl_3$) δ 8.20 (s, 1H), 8.18 (t, J=4.4 Hz, 1H), 7.69-7.66 (m, 1H), 7.47 (dd, J=8.0, 1.2 Hz, 1H), 7.42-7.35 (m, 2H), 7.25-7.17 (m, 4H), 7.10-7.04 (m, 2H), 6.54 (dd, J=2.0, 1.0 Hz, 1H), 4.84 (d, J=5.1 Hz, 2H), 3.08-2.97 (m, 2H), 2.37 (s, 214), 1.85-1.77 (m, 4H), 1.69-1.63 (m, 5H). LCMS calcd for $C_{24}H_{27}N_4O$; 387.2 (M+H$^+$), found: 387.2.

AJ2-14

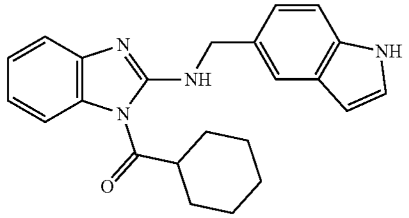

(2-(((1H-indol-5-yl)methyl)amino)-1H-benzo[d]imidazol-1-yl)(cyclohexyl)methanone (AJ2-14): Synthesized according to scheme 1 and following general procedure 4, purified by PTLC (Hexane/Ethyl acetate 3:2) to afford AJ2-14 as off white solid (6 mg, 47%) $^1$H NMR (400 MHz, $CDCl_3$) δ 8.32 (s, 1H), 8.15 (t, J=5.2 Hz, 1H), 7.58 (d, J=1.6 Hz, 1H), 7.38 (dd, J=7.9, 1.2 Hz, 1H), 7.27 (d, J=8.3 Hz, 1H), 7.22-7.13 (m, 4H), 7.04-6.96 (m, 2H), 6.49-6.42 (m, 1H), 4.74 (d, J=5.1 Hz, 2H), 3.12-3.07 (m, 1H), 2.02-1.93 (m, 2H), 1.87-1.81 (m, 2H), 1.75-1.65 (m, 2H), 1.57-1.50 (m, 2H), 1.37 (dt, J=12.7, 3.3 Hz, 2H). $^{13}$C NMR (151 MHz, $CDCl_3$) δ 178.08, 155.28, 143.83, 135.37, 129.83, 129.18, 128.08, 124.87, 124.78, 122.35, 120.39, 120.17, 117.12, 112.82, 111.36, 102.62, 47.67, 44.79, 29.04, 28.73, 25.63, 25.47, 25.42. LCMS calcd for $C_{23}H_{25}N_4O$; 373.2 (M+H$^+$), found: 373.2.

AJ2-15

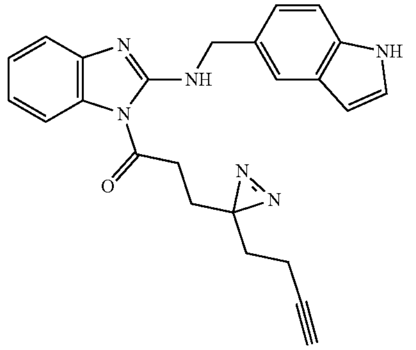

1-(2-(((1H-indol-5-yl)methyl)amino)-1H-benzo[d]imidazol-1-yl)-3-(3-(but-3-yn-1-yl)-3H-diazirin-3-yl)propan-1-one (AJ2-15): Synthesized according to scheme 1 and general procedure 1, purified by biotage (Hexane/Ethyl acetate 12) to afford AJ2-15 as colorless liquid (14 mg, 54%) $^1$H NMR (400 MHz, $CDCl_3$) δ 8.36 (s, 1H), 8.06 (t, J=5.2 Hz, 1H), 7.67 (s, 1H), 7.45 (d, J=7.8 Hz, 1H), 7.35 (d, J=8.4 Hz, 1H), 7.30-7.20 (m, 4H), 7.06 (t, J=7.8 Hz, 1H), 6.52 (s, 1H), 4.84 (d, J=5.1 Hz, 2H), 2.76 (t, J=7.4 Hz, 2H), 2.10-1.98 (m, 5H), 1.73 (d, J=7.3 Hz, 2H). LCMS calcd for $C_{24}H_{23}N_6O$; 411.2 (M+H$^+$), found: 411.0.

AJ2-16

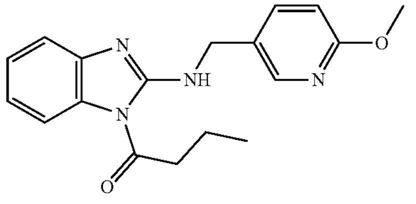

1-(2-(((6-methoxypyridin-3-yl)methyl)amino)-1H-benzo[d]imidazol-1-yl)butan-1-one (AJ2-16): Synthesized according to scheme 1 and general procedure 4, purified by biotage (Hexane/Ethyl acetate 3:2) to afford AJ2-16 as off white solid (12 mg, 47%); $^1$H NMR (400 MHz, DMSO) δ 8.41 (t, J=6.1 Hz, 1H), 8.22 (d, J=2.4 Hz, 1H), 7.78 (dd, J=8.5, 2.5 Hz, 1H), 7.57 (d, J=8.1 Hz, 1H), 7.27 (dd, J=7.9, 1.4 Hz, 1H), 7.17 (td, J=7.6, 1.1 Hz, 1H), 7.03 (ddd, J=8.3, 7.5, 1.3 Hz, 1H), 6.78 (d, J=8.5 Hz, 1H), 4.59 (d, J=6.1 Hz, 2H), 3.82 (s, 3H), 3.10 (t, J=7.0 Hz, 2H), 1.73 (q, J=7.2 Hz, 3H), 1.02 (t, J=7.4 Hz, 3H). LCMS calcd for $C_{18}H_{21}N_4O_2$; 325.1 (M+H$^+$), found: 325.0.

AJ2-17A

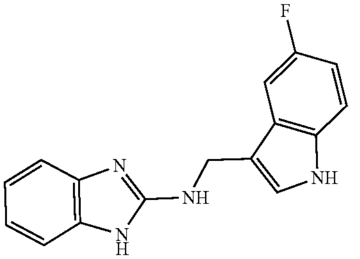

1-(2-(((5-fluoro-1H-indol-3-yl)methyl)amino)-1H-benzo[d]imidazol-1-yl)butan-1-one (AJ2-17A): Synthesized according to scheme 1 and general procedure 1, purified by biotage (Hexane/Ethyl acetate 4:6) to afford AJ2-17A as brown solid (74 mg, 54%) $^1$H NMR (400 MHz, $CD_3OD$_SPE) δ 7.32-7.24 (m, 2H), 7.16 (d, J=7.6, Hz, 2H), 6.92 (d, J=7.1 Hz, 2H), 6.82 (td, J=9.2, 2.6 Hz, 1H), 4.63 (s, 2H). LCMS calcd for $C_{68}H_{14}FN_4$; 281.1 (M+H$^+$), found: 281.1.

AJ2-17

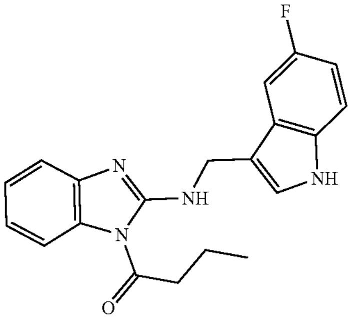

1-(2-(((5-fluoro-1H-indol-3-yl)methyl)amino)-1H-benzo[d]imidazol-1-yl)butan-1-one (AJ2-17): Synthesized according to scheme 1 and general procedure 4, purified by biotage (Hexane/Ethyl acetate 3:2) to afford AJ2-17 as off white solid (5 mg, 42%)$^1$H NMR (400 MHz, $CDCl_3$) δ 8.47 (s, 1H), 8.07 (t, J=5.0 Hz, 1H), 7.49 (dd, J=7.9, 1.2 Hz, 114), 7.42-7.36 (m, 1H), 7.33 (dd, J=9.5, 2.5 Hz, 1H), 7.29-7.26 (m, 1H), 7.26-7.22 (m, 2H), 7.07 (ddd, J=8.6, 7.5, 1.3 Hz, 1H), 6.94 (td, J=9.1, 2.5 Hz, 1H), 4.88 (dd, J=5.0, 0.8 Hz, 2H), 2.97 (t, J=7.2 Hz, 2H), 1.84 (p, J=7.3 Hz, 2H), 1.07 (t, J=7.4 Hz, 314). LCMS calcd for $C_{20}H_{19}FN_4O$; 351.2 (M+H$^+$), found: 351.0.

AJ2-18

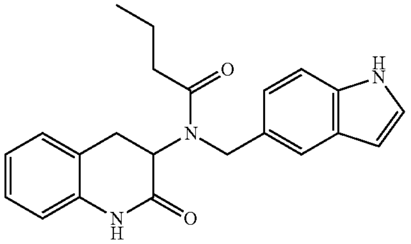

N-((1H-indol-5-yl)methyl)-N-(2-oxo-1,2,3,4-tetrahydroquinolin-3-yl)butyramide (AJ2-18): Synthesized according to scheme 1 and general procedure 4, purified by biotage (Hexane/Ethyl acetate 6:4) to afford AJ2-18 as off white solid (8 mg, 47%); $^1$H NMR (400 MHz, $CDCl_3$) δ 8.46 (s, 1H), 8.31 (s, 1H), 7.48 (d, J=1.6 Hz, 1H), 7.32 (d, J=8.3 Hz, 1H), 7.19-7.13 (m, 1H), 7.02 (dd, J=8.3, 1.7 Hz, 2H), 6.87 (d, J=7.6 Hz, 1H), 6.79 (td, J=7.4, 1.1 Hz, 1H), 6.62 (dd, J=7.9, 1.1 Hz, 1H), 6.49-6.42 (m, 1H), 5.00-4.85 (m, 1H), 4.77 (d, J=17.1 Hz, 1H), 4.63 (d, J=17.0 Hz, 1H), 3.34 (t, J=14.8 Hz, 1H), 2.69 (dd, J=15.3, 6.7 Hz, 1H), 2.51-2.32 (m, 2H), 1.68 (q, J=7.4 Hz, 2H), 0.88 (t, J=7.4 Hz, 314). $^{13}$C NMR (101 MHz, $CDCl_3$) δ 174.69, 169.14, 136.32, 135.33, 128.58, 128.32, 128.13, 127.62, 125.12, 122.95, 122.50, 120.65, 118.54, 115.14, 111.61, 102.50, 55.30, 51.88, 35.64, 30.32, 18.75, 13.90. LCMS calcd for $C_{22}H_{24}N_3O_2$; 362.1 ($M+H^+$), found: 362.1.

AJ2-19

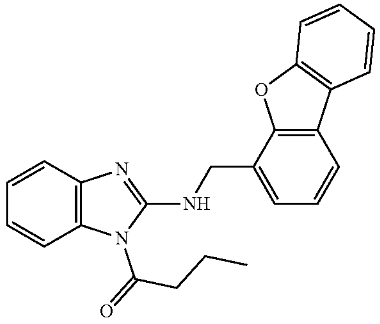

1-(2-((dibenzo[b,d]furan-4-ylmethyl)amino)-1H-benzo[d]imidazol-1-yl)butan-1-one (AJ2-19): Synthesized according to scheme 1 and general procedure 4, purified by biotage (Hexane/Ethyl acetate 3:2) to afford AJ2-19 as white solid (14 mg, 62%); $^1$H NMR (400 MHz, $CDCl_3$) δ 7.95 (dd, J=7.7, 1.4 Hz, 1H), 7.89 (dd, J=7.8, 1.3 Hz, 1H), 7.60 (dt, J=8.2, 0.9 Hz, 1H), 7.54 (dd, J=7.5, 1.2 Hz, 1H), 7.46 (dd, J=8.4, 1.4 Hz, 2H), 7.41-7.36 (m, 1H), 7.36-7.33 (m, 1H), 7.31 (d, J=7.6 Hz, 1H), 7.28-7.23 (m, 2H), 7.06 (dd, J=8.5, 1.3 Hz, 1H), 5.16 (d, J=4.0 Hz, 2H), 2.98 (t, J=7.2 Hz, 2H), 1.85 (q, J=7.3 Hz, 2H), 1.08 (t, J=7.4 Hz, 3H). LCMS calcd for $C_{24}H_{22}N_3O_2$; 384.2 ($M+H^+$), found: 384.2.

AJ2-20

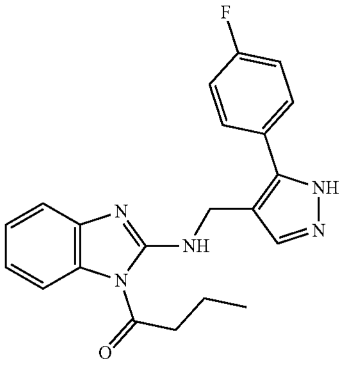

1-(2-(((5-(4-fluorophenyl)-1H-pyrazol-4-yl)methyl)amino)-1H-benzo[d]imidazol-1-yl)butan-1-one (AJ2-20): Synthesized according to scheme 1 and general procedure 4, purified by PTLC (DCM/MeOH 9:1) to afford AJ2-20 as brown viscous liquid (6 mg, 42%): $^1$H NMR (400 MHz, $CDCl_3$) δ 8.01 (t, J=5.5 Hz, 1H), 7.70 (s, 1H), 7.62-7.51 (m, 2H), 7.41 (dd, J=16.1, 8.0 Hz, 2H), 7.24 (d, J=7.3 Hz, 3H), 7.20-7.07 (m, 3H), 6.98 (s, 1H), 4.71 (d, J=4.8 Hz, 2H), 2.97 (t, J=7.2 Hz, 2H), 1.93-1.78 (m, 2H), 1.08 (t, J=7.4 Hz, 3H). LCMS calcd for $C_{21}H_{21}FN_5O$; 378.1 ($M+H^+$), found: 378.0.

AJ2-21

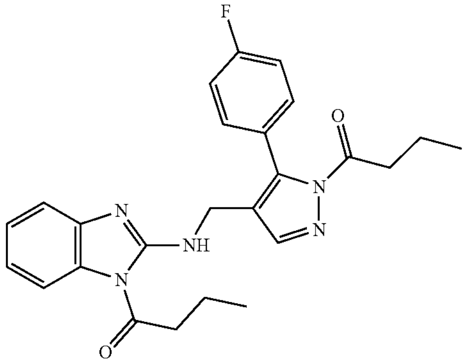

1-(4-(((1-butyryl-1H-benzo[d]imidazol-2-yl)amino)methyl)-5-(4-fluorophenyl)-1H-pyrazol-1-yl)butan-1-one (AJ2-21): Synthesized according to scheme 1 and general procedure 4, purified by PTLC (DCM/MeOH 9.5:0.5) to afford AJ2-21 as brown viscous liquid (4 mg, 48%); $^1$H NMR (400 MHz, $CDCl_3$) δ 8.34 (s, 1H), 8.10 (t, J=5.3 Hz, 1H), 7.76-7.66 (m, 2H), 7.49-7.35 (m, 2H), 7.31-7.24 (m, 1H), 7.18-7.05 (m, 3H), 4.77 (d, J=5.4, 2H), 3.14 (t, J=7.4 Hz, 2H), 2.99 (t, J=7.2 Hz, 2H), 1.88-1.80 (m, 4H), 1.09 (t, J=7.4 Hz, 3H), 1.04 (t, J=7.4 Hz, 3H). LCMS calcd for $C_{25}H_{27}FN_5O_2$; 448.2 ($M+H^+$), found: 448.1.

AJ2-22

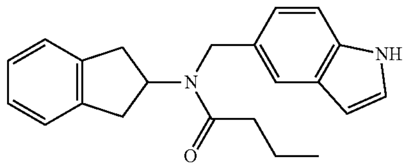

N-((1H-indol-5-yl)methyl)-N-(2,3-dihydro-1H-inden-2-yl)butyramide (AJ2-22): Synthesized according to scheme 1 and general procedure 4, purified by biotage (Hexane/Ethyl acetate 7:3) to afford AJ2-22 as brown viscous liquid (17 mg, 68%); $^1$H NMR (400 MHz, $CDCl_3$) δ 8.79 (s, 1H), 8.55 (s, 0.39H), 7.41 (d, J=1.8 Hz, 1H), 7.39-7.32 (m, 1.61H), 7.26 (d, J=8.4 Hz, 0.5H), 7.19 (t, J=2.8 Hz, 1.12H), 7.17-7.12 (m, 1.93H), 7.00 (d, J=8.4 Hz, 0.45H), 6.95-6.93 (dd, J=8.4, 1.9 Hz, 1.19H), 6.50 (t, J=2.7 Hz, 1.10H), 6.45 (s, 0.42H), 5.58-5.50 (m, 1.14H), 4.90 (t, J=8.2 Hz, 0.43H), 4.74 (s, 0.89H), 4.64 (s, 2.20H), 3.17-2.93 (m, 6.63H), 2.57 (t, J=7.6 Hz, 0.93H), 2.32 (t, J=7.5 Hz, 2.28H), 1.83 (q, J=7.5 Hz, 1.01H), 1.74-1.65 (m, 2.49H), 1.04 (t, J=7.4 Hz, 1.43H), 0.89 (t, J=7.4 Hz, 3.53H). Note: rotomeric isomers observed. LCMS calcd for $C_{22}H_{24}N_2O$; 333.1 ($M+H^+$), found: 333.1.

AJ2-23

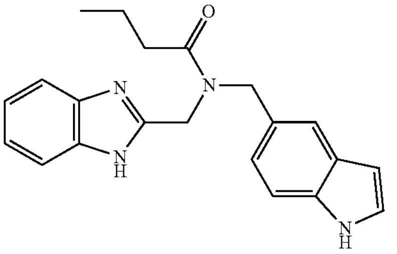

N-((1H-benzo[d]imidazol-2-yl)methyl)-N-((1H-indol-5-yl)methyl)butyramide (AJ2-23): Synthesized according to scheme 1 and general procedure 4, purified by PTLC to afford AJ2-23 as viscous liquid (13 mg, 57%); $^1$H NMR (400 MHz, $CDCl_3$) δ 10.50 (s, 1H), 9.17 (s, 1H), 7.79-7.69 (m, 1H), 7.47-7.39 (m, 2H), 7.28-7.23 (m, 4H), 6.89 (dd, J=8.3, 1.7 Hz, 1H), 6.53-6.47 (m, 1H), 4.70 (s, 2H), 4.69 (s, 214), 2.48 (t, J=7.5 Hz, 2H), 1.74 (h, J=7.4 Hz, 2H), 0.96 (t, J=7.4 Hz, 3H). LCMS calcd for $C_{21}H_{23}N_4O$; 347.1 ($M+H^+$), found: 347.1.

AJ2-24

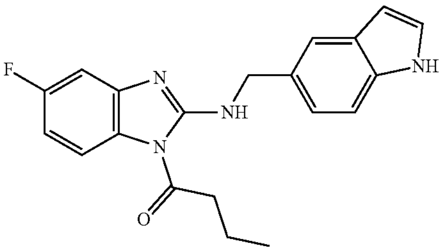

1-(2-(((1H-indol-5-yl)methyl)amino)-5-fluoro-1H-benzo[d]imidazol-1-yl)butan-1-one (AJ2-24): Synthesized according to scheme 1 and general procedure 4, purified by biotage (Hexane/Ethyl acetate 6:4) to afford AJ2-24 as viscous liquid (6 mg, 43%); $^1$H NMR (400 MHz, $CDCl_3$) δ 8.24 (s, 1H), 8.22 (s, 1H), 7.68 (d, J=1.6 Hz, 1H), 7.39 (dd, J=8.3, 0.9 Hz, 1H), 7.31-7.26 (m, 1H), 7.23-7.24 (m, 2H), 7.14 (dd, J=9.2, 2.6 Hz, 1H), 6.75 (td, J=9.0, 2.6 Hz, 1H), 6.55-6.53 (m, 1H), 4.83 (d, J=5.2 Hz, 2H), 2.94 (t, J=7.2 Hz, 2H), 1.84 (h, J=7.3 Hz, 2H), 1.08 (t, J=7.4 Hz, 3H). LCMS col at $C_{20}H_{20}FN_4O$; 351.1 ($M+H^+$), found: 351.1.

AJ2-25A

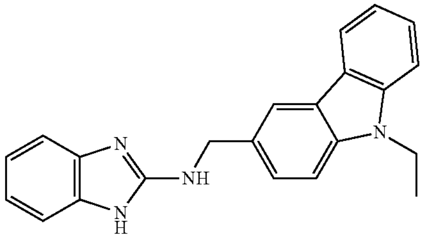

N-((9-ethyl-9H-carbazol-3-yl)methyl)-1H-benzo[d]imidazol-2-amine (AJ2-25A): Synthesized according to scheme 1 and general procedure 1, purified by biotage (Hexane/Ethyl acetate 4:6) to afford AJ2-25A as yellow solid (254 mg, 78%); $^1$H NMR (400 MHz, DMSO) δ 8.15 (d, J=1.6 Hz, 1H), 8.10 (dt, J=7.8, 1.0 Hz, 1H), 7.61-7.54 (m, 2H), 7.51 (dd, J=8.5, 1.7 Hz, 1H), 7.43 (ddd, J=8.3, 7.1, 1.2 Hz, 1H), 7.27 (s, 1H), 7.21-7.11 (m, 3H), 6.88 (dd, J=5.8, 3.2 Hz, 2H), 4.67 (d, J=5.4 Hz, 2H), 4.42 (q, J=7.1 Hz, 2H), 1.28 (t, J=7.1 Hz, 3H). LCMS calcd for $C_{20}H_{21}FN_4$; 341.1 ($M+H^+$), found: 341.0.

AJ2-25

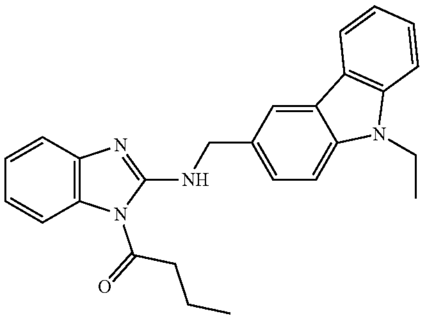

1-(2-(((9-ethyl-9H-carbazol-3-yl)methyl)amino)-1H-benzo[d]imidazol-1-yl)butan-1-one (AJ2-25): Synthesized according to scheme 1 and general procedure 4, purified by biotage (Hexane/Ethyl acetate 6:4) to afford AJ2-25 as of yellow solid (16 mg, 68%); $^1$H NMR (400 MHz, $CDCl_3$) δ 8.21 (s, 1H), 8.14 (s, 1H), 8.09 (d, J=7.8 Hz, 1H), 7.54 (dd, J=8.4, 1.5 Hz, 1H), 7.51-7.44 (m, 2H), 7.44-7.37 (m, 3H), 7.26-7.19 (m, 2H), 7.11-7.03 (m, 1H), 4.94 (d, J=5.2 Hz, 2H), 4.38 (q, J=7.2 Hz, 2H), 3.00 (t, J=7.2 Hz, 2H), 1.85 (h, J=7.4 Hz, 2H), 1.49-1.37 (m, 3H), 1.14-1.04 (m, 3H). LCMS calcd for $C_{26}H_{27}N_4O$; 411.2 ($M+H^+$), found: 411.0.

AJ2-26

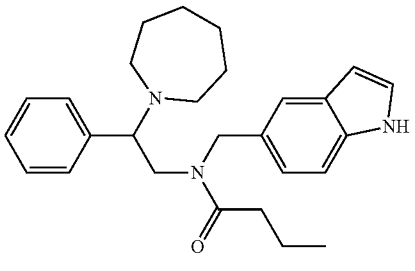

N-((1H-indol-5-yl)methyl)-N-(2-(azepan-1-yl)-2-phenylethyl)butyramide (AJ2-26): Synthesized according to scheme 1 and general procedure 4, purified PTLC (Hexane/Ethyl acetate 7:3) to afford AJ2-26 as a colorless liquid (22 mg, 74%); $^1$H NMR (400 MHz, $CD_2Cl_2$) δ 8.97 (s, 1H), 7.67-7.48 (m, 2H), 7.42-7.31 (m, 2H), 7.25 (d, J=8.3 Hz, 2H), 7.13 (t, J=2.6 Hz, 2H), 6.69 (dd, J=8.4, 1.7 Hz, 1H), 6.36 (t, J=2.4 Hz, 1H), 4.41-4.29 (m, 2H), 3.62-3.51 (m, 2H), 3.05 (s, 2H), 2.29-2.09 (m, 3H), 1.79-1.69 (m, 3H), 1.50 (dt, J=14.8, 9.3 Hz, 9H), 0.80 (d, J=7.4 Hz, 3H). Note: rotomeric isomers observed, LCMS calcd for $C_{27}H_{36}N_3O$; 418.2 ($M+H^+$), found: 418.1.

AJ2-27

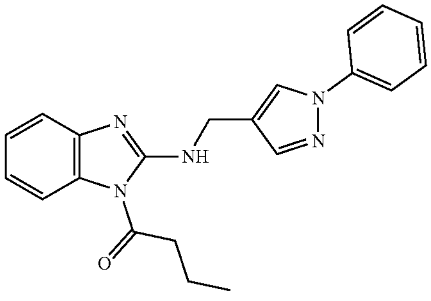

1-(2-(((l-phenyl-1H-pyrazol-4-yl)methyl)amino)-1H-benzo[d]imidazol-1-yl)butan-1-one (AJ2-27): Synthesized according to scheme 1 and general procedure 4, purified PTLC (Hexane/Ethyl acetate 6:4) to afford AJ2-27 as a colorless liquid (16 mg, 62%); $^1$H NMR (400 MHz, $CDCl_3$) δ 8.11 (t, J=5.6 Hz, 1H), 8.01 (d, J=0.8 Hz, 1H), 7.77 (d, J=0.7 Hz, 1H), 7.69-7.63 (m, 2H), 7.49-7.37 (m, 4H), 7.31-7.24 (m, 3H), 7.08 (ddd, J=8.5, 7.5, 1.3 Hz, 1H), 4.71 (d, J=5.5 Hz, 2H), 3.00 (t, J=7.2 Hz, 2H), 1.87 (h, J=7.3 Hz, 2H), 1.09 (t, J=7.4 Hz, 3H). LCMS calcd for $C_{21}H_{22}N_5O$; 360.1 (M+H$^+$), found: 360.1.

AJ2-28

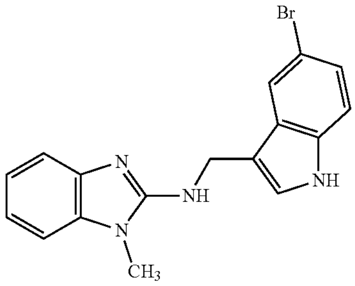

N-((5-bromo-1H-indol-3-yl)methyl)-1-methyl-1H-benzo[d]imidazol-2-amine A(AJ2-28): Synthesized according to scheme 1, purified by biotage (DCM/MeOH; 9:1) to afford AJ2-28 as a brown solid (178 mg, 65%); $^1$H NMR (400 MHz, DMSO) δ 11.15 (s, 1H), 7.94 (d, J=1.9 Hz, 1H), 7.42 (d, J=2.4 Hz, 1H), 7.33 (d, J=8.5 Hz, 1H), 7.26-7.22 (m, 1H), 7.18 (dd, J=8.6, 2.0 Hz, 1H), 7.14-7.10 (m, 1H), 7.01-6.97 (m, 1H), 6.97-6.87 (m, 2H), 4.69 (d, J=5.6 Hz, 2H), 3.48 (s, 3H). $^{13}$C NMR (101 MHz, DMSO) δ 155.65, 143.07, 135.83, 135.44, 129.10, 126.24, 123.93, 121.90, 120.64, 118.66, 115.35, 113.86, 113.50, 111.63, 107.63, 38.12, 28.69. LCMS(ESI) calcd for $C_{17}H_{16}BrN_4$; 355.0 (M+H$^+$), found: 354.9.

AJ2-29

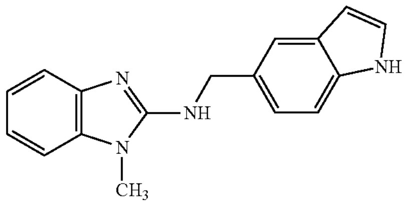

N-((1H-indol-5-yl)methyl)-1-methyl-1H-benzo[d]imidazol-2-amine (AJ2-29): Synthesized according to scheme 1, purified by biotage (DCM/MeOH; 9:1) to afford AJ2-29 as a brown solid (165 mg, 72%); $^1$H NMR (400 MHz, $CDCl_3$) δ 8.40 (s, 1H), 7.70 (d, J=1.6 Hz, 1H), 7.53 (dt, J=7.7, 1.0 Hz, 1H), 7.42-7.36 (m, 1H), 7.31-7.24 (m, 3H), 7.13 (ddd, J=7.7, 5.0, 3.7 Hz, 1H), 7.10-7.05 (m, 2H), 6.55 (d, J=1.1 Hz, 1H), 4.81 (d, J=5.1 Hz, 2H), 4.24 (d, J=5.5 Hz, 1H), 3.46 (s, 3H). LCMS calcd for $C_{17}H_{17}N_4$; 277.1 (M+H$^+$), found: 277.1.

AJ2-30

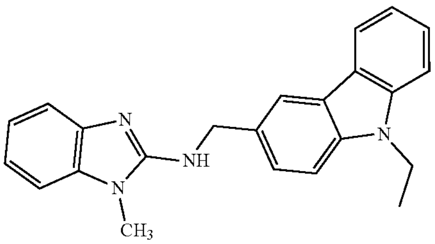

N-((9-ethyl-9H-carbazol-3-yl)methyl)-1-methyl-1H-benzo[d]imidazol-2-amine (AJ2-30): Synthesized according to scheme 1, purified on biotage (Hexane/Ethyl acetate; 3:7) to afford AJ2-30 as a yellow solid (248 mg, 76%); $^1$H NMR (400 MHz, DMSO) δ 8.17 (t, J=1.1 Hz, 1H), 8.12 (dt, J=7.8, 1.0 Hz, 1H), 7.61-7.53 (m, 3H), 7.43 (ddd, J=8.3, 7.1, 1.2 Hz, 1H), 7.23 (t, J=5.9 Hz, 1H), 7.23-7.13 (m, 3H), 7.00-6.84 (m, 2H), 4.75 (d, J=5.8 Hz, 2H), 4.42 (q, J=7.1 Hz, 2H), 3.55 (s, 3H), 1.28 (t, J=7.1 Hz, 3H). $^{13}$C NMR (101 MHz, $CDCl_3$) δ 154.38, 142.32, 140.31, 139.55, 135.03, 128.90, 126.27, 125.89, 123.13, 122.67, 121.24, 120.52, 120.38, 119.61, 118.96, 116.53, 108.68, 108.59, 107.05, 48.26, 37.63, 28.24, 13.82. LCMS calcd for $C_{23}H_{23}N_4$; 355.1 (M+H$^+$), found: 355.1.

AJ2-31

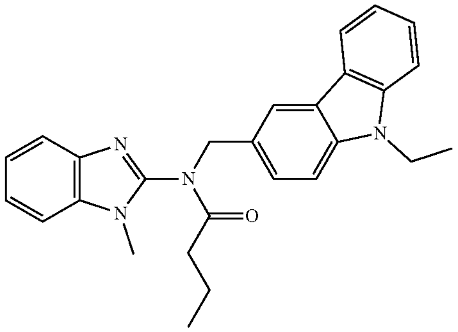

N-((9-ethyl-9H-carbazol-3-yl)methyl)-N-(1-methyl-1H-benzo[d]imidazol-2-yl)butyramide (AJ2-31): Synthesized according to scheme 1 and general procedure 3, purified on biotage (DCM/MeOH; 9.5:0.5) to afford AJ2-31 as a white solid (64 mg, 52%); $^1$H NMR (400 MHz, DMSO) δ 8.15-7.86 (m, 2H), 7.64 (d, J=7.6 Hz, 1H), 7.57 (d, J=8.2 Hz, 1H), 7.50 (dd, J=11.8, 8.1 Hz, 2H), 7.45-7.43 (m, 1H), 7.35 (d, J=8.5 Hz, 1H), 7.25 (p, J=7.4 Hz, 2H), 7.19-7.12 (m, 1H), 5.07 (s, 2H), 4.40 (q, J=7.1 Hz, 2H), 3.39 (s, 3H), 2.00 (s, 2H), 1.62-1.48 (m, 2H), 1.28 (t, J=7.1 Hz, 3H), 0.81 (d, J=7.7 Hz, 3H). $^{13}$C NMR (151 MHz, DMSO) δ 171.61, 147.34, 139.80, 139.16, 138.30, 133.94, 126.53, 125.82, 125.15, 122.23, 121.58, 121.29, 119.82, 119.61, 118.74, 118.12, 110.28, 108.53, 108.33, 50.42, 36.34, 34.55, 28.66, 17.24, 13.05, 12.90. Note: rotomeric isomers observed, LCMS calcd for $C_{27}H_{28}N_4O$; 425.2 (M+H$^+$), found: 425.1.

AJ2-32

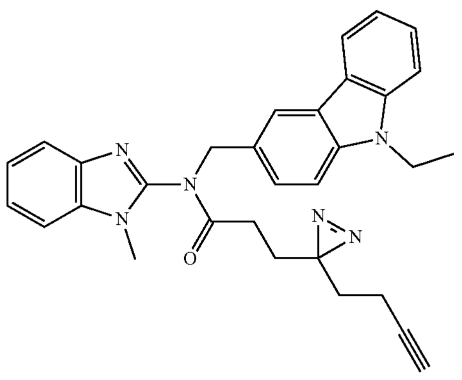

3-(3-(but-3-yn-1-yl)-3H-diazirin-3-yl)-N-((9-ethyl-9H-carbazol-3-yl)methyl)-N-(1-methyl-1H-benzo[d]imidazol-2-yl)propanamide (AJ2-32): Synthesized according to scheme 1 and general procedure 3, purified biotage (DCM/MeOH; 9.5:0.5) to afford AJ2-32 as a light brown viscous liquid (12 mg, 46%); $^1$H NMR (400 MHz, $CDCl_3$) δ 8.00 (d, J=7.8 Hz, 1H), 7.97 (d, J=1.6 Hz, 1H), 7.83 (dd, J=6.9, 2.1 Hz, 1H), 7.50-7.46 (m, 1H), 7.41 (dt, J=8.3, 1.0 Hz, 1H), 7.39-7.26 (m, 4H), 7.25-7.18 (m, 2H), 5.19 (s, 2H), 4.34 (q, J=7.2 Hz, 2H), 3.05 (s, 3H), 1.99 (td, J=7.4, 2.6 Hz, 3H), 1.95-1.81 (m, 4H), 1.62 (t, J=7.4 Hz, 2H), 1.42 (t, J=7.2 Hz, 3H). Note: rotomeric isomers observed, LCMS calcd for $C_{31}H_{31}N_6O$; 503.2 (M+H$^+$), found: 503.0.

AJ2-33

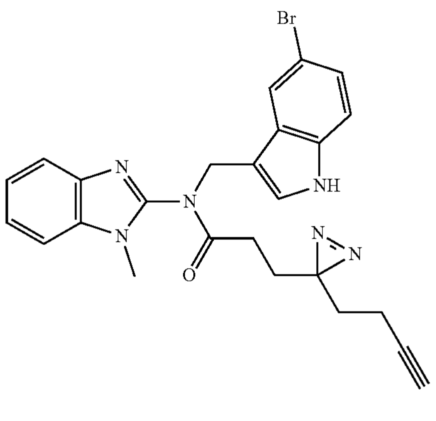

N-((5-bromo-1H-indol-3-yl)methyl)-3-(3-(but-3-yn-1-yl)_3H-diazirin-3-yl)-N-(1-methyl-1H-benzo[d]imidazol-2-yl)propanamide (AJ2-32): Synthesized according to scheme 1 and general procedure 3, purified by PTLC (DCM/MeOH; 9.5:0.5) to afford AJ2-33 as a light brown viscous liquid (4 mg, 27%); $^1$H NMR (400 MHz, $CDCl_3$) δ 8.33 (d, J=8.8 Hz, 1H), 7.81 (d, J=2.0 Hz, 1H), 7.59-7.52 (m, 2H), 7.48 (dd, J=8.8, 2.0 Hz, 1H), 7.16 (dd, J=7.8, 4.2 Hz, 1H), 7.15-7.11 (m, 2H), 5.12 (s, 1H), 4.85 (s, 2H), 4.30 (s, 1H), 3.72-3.59 (m, 3H), 3.52 (s, 3H), 3.35 (s, 2H), 2.68 (t, J=7.4 Hz, 2H), 2.36 (t, J=7.6 Hz, 1H), 2.11-1.97 (m, 7H), 1.73 (s, 2H). Note: rotomeric isomers observed, LCMS calcd for $C_{25}H_{24}BrN_6O$; 503.1 (M+H$^+$), found: 503.0.

AJ2-34

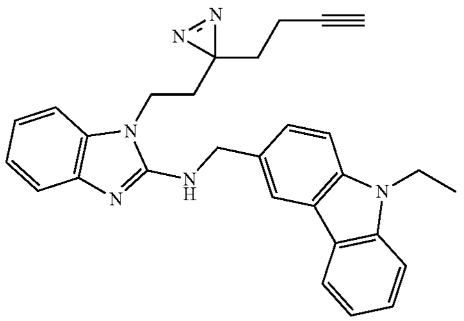

1-(2-(3-(but-3-yn-1-yl)-3H-diazirin-3-yl)ethyl)-N-((9-ethyl-9H-carbazol-3-yl)methyl)-1H-benzo[d]imidazol-2-amine (AJ2-34): Synthesized according to scheme 1 and general procedure 5, purified biotage (Hexane/Ethyl acetate; 4:6) to afford AJ2-34 as a yellow viscous liquid (43 mg, 64%); $^1$H NMR (400 MHz, $CDCl_3$) δ 8.17 (dd, J=1.7, 0.7 Hz, 1H), 8.10 (dt, J=7.9, 1.0 Hz, 1H), 7.60-7.54 (m, 2H), 7.52-7.38 (m, 3H), 7.25-7.21 (m, 1H), 7.18-7.14 (m, 1H), 7.13-7.05 (m, 2H), 4.92 (d, J=5.1 Hz, 2H), 4.59 (t, J=5.2 Hz, 1H), 4.38 (q, J=7.2 Hz, 2H), 3.79-3.69 (m, 2H), 1.93-1.84 (m, 4H), 1.80 (t, J=2.7 Hz, 1H), 1.46-1.42 (m 5H). $^{13}$C NMR (101 MHz, $CDCl_3$) δ 153.72, 142.47, 140.30, 139.53, 133.94, 128.81, 126.23, 125.89, 123.11, 122.67, 121.61, 120.55, 120.37, 119.84, 118.96, 116.78, 108.70, 108.60, 107.20, 82.52, 69.62, 48.33, 37.62, 36.80, 32.20, 26.63, 13.84, 13.16. LCMS calcd for $C_{29}H_{29}N_6$; 461.2 (M+H$^+$), found: 461.0.

AJ2-35

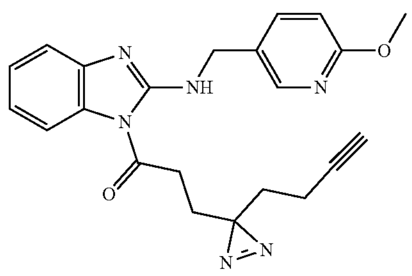

3-(3-(but-3-yn-1-yl)-3H-diazirin-3-yl)-1-(2-(((6-methoxypyridin-3-yl)methyl)amino)-1H-benzo[d]imidazol-1-yl)propan-1-one (AJ2-35): Synthesized according to scheme 1 and general procedure 3, purified biotage (Hexane/Ethyl acetate; 4:6) to afford AJ2-35 as a light brown viscous liquid (12 mg, 62%); $^1$H NMR (400 MHz, $CDCl_3$) δ 8.26-8.16 (m, 1H), 8.02 (t, J=5.6 Hz, 1H), 7.67 (dd, J=8.5, 2.5 Hz, 1H), 7.44 (ddd, J=7.9, 1.2, 0.6 Hz, 1H), 7.32-7.24 (m, 2H), 7.08 (dd, J=8.1, 1.3 Hz, 1H), 6.73 (dd, J=8.5, 0.7 Hz, 1H), 4.69 (d, J=5.6 Hz, 2H), 3.93 (s, 3H), 2.85-2.75 (m, 2H), 2.15-1.95 (m, 5H), 1.74 (t, J=7.3 Hz, 2H). LCMS calcd for $C_{22}H_{23}N_6O_2$; 403.1 (M+H$^+$), found: 403.0.

AJ2-36

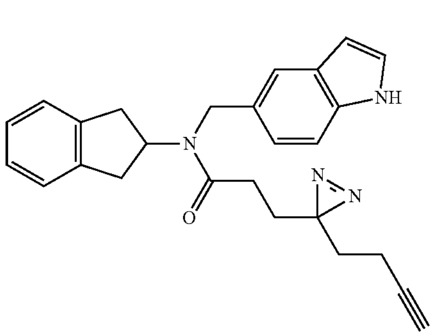

N-((1H-indol-5-yl)methyl)-3-(3-(but-3-yn-1-yl)-3H-diazirin-3-yl)-N-(2,3-dihydro-1H-inden-2-yl)propenamide (AJ2-36): Synthesized according to scheme 1 and general procedure 2, purified biotage (Hexane/Ethyl acetate; 4:6) to afford AJ2-36 as a light brown viscous liquid (12 mg, 46%); $^1$H NMR (400 MHz, $CDCl_3$) δ 8.33 (s, 1H), 7.44-7.35 (m, 3H), 7.34-7.22 (m, 2H), 7.21-7.12 (m, 2H), 7.03-6.91 (m, 2H), 6.53 (t, J=2.7 Hz, 1H), 6.47 (s, 1H), 5.52 (q, J=8.6 Hz, 1H), 4.84-4.66 (m, 1H), 4.60 (s, 2H), 3.18-3.11 (m, 2H), 3.01-2.97 (m, 4H), 2.31 (t, J=7.6 Hz, 1H), 2.08 (t, J=7.5 Hz, 2H), 1.98-1.88 (m 3H), 1.83 (t, J=7.4 Hz, 2H), 1.71 (t, J=7.5 Hz, 1H), 1.56 (t, J=7.5 Hz, 2H). Note: rotomeric isomers observed. LCMS calcd for $C_{26}H_{27}N_4O$; 411.2 (M+H$^+$), found: 411.2.

AJ2-37

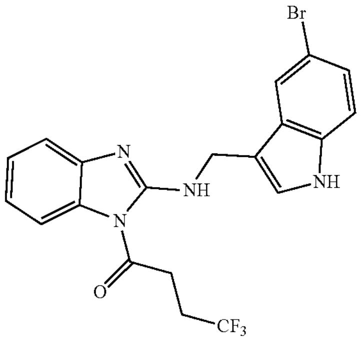

1-(2-(((S-bromo-1H-indol-3-yl)methyl)amino)-1H-benzo[d]imidazol-1-yl)-4,4,4-trifluorobutan-1-one (AJ2-37): Synthesized according to scheme 1 and general procedure 4, purified on biotage (DCM/MeOH; 9.5:0.5) to afford AJ2-37 as a light brown viscous liquid (12 mg, 46%); $^1$H NMR (400 MHz, $CDCl_3$) δ 8.18 (s, 1H), 7.89 (s, 1H), 7.84 (dd, J=1.7, 0.8 Hz, 1H), 7.51 (dd, J=8.0, 1.3 Hz, 1H), 7.37-7.31 (m, 2H), 7.31-7.27 (m, 3H), 7.11 (ddd, J=8.1, 7.5, 1.2 Hz, 1H), 4.89 (dd, J=5.1, 0.8 Hz, 2H), 3.35-3.24 (m, 2H), 2.74-2.55 (m, 2H). LCMS calcd for $C_{20}H_{17}BrF_3N_4O$; 465.0 (M+H$^+$), found: 466.8.

AJ2-38

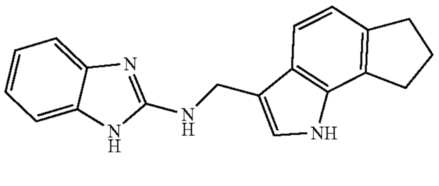

N-((1,6,7,8-tetrahydrocyclopenta[g]indol-3-yl)methyl)-1H-benzo[d]imidazol-2-amine (AJ2-38): Synthesized according to scheme 1, purified on biotage (DCM/MeOH; 9.5:0.5) to afford AJ2-38 as an off white solid (64 mg, 72%); $^1$H NMR (400 MHz, $CD_3OD$) δ 7.38 (d, J=8.0 Hz, 1H), 7.22 (dd, J=5.8, 3.2 Hz, 2H), 7.17 (s, 1H), 6.99 (dd, J=5.8, 3.2 Hz, 2H), 6.91 (d, J=8.0 Hz, 1H), 4.70 (s, 2H), 2.97 (dt, J=23.9, 7.3 Hz, 4H), 2.11 (p, J=7.4 Hz, 2H). $^{13}$C NMR (101 MHz, $CD_3OD$) δ 154.74, 137.63, 136.51, 133.87, 125.45, 125.30, 122.36, 120.45, 116.22, 115.69, 112.07, 111.32, 47.52, 47.31, 47.09, 38.70, 32.64, 29.49, 25.02. LCMS calcd for $C_{19}H_{19}N_4$; 303.1 (M+H$^+$), found: 303.1.

AJ2-39

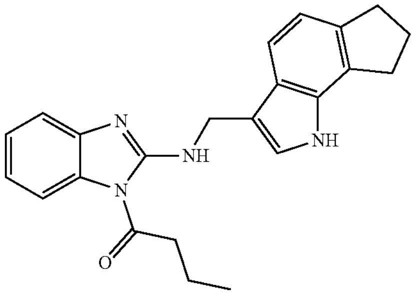

1-(2-(((1,6,7,8-tetrahydrocyclopenta[g]indol-3-yl)methyl)amino)-1H-benzo[d]imidazol-1-yl)butan-1-one (AJ2-39): Synthesized according to scheme 1, and general procedure 4, purified by biotage (Hexane/Ethyl acetate; 5:5) to afford AJ2-39 as a white solid (64 mg, 72%); $^1$H NMR (400 MHz, $CDCl_3$) δ 8.06 (s, 1H), 7.92 (s, 1H), 7.54-7.45 (m, 2H), 7.38 (d, J=8.1 Hz, 1H), 7.28-7.21 (m, 2H), 7.06 (td, J=7.8, 1.5 Hz, 2H), 4.93 (d, J=4.9 Hz, 2H), 3.04 (t, J=7.3 Hz, 4H), 2.96 (t, J=7.2 Hz, 2H), 2.21 (p, J=7.4 Hz, 2H), 1.82 (h, J=7.4 Hz, 2H), 1.06 (t, J=7.4 Hz, 3H). LCMS calcd for $C_{23}H_{25}N_4O$; 373.2 (M+H$^+$), found: 373.1.

AJ2-40

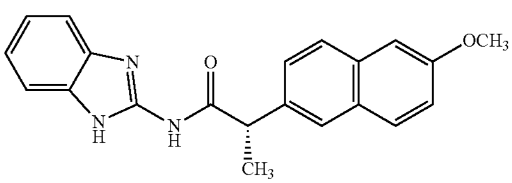

(S)—N-(1H-benzo[d]imidazol-2-yl)-2-(6-methoxynaphthalen-2-yl)propenamide (AJ2-40): Synthesized according to scheme 1, and general procedure 2, purified on biotage (Hexane/Ethyl acetate; 3:7) to afford AJ2-40 as a white solid (67 mg, 68%); $^1$H NMR (400 MHz, DMSO) δ 12.07 (s, 1H), 11.74 (s, 1H), 7.87-7.73 (m, 3H), 7.54 (dd, J=8.6, 1.8 Hz, 1H), 7.42-7.38 (m, 2H), 7.29 (d, J=2.6 Hz, 1H), 7.15 (dd, J=9.0, 2.6 Hz, 1H), 7.06 (t, J=4.4 Hz, 2H), 4.13 (q, J=7.0 Hz, 1H), 3.86 (s, 3H), 1.55 (d, J=6.9 Hz, 3H). LCMS calcd for $C_{21}H_{20}N_3O_2$; 346.1 (M+H$^+$), found: 346.0.

AJ2-41

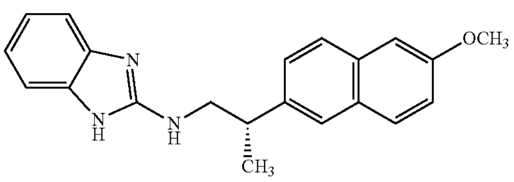

(S)—N-(2-(6-methoxynaphthalen-2-yl)propyl)-1H-benzo[d]imidazol-2-amine (AJ2-41): Synthesized according to scheme 1, purified on biotage (Hexane/Ethyl acetate; 3:7) to afford AJ2-41 as a light brown solid (22 mg, 57%); $^1$H NMR (400 MHz, $CDCl_3$) δ 7.49 (d, J=8.5 Hz, 1H), 7.42 (d, J=8.9 Hz, 1H), 7.28 (d, J=1.9 Hz, 1H), 7.17 (dd, J=5.8, 3.2 Hz, 2H), 7.05-7.02 (m, 2H), 7.01-6.92 (m, 3H), 3.82 (s, 3H), 3.57 (dd, J=12.8, 6.1 Hz, 1H), 3.36 (dd, J=12.8, 8.5 Hz, 1H), 2.95 (q, J=7.1 Hz, 1H), 1.15 (d, J=6.9 Hz, 3H). $^{13}$C NMR (101 MHz, $CDCl_3$) δ 157.42, 155.10, 138.80, 137.18, 133.47, 129.08, 128.92, 127.26, 125.71, 125.59, 120.81, 118.85, 112.06, 105.58, 55.29, 49.77, 39.63, 19.33. LCMS calcd for $C_{21}H_{22}N_3O$; 332.1 (M+H$^+$), found: 332.1.

AJ2-42

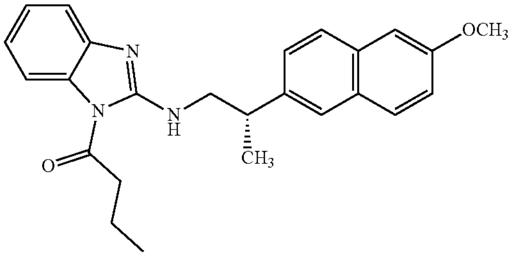

(S)-1-(2-((2-(6-methoxynaphthalen-2-yl)propyl)amino)-1H-benzo[d]imidazol-1-yl)butan-1-one (AJ2-42): Synthesized according to scheme 1 and general procedure 4, purified on biotage (Hexane/Ethyl acetate; 6:4) to afford AJ2-42 as a light brown solid (22 mg, 57%); $^1$H NMR (400 MHz, $CDCl_3$) δ 7.89 (t, J=5.4 Hz, 1H), 7.70 (dd, J=8.5, 5.7 Hz, 2H), 7.64 (d, J=1.8 Hz, 1H), 7.44-7.38 (m, 2H), 7.33 (d, J=8.1 Hz, 1H), 7.22 (td, J=7.7, 1.1 Hz, 1H), 7.16-7.09 (m, 2H), 7.05-7.00 (m, 1H), 3.91 (s, 3H), 3.88 (dd, J=13.5, 7.0 Hz, 1H), 3.81-3.74 (m, 1H), 3.39-3.23 (m, 1H), 2.90 (td, J=7.1, 1.0 Hz, 2H), 1.78 (h, J=7.4 Hz, 3H), 1.45 (d, J=7.0 Hz, 3H), 1.02 (t, J=7.4 Hz, 311). LCMS calcd for $C_{25}H_{28}N_3O_2$; 402.2 (M+H$^+$), found: 402.1.

AJ2-43

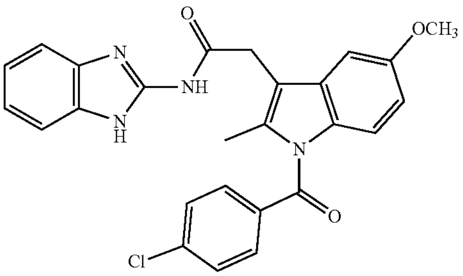

N-(1H-benzo[d]imidazol-2-yl)-2-(1-(4-chlorobenzoyl)-5-methoxy-2-methyl-1H-indol-3-yl)acetamide (AJ2-43): Synthesized according to scheme 1, purified on biotage (Hexane/Ethyl acetate; 4:6) to afford AJ2-43 as a light brown solid (42 mg, 64%); $^1$H NMR (400 MHz, $CDCl_3$) δ 7.74-7.64 (m, 2H), 7.58-7.42 (m, 4H), 7.22 (dd, J=6.0, 3.2 Hz, 2H), 6.92 (d, J=2.5 Hz, 1H), 6.82 (d, J=9.0 Hz, 1H), 6.65 (dd, J=9.1, 2.5 Hz, 1H), 4.02 (s, 2H), 3.66 (s, 3H), 2.42 (s, 3H). LCMS calcd for $C_{26}H_{22}ClN_4O_3$; 473.1 (M+H$^+$), found: 472.9.

AJ2-44

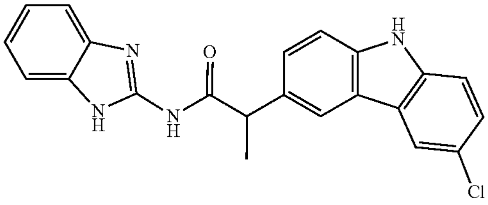

N-(1H-benzo[d]imidazol-2-yl)-2-(6-chloro-9H-carbazol-3-yl)propenamide (AJ2-44): Synthesized according to general procedure 2 purified on biotage (Hexane/Ethyl acetate; 4:6) to afford AJ2-44 as an off white solid (24 mg, 54%); $^1$H NMR (400 MHz, DMSO) δ 11.36 (s, 1H), 8.23 (s, 2H), 8.17 (d, J=2.1 Hz, 1H), 8.09 (d, J=8.1 Hz, 1H), 7.49 (d, J=8.5 Hz, 1H), 7.43-7.39 (m, 1H), 7.39-7.30 (m, 3H), 7.19 (dd, J=5.9, 3.2 Hz, 2H), 7.11 (dd, J=8.2, 1.5 Hz, 1H), 3.84 (t, J=7.1 Hz, 1H), 1.44 (d, J=7.1 Hz, 3H). LCMS calcd for $C_{22}H_{18}ClN_4O$; 389.1 (M+H$^+$), found: 389.0.

AJ2-45

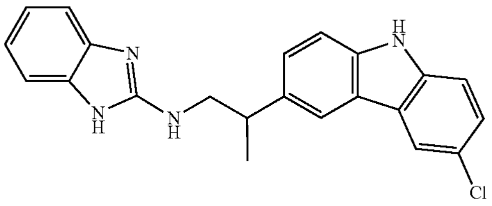

N-(2-(6-chloro-9H-carbazol-3-yl)propyl)-1H-benzo[d]imidazol-2-amine (AJ2-45): Synthesized according to scheme 1 and general procedure 1, purified on biotage (Hexane/Ethyl acetate; 3:7) to afford AJ2-45 as an brown solid (8 mg, 42%); $^1$H NMR (400 MHz, $CDCl_3$) δ 8.19 (s, 1H), 7.93 (d, J=1.8 Hz, 1H), 7.82 (d, J=8.0 Hz, 1H), 7.33 (dd, J=4.1, 1.3 Hz, 1H), 7.20 (dd, J=5.8, 3.2 Hz, 2H), 7.04 (dd, J=5.8, 3.2 Hz, 2H), 6.96-6.87 (m, 2H), 3.62 (dd, J=12.7, 5.6 Hz, 1H), 3.36 (dd, J=12.8, 9.0 Hz, 1H), 3.04 (t, J=7.4 Hz, 1H), 1.24 (d, J=7.0 Hz, 3H) LCMS cared for $C_{22}H_{20}ClN_4$; 375.1 (M+H$^+$), found: 375.1.

AJ2-46

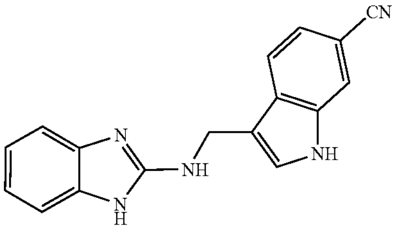

3-(((1H-benzo[d]imidazol-2-yl)amino)methyl)-1H-indole-6-carbonitrile (AJ2-46): Synthesized according to scheme 1 and general procedure 1, purified on biotage (Hexane/Ethyl acetate; 3:7) to afford AJ2-46 as an brown solid (35 mg, 58%); $^1$H NMR (400 MHz, $CD_3OD$) δ 7.83-7.75 (m, 2H), 7.58 (d, J=0.9 Hz, 1H), 7.30 (dd, J=8.2, 1.5 Hz, 1H), 7.23 (dd, J=5.8, 3.2 Hz, 2H), 7.00 (dd, J=5.8, 3.2 Hz, 2H), 4.77 (d, J=0.8 Hz, 2H). LCMS calcd for $C_{17}H_{14}N_5$; 288.1 (M+H$^+$), found: 288.1.

AJ2-47

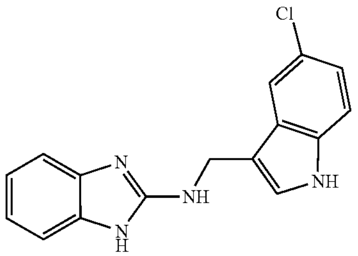

N-((5-chloro-1H-indol-3-yl)methyl)-1H-benzo[d]imidazol-2-amine (AJ2-47): Synthesized according to scheme 1 and general procedure 1, purified on biotage (Hexane/Ethyl acetate; 3:7) to afford AJ2-47 as an brown solid (43 mg, 64%); $^1$H NMR (400 MHz, $CDCl_3$) δ 8.38 (s, 1H), 7.49 (d, J=2.0 Hz, 1H), 7.29-7.23 (m, 2H), 7.20 (d, J=8.6 Hz, 1H), 7.11 (dd, J=8.6, 2.0 Hz, 1H), 7.05 (dd, J=5.8, 3.2 Hz, 2H), 6.99 (s, 1H), 5.12 (s, 1H), 4.61 (s, 2H). LCMS calcd for $C_{16}H_4ClN_4$; 297.0 (M+H$^+$), found: 297.0.

AJ2-48

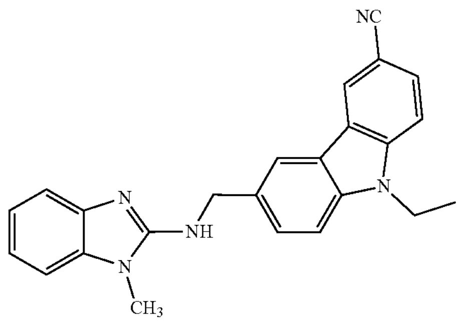

9-ethyl-6-(((1-methyl-1H-benzo[d]imidazol-2-yl)amino)methyl)-9H-carbazole-3-carbonitrile (AJ2-48): Synthesized according to scheme 1 and general procedure 1, purified on biotage (Hexane/Ethyl acetate; 3:7) to afford AJ2-48 as an brown solid (32 mg, 65%); $^1$H NMR (400 MHz, $CDCl_3$)$^1$H NMR (400 MHz, $CDCl_3$) δ 7.89 (dd, J=3.4, 1.6 Hz, 2H), 7.48 (dd, J=8.4, 1.7 Hz, 1H), 7.42 (dt, J=8.5, 1.6 Hz, 2H), 7.15 (dd, J=16.5, 8.5 Hz, 2H), 7.19-7.12 (m, 2H), 6.89 (dd, J=7.7, 1.3 Hz, 1H), 6.00 (s, 1H), 4.82 (s, 2H), 4.08 (q, J=7.1 Hz, 2H), 3.34 (s, 3H), 1.26 (t, J=7.2 Hz, 3H). $^{13}$C NMR (101 MHz, $CDCl_3$) δ 154.84, 142.15, 141.58, 139.69, 135.13, 131.07, 128.58, 127.33, 125.01, 122.61, 121.84, 121.13, 120.74, 119.90, 119.52, 115.89, 109.09, 108.95, 107.11, 100.85, 47.42, 37.77, 28.35, 13.78. LCMS calcd for $C_{24}H_{22}N_5$; 380.1 (M+H$^+$), found: 380.1.

AJ2-49

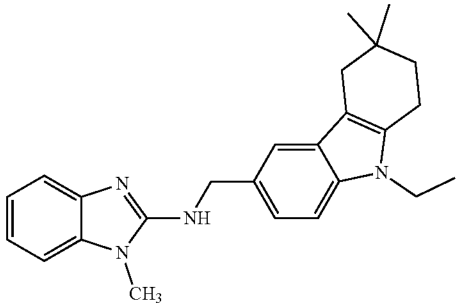

N-((9-ethyl-3,3-dimethyl-2,3,4,9-tetrahydro-1H-carbazol-6-yl)methyl)-1-methyl-1H-benzo[d]imidazol-2-amine (AJ2-49): Synthesized according to scheme 3 and general procedure 1, purified on biotage (Hexane/Ethyl acetate; 3:7) to afford AJ2-49 as an brown solid (32 mg, 65%); $^1$H NMR (400 MHz, $CDCl_3$) δ 7.59-7.46 (m, 2H), 7.31-7.18 (m, 2H), 7.12 (ddd, J=7.9, 6.3, 2.3 Hz, 1H), 7.09-7.03 (m, 2H), 4.78 (d, J=4.8 Hz, 2H), 4.22 (d, J=5.5 Hz, 1H), 4.08 (q, J=7.2 Hz, 2H), 3.40 (d, J=2.1 Hz, 3H), 2.69 (t, J=6.3 Hz, 2H), 2.51 (d, J=1.6 Hz, 2H), 1.69 (t, J=6.4 Hz, 2H), 1.31 (t, J=7.2 Hz, 3H), 1.04 (s, 6H). $^{13}$C NMR (101 MHz, $CDCl_3$) δ 154.41, 142.41, 135.69, 135.01, 134.67, 128.36, 127.87, 121.16, 119.49, 117.84, 116.51, 108.88, 108.84, 106.96, 48.68, 37.66, 36.09, 35.06, 30.10, 28.20, 28.06, 19.61, 15.52. LCMS calcd for $C_{25}H_{31}N_4$; 387.2 (M+H$^+$), found: 387.1.

AJ2-50

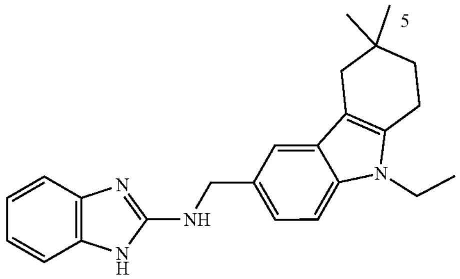

N-((9-ethyl-3,3-dimethyl-2,3,4,9-tetrahydro-1H-carbazol-6-yl)methyl)-1H-benzo[d]imidazol-2-amine (AJ2-50): Synthesized according to scheme 3 and general procedure 1, purified on biotage (Hexane/Ethyl acetate; 6:4) to afford AJ2-50 as brown solid (45 mg, 62%); $^1$H NMR (400 MHz, $CDCl_3$) δ 7.43 (d, J=1.6 Hz, 1H), 7.23 (dd, J=5.8, 3.2 Hz, 2H), 7.19 (d, J=8.3 Hz, 1H), 7.10 (dd, J=8.4, 1.7 Hz, 1H), 7.02 (dd, J=5.8, 3.2 Hz, 2H), 4.61 (s, 2H), 4.05 (q, J=7.2 Hz, 2H), 2.69 (t, J=6.3 Hz, 2H), 2.46 (d, J=1.6 Hz, 2H), 1.69 (t, J=6.4 Hz, 2H), 1.30 (t, J=7.2 Hz, 3H), 1.04 (s, 6H). LCMS calcd for $C_{24}H_{29}N_4$; 373.2 (M+H$^+$), found: 373.1.

AJ2-51

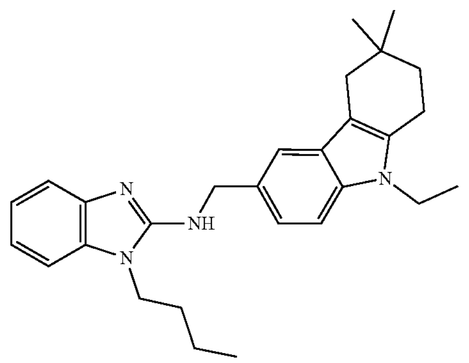

1-butyl-N-((9-ethyl-3,3-dimethyl-2,3,4,9-tetrahydro-1H-carbazol-6-yl)methyl)-1H-benzo[d]imidazol-2-amine (AJ2-51): Synthesized according to scheme 3 and general procedure 1 and following general procedure 4, purified on biotage (Hexane/Ethyl acetate; 6:4) to afford AJ2-51 as a brown solid (22 mg, 56%); $^{1}$H NMR (400 MHz, $CDCl_3$) δ 7.45 (dd, J=7.2, 1.3 Hz, 2H), 7.19-7.12 (m, 2H), 7.06-6.99 (m, 1H), 7.00-6.94 (m, 2H), 4.76 (d, J=3.8 Hz, 2H), 3.96 (q, J=7.2 Hz, 2H), 3.80 (t, J=7.3 Hz, 2H), 2.59 (t, J=6.4 Hz, 2H), 2.40 (d, J=1.5 Hz, 2H), 1.60 (td, J=6.9, 6.4, 2.5 Hz, 4H), 1.32-1.25 (m, 2H), 1.22 (q, J=6.9 Hz, 4H), 0.81 (t, J=7.3 Hz, 3H). $^{13}$C NMR (101 MHz, $CDCl_3$) δ 153.04, 139.89, 135.64, 134.52, 133.84, 128.07, 127.77, 121.51, 121.07, 120.12, 117.67, 115.74, 108.83, 107.55, 48.43, 42.29, 37.62, 36.09, 35.00, 30.96, 30.06, 28.04, 20.18, 19.59, 15.51, 13.79. LCMS calcd for $C_{28}H_{37}N_4$; 428.2 (M+H$^+$), found: 429.2.

AJ2-52

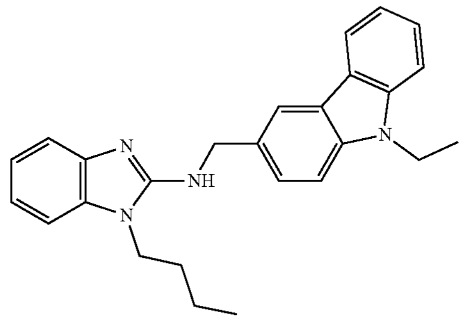

1-butyl-N-((9-ethyl-9H-carbazol-3-yl)methyl)-1H-benzo[d]imidazol-2-amine (AJ2-52): Synthesized according to general procedure 1, and following general procedure 5, purified on biotage (Hexane/Ethyl acetate; 5:5) to afford AJ2-52 as a yellow solid (18 mg, 62%); $^{1}$H NMR (400 MHz, $CDCl_3$) δ 8.12 (d, J=1.7 Hz, 1H), 8.07 (dt, J=7.8, 1.0 Hz, 1H), 7.58-7.51 (m, 2H), 7.47 (ddd, J=8.3, 7.0, 1.2 Hz, 1H), 7.43-7.34 (m, 2H), 7.27-7.21 (m, 1H), 7.15-7.11 (m, 1H), 7.07 (dd, J=3.8, 1.0 Hz, 2H), 4.90 (d, J=4.9 Hz, 2H), 4.35 (q, J=7.3 Hz, 3H), 3.82 (t, J=7.2 Hz, 2H), 1.77-1.61 (m, 2H), 1.41 (t, J=7.2 Hz, 3H), 1.39-1.29 (m, 2H), 0.89 (t, J=7.3 Hz, 3H). $^{13}$C NMR (101 MHz, $CDCl_3$) δ 153.90, 142.19, 140.32, 139.55, 134.61, 128.99, 126.16, 125.90, 123.13, 122.67, 121.17, 120.50, 120.26, 119.60, 118.97, 116.51, 108.71, 108.59, 107.37, 48.28, 42.10, 37.63, 31.12, 20.24, 13.83, 13.79, LCMS calcd for $C_{26}H_{29}N_4$; 397.2 (M+H$^+$), found: 397.2.

AJ2-53

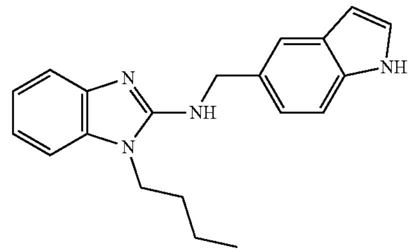

N-((1H-indol-5-yl)methyl)-1-butyl-1H-benzo[d]imidazol-2-amine (AJ2-53): Synthesized according to general procedure 1 and following general procedure 5, purified on biotage (Hexane/Ethyl acetate; 6:4) to afford AJ2-53 as a light brown liquid (16 mg, 56%); $^{1}$H NMR (400 MHz, $CDCl_3$) δ 9.13 (s, 1H), 7.51 (d, J=1.7 Hz, 1H), 7.45-7.38 (m, 1H), 7.21 (d, J=8.3 Hz, 1H), 7.11-6.95 (m, 5H), 6.38 (ddd, J=3.0, 2.0, 0.9 Hz, 1H), 4.67 (s, 2H), 4.57 (s, 1H), 3.70 (t, J=7.2 Hz, 2H), 1.57 (dq, J=9.6, 7.4 Hz, 2H), 1.33-1.12 (m, 3H), 0.79 (t, J=7.3 Hz, 3H). $^{13}$C NMR (101 MHz, $CDCl_3$) δ 153.76, 141.46, 135.55, 134.37, 129.41, 128.06, 125.21, 122.22, 121.31, 120.13, 119.80, 116.06, 111.61, 107.51, 102.20, 48.37, 42.12, 31.02, 20.21, 13.77. LCMS calcd for $C_{20}H_{23}N_4$; 319.1 (M+H$^+$), found: 319.1.

AJ2-54

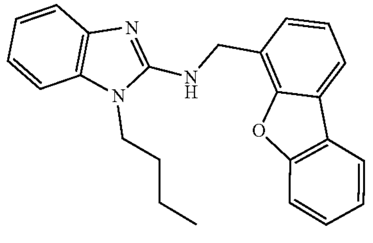

1-butyl-N-(dibenzo[b,d]furan-4-ylmethyl)-1H-benzo[d]imidazol-2-amine (AJ2-54): Synthesized according to general procedure 1 and following general procedure 4, purified on biotage (Hexane/Ethyl acetate; 6:4) to afford AJ2-54 as a light brown liquid (24 mg, 68%); $^{1}$H NMR (400 MHz, $CDCl_3$) δ 7.95 (ddd, J=7.7, 1.4, 0.7 Hz, 1H), 7.87 (dd, J=7.7, 1.3 Hz, 1H), 7.59-7.50 (m, 3H), 7.48-7.44 (m, 1H), 7.39-7.27 (m, 2H), 7.14-7.10 (m, 1H), 7.08-7.04 (m, 2H), 5.12 (d, J=5.4 Hz, 2H), 4.84 (t, J=5.6 Hz, 1H), 3.84 (t, J=7.2 Hz, 2H), 1.76-1.63 (m, 2H), 1.41-1.28 (m, 2H), 0.86 (t, J=7.3 Hz, 3H). $^{13}$C NMR (101 MHz, $CDCl_3$) δ 156.04, 154.37, 153.90, 142.23, 134.66, 127.33, 127.09, 124.40, 124.21, 123.10, 123.00, 122.58, 121.15, 120.85, 120.07, 119.61, 116.61, 111.66, 107.36, 43.02, 42.16, 31.13, 20.25, 13.74. LCMS calcd for $C_{24}H_{24}N_3O$; 370.1 (M+H$^+$), found: 370.1.

AJ2-55

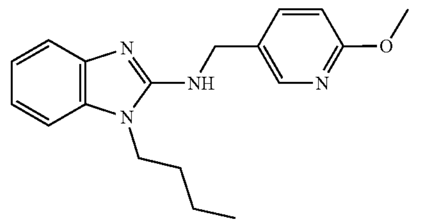

1-butyl-N-((6-methoxypyridin-3-yl)methyl)-1H-benzo[d]imidazol-2-amine (AJ2-55): Synthesized according to general procedure 1 and following general procedure 4, purified on biotage (Hexane/Ethyl acetate; 4:6) to afford AJ2-55 as a light brown liquid (18 mg, 62%); $^1$H NMR (400 MHz, $CDCl_3$) δ 8.11 (t, J=1.8 Hz, 1H), 7.60 (ddd, J=8.6, 2.6, 1.4 Hz, 1H), 7.41 (dd, J=7.5, 1.3 Hz, 1H), 7.09-6.98 (m, 3H), 6.64 (dd, J=8.5, 0.9 Hz, 1H), 4.60 (s, 3H), 3.84 (s, 3H), 3.81 (t, J=7.3 Hz, 2H), 1.72-1.59 (m, 2H), 1.36-1.22 (m, 2H), 0.85 (t, J=7.3 Hz, 3H). LCMS calcd for $C_{18}H_{23}N_4O$; 311.2 (M+H$^+$), found: 311.2.

AJ2-56

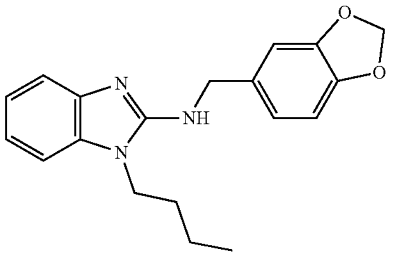

N-(benzo[d][1,3]dioxol-5-ylmethyl)-1-butyl-1H-benzo[d]imidazol-2-amine (AJ2-56): Synthesized according to general procedure 1 and following general procedure 4, purified on biotage (Hexane/Ethyl acetate; 4:6) to afford AJ2-56 as a light brown liquid (8 mg, 56%); NMR (400 MHz, $CDCl_3$) δ 7.39 (dt, 0.1=7.7, 1.0 Hz, 1H), 7.03-6.97 (m, 1H), 7.05-7.00 (m, 2H), 6.81 (d, J=1.7 Hz, 1H), 6.75 (dd, J=7.9, 1.7 Hz, 1H), 6.67 (d, J=7.9 Hz, 1H), 5.84 (s, 2H), 4.55 (d, J=4.5 Hz, 2H), 4.48 (s, 1H), 3.77 (t, J=7.2 Hz, 2H), 1.68-1.55 (m, 2H), 1.34-1.21 (m, 2H), 0.84 (t, J=7.3 Hz, 3H). $^{13}$C NMR (101 MHz, $CDCl_3$) δ 153.61, 147.89, 147.06, 141.60, 134.44, 132.52, 121.26, 121.16, 119.77, 116.29, 108.48, 108.30, 107.46, 101.08, 47.37, 42.17, 31.09, 20.23, 13.79. LCMS calcd for $C_{19}H_{22}N_3O_2$; 324.1 (M+H$^+$), found: 324.1.

AJ2-57

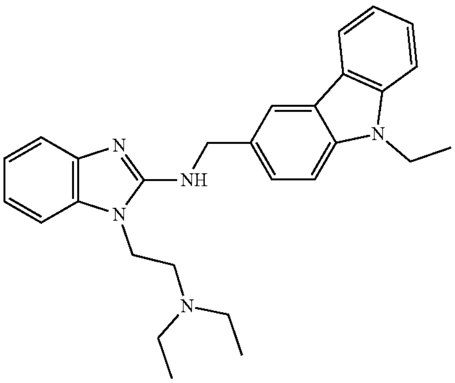

1-(2-(diethylamino)ethyl)-N-((9-ethyl-9H-carbazol-3-yl)methyl)-1H-benzo[d]imidazol-2-amine (AJ2-57): Synthesized according to general procedure 1, purified on biotage (DCM/Methanol; 9.5:0.5) to afford AJ2-57 as a yellow solid (35 mg, 74%); $^1$H NMR (400 MHz, $CDCl_3$) δ 8.06 (d, J=1.7 Hz, 1H), 8.00 (dt, J=7.8, 1.0 Hz, 1H), 7.94 (s, 1H), 7.50-7.45 (m, 2H), 7.39 (ddd, J=8.2, 7.0, 1.2 Hz, 1H), 7.35-7.25 (m, 2H), 7.14 (ddd, J=8.0, 7.0, 1.1 Hz, 1H), 7.04 (td, J=7.5, 1.5 Hz, 1H), 7.00-6.89 (m, 2H), 4.74 (d, J=3.9 Hz, 2H), 4.28 (q, J=7.2 Hz, 2H), 3.91-3.81 (m, 2H), 2.67-2.58 (m, 2H), 2.28 (q, J=7.2 Hz, 4H), 1.33 (t, J=7.2 Hz, 3H), 0.61 (t, J=7.1 Hz, 6H). LCMS calcd for $C_{28}H_{34}N_5$; 440.2 (M+H$^+$), found: 440.1.

AJ2-58

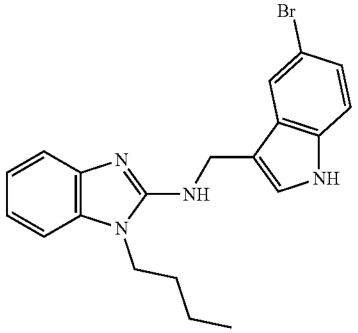

N-((5-bromo-1H-indol-3-yl)methyl)-1-butyl-1H-benzo[d]imidazol-2-amine (AJ2-58): Synthesized according to scheme 1 and general procedure 5, purified on biotage (Hexane/Ethyl acetate; 4:6) to afford AJ2-58 as a light brown liquid (6 mg, 43%); $^1$H NMR (400 MHz, $CDCl_3$) δ 9.17 (s, 1H), 7.51-7.46 (m, 1H), 7.43-7.37 (m, 1H), 7.24 (s, 1H), 7.06-7.00 (m, 3H), 6.99-6.89 (m, 2H), 4.60 (s, 2H), 3.85 (t, J=7.2 Hz, 2H), 1.61-1.54 (m, 2H), 1.29-1.21 (m, 2H), 0.77 (t, J=7.3 Hz, 4H). LCMS calcd for $C_{20}H_{22}BrN_4$; 397.0 (M+H$^+$), found: 397.0.

AJ2-59

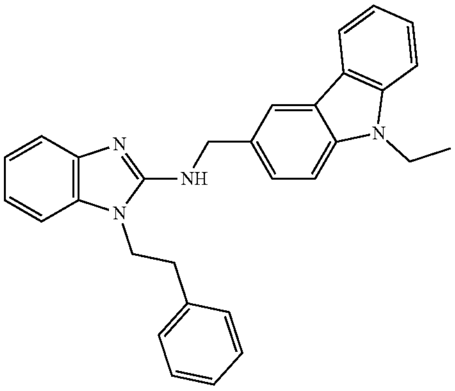

N-((9-ethyl-9H-carbazol-3-yl)methyl)-1-phenethyl-1H-benzo[d]imidazol-2-amine (AJ2-59): Synthesized according to scheme 1 and general procedure 5, purified on biotage (Hexane/Ethyl acetate; 6:4) to afford AJ2-59 as a light yellow liquid (12 mg, 47%); $^1$H NMR (400 MHz, $CDCl_3$) δ 7.96 (d, J=7.7 Hz, 1H), 7.91 (s, 1H), 7.49 (d, J=7.8 Hz, 1H), 7.40-7.27 (m, 3H), 7.20 (d, J=8.4 Hz, 1H), 7.14-7.09 (m, 1H), 7.09-7.03 (m, 4H), 6.99 (td, J=7.6, 1.2 Hz, 1H), 6.95-6.87 (m, 3H), 4.61 (s, 2H), 4.22 (q, J=7.2 Hz, 2H), 4.08 (t, J=6.6 Hz, 2H), 2.92 (t, J=6.6 Hz, 2H), 1.30 (t, J=7.2 Hz, 3H). $^{13}$C NMR (101 MHz, $CDCl_3$) δ 152.73, 140.20, 139.47, 137.86, 128.95, 128.87, 127.96, 127.12, 126.26, 125.76, 122.91, 122.67, 122.04, 120.75, 120.51, 120.44, 118.88, 115.54, 108.50, 107.67, 48.07, 44.63, 37.55, 35.01, 13.79. LCMS calcd for $C_{30}H_{29}N_4$; 445.2 ($M+H^+$), found: 445.1.

AJ2-60

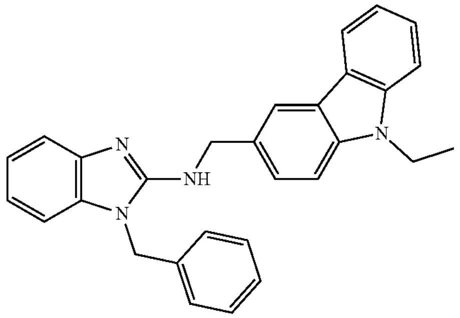

1-benzyl-N-((9-ethyl-9H-carbazol-3-yl)methyl)-1H-benzo[d]imidazol-2-amine (AJ2-60): Synthesized according to general procedure 1, purified on biotage (Hexane/Ethyl acetate; 6:4) to afford AJ2-60 as a light yellow solid (43 mg, 67%), $^1$H NMR (400 MHz, $CDCl_3$) δ 7.93 (dd, J=7.9, 1.0 Hz, 1H), 7.86 (d, J=1.7 Hz, 1H), 7.49 (d, J=7.8 Hz, 1H), 7.38 (ddd, J=8.2, 7.0, 1.2 Hz, 1H), 7.33-7.27 (m, 2H), 7.23-7.16 (m, 4H), 7.13 (td, J=7.4, 6.9, 1.0 Hz, 1H), 7.10-7.01 (m, 3H), 6.98 (d, J=4.1 Hz, 2H), 5.01 (d, J=2.3 Hz, 2H), 4.76 (d, J=4.3 Hz, 2H), 4.51 (s, 1H), 4.24 (q, J=7.2 Hz, 2H), 1.31 (t, J=7.2 Hz, 3H). $^{13}$C NMR (101 MHz, $CDCl_3$) δ 154.05, 140.26, 139.45, 135.36, 134.72, 129.16, 128.70, 128.11, 126.55, 125.87, 125.82, 123.05, 122.65, 121.62, 120.51, 120.03, 119.86, 118.87, 116.54, 108.57, 108.54, 107.45, 48.05, 45.75, 37.59, 13.81. LCMS calcd for $C_{29}H_{27}N_4$; 431.2 ($M+H^+$), found: 431.1.

AJ2-61

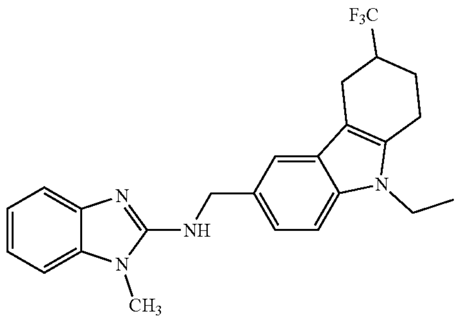

N-((9-ethyl-3-(trifluoromethyl)-2,3,4,9-tetrahydro-1H-carbazol-6-yl)methyl)-1-methyl-1H-benzo[d]imidazol-2-amine (AJ2-61): Synthesized according to scheme 3 and general procedure 1, purified on biotage (Hexane/Ethyl acetate; 5:5) to afford AJ2-61 as a brown solid (24 mg, 72%), $^1$H NMR (400 MHz, $CDCl_3$) δ 7.37-7.31 (m, 2H), 7.14-7.07 (m, 2H), 6.95 (dtd, J=16.4, 7.3, 1.4 Hz, 2H), 6.90-6.85 (m, 1H), 4.98 (s, 1H), 4.66 (s, 2H), 3.90 (qd, J=7.3, 3.0 Hz, 2H), 3.25 (s, 3H), 2.85 (dd, J=15.1, 5.2 Hz, 1H), 2.77-2.66 (m, 1H), 2.66-2.51 (m, 2H), 2.40-2.25 (m, 1H), 2.24-2.14 (m, 1H), 1.71 (qd, J=12.2, 5.9 Hz, 1H), 1.18 (t, J=7.2 Hz, 3H). $^{13}$C NMR (101 MHz, $CDCl_3$) δ 154.27, 141.58, 135.59, 134.83, 134.34, 129.48, 129.01, 126.99, 126.71, 121.59, 121.24, 119.66, 117.48, 116.02, 109.05, 107.08, 106.44, 48.23, 39.50 (q, J=27.0 Hz), 37.74, 28.27, 22.29 (d, J=3.0 Hz), 20.96, 20.71 (d, J=2.9 Hz), 15.48. $^{19}$F NMR (376 MHz, $CDCl_3$) δ −72.78 (d, J=8.4 Hz). LCMS calcd for $C_{24}H_{26}F_3N_4$; 427.2 ($M+H^+$), found: 427.2.

AJ2-62

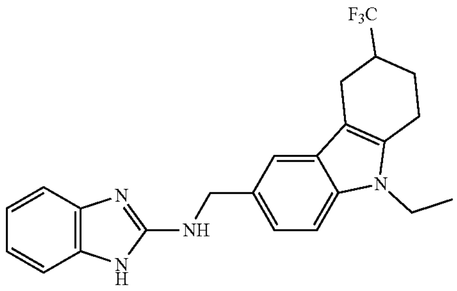

N-((9-ethyl-3-(trifluoromethyl)-2,3,4,9-tetrahydro-1H-carbazol-6-yl)methyl)-1H-benzo[d]imidazol-2-amine (AJ2-62): Synthesized according to scheme 3 and general procedure 1, purified on biotage (Hexane/Ethyl acetate; 5:5) to afford AJ2-62 as a brown solid (34 mg, 63%), $^1$H NMR (400 MHz, MeOD) δ 7.41 (s, 1H), 7.19 (dd, J=5.8, 3.2 Hz, 2H), 7.14 (s, 2H), 6.95 (dd, J=5.8, 3.2 Hz, 2H), 4.60 (s, 2H), 3.85 (qd, J=7.3, 2.6 Hz, 2H), 2.87 (dd, J=14.8, 5.1 Hz, 1H), 2.69-2.42 (m, 3H), 2.40-2.25 (m, 1H), 2.22-2.07 (m, 1H), 1.65 (tt, J=12.3, 6.1 Hz, 1H), 1.13 (t, J=7.1 Hz, 3H). $^{13}$C NMR (101 MHz, MeOD) δ 155.36, 137.45, 135.51, 134.13, 129.61, 128.97, 126.99, 126.85, 120.43, 120.03, 116.14, 111.37, 108.55, 105.58, 47.02, 46.86, 39.17 (q, J=26.7 Hz), 36.98, 21.96, 20.20, 14.27. $^{19}$F NMR (376 MHz, $CD_3OD$) δ −74.25 (d, J=8.5 Hz). LCMS calcd for $C_{23}H_{24}F_3N_4$; 413.1 ($M+H^+$), found: 413.1.

AJ2-63

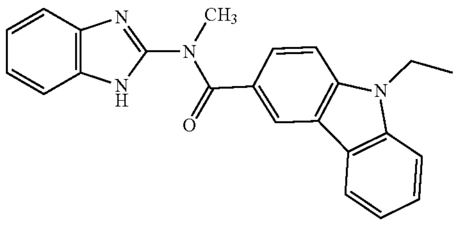

N-(1H-benzo[d]imidazol-2-yl)-9-ethyl-N-methyl-9H-carbazole-3-carboxamide (AJ2-63): Synthesized according to general procedure 3, purified on biotage (Hexane/Ethyl acetate; 6:4) to afford AJ2-63 as a brown solid (34 mg, 63%), $^1$H NMR (400 MHz, $CDCl_3$) δ 11.62 (s, 1H), 8.40 (d, J=1.6 Hz, 1H), 8.14 (dt, J=7.9, 0.9 Hz, 1H), 7.73 (dd, J=8.5, 1.7 Hz, 2H), 7.59-7.44 (m, 4H), 7.33-7.29 (m, 1H), 4.43 (q, J=7.3 Hz, 2H), 3.82 (s, 3H), 1.48 (t, J=7.2 Hz, 3H). LCMS calcd for $C_{23}H_{21}N_4O$; 369.1 ($M+H^+$), found: 369.1.

AJ2-64

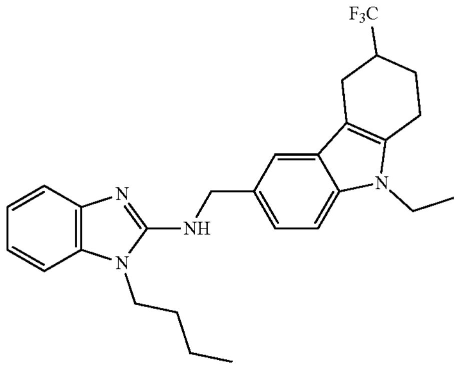

1-butyl-N-((9-ethyl-3-(trifluoromethyl)-2,3,4,9-tetrahydro-1H-carbazol-6-yl)methyl)-1H-benzo[d]imidazol-2-amine (AJ2-64): Synthesized according to scheme 3 and following general procedure 5, purified on biotage (Hexane/Ethyl acetate; 6:4) to afford AJ2-64 as a brown solid (42 mg, 64%), $^{1}$H NMR (400 MHz, $CDCl_3$) δ 7.46-7.37 (m, 2H), 7.24-7.13 (m, 2H), 7.08-6.94 (m, 3H), 4.97-4.80 (m, 1H), 4.74 (d, J=3.1 Hz, 2H), 4.01-3.94 (m, 2H), 3.79 (t, J=7.2 Hz, 2H), 2.99-2.87 (m, 1H), 2.86-2.79 (m, 1H), 2.75-2.56 (m, 2H), 2.47-2.33 (m, 1H), 2.30-2.21 (m, 1H), 1.84-1.73 (m, 1H), 1.65-1.58 (m, 2H), 1.31-1.18 (m, 5H), 0.82 (t, J=7.3 Hz, 314). $^{13}$C NMR (101 MHz, $CDCl_3$) δ 153.36, 135.59, 134.37, 134.13, 129.40, 128.91, 126.94, 126.63, 121.66, 121.36, 119.92, 117.51, 116.00, 109.13, 107.47, 106.53, 48.30, 42.23, 39.54 (q, J=27.0 Hz) 37.77, 31.03, 22.32, 22.29, 20.99, 20.70, 20.21, 15.48, 13.76. $^{19}$F NMR (376 MHz, $CDCl_3$) δ −72.89 (d, J=8.4 Hz). LCMS calcd for $C_{27}H_{32}F_3N_4$; 369.2 (M+H$^+$), found: 369.2.

AJ2-65

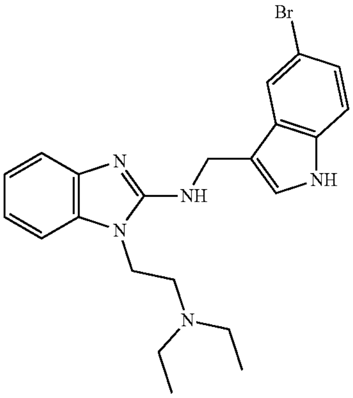

N-((5-bromo-1H-indol-3-yl)methyl)-1-(2-(diethylamino)ethyl)-1H-benzo[d]imidazol-2-amine (AJ2-65): Synthesized according to general scheme 3, purified on biotage (Hexane/Ethyl acetate; 4:6) to afford AJ2-65 as a yellow solid (24 mg, 66%), $^{1}$H NMR (400 MHz, DMSO) δ 11.15 (s, 1H), 7.87 (d, J=2.0 Hz, 1H), 7.43 (d, J=2.5 Hz, 1H), 7.41-7.30 (m, 2H), 7.24 (d, J=7.5 Hz, 1H), 7.23-7.10 (m, 2H), 6.93 (dt, J=20.8, 7.1 Hz, 2H), 4.66 (d, J=3.7 Hz, 2H), 4.00 (t, J=5.8 Hz, 2H), 2.57 (t, J=5.7 Hz, 2H), 2.38 (q, J=7.1 Hz, 4H), 0.72 (t, J=7.1 Hz, 6H). LCMS calcd for $C_{22}H_{27}BrN_5$; 440.1 (M+H$^+$), found: 440.1.

AJ2-66

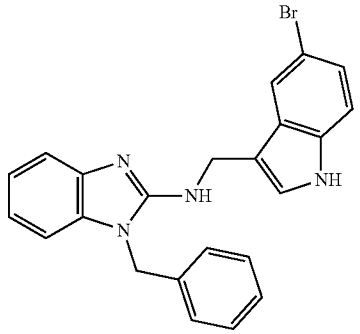

1-Benzyl-N-((5-bromo-1H-indol-3-yl)methyl)-1H-benzo[d]imidazol-2-amine (AJ2-66): Synthesized according to general scheme 3, purified on biotage (Hexane/Ethyl acetate; 6:4) to afford AJ2-66 as a brown solid (48 mg, 63%), $^{1}$H NMR (400 MHz, $CDCl_3$) δ 9.64-9.52 (m, 1H), 7.38-7.30 (m, 2H), 7.09 (dd, J=5.0, 1.9 Hz, 3H), 7.03-6.97 (m, 3H), 6.94 (ddd, J=6.6, 4.9, 2.3 Hz, 4H), 6.83 (d, J=2.3 Hz, 1H), 4.92 (s, 2H), 4.51 (s, 2H). $^{13}$C NMR (101 MHz, $CDCl_3$) δ 153.72, 140.70, 135.15, 134.96, 134.32, 129.16, 128.24, 128.10, 126.53, 124.88, 124.68, 121.86, 121.07, 120.48, 115.77, 113.02, 112.76, 111.71, 107.89, 45.80, 39.24. LCMS calcd for $C_{23}H_{20}BrN_4$; 431.0 (M+H$^+$), found: 431.0.

AJ2-67

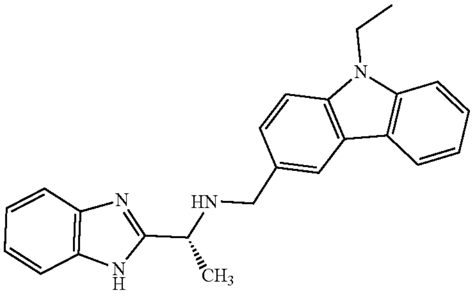

(R)-1-(1H-benzo[d]imidazol-2-yl)-N-((9-ethyl-9H-carbazol-3-yl)methyl)ethan-1-amine (AJ2-67): Synthesized according to general procedure 1, purified on biotage (Hexane/Ethyl acetate; 6:4) to afford AJ2-67 as a brown solid (34 mg, 63%), $^{1}$H NMR (400 MHz, $CDCl_3$) δ 8.02-7.92 (m, 2H), 7.71 (dd, J=6.1, 3.2 Hz, 2H), 7.53 (td, J=7.6, 7.0, 1.2 Hz, 1H), 7.41 (d, J=8.2 Hz, 1H), 7.37-7.24 (m, 4H), 7.20 (d, J=8.3 Hz, 1H), 4.40 (q, J=6.6 Hz, 1H), 4.26 (q, J=7.1 Hz, 2H), 4.01-3.83 (m, 2H), 1.61 (d, J=6.7 Hz, 3H), 1.38 (t, J=7.2 Hz, 3H). $^{13}$C NMR (101 MHz, $CDCl_3$) δ 158.50, 140.27, 139.30, 129.82, 126.30, 125.77, 123.01, 122.78, 122.39, 120.55, 120.13, 118.88, 108.59, 108.41, 52.50, 52.31, 37.53, 21.83, 13.83. LCMS calcd for $C_{24}H_{25}N_4$; 369.2 (M+H$^+$), found: 369.2.

AJ2-68

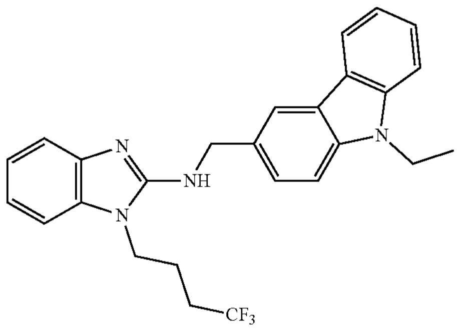

N-((9-ethyl-9H-carbazol-3-yl)methyl)-1-(4,4,4-trifluorobutyl)-1H-benzo[d]imidazol-2-amine (AJ2-68): Synthesized according to scheme 1 and general procedure 5, purified on biotage (Hexane/Ethyl acetate; 6:4) to afford AJ2-68 as a brown solid (34 mg, 63%), $^1$H NMR (400 MHz, $CDCl_3$) δ 8.02 (d, J=1.7 Hz, 1H), 7.96 (dt, J=7.8, 1.0 Hz, 1H), 7.50-7.36 (m, 3H), 7.34-7.24 (m, 2H), 7.21-7.10 (m, 1H), 7.07 (td, J=7.6, 1.3 Hz, 1H), 7.00 (td, J=7.6, 1.2 Hz, 1H), 6.97-6.89 (m, 1H), 4.81 (s, 2H), 4.25 (q, J=7.2 Hz, 2H), 3.82 (t, J=7.0 Hz, 2H), 2.10-1.98 (m, 2H), 1.98-1.84 (m, 2H), 1.32 (t, J=7.2 Hz, 3H). $^{19}$F NMR (376 MHz, $CDCl_3$) δ −65.84 (t, J=10.4 Hz). LCMS calcd for $C_{26}H_{26}F_3N_4$; 451.2 (M+H$^+$), found: 451.2.

AJ2-69

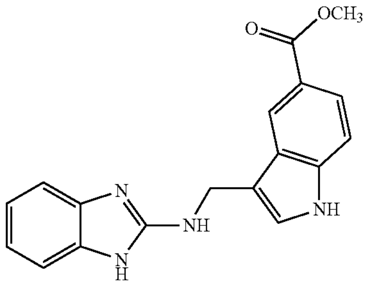

Methyl 3-(((1H-benzo[d]imidazol-2-yl)amino)methyl)-1H-indole-5-carboxylate (AJ2-69): Synthesized according to general procedure 1, purified on biotage (Hexane/Ethyl acetate; 3:7) to afford AJ2-69 as a brown solid (30 mg, 23%), $^1$H NMR (400 MHz, MeOD) δ 8.30 (dd, J=1.7, 0.7 Hz, 1H), 7.69 (dd, J=8.6, 1.7 Hz, 1H), 7.34-7.26 (m, 2H), 7.14 (dd, J=5.8, 3.2 Hz, 3H), 6.92 (dd, J=5.8, 3.2 Hz, 2H), 4.69-4.62 (m, 2H), 3.70 (s, 3H). LCMS calcd for $C_{18}H_{17}N_4O_2$; 321.1 (M+H$^+$), found: 321.1.

AJ2-70

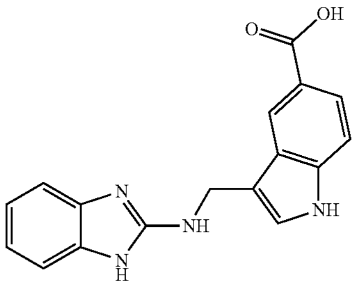

3-(((1H-benzo[d]imidazol-2-yl)amino)methyl)-1H-indole-5-carboxylic acid (AJ2-70): To a solution of methyl 3-(((1H-benzo[d]imidazol-2-yl)amino)methyl)-1H-indole-5-carboxylate (AJ2-69) (0.078 mmol) in tetrahydrofuran (1 mL) and water (1 mL), at 0° C. was added lithium hydroxide (0.023 mmol) the reaction mixture was stirred at room temperature for 6 hours, after completion the reaction mixture was neutralized (pH 6-7) with 1 N. HCl, and solid was filtered to afford AJ2-70 as a brown solid (6 mg, 42%), $^1$H NMR (400 MHz, DMSO-$d_6$) δ 11.26 (s, 1H), 8.40 (s, 1H), 7.72 (d, J=8.6 Hz, 1H), 7.45 (d, J=2.3 Hz, 1H), 7.41 (d, J=8.6 Hz, 1H), 7.18-7.09 (m, 2H), 7.05 (s, 1H), 6.86 (dd, J=5.8, 3.2 Hz, 2H), 4.66 (d, J=5.6 Hz, 2H). $^{13}$C NMR (151 MHz, DMSO-$d_6$) δ 169.03, 155.85, 139.27, 126.62, 125.93, 122.94, 122.23, 121.72, 114.70, 111.61, 38.09. LCMS calcd for $C_{17}H_{15}N_4O_2$; 307.1 (M+H$^+$), found: 307.1.

AJ2-71

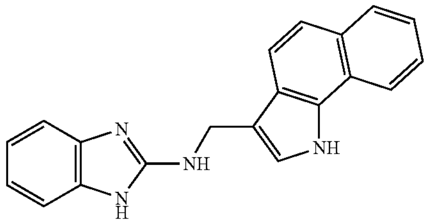

N-((1H-benzo[g]indol-3-yl)methyl)-1H-benzo[d]imidazol-2-amine (AJ2-71): Synthesized according to general procedure 1, purified on biotage (Hexane/Ethyl acetate; 2:8) to afford AJ2-71 as an off white solid (34 mg, 63%), $^1$H NMR (400 MHz, DMSO) δ 11.88 (s, 1H), 10.63 (s, 1H), 8.34 (d, J=8.2 Hz, 1H), 7.91 (d, J=8.1 Hz, 1H), 7.80 (d, J=8.6 Hz, 1H), 7.57-7.50 (m, 1H), 7.50-7.36 (m, 3H), 7.16 (s, 2H), 6.86 (t, J=7.7 Hz, 3H), 4.72 (d, J=5.8 Hz, 2H). LCMS calcd for $C_{20}H_{17}N_4$; 313.1 (M+H$^+$), found: 313.1.

AJ2-72

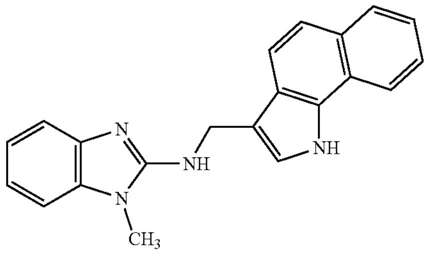

N-((1H-benzo[g]indol-3-yl)methyl)-1-methyl-1H-benzo[d]imidazol-2-amine (AJ2-72): Synthesized according to general procedure 1, purified on biotage (Hexane/Ethyl acetate; 3:7) to afford AJ2-62 as a brown solid (34 mg, 63%). NMR (400 MHz, DMSO-$d_6$) δ 11.89 (d, J=2.6 Hz, 1H), 8.35 (dd, J=8.2, 1.1 Hz, 1H), 7.91 (dd, J=8.3, 1.2 Hz, 1H), 7.82 (d, J=8.6 Hz, 1H), 7.52 (ddd, J=8.2, 6.8, 1.3 Hz, 1H), 7.48-7.43 (m, 2H), 7.39 (ddd, J=8.1, 6.9, 1.3 Hz, 1H), 7.29-7.23 (m, 1H), 7.14 (dd, J=7.9, 1.2 Hz, 1H), 7.03-6.89

(m, 3H), 4.82 (d, J=5.4 Hz, 2H), 3.50 (s, 3H). LCMS calcd for $C_{21}H_{19}N_4$; 327.1 (M+H$^+$), found: 327.1.

AJ2-73

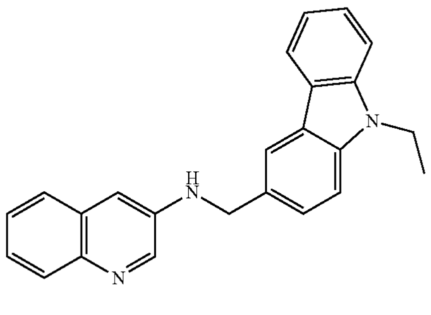

N-((9-ethyl-9H-carbazol-3-yl)methyl)quinolin-3-amine (AJ2-73): Synthesized according to general procedure 1, purified on biotage (Hexane/Ethyl acetate; 6:4) to afford AJ2-73 as an off white solid (76 mg, 71%), $^1$H NMR (400 MHz, $CDCl_3$) δ 8.54 (dd, J=2.9, 1.0 Hz, 1H), 8.16 (d, J=1.8 Hz, 1H), 8.13 (dd, J=7.8, 1.0 Hz, 1H), 8.00 (dd, J=6.2, 3.2 Hz, 1H), 7.62 (dd, J=6.3, 3.3 Hz, 1H), 7.52 (ddt, J=9.4, 7.0, 1.4 Hz, 2H), 7.47-7.41 (m, 4H), 7.31-7.24 (m, 1H), 7.14 (d, J=2.6 Hz, 1H), 4.58 (t, J=3.1 Hz, 2H), 4.47 (s, 1H), 4.39 (qd, J=7.4, 2.6 Hz, 2H), 1.46 (td, J=7.1, 1.2 Hz, 3H). $^{13}$C NMR (101 MHz, $CDCl_3$) δ 143.45, 142.18, 141.63, 140.34, 139.53, 129.57, 129.03, 128.46, 126.91, 126.07, 125.92, 125.56, 124.92, 123.26, 122.65, 120.52, 119.77, 118.97, 110.38, 108.75, 108.62, 48.53, 37.65, 13.84.

LCMS calcd for $C_{24}H_{22}N_3$; 352.2 (M+H$^+$), found: 352.2.

AJ2-74

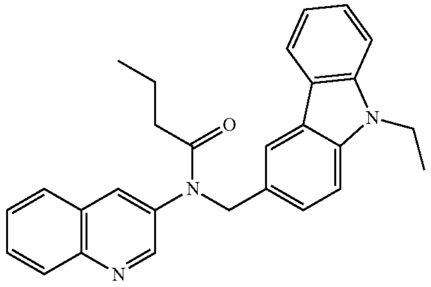

N-((9-ethyl-9H-carbazol-3-yl)methyl)-N-(quinolin-3-yl) butyramide (AJ2-74): Synthesized according to general procedure 1 and followed by general procedure 4, purified on PTLC (Hexane/Ethyl acetate; 6:4) to afford AJ2-62 as a brown solid (17 mg, 68%), $^1$H NMR (400 MHz, $CDCl_3$) δ 8.61-8.32 (m, 1H), 8.02 (d, J=8.5 Hz, 1H), 7.92 (d, J=7.7 Hz, 1H), 7.85 (d, J=1.2 Hz, 1H), 7.71-7.57 (m, 3H), 7.46 (ddd, J=8.1, 6.8, 1.1 Hz, 1H), 7.41-7.28 (m, 2H), 7.21-7.16 (m, 1H), 7.10 (ddd, J=7.9, 7.0, 1.1 Hz, 1H), 5.10 (s, 2H), 4.26 (q, J=7.2 Hz, 2H), 2.06-1.92 (m, 2H), 1.61 (q, J=7.4 Hz, 2H), 1.34 (t, J=7.2 Hz, 3H), 0.77 (t, J=7.4 Hz, 3H). LCMS calcd for $C_{28}H_{28}N_3O$; 422.2 (MAT), found: 422.1.

AJ2-75

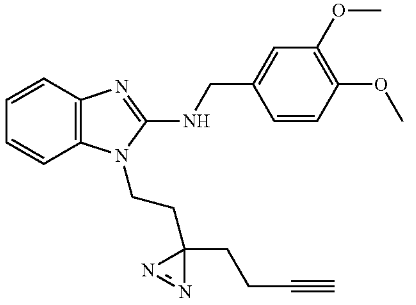

1-(2-(3-(but-3-yn-1-yl)-3H-diazirin-3-yl)ethyl)-N-(3,4-dimethoxybenzyl)-1H benzo[d]imidazol-2-amine (AJ2-75): Synthesized according to general procedure 1 and followed by general procedure 5, purified PTLC (Hexane/Ethyl acetate; 6:4) to afford AJ2-75 as a brown solid (12 mg, 64%). $^1$H NMR (600 MHz, $CDCl_3$) δ 7.43 (dd, J=7.7, 4.7 Hz, 1H), 7.07 (dt, J=8.4, 4.2 Hz, 1H), 7.05-6.98 (m, 2H), 6.97-6.88 (m, 2H), 6.76 (dd, J=8.1, 4.7 Hz, 1H), 4.60 (d, J=4.6 Hz, 3H), 3.79 (t, J=5.3 Hz, 6H), 3.66 (q, J=6.4, 5.8 Hz, 2H), 1.81 (tt, J=12.3, 5.1 Hz, 5H), 1.37 (q, J=6.3 Hz, 2H). $^{13}$C NMR (151 MHz, $CDCl_3$) δ 153.55, 149.17, 148.66, 142.23, 133.86, 131.05, 121.69, 120.40, 119.97, 116.77, 111.55, 111.21, 107.23, 82.47, 69.66, 55.97, 55.94, 47.66, 36.82, 32.25, 26.66, 13.17. LCMS calcd for $C_{23}H_{26}N_5O_2$; 404.2 (M+H$^+$), found: 404.2.

AJ2-76

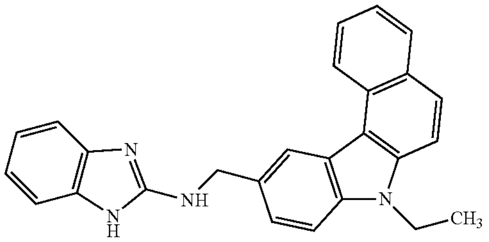

N-((7-ethyl-7H-benzo[c]carbazol-10-yl)methyl)-1H-benzo[d]imidazol-2-amine (AJ2-76): Synthesized according to general procedure 1, purified by biotage (Hexane/Ethyl acetate; 2:8) to afford AJ2-76 as a brown solid (27 mg, 56%), $^1$H NMR (400 MHz, $CDCl_3$) δ 8.59 (d, J=8.3 Hz, 1H), 8.41 (s, 1H), 7.91 (dt, J=8.1, 0.9 Hz, 1H), 7.81 (d, J=8.9 Hz, 1H), 7.64-7.54 (m, 1H), 7.52 (d, J=8.9 Hz, 1H), 7.38-7.40 (m, 1H), 7.35-7.30 (m, 2H), 7.16 (dd, J=5.9, 3.2 Hz, 2H), 6.94 (dd, J=5.8, 3.2 Hz, 2H), 4.69 (s, 2H), 4.32 (q, J=7.2 Hz, 2H), 1.33 (t, J=7.2 Hz, 3H). LCMS calcd for $C_{26}H_{23}N_4$; 391.1 (M+H$^+$), found: 391.1.

AJ2-77

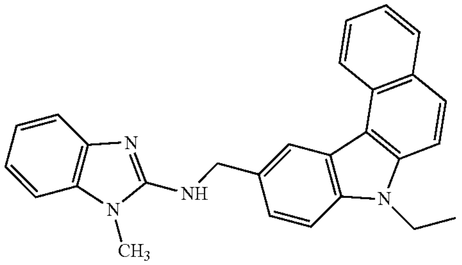

N-((7-ethyl-7H-benzo[c]carbazol-10-yl)methyl)-1-methyl-1H-benzo[d]imidazol-2-amine (AJ2-77): Synthesized according to general procedure 1, purified by biotage (Hexane/Ethyl acetate; 3:7) to afford AJ2-77 as a brown solid (48 mg, 66%), $^{1}$H NMR (400 MHz, $CDCl_3$) δ 8.78 (dd, J=8.4, 1.1 Hz, 1H), 8.67 (d, J=1.6 Hz, 1H), 8.03 (dt, J=8.1, 0.8 Hz, 1H), 7.94 (d, J=8.9 Hz, 1H), 7.74-7.70 (m, 1H), 7.67 (d, J=8.9 Hz, 1H), 7.64-7.58 (m, 2H), 7.58-7.47 (m, 2H), 7.21-7.17 (m, 1H), 7.16-7.05 (m, 2H), 5.00 (d, J=5.2 Hz, 2H), 4.51 (q, J=7.2 Hz, 3H), 3.45 (s, 3H), 1.50 (t, J=7.2 Hz, 3H). LCMS calcd, for $C_{27}H_{25}N_4$; 405.2 (M+H$^+$), found: 405.1.

AJ2-78

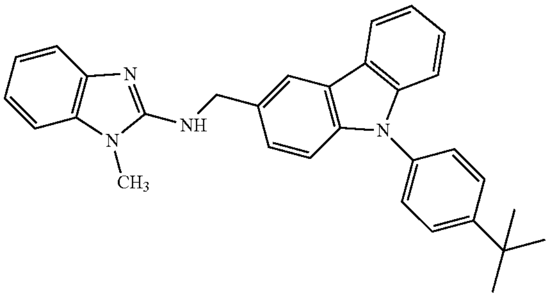

N-((9-(4-(tert-butyl)phenyl)-9H-carbazol-3-yl)methyl)-1-methyl-1H-benzo[d]imidazol-2-amine (AJ2-78): Synthesized according to general procedure 1, purified by biotage (Hexane/Ethyl acetate; 3:7) to afford AJ2-78 as a brown solid (65 mg, 72%), $^{1}$H NMR (400 MHz, $CDCl_3$) δ 8.22 (dd, J=1.7, 0.7 Hz, 1H), 8.16 (dt, J=7.8, 1.0 Hz, 1H), 7.65-7.61 (m, 2H), 7.58 (dt, J=7.8, 1.0 Hz, 1H), 7.54-7.47 (m, 3H), 7.47-7.41 (m, 3H), 7.34-7.29 (m, 1H), 7.17 (ddd, J=7.8, 5.0, 3.6 Hz, 1H), 7.13-7.08 (m, 2H), 4.94 (d, J=5.3 Hz, 2H), 4.35 (t, J=5.3 Hz, 1H), 3.51 (s, 3H), 1.46 (s, 9H). LCMS calcd for $C_{31}H_{31}N_4$; 459.2 (M+H$^+$), found: 459.1.

AJ2-79

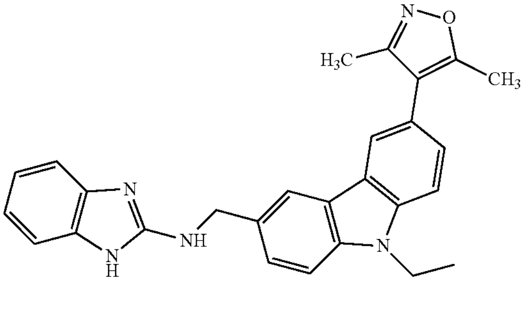

N-((6-(3,5-dimethylisoxazol-4-yl)-9-ethyl-9H-carbazol-3-yl)methyl)-1H-benzo[d]imidazol-2-amine (AJ2-79): Synthesized according to general synthetic scheme 2 and followed by general procedure 1, purified by biotage (Hexane/Ethyl acetate; 3:7) to afford AJ2-79 as a brown solid (10 mg, 52%). $^{1}$H NMR (400 MHz, $CDCl_3$) δ 8.04-7.96 (m, 1H), 7.75 (d, J=1.6 Hz, 1H), 7.38-7.35 (m, 2H), 7.26-7.20 (m, 2H), 7.14 (dd, J=5.8, 3.2 Hz, 2H), 6.91 (dd, J=5.8, 3.2 Hz, 2H), 4.67 (s, 2H), 4.25 (q, J=7.2 Hz, 2H), 2.30 (s, 3H), 2.18 (s, 3H), 1.34 (t, J=7.2 Hz, 3H). $^{13}$C NMR (101 MHz, $CDCl_3$) δ 164.97, 159.15, 154.73, 139.87, 139.56, 128.61, 127.13, 125.69, 122.90, 122.81, 121.16, 120.92, 120.85, 119.38, 117.28, 112.32, 109.10, 108.89, 53.45, 47.67, 37.76, 13.88, 11.55, 10.87. LCMS calcd for $C_{27}H_{26}N_5O$; 436.2 (M+H$^+$), found: 436.1.

AJ2-80

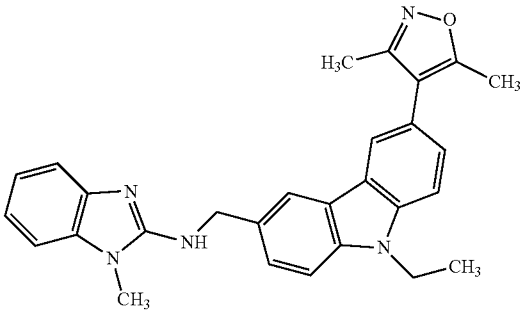

N-((6-(3,5-dimethylisoxazol-4-yl)-9-ethyl-9H-carbazol-3-yl)methyl)-1-methyl-1H-benzo[d]imidazol-2-amine (AJ2-80): Synthesized according to general procedure scheme 2 followed by general procedure 1, purified by biotage (Hexane/Ethyl acetate; 3:7) to afford AJ2-80 as a brown solid (34 mg, 62%), $^{1}$H NMR (400 MHz, $CDCl_3$) δ 8.19 (d, J=1.7 Hz, 1H), 7.96 (d, J=1.7 Hz, 1H), 7.65-7.54 (m, 2H), 7.53-7.42 (m, 2H), 7.36 (dt, J=8.4, 1.3 Hz, 1H), 7.16 (ddd, J=7.8, 4.1, 1.5 Hz, 1H), 7.10 (dt, J=4.1, 1.1 Hz, 2H), 4.95 (d, J=5.1 Hz, 2H), 4.43 (dt, J=8.3, 6.6 Hz, 3H), 3.50 (s, 3H), 2.46 (s, 3H), 2.33 (s, 3H), 1.55-1.42 (m, 3H). LCMS calcd for $C_{28}H_{28}N_5O$ 450.2 (M+H$^+$), found: 450.2.

AJ2-81

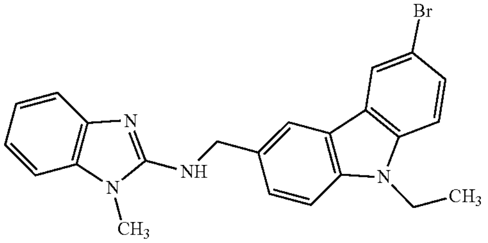

N-((6-bromo-9-ethyl-9H-carbazol-3-yl)methyl)-1-methyl-1H-benzo[d]imidazol-2-amine (AJ2-81): Synthesized according to general procedure 1, purified by biotage (Hexane/Ethyl acetate; 3:7) to afford AJ2-81 as a brown solid (85 mg, 76%), $^{1}$H NMR (400 MHz, $CDCl_3$) δ 8.21 (d, J=1.9 Hz, 1H), 8.11 (dd, J=1.7, 0.7 Hz, 1H), 7.63-7.54 (m, 3H), 7.42 (dd, J=8.4, 0.6 Hz, 1H), 7.31 (d, J=8.7 Hz, 1H), 7.22-7.14 (m, 1H), 7.14-7.09 (m, 2H), 4.92 (d, J=5.0 Hz, 2H), 4.37 (q, J=7.2 Hz, 3H), 3.51 (s, 3H), 1.44 (t, J=7.2 Hz, 3H). LCMS calcd for $C_{23}H_{22}BrN_4$; 433.0 (M+H$^+$), found: 433.0.

AJ2-82

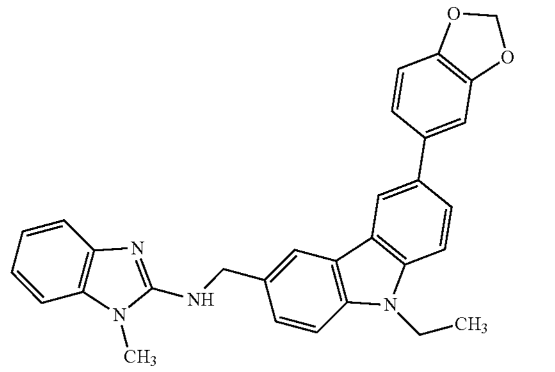

N-((6-(benzo[d][1,3]diozol-5-yl)-9-ethyl-9H-carbazol-3-yl)methyl)-1-methyl-1H-benzo[d]imidazol-2-amine (AJ2-82): Synthesized according to general scheme 2 and general procedure 1, purified by biotage (Hexane/Ethyl acetate; 2:8) to afford AJ2-82 as a brown solid (13 mg, 52%), $^{1}$H NMR (400 MHz, $CDCl_3$) δ 7.96 (d, J=1.8 Hz, 1H), 7.88 (d, J=1.6 Hz, 1H), 7.50-7.38 (m, 2H), 7.35 (dd, J=8.4, 1.7 Hz, 1H), 7.18-7.10 (m, 3H), 7.06 (dt, J=7.7, 1.2 Hz, 1H), 7.01-6.93 (m, 2H), 6.87 (d, J=7.7 Hz, 1H), 6.84-6.77 (m, 1H), 5.22 (s, 2H), 4.77 (s, 3H), 4.09 (q, J=6.9 Hz, 2H), 3.25 (s, 3H), 1.21 (s, 3H). LCMS calcd for $C_{30}H_{27}N_4O_2$; 475.2 (M+H$^+$), found: 475.1.

AJ2-83

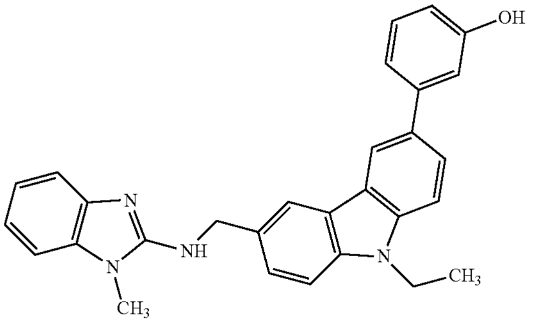

3-(9-ethyl-6-(((1-methyl-1H-benzo[d]imidazol-2-yl)amino)methyl)-9H-carbazol-3-yl)phenol (AJ2-83): Synthesized according to general scheme 2 and general procedure 1, purified by biotage (Hexane/Ethyl acetate; 3:7) to afford AJ2-83 as an off white solid (35 mg, 62%), $^{1}$H NMR (600 MHz, DMSO) δ 9.56 (s, 1H), 8.40 (s, 1H), 8.30 (s, 1H), 7.76-7.62 (m, 2H), 7.59 (s, 2H), 7.35-7.27 (m, 2H), 7.21 (dt, J=22.1, 7.7 Hz, 4H), 6.96 (dt, J=23.9, 7.9 Hz, 2H), 6.78 (d, J=8.1 Hz, 1H), 4.93-4.71 (m, 2H), 4.61-4.29 (m, 2H), 3.59 (s, 3H), 1.32 (t, J=7.4 Hz, 3H). $^{13}$C NMR (151 MHz, DMSO) δ 158.29, 155.72, 143.10, 142.97, 139.84, 139.70, 135.86, 131.73, 131.20, 130.31, 126.42, 125.08, 123.15, 122.64, 120.68, 120.03, 118.76, 118.70, 118.04, 115.41, 114.05, 113.94, 109.88, 109.48, 107.69, 46.81, 37.56, 28.76, 14.18. LCMS calcd for $C_{29}H_{27}N_4O$; 447.2 (MAT), found: 447.1.

AJ2-85

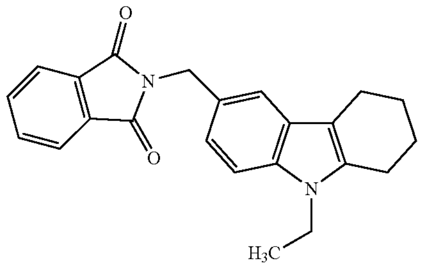

2-((9-ethyl-2,3,4,9-tetrahydro-1H-carbazol-6-yl)methyl)isoindoline-1,3-dione (AJ2-83): Synthesized according to general procedure 4, purified by biotage (Hexane/Ethyl acetate; 6:4) to afford AJ2-85 as yellow solid (45 mg, 62%), $^{1}$H NMR (400 MHz, $CDCl_3$) δ 7.72 (dd, J=5.5, 3.1 Hz, 2H), 7.56 (dd, J=5.5, 3.0 Hz, 2H), 7.49 (d, J=1.7 Hz, 1H), 7.19 (dd, J=8.4, 1.7 Hz, 1H), 7.10 (dd, J=8.4, 0.7 Hz, 1H), 4.85 (s, 2H), 3.93 (q, J=7.2 Hz, 2H), 2.67-2.51 (m, 4H), 1.91-1.79 (m, 2H), 1.74 (dtd, J=11.2, 5.9, 2.3 Hz, 2H), 1.18 (t, J=7.2 Hz, 3H). $^{13}$C NMR (101 MHz, $CDCl_3$) δ 168.23, 135.63, 135.17, 133.74, 132.35, 127.42, 126.76, 123.14, 121.66, 118.53, 109.48, 108.54, 42.35, 37.43, 23.26, 23.22, 22.06, 21.11, 15.47, 15.31. LCMS calcd for $C_{23}H_{23}N_2O_2$; 359.1 (M+H$^+$), found: 359.1.

AJ2-86

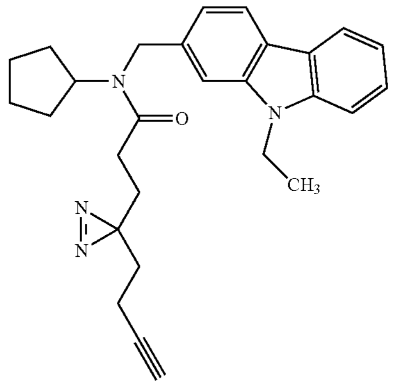

3-(3-(but-3-yn-1-yl)-3H-diazirin-3-yl)-N-cyclopentyl-N-((9-ethyl-9H-carbazol-2-yl)methyl)propenamide (AJ2-86): Synthesized according to general procedure 2, purified by biotage (Hexane/Ethyl acetate; 6:4) to afford AJ2-86 as colorless oil (14 mg, 62%), Note: rotomeric isomers observed. $^{1}$H NMR (400 MHz, $CDCl_3$) δ 8.13 ((L J=7.9 Hz, 1H), 7.95-7.91 (m, 1H), 7.50 (t, J=7.6 Hz, 1H), 7.48-7.38 (m, 3H), 7.32-7.19 (m, 3H), 5.03-4.95 (m, 1H), 4.76 (s, 1H), 4.71-4.65 (m, 2H), 4.42-4.34 (m, 3H), 2.30 (t, J=7.5 Hz, 1H), 2.08 (t, J=7.4 Hz, 3H), 1.99-188 (m, 4H), 1.90-1.79 (m, 4H), 1.69 (td, J=8.0, 6.6, 3.3 Hz, 3H), 1.58 (q, J=7.4, 6.6 Hz, 6H), 1.48 (d, J=7.2 Hz, 3H). Note: rotomeric isomers observed, LCMS calcd for $C_{28}H_{33}N_4O$; 441.2 (M+H$^+$), found: 441.1.

AJ2-87

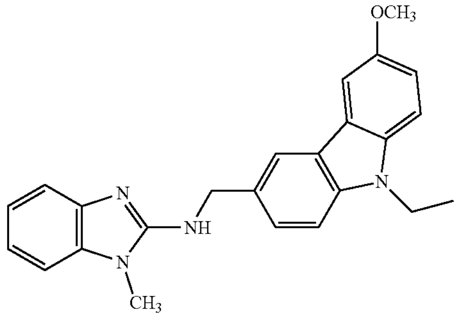

N-((9-ethyl-6-methoxy-9H-carbazol-3-yl)methyl)-1-methyl-1H-benzo[d]imidazol-2-amine (AJ2-87): Synthesized according to general procedure 1, purified by biotage (Hexane/Ethyl acetate; 4:6) to afford AJ2-87 as yellow solid (72 mg, 64%), $^{1}H$ NMR (400 MHz, $CDCl_3$) δ 7.99 (d, J=1.7 Hz, 1H), 7.46 (dd, J=7.3, 1.6 Hz, 2H), 7.42 (dt, J=8.3, 1.5 Hz, 1H), 7.25 (dd, J=8.4, 1.5 Hz, 1H), 7.22 (d, J=8.8 Hz, 1H), 7.09-7.01 (m, 2H), 7.01-6.94 (m, 2H), 4.78 (d, J=4.1 Hz, 2H), 4.37 (s, 1H), 4.23 (qd, J=7.2, 1.4 Hz, 2H), 3.83 (s, 3H), 3.34 (s, 3H), 1.31 (t, J=7.2 Hz, 3H). $^{13}C$ NMR (101 MHz, $CDCl_3$) δ 154.38, 153.65, 142.29, 140.02, 135.35, 135.02, 128.37, 126.24, 122.94, 122.90, 121.25, 120.35, 119.60, 116.50, 115.21, 109.33, 108.78, 107.05, 103.34, 56.16, 48.27, 37.72, 28.24, 13.90. LCMS calcd for $C_{24}H_{25}N_4O$; 385.2 (M+H$^+$), found: 384.1.

AJ2-88

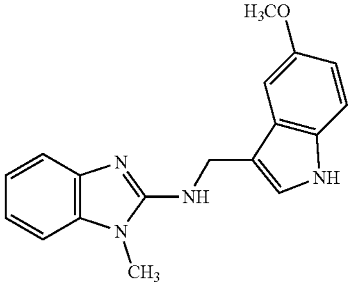

N-((5-methoxy-1H-indol-3-yl)methyl)-1-methyl-1H-benzo[d]imidazol-2-amine (AJ2-88): Synthesized according to general procedure 1, purified by biotage (Hexane/Ethyl acetate; 2:8) to afford AJ2-87 as a yellow solid (72 mg, 64%), $^{1}H$ NMR (400 MHz, $CDCl_3$) δ 8.43 (s, 1H), 7.47 (dt, J=7.8, 1.0 Hz, 1H), 7.20-7.16 (m, 1H), 7.14 (d, J=2.5 Hz, 1H), 7.08 (dd, J=2.5, 1.6 Hz, 1H), 7.08-7.03 (m, 1H), 7.02-6.98 (m, 2H), 6.80 (dd, J=8.8, 2.5 Hz, 1H), 4.85-4.73 (m, 2H), 4.13 (s, 1H), 3.69 (s, 3H), 3.34 (s, 3H). $^{13}C$ NMR (101 MHz, $CDCl_3$) δ 154.43, 154.35, 142.28, 134.98, 131.50, 127.19, 124.22, 121.28, 119.67, 116.43, 112.92, 112.86, 112.18, 107.09, 100.61, 55.88, 39.39, 28.24. LCMS calcd for $C_{18}H_{19}N_4O$; 307.1 (M+H$^+$), found: 307.1.

AJ2-89

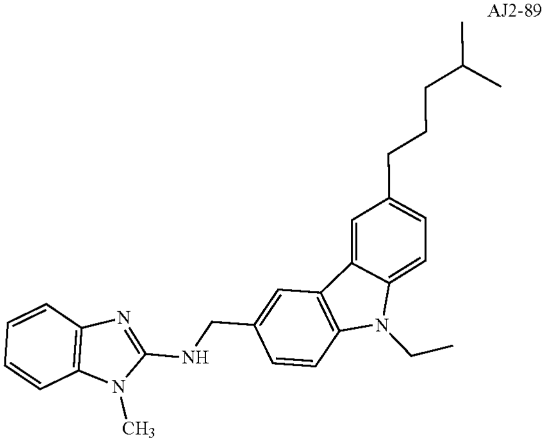 [SMILES: CCn1c2ccc(CCCC(C)C)cc2c2cc(CNc3nc4ccccc4n3C)ccc21]

N-((9-ethyl-6-(4-methylpentyl)-9H-carbazol-3-yl)methyl)-1-methyl-1H-benzo[d]imidazol-2-amine (AJ2-89): Synthesized according to general scheme 4, followed by general procedure 1, purified by biotage (Hexane/Ethyl acetate; 4:6) to afford AJ2-89 as a yellow solid (68 mg, 72%), $^{1}H$ NMR (600 MHz, $CDCl_3$) δ 8.11 (s, 1H), 7.92 (s, 1H), 7.60 (d, J=7.8 Hz, 1H), 7.51 (d, J=8.3 Hz, 1H), 7.39-7.32 (m, 3H), 7.20 (t, J=7.6 Hz, 1H), 7.13 (d, J=7.6 Hz, 1H), 7.06 (d, J=7.8 Hz, 1H), 4.89 (d, J=5.1 Hz, 2H), 4.79 (s, 1H), 4.34 (q, J=7.2 Hz, 2H), 3.38 (s, 3H), 2.83 (t, J=7.8 Hz, 2H), 1.80-1.74 (m, 2H), 1.69-1.64 (m, 1H), 1.44 (t, J=7.2 Hz, 3H), 1.40-1.30 (m, 2H), 1.01-0.93 (m, 6H). $^{13}C$ NMR (151 MHz, $CDCl_3$) δ 154.55, 142.38, 139.75, 138.83, 135.09, 133.65, 128.64, 126.68, 126.06, 123.00, 122.75, 121.21, 120.24, 119.90, 119.54, 116.39, 108.55, 108.32, 107.08, 48.24, 38.80, 37.63, 36.35, 30.36, 28.18, 28.05, 22.76, 13.90. LCMS calcd for $C_{29}H_{35}N_4$; 439.2 (M+H$^+$), found: 439.2.

AJ2-90

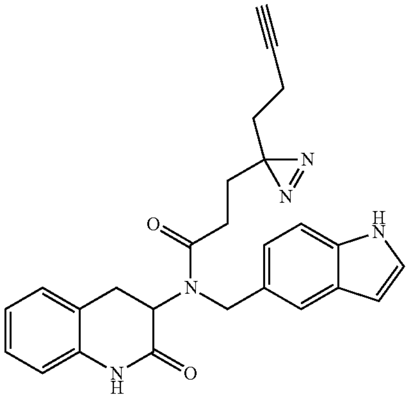

N-((1H-indol-5-yl)methyl)-3-(3-(but-3-yn-1-yl)-3H-diazirin-3-yl)-N-(2-oxo-1,2,3,4 tetrahydroquinolin-3-yl)propenamide (AJ2-90): Synthesized according to general scheme 1 and general procedure 2, purified by PTLC (Hexane/Ethyl acetate; 5:5) to afford AJ2-90 as white solid (22 mg, 46%), $^{1}H$ NMR (400 MHz, $CDCl_3$) δ 8.27 (s, 1H), 7.87 (s, 1H), 7.48 (d, J=1.7 Hz, 1H), 7.34 (d, J=8.4 Hz, 1H), 7.19 (d, J=2.4 Hz, 1H), 7.04 (td, J=6.7, 3.4 Hz, 2H), 6.91 (d, J=7.4 Hz, 1H), 6.82 (td, J=7.5, 1.1 Hz, 1H), 6.61 (dd, J=7.9, 1.1 Hz, 1H), 6.48-6.49 (m, 1H), 4.88-4.83 (m, 1H), 4.72-

4.59 (m, 2H), 3.38 (t, J=14.8 Hz, 1H), 2.72 (dd, J=15.4, 6.7 Hz, 1H), 2.27-2.15 (m, 2H), 1.89-1.77 (m, 4H), 1.56-1.49 (m, 2H). LCMS calcd for $C_{26}H_{26}N_5O_2$; 440.2 (M+H$^+$), found: 440.1.

AJ2-91

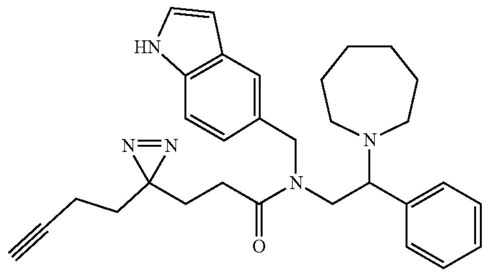

N-((1H-indol-5-yl)methyl)-N-(2-(azepan-1-yl)-2-phenylethyl)-3-(3-(but-3-yn-1-yl)-3H-diazirin-3-yl)propenamide (AJ2-91): Synthesized according to general procedure 1 followed by general procedure 2, purified by PTLC (Hexane/Ethyl acetate; 7:3) to afford AJ2-91 as a colorless oil (14 mg, 46%), $^1$H NMR (400 MHz, $CDCl_3$) δ 8.25 (s, 1H), 8.18 (s, 1H), 7.33 (d, J=1.5 Hz, 1H), 7.29-7.16 (m, 10H), 6.95 (dd, J=8.4, 1.7 Hz, 1H), 6.78 (dd, J=8.3, 1.7 Hz, 1H), 6.43 (q, J=2.8 Hz, 2H), 4.40-4.30 (m, 2H), 4.08 (dd, J=13.2, 6.9 Hz, 1H), 3.95 (t, J=7.4 Hz, 1H), 3.89-3.85 (m, 1H), 3.75-3.60 (m, 1H), 3.39-3.26 (m, 1H), 2.68-2.58 (m, 2H), 2.51 (qt, J=9.9, 5.5 Hz, 4H), 2.00 (t, J=7.6 Hz, 2H), 1.97-1.85 (m, 5H), 1.74 (td, J=7.9, 7.4, 2.8 Hz, 3H), 1.54-1.50 (m, 4H). Note: rotomeric isomers observed. LCMS calcd for $C_{31}H_{38}N_5O$; 496.30 (M+H$^+$), found: 496.1.

AJ2-92

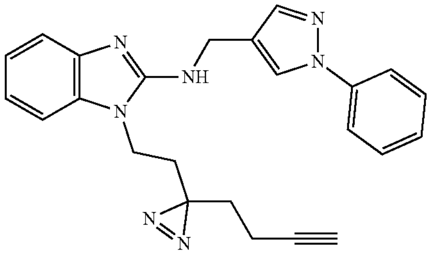

1-(2-(3-(but-3-yn-1-yl)-3H-diazirin-3-yl)ethyl)-N-((1-phenyl-1H-pyrazol-4-yl)methyl)-1H-benzo[d]imidazol-2-amine (AJ2-92): Synthesized according to general procedure 1 followed by general procedure 5, purified by PTLC (Hexane/Ethyl acetate; 5:5) to afford AJ2-92 as yellow sticky liquid (8 mg, 52%), $^1$H NMR (600 MHz, $CDCl_3$) δ 7.95 (s, 1H), 7.69 (s, 1H), 7.60-7.55 (m, 2H), 7.46 (d, J=7.9 Hz, 1H), 7.39-7.32 (m, 2H), 7.23-7.17 (m, 1H), 7.10-7.07 (m, 1H), 7.04-6.98 (m, 2H), 4.68 (s, 1H), 4.62 (s, 2H), 3.66 (t, J=7.3 Hz, 2H), 1.86-1.77 (m, 5H), 1.36 (t, J=7.0 Hz, 2H). $^{13}$C NMR (151 MHz, $CDCl_3$) δ 153.38, 142.28, 140.82, 139.99, 133.92, 129.47, 126.59, 126.37, 121.71, 120.88, 120.05, 119.10, 116.88, 107.31, 82.44, 69.65, 38.00, 36.82, 32.24, 26.68, 13.14. LCMS(ESI) calcd for $C_{24}H_{24}N_7$; 410.2 (M+H$^+$), found: 410.1.

AJ2-CP53

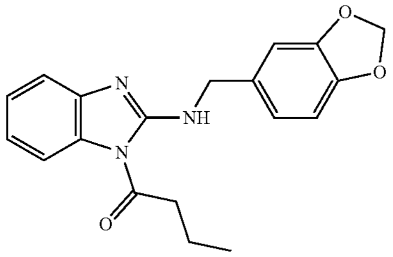

1-(2-((benzo[d][1,3]dioxol-5-ylmethyl)amino)-1H-benzo[d]imidazol-1-yl)butan-1-one (AJ2-CP53): Synthesized according to scheme 1 and general procedure 4, purified PTLC (Hexane/Ethyl acetate 5:5) to afford AJ2-CP53 as an off white solid (18 mg, 45%); $^1$H NMR (400 MHz, $CDCl_3$) δ 8.11 (d, J=5.8 Hz, 1H), 7.44 (dd, J=8.2, 1.1 Hz, 1H), 7.39 (d, J=8.1 Hz, 1H), 7.24 (dd, J=7.8, 1.1 Hz, 1H), 7.07 (ddd, J=8.6, 7.5, 1.3 Hz, 1H), 6.91 (d, J=1.7 Hz, 1H), 6.89-6.84 (m, 1H), 6.78 (d, J=7.9 Hz, 1H), 5.95 (s, 2H), 4.67 (d, J=5.4 Hz, 2H), 3.00 (t, J=7.2 Hz, 2H), 1.87 (h, J=7.3 Hz, 2H), 1.10 (t, J=7.4 Hz, 3H). LCMS calcd, for $C_{19}H_{20}N_3O_3$; 338.1 (M+H$^+$), found: 338.1.

Example 3. Fragment-Based Chemical Proteomic Approach to Develop SLC Inhibitors

Chemical probes offer a valuable way to directly interrogate the function and disease-relevance of proteins and complement genetic approaches by producing reversible and graded gains or losses of protein activity, as well as, in various instances, neo-functional outcomes. Chemical probes are typically discovered through the high throughput screening (HTS) of large chemical libraries (~$10^6$) against desired targets or phenotypes. Despite several successful implementations of HTS, this approach continues to face major technical hurdles that limit its general utility. First, they are often conducted using large libraries of structurally elaborate (MW 400-600 Da) compounds that can be difficult to optimize due to their suboptimal ligand efficiency[42]. In addition, such high-molecular weight compound libraries have vast possible atomic combinations and therefore tend to inefficiently and incompletely explore biologically relevant ("druggable") chemical space across the human proteome[43,44]. Fragment-based ligand discovery (FBLD) has the potential to address some of the limitations of conventional HTS by assaying smaller libraries (~1000) of low-molecular weight compounds (<300 Da) for binding to protein targets (42, 43). By setting low molecular weight limits for compound screening. FBLD reduces the total possible number of atomic combinations by tens of orders of magnitude compared to traditional molecular weight cutoffs (~500 Da) used for HTS[45]. Fragment screens accordingly enable the exploration of a larger fraction of small-molecule-protein interaction space with a much smaller and more simplified library of compounds that tend to have superior ligand efficiencies compared to HTS hits[43]. Fragment screens typically have higher hit rates than HTS, but, due to the low-affinity of these hits, FBLD has, to date, been limited to the study of purified protein targets, where ligand-protein interactions can be characterized by biophysical methods (e.g. NMR, X-ray)[42].

To addresses these limitations, we developed a powerful approach that integrates fragment-based ligand discovery with chemical proteomics, called fragment-based ligand mapping in cells (FbLMiC, FIG. 1A), to globally survey ligandable proteins and their ligandable sites[46, 47]. In this approach, small-molecule probes, called fully functionalized fragment (FFF) probes contain (FIG. 1B-C): 1) a structurally minimized "constant" region bearing a photoactivatable diazirine group and alkyne handle, which together enable UV light-induced covalent modification and detection, enrichment, and identification of compound-bound protein targets; and 2) a "variable" recognition region consisting of structurally diverse small-molecule fragments (MW<300 Da) to promote interactions with a subset of the proteome. Notable strengths of FbLMiC are: 1) probe-protein interactions can be trapped and identified from living cells, preserving labile interactions that might be disrupted by cell lysis; 2) FFF probes interact at functional protein sites (e.g. active sites, allosteric sites, and sites of protein-protein interactions); 3) efficient enrichment and identification of low-abundance and low-affinity proteins enabled by covalent trapping; and 4) fragments can be optimized into higher affinity ligands through a FbLMiC-guided medicinal chemistry. This platform has outstanding proteomic coverage with a still growing unprecedented ligandability map of 4000+ human proteins, including proteins that fall out of traditional "druggable" classes (e.g. adaptor proteins, transcription factors) and the vast majority currently lack chemical probes (FIG. 1C).

Using our FbLMiC platform, we have identified over 100 SLC-FFF interactions directly in human cell lines and primary immune cells. Furthermore, we demonstrated that these FFF-SLC interactions can be starting points for SLC inhibitor development[46]. For example, we recently identified a coumarin-based FFF (FFF 3) that highly engages the acylcaritine transporter SLC25A20[46]. Through FbLMiC-assisted medicinal chemistry, we developed a first-in-class inhibitor (CP22) for SLC25A20 and used it to characterize SLC25A20 function in the context of fatty acid metabolism. Using a combination of FFF 3, the structurally similar CP26 that does not engage SLC25A20 and CP22, we demonstrated that 1) pharmacological inhibitors engage the intermembrane side of the transport domain of SLC25A20 (FIG. 2C); 2) blockade of SLC25A20 transport led to the build-up of long-chain acylcarnitines (>C14) (FIG. 2D), suggesting these as the main SLC25A20 substrates; and 3) blockade of SLC25A20 transport inhibits fatty-acid oxidation. As noted in the next sections, we have used FbLMiC do develop first generation inhibitors of SLC15A4. Herein, we propose to use these chemical probes to investigate the mechanism(s) by which SLC15A4 drives cytokine production in immune cells and to assess its potential as therapeutic target for the treatment of autoimmune conditions, such as lupus.

Previous studies have established that SLC15A4 has a unique and critical role in the production of IFN-1 and other inflammatory cytokines in pDCs as well as in the pathogenesis of autoimmune conditions, elevating SLC15A4 as a potential therapeutic target for such disorders. However. SLC15A4 heretofore remains undrugged and no inhibitors have been disclosed. Our application describes an enabling chemical proteomic strategy for the development of first-in-class inhibitors of SLC15A4 that block SLC15A4 transport and suppress IFN-I production in human and mouse pDCs, in-cell target engagement capabilities, structurally similar but inactive control compounds. Currently our lead inhibitors can suppress IFN-I production with an IC50~200 nM in primary human pDCs.

Figure 2A:
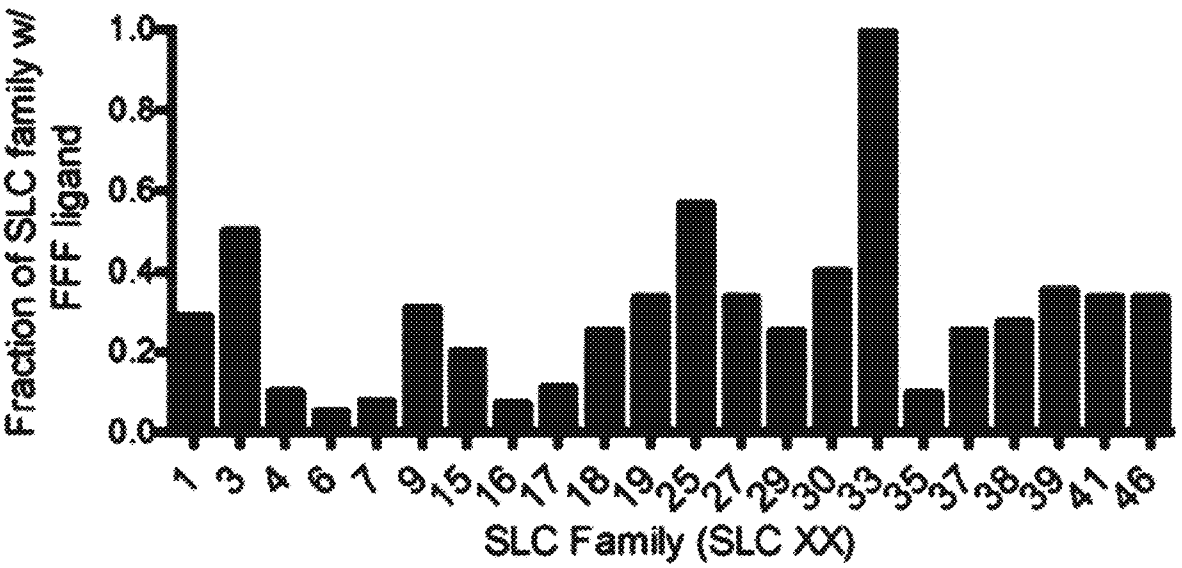
FIGS. 2A-2D represent the chemical proteomic development of SLC chemical probes. (A) Overview of identified fragment-SLC interactions using FbLMiC in HEK293T, K562 and human PBMC cells. SLCs are considered FFF targets if they are reproducibility enriched >5-fold over a control methyl FFF probe (in at least biological replicate)
Figure 2B:
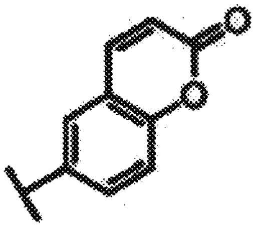
Figure 2B:
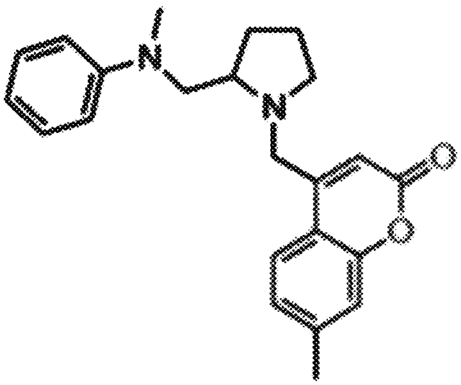
Figure 2B:
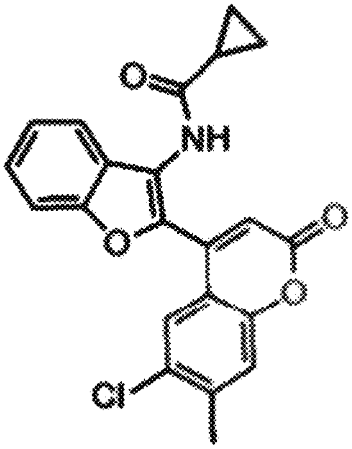
Figure 2C:
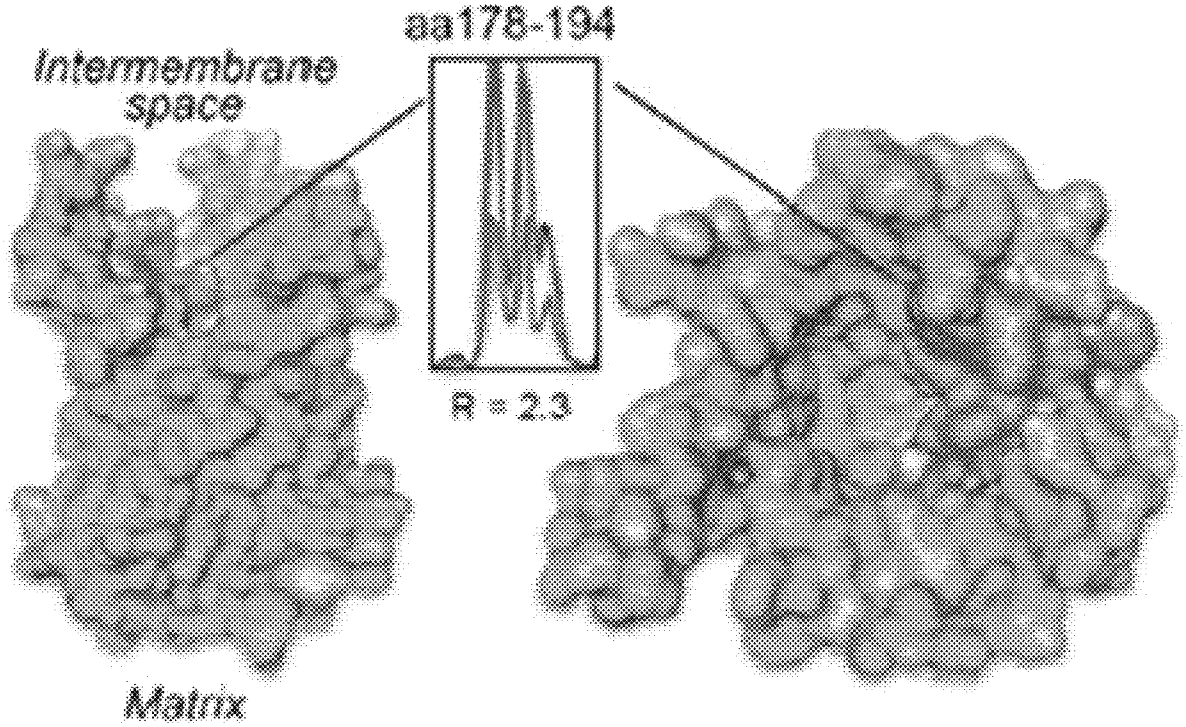
Figure 2D:
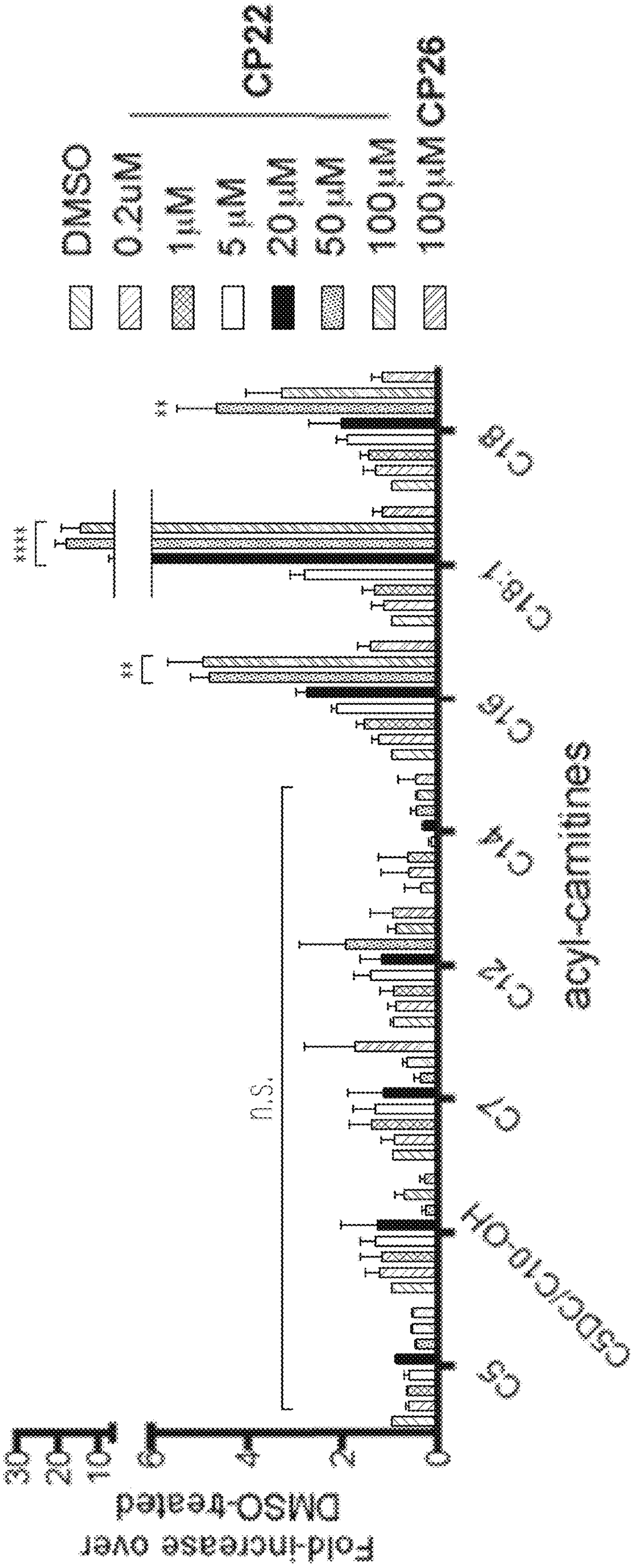
Figure 3A:
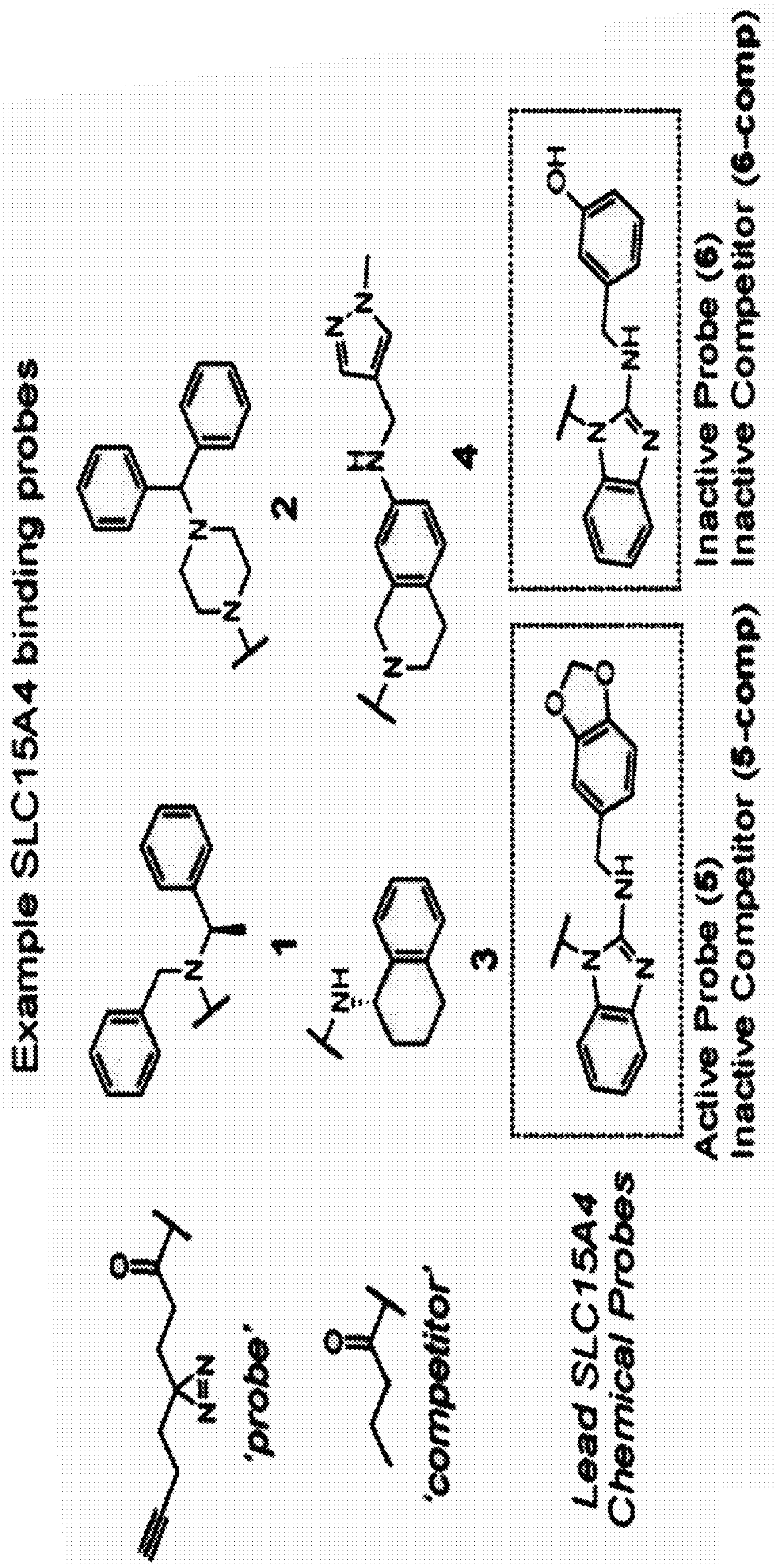
Figure 3B:
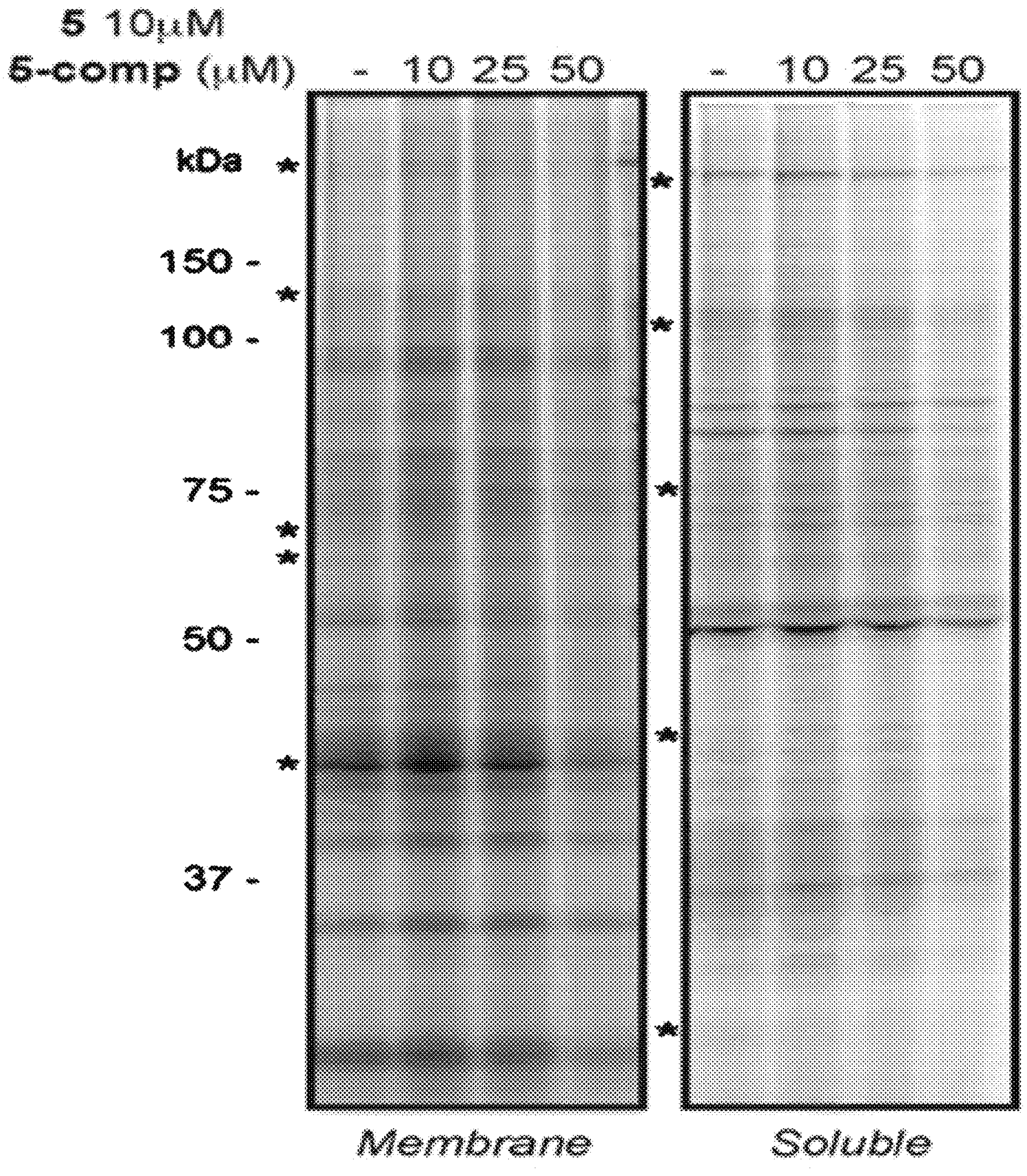
Figure 3C:
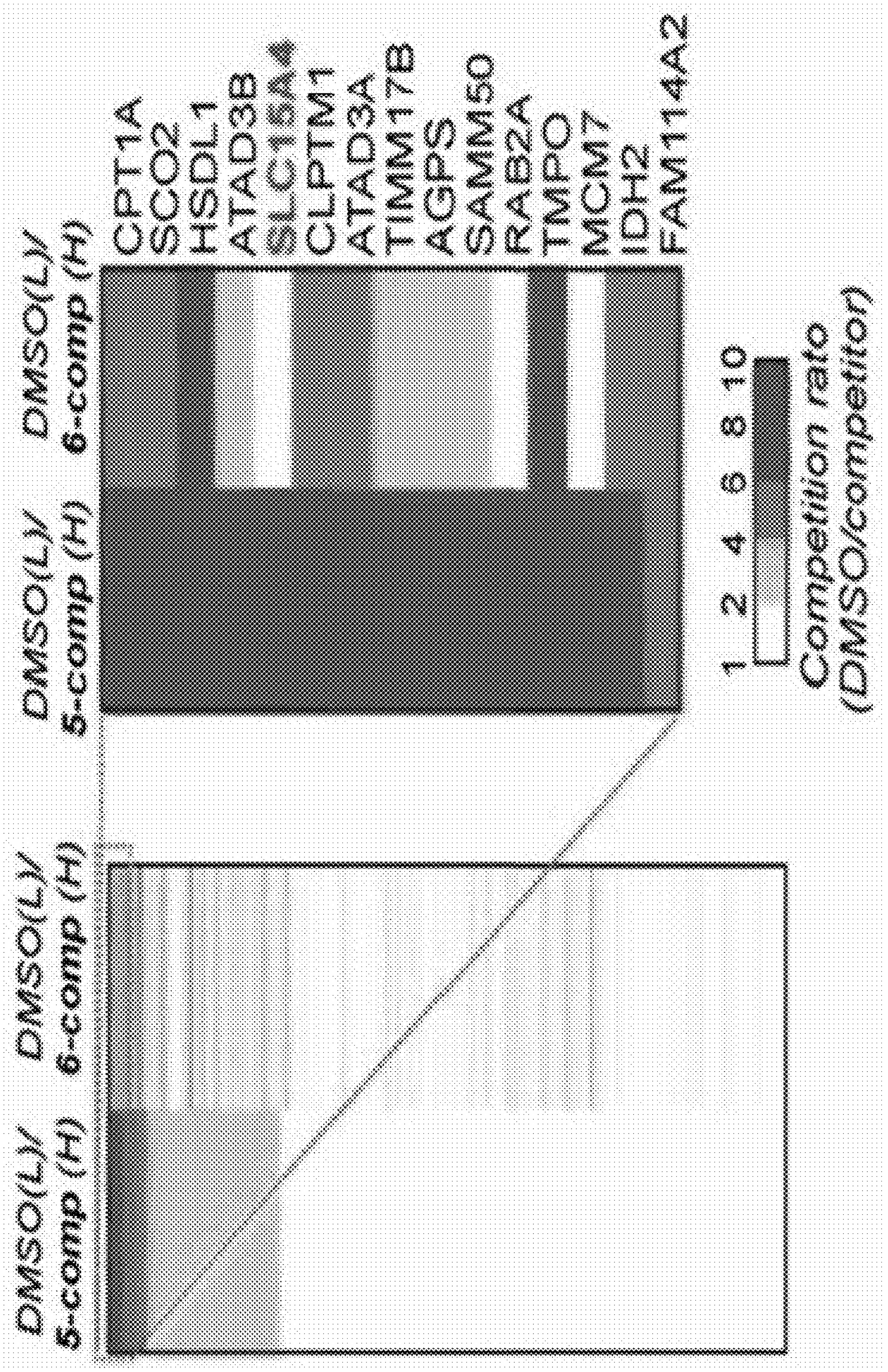
Figure 3D:
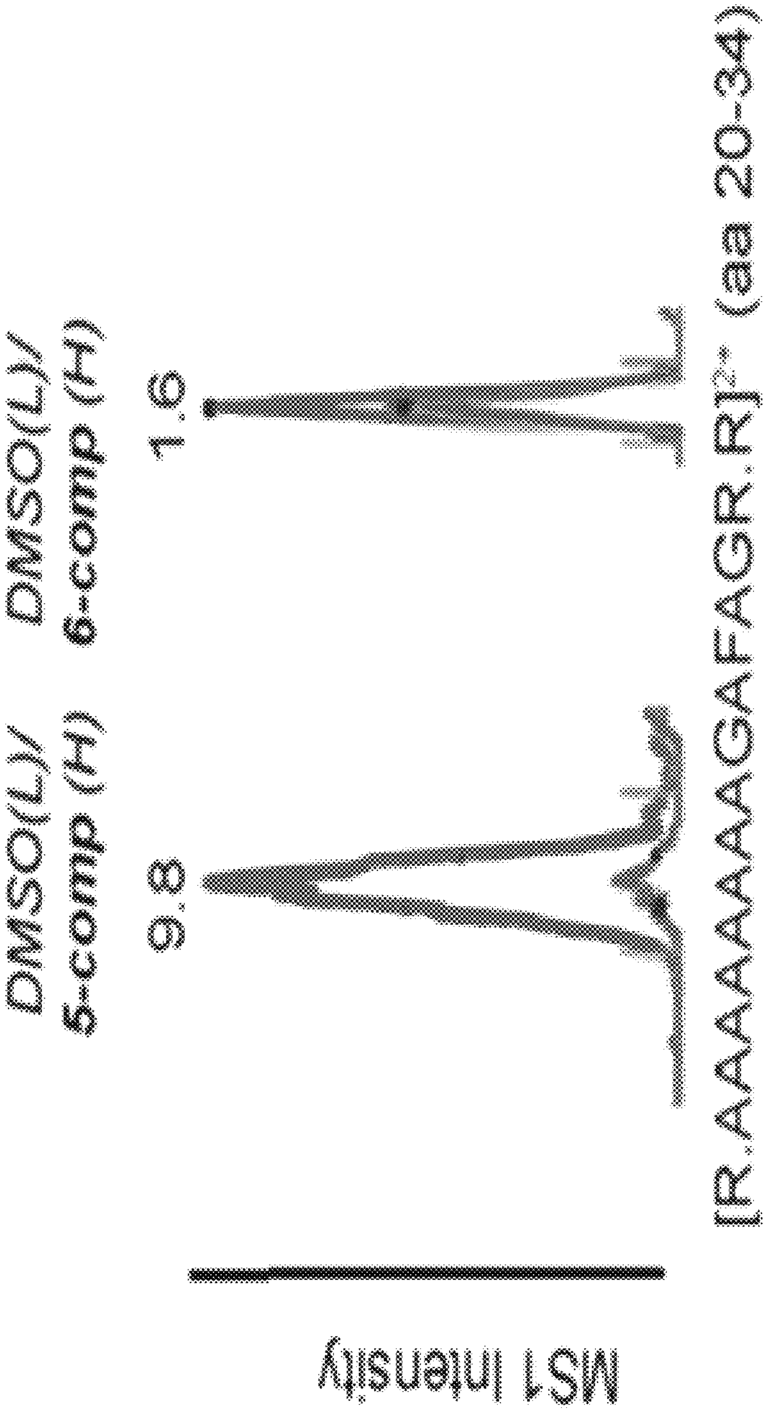
Figure 4A:
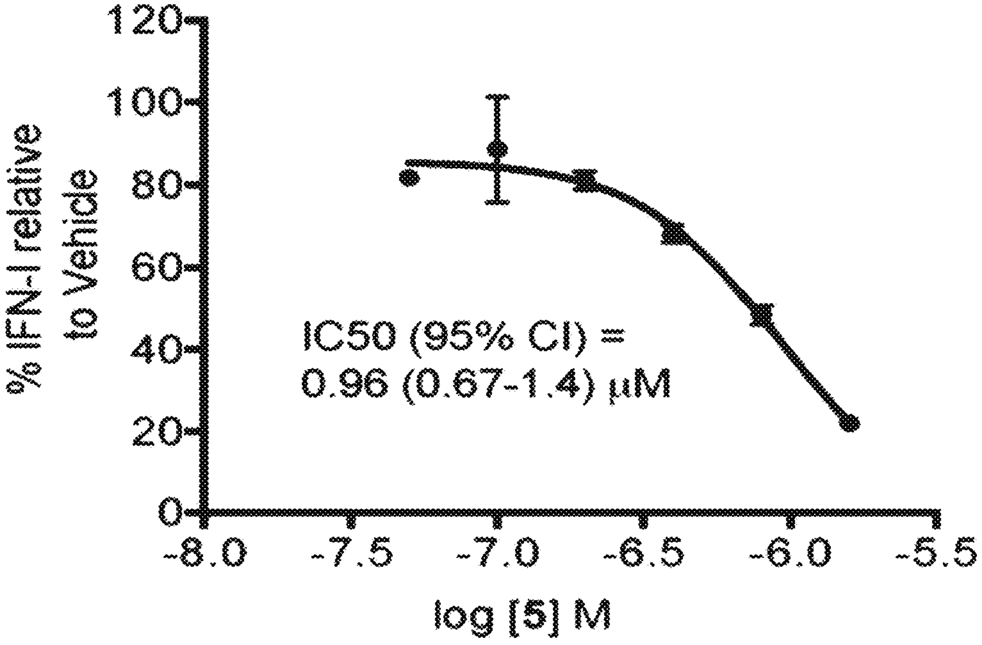
Figure 4B:
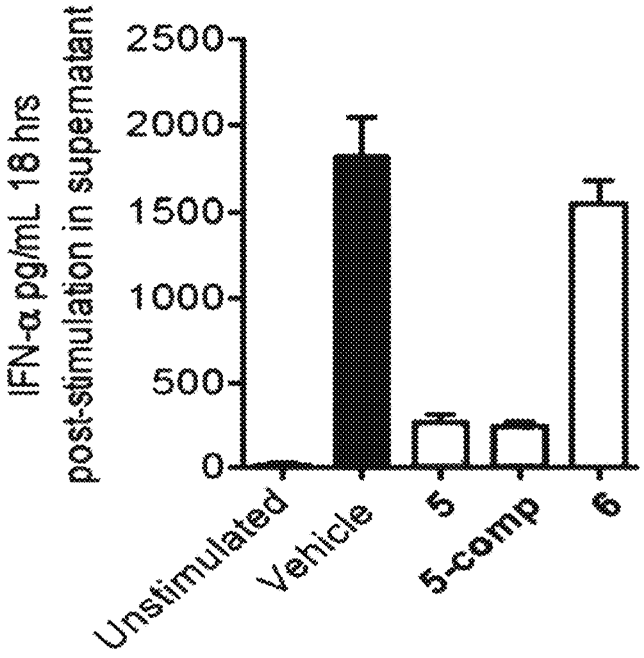
Figure 4C:
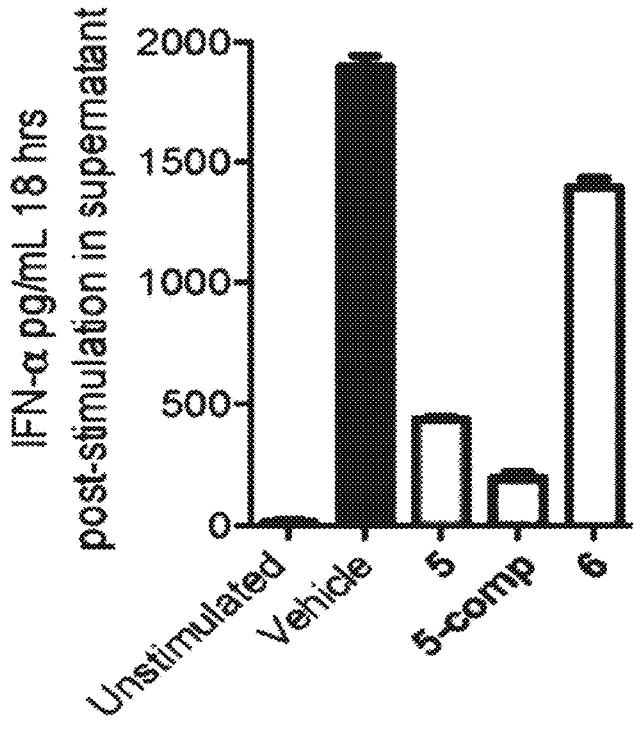
Figure 4D:
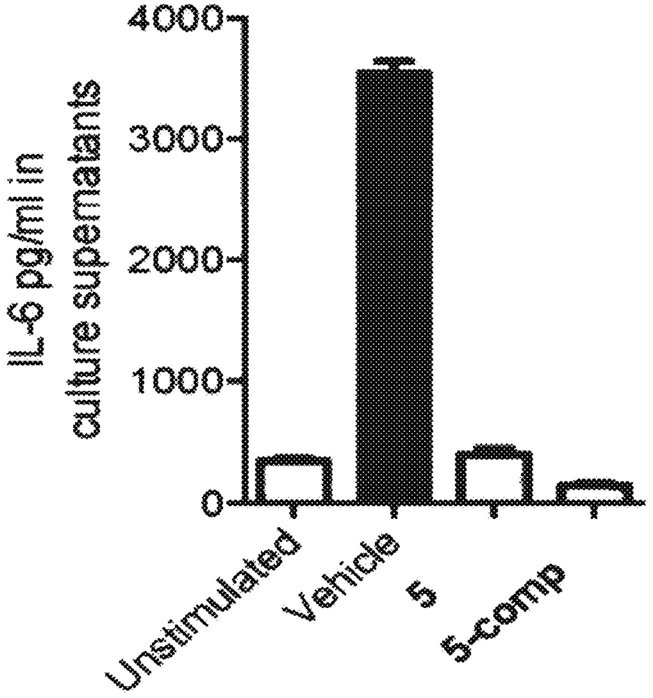

Chemoproteomic Development of SLC15A4 Chemical Probes. To identify small molecule fragments that might serve as leads for SLC15A4 inhibitor development, we searched our previously published data sets using FbLMiC[46, 47] and screened a small (~30) in-house library of FFFs in human peripheral blood mononuclear cells (PBMCs) (20 and 200 mM) via multiplexed proteomics, as previously described[47]. Briefly (FIG. 1A), freshly isolated PBMCs from healthy donor blood were treated with FFF for 30 min, exposed to UV irradiation to capture fragment-bound proteins, lysed, conjugated to a biotin-azide tag by copper (I)-catalyzed alkyne-azide cycloaddition (CuAAC, or 'click chemistry'), and fragment-labeled proteins enriched with streptavidin-coated beads. Enriched proteins were trypsinized, the resulting peptides labeled with tandem mass tags (TMT, for quantitation), analyzed by LC-MS/MS/MS and proteins were identified and quantified by their MS1/MS2 and MS3 signals respectively. Candidate targets were defined as proteins that were enriched (>5-fold) by the hit FFF over a control FFF (a methyl fragment). We identified several fragments that substantially enriched endogenous SLC15A4 (FIG. 3A). To prioritize potential leads that might perturb SLC15A4 function, we examined whether they modulated IFN-I production in TLR-stimulated human pDCs. Briefly, human pDCs were isolated from PBMCs using a commercially available negative selection kit (Miltenyi), treated with CpG-A DNA (4 ug/mL) for 1 hr, followed by FFF (20 μM) and incubated overnight at 37° C. The following day supernatants were harvested and IFN-α levels quantified by ELISA. FFF 5 was found to substantially suppress IFN-I levels (FIG. 4) while others did so moderately (not shown). In addition, we identified a structurally similar probe (FFF 6) that did not engage SLC15A4 nor suppress IFN-1. We subsequently synthesized 'non-clickable' versions of FFF 5 and FFF 6 in order to identify high-stoichiometry ligand-protein interactions via competition experiments with FFF 5+/− excess of 'non-clickable' competitors by both fluorescence gel-based (FIG. 3B) and MS-based experiments (FIG. 3C). We identified 14 proteins that were substantially enriched by FFF 5 (20 μM) and competed (>4-fold) by treatment with excess 5-comp, several of which were also competed by inactive control 6-comp. Among the highest competed targets was SLC15A4, which was not competed by inactive 6-comp, indicating it to be a high stoichiometry target of FFF 5 and 5-comp (FIG. 2C-D). Furthermore, we observe no evidence of 5 interacting with SLC15A3 in any of our proteomic studies. We subsequently confirmed that FFF 5 suppresses IFN-1 production in a dose-dependent (1050~1 mM) fashion (FIG. 4A) and both FFF 5 and 5-comp, but not inactive analog 6, can suppress inflammatory cytokine production in both human and mouse pDCs (isolation described in Aim 1) (FIG. 4B-D).

Development of SLC15A4-Transport Luciferase Reporter Assay. To assess whether FFF 5 and related compounds inhibit SLC15A4 transport, we generated a SLC15A4 transport-based reporter cell line. The precise substrate scope of endolysosomal SLC15A4 is not established. However, several studies have implicated SLC15A4 to be a transporter of the bacterial-derived peptidoglycans, such as MDP and Tri-DAP, which are ligands of the immune sensors NOD1 and NOD2[27-29, 48]. Recently, it has been shown that disruption of the dileucine motifs (DE)-XXXL-(L/I) or DXXLL of SLC15A3[49] and SLC15A4[50] can result in successful targeting to the plasma membrane. Considering that NODs signal through the NFκB pathway, we sought to develop an NFκB reporter assay as a strategy to measure SLC15A4 transport in cells.

Briefly, both wildtype (WT) human SLC15A4 and a dileucine mutant (L14A, LISA, L318A, V319A) were cloned in frame with the mCherry using a $(GGGGS)_3$ linker in the pLPC lentiviral backbone. Lentiviral vectors were packaged in psPAX2 and pMD2.G packing plasmids and used to generate stable cell lines expressing either SLC15A4 WT or membrane-trafficked SLC15A4 mutant A549 cells (FIG. 5A). Stable reporter cells were subsequently generated from these SLC15A4 cell lines using the Promega Dual-Luciferase Reporter system (pGLA4.32 [luc2P/NFκB-RE/Hygro]) containing five copies of an NF-κB response element. We confirmed the production of luciferase upon exposure to MDP or Tri-DAP NOD ligands (FIG. 6B-C), which is suppressed when exposed to either triptolide (an NF□B inhibitor, FIG. 5C) ML130 (NOD1 inhibitor, not shown) or GSK717 (NOD2 inhibitor, not shown). Further, FFF 5, but not FFF 6 blocked MDP-induced luciferase, together demonstrating that FFF 5 blocks SLC15A4-mediated transport.

Figure 6D:
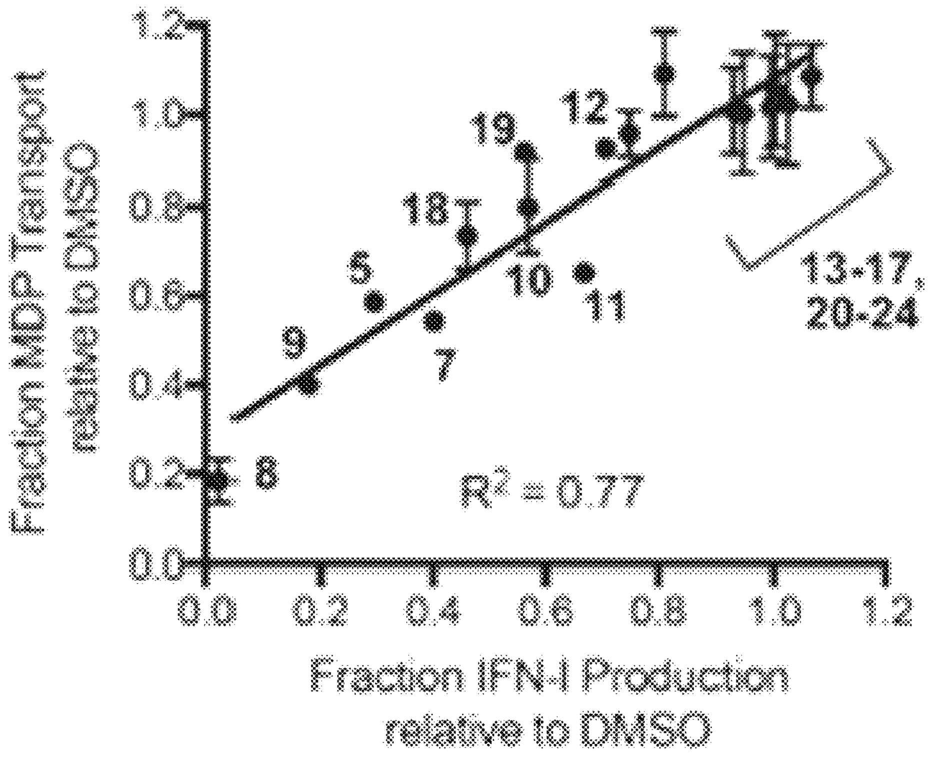
Figure 6E:
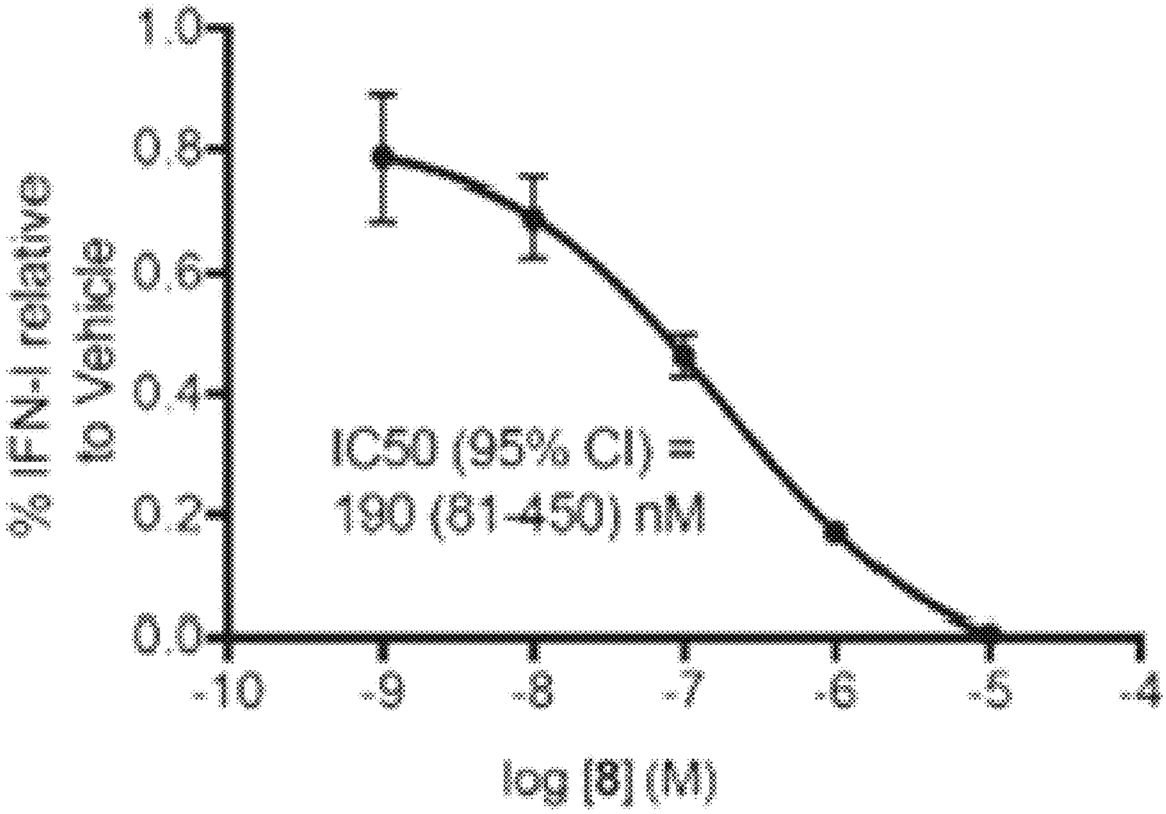

Preliminary Structure-Activity Relationship (SAR) Studies. With no structures or prior art—we set out to develop a robust and simple synthetic strategy that would provide access to numerous and diverse scaffolds in 2-3 simple synthetic steps from readily available starting materials to enable rapid synthetic exploration of chemical features that would enhance SLC15A4 inhibitory activity and if necessary, improve PK properties for in vivo studies (Aim 2). To this end, we divided 5-comp into three primary chemical regions: benzimidazole—purple, butanoyl—red, and benzodioxole/aromatic—green (FIG. 6A) and in preliminary studies synthesized 18 analogs of 5-comp (7-24, FIG. 6B) through the simple synthetic routes (FIG. 6A). Briefly, readily available aromatic aldehydes (green) are coupled to benzimidzole (Int-1A, top route) or other aromatic-containing amines (Int-1B, bottom route) using standard reductive amination conditions to furnish intermediate Int-A2/Int-B2 which can then be used to diversify at the N1 position of the benzimidazole through treatment with a wide variety of acyl chlorides or coupling to acids (3) or through alkylation reactions. We first examined the cytoxicity of analogs at in primary human pDCs at 10 □M, revealing no signs of substational toxic effects. We next examined the ability of 7-24 to 1) suppress IFN-I production in TLR7 (CpG)-stimulated human pDCs; and 2) block SLC15A4-mediated MDP transport (FIG. 7D). Virtually all substitutions of the benzimidazole ring (21-24) disrupted activity, while various substitutions at the butanoyl (red, 16-20) and benzodioxole (green, 7-15) positions were more tolerated. Specifically, we found the 5-bromoindole analog 8 to be the most potent in both assays, with an IFN-I suppression IC50 of 190 nM (FIG. 6E), a ~5-fold improvement over 5-comp. We also identified several analogs (13-17, 20-24) that showed no activity, representing additional valuable control compounds for functional investigations. Notably, we found a strong correlation of activity for each compound in both assays; that is, analogs that suppressed IFN-1 production also blocked MDP transport to a similar magnitude (FIG. 6D). The concurrence between assays is suggestive of a mechanism in which inhibitor interactions with SLC15A4 affects both activities similarly and is therefore in alignment with a hypothesis that transport function be mechanistically connected to subsequent TLR-signaling in pDCs.

INCORPORATION BY REFERENCE

All of the U.S. patents and U.S. patent application publications cited herein are hereby incorporated by reference.

EQUIVALENTS

Those skilled in the art will recognize or be able to ascertain using no more than routine experimentation, many equivalents to the specific embodiments of the disclosure described herein. Such equivalents are encompassed by the following claims.

REFERENCES

1. Pandey S, Kawai T, Akira S. Microbial sensing by Toll-like receptors and intracellular nucleic acid sensors. Cold Spring Harb Perspect Biol. 2014:7(1):a016246. Epub 2014 Oct. 11. doi: 10.1101/cshperspect.a016246. PubMed PMID: 25301932; PMCID: PMC4292165.
2. Blasius A L, Beutler B. Intracellular toll-like receptors. Immunity. 2010; 32(3):305-15. Epub 2010 Mar. 30. doi: 10.1016/j.immuni.2010.03.012. PubMed PMID: 20346772.
3. Wen H, Miao E A, Ting J P. Mechanisms of NOD-like receptor-associated inflammasome activation. Immunity. 2013; 39(3):432-41. Epub 2013 Sep. 24. doi: 10.1016/j.immuni.2013.08.037. PubMed PMID: 24054327; PMCID: PMC3835203.
4. Richez C, Blanco P, Rifkin I, Moreau J F, Schaeverbeke T. Role for toll-like receptors in autoimmune disease: The example of systemic lupus erythematosus. Joint Bone Spine. 2011; 78(2):124-30. doi: 10.1016/j.jbspin.2010.09.005. PubMed PMID: WOS: 000288017400005.
5. Ma Z Y, Zhang E J, Yang D L, Lu M J. Contribution of Toll-like receptors to the control of hepatitis B virus infection by initiating antiviral innate responses and promoting specific adaptive immune responses. Cellular & Molecular Immunology. 2015; 12(3):273-82. doi: 10.1038/cmi.2014.112. PubMed PMID: WOS: 000353919700006.
6. Iwasaki A, Medzhitov R. Toll-like receptor control of the adaptive immune responses. Nature Immunology. 2004; 5(10):987-95. doi: 10.1038/ni1112. PubMed PMID: WOS:000224156600005.
7. Theofilopoulos A N, Kono D H, Baccala R. The multiple pathways to autoimmunity. Nat Immunol. 2017; 18(7): 716-24. Epub 2017 Jun. 21. doi: 10.1038/ni.3731. PubMed PMID: 28632714; PMCID: PMC5791156.
8. Kono D H, Baccala R, Theofilopoulos A N. TLRs and interferons: a central paradigm in autoimmunity. Cuff Opin Immunol. 2013; 25(6):720-7. Epub 2013 Nov. 20. doi: 10.1016/j.coi.2013.10.006. PubMed PMID: 24246388; PMCID: PMC4309276.
9. Reizis B, Bunin A, Ghosh H S, Lewis K L, Sisirak V. Plasmacytoid dendritic cells: recent progress and open questions. Annu Rev Immunol. 2011; 29:163-83. Epub 2011 Jan. 12. doi: 10.1146/annurev-immunol-031210-101345. PubMed PMID: 21219184; PMCID: PMC4160806.
10. Gilliet M, Cao W, Liu Y J. Plasmacytoid dendritic cells: sensing nucleic acids in viral infection and autoimmune diseases. Nat Rev Immunol. 2008; 8(8):594-606. Epub 2008 Jul. 22. doi: 10.1038/nri2358. PubMed PMID: 18641647.
11. Penna G, Vulcano M, Roncari A, Facchetti F, Sozzani S, Adorini L. Cutting edge: differential chemokine production by myeloid and plasmacytoid dendritic cells. J Immunol. 2002:169(12):6673-6. Epub 2002 Dec. 10. doi: 10.4049/jimmunol.169.12.6673. PubMed PMID: 12471096.
12. Ochando J C, Homma C, Yang Y, Hidalgo A, Garin A, Tacke F, Angeli V, Li Y, Boros P, Ding Y, Jessberger R, Trinchieri G, Lira S A, Randolph G J, Bromberg J S. Alloantigen-presenting plasmacytoid dendritic cells mediate tolerance to vascularized grafts. Nat Immunol. 2006; 7(6):652-62. Epub 2006/04/25. doi: 10.1038/ni1333. PubMed PMID: 1663334.6.

13. Villadangos J A, Young L. Antigen-presentation properties of plasmacytoid dendritic cells. Immunity. 2008; 29(3):352-61. Epub 2008 Sep. 19. doi: 10.1016/j.immuni.2008.09.002. PubMed PMID: 18799143.
14. Ding C, Cai Y, Marroquin J, Ildstad S T, Yan J. Plasmacytoid dendritic cells regulate autoreactive B cell activation via soluble factors and in a cell-to-cell contact manner. J Immunol. 2009; 183(11):7140-9. Epub 2009 Nov. 6. doi: 10.4049/jimmunol.0901175. PubMed PMID: 19890051; PMCID: PMC3351849.
15. Jego G. Palucka A K, Blanck J P, Chalouni C, Pascual V, Banchereau J. Plasmacytoid dendritic cells induce plasma cell differentiation through type I interferon and interleukin 6. Immunity. 2003; 19(2):225-34. Epub 2003 Aug. 23. doi: 10.1016/s1074-7613(03)00208-5. PubMed PMID: 12932356.
16. Yuan Y, Ma H, Ye Z, Jing W, Jiang Z. Interferon-stimulated gene 15 expression in systemic lupus erythematosus: Diagnostic value and association with lymphocytopenia. Z Rheumatol. 2018; 77(3):256-62. doi: 10.1007/s00393-017-0274-8. PubMed PMID: 28204879.
17. Pashenkov M, Huang Y M, Kostulas V, Haglund M, Soderstrom M, Link H. Two subsets of dendritic cells are present in human cerebrospinal fluid. Brain. 2001; 124(Pt 3):480 92. PubMed PMID: 11222448.
18. Serafini B, Rosicarelli B, Franciotta D, Magliozzi R, Reynolds R, Cinque P, Andreoni L, Trivedi P, Salvetti M, Faggioni A, Aloisi F. Dysregulated Epstein-Barr virus infection in the multiple sclerosis brain. J Exp Med. 2007; 204(12):2899-912. doi: 10.1084/jem.20071030. PubMed PMID: 17984305; PMCID: PMC2118531.
19. Li P, Zheng Y, Chen X. Drugs for Autoimmune Inflammatory Diseases: From Small Molecule Compounds to Anti-TNF Biologics. Front Pharmacol. 2017; 8:460. Epub 2017 Aug. 9. doi: 10.3389/fphar.2017.00460. PubMed PMID: 28785220; PMCID: PMC5506195.
20. Darvin P, Toor S M, Sasidharan Nair V, Elkord E. Immune checkpoint inhibitors: recent progress and potential biomarkers. Exp Mol Med. 2018; 50(12):165. Epub 2018 Dec. 14. doi: 10.1038/s12276-018-0191-1. PubMed PMID: 30546008; PMCID: PMC6292890.
21. Gao W, Xiong Y, Li Q, Yang H. Inhibition of Toll-Like Receptor Signaling as a Promising Therapy for Inflammatory Diseases: A Journey from Molecular to Nano Therapeutics. Frontiers in Physiology. 2017; 8. doi: ARTN 508 10.3389/fphys.2017.00508. PubMed PMID: WOS:000405889400001.
22. Botka C W, Wittig T W, Graul R C, Nielsen C U, Higaka K, Amidon G L, Sadee W. Human proton/oligopeptide transporter (POT) genes: identification of putative human genes using bioinformatics. AAPS PharmSci. 2000; 2(2): E16. Epub 2001 Dec. 14. doi: 10.1208/ps020216. PubMed PMID: 11741232; PMCID: PMC2751030.
23. Sakata K, Yamashita T, Maeda M, Moriyama Y, Shimada S, Tohyama M. Cloning of a lymphatic peptide/histidine transporter. Biochem J. 2001:356(Pt 1):53-60. Epub 2001 May 5. doi: 10.1042/0264-6021:3560053. PubMed PMID: 11336635; PMCID: PMC1221811.
24. Yamashita T, Shimada S, Guo W, Sato K, Kohmura E, Hayakawa T, Takagi T, Tohyama M. Cloning and functional expression of a brain peptide/histidine transporter. J Biol Chem. 1997; 272(15):10205-11. Epub 1997 Apr. 11. doi: 10.1074/jbc.272.15.10205. PubMed PMID: 9092568.
25. Nakamura N, Tanaka S, Teko Y, Mitsui K, Kanazawa H. Four Na+/H+ exchanger isoforms are distributed to Golgi and post-Golgi compartments and are involved in organelle pH regulation. J Biol Chem. 2005; 280(2):1561-72. Epub 2004 Nov. 4. doi: 10.1074/jbc.M410041200. PubMed PMID: 15522866.
26. Mellman I, Fuchs R, Helenius A. Acidification of the endocytic and exocytic pathways. Annu Rev Biochem. 1986; 55:663-700. Epub 1986 Jan. 1. doi: 10.1146/annurev.bi 0.55.070186.003311. PubMed PMID: 2874766.
27. Caruso R, Warner N, Inohara N, Nunez G. NOD1 and NOD2: signaling, host defense, and inflammatory disease. Immunity. 2014; 41(6):898-908. Epub 2014 Dec. 20. doi: 10.1016/j.immuni.2014.12.010. PubMed PMID: 25526305; PMCID: PMC4272446.
28. Hu Y, Song F, Jiang H, Nunez G. Smith D E. SLC15A2 and SLC15A4 Mediate the Transport of Bacterially Derived Di/Tripeptides To Enhance the Nucleotide-Binding Oligomerization Domain-Dependent Immune Response in Mouse Bone Marrow-Derived Macrophages. J Immunol. 2018; 201(2):652-62. Epub 2018 May 23. doi: 10.4049/jimmunol.1800210. PubMed PMID: 29784761; PMCID: PMC6039277.
29. Nakamura N, Lill J R, Phung Q. Jiang Z. Bakalarski C, de Maziere A, Klumperman J, Schlatter M, Delamarre L, Mellman I. Endosomes are specialized platforms for bacterial sensing and NOD2 signalling. Nature. 2014; 509(7499):240-4. Epub 2014 Apr. 4. doi: 10.1038/nature13133. PubMed PMID: 24695226.
30. Sasawatari S, Okamura T. Kasumi E. Tanaka-Furuyama K, Yanobu-Takanashi R, Shirasawa S. Kato N, Toyama-Sorimachi N. The solute carrier family 15A4 regulates TLR9 and NOD functions in the innate immune system and promotes colitis in mice. Gastroenterology. 2011; 140(5):1513-25. Epub 2011 Feb. 1. doi: 10.1053/j.gastro.2011.01.041. PubMed PMID: 21277849.
31. Blasius A L, Arnold C N, Georgel P, Rutschmann S, Xia Y, Lin P, Ross C, Li X, Smart N G, Beutler B. Slc15a4, AP-3, and Hermansky-Pudlak syndrome proteins are required for Toll-like receptor signaling in plasmacytoid dendritic cells. Proc Natl Acad Sci USA. 2010; 107(46): 19973-8. Epub 2010 Nov. 4. doi: 10.1073/pnas.1014051107. PubMed PMID: 21045126; PMCID: PMC2993408.
32. Baccala R, Gonzalez-Quintial R, Blasius A L, Rimann I, Ozato K, Kono D H, Beutler B, Theofilopoulos A N. Essential requirement for IRF8 and SLC15A4 implicates plasmacytoid dendritic cells in the pathogenesis of lupus. Proc Natl Acad Sci USA. 2013; 110(8):2940-5. Epub 2013 Feb. 6. doi: 10.1073/pnas.1222798110. PubMed PMID: 23382217; PMCID: 3581947.
33. Zuo X B, Sheng Y J, Hu S J, Gao J P, Li Y, Tang H Y, Tang X F, Cheng H, Yin X Y, Wen L L, Sun L D, Yang S, Cui Y, Zhang X J. Variants in TNFSF4, TNFAIP3, TNIP1, BLK, SLC15A4 and UBE2L3 interact to confer risk of systemic lupus erythematosus in Chinese population. Rheumatology International. 2014; 34(4):459-64. doi: 10.1007/s00296-013-2864 3. PubMed PMID: WOS: 000333080300003.
34. Takeuchi F, Ochiai Y, Serizawa M, Yanai K, Kuzuya N, Kajio H, Honjo S, Takeda N, Kaburagi Y. Yasuda K, Shirasawa S, Sasazuki T. Kato N. Search for type 2 diabetes susceptibility genes on chromosomes 1q, 3q and 12q. Journal of Human Genetics. 2008; 53(4):314-24. doi: 10.1007/s10038-008-0254-6. PubMed PMID: WOS: 000254624500004.

35. Cesar-Razquin A, Snijder B, Frappier-Brinton T. Isserlin R, Gyimesi G, Bai X. Reithmeier R A, Hepworth D, Hediger M A, Edwards A M, Superti-Furga G. A Call for Systematic Research on Solute Carriers. Cell. 2015; 162 (3):478-87. doi: 10.1016/j.cell.2015.07.022. PubMed PMID: 26232220.

36. Lin L, Yee S W, Kim R B, Giacomini K M. SLC transporters as therapeutic targets: emerging opportunities. Nat Rev Drug Discov. 2015; 14(8):543-60. doi: 10.1038/nrd4626. PubMed PMID: WOS: 000359032700017.

37. O'Sullivan D. Pearce E L. Targeting T cell metabolism for therapy. Trends in Immunology. 201536(2):71-80. doi: 10.1016/j.it.2014.12.004. PubMed PMID: WOS: 000349731200004.

38. Wang W W, Gallo L, Jadhav A. Hawkins R, Parker C G. The Druggability of Solute Carriers. J Med Chem. 2019. Epub 2019 Nov. 28. doi: 10.1021/acs.jmedchem.9b01237. PubMed PMID: 31774679.

39. Bai X, Moraes T F, Reithmeier R A F. Structural biology of solute carrier (SLC) membrane transport proteins. Mol Membr Biol. 201734(1-2):1-32. Epub 2018 Apr. 14. doi: 10.1080/09687688.2018.1448123. PubMed PMID: 29651895.

40. Blagg J, Workman P. Chemical biology approaches to target validation in cancer. Curr Opin Pharmacol. 2014; 17:87-100. doi: 10.1016/j.coph.2014.07.007. PubMed PMID: 25175311.

41. Blagg J. Workman P. Choose and Use Your Chemical Probe Wisely to Explore Cancer Biology. Cancer Cell. 2017; 32(2):268-70. doi: 10.1016/j.cell.2017.07.010. PubMed PMID: 28810148; PMCID: PMC5559281.

42. Hajduk P J, Greer J. A decade of fragment-based drug design: strategic advances and lessons learned. Nature reviews Drug discovery. 2007; 6(3):211-9. doi: 10.1038/nrd2220. PubMed PMID: 17290284.

43. Bembenek S D, Tounge B A, Reynolds C H. Ligand efficiency and fragment-based drug discovery. Drug discovery today. 2009; 14(5-6):278-83. doi: 10.1016/j.drudis.2008.11.007. PubMed PMID: 19073276.

44. Lipinski C, Hopkins A. Navigating chemical space for biology and medicine. Nature. 2004; 432(7019):855-61. doi: 10.1038/nature03193. PubMed PMID: 15602551.

45. Fink T, Bruggesser H, Reymond J L. Virtual exploration of the small-molecule chemical universe below 160 Daltons. Angew Chem Int Ed Engl. 2005; 44(10):1504-8. doi: 10.1002/anie.200462457. PubMed PMID: 15674983.

46. Parker C G, Galmozzi A, Wang Y, Correia B E, Sasaki K, Joslyn C M, Kim A S, Cavallaro C L, Lawrence R M, Johnson S R, Narvaiza I, Saez E, Cravatt B F. Ligand and Target Discovery by Fragment-Based Screening in Human Cells. Cell. 2017; 168(3):527-41 e29. Epub 2017 Jan. 24. doi: 10.1016/j.cell.2016.12.029. PubMed PMID: 28111073; PMCID: PMC5632530.

47. Wang Y. Dix M M, Bianco G, Remsberg J R, Lee H Y, Kalocsay M, Gygi S P, Forli S. Vite G, Lawrence R M, Parker C G, Cravatt B F. Expedited mapping of the ligandable proteome using fully functionalized enantiomeric probe pairs. Nat Chem. 2019:11(12):1113-23. Epub 2019 Oct. 30. doi: 10.1038/s41557-019-0351-5. PubMed PMID: 31659311; PMCID: PMC6874898.

48. Lee J, Tattoli I, Wojtal K A, Vavricka S R, Philpott D J, Girardin S E. pH-dependent internalization of muramyl peptides from early endosomes enables Nod1 and Nod2 signaling. J Biol Chem. 2009; 284(35):23818-29. Epub 2009/07/03. doi: 10.1074/jbc.M109.033670. PubMed PMID: 19570976; PMCID: PMC2749154.

49. Nakamura N, Lill J R, Phung Q, Jiang Z S, Bakalarski C, de Maziere A. Klumperman J, Schlatter M, Delamarre L, Mellman I. Endosomes are specialized platforms for bacterial sensing and NOD2 signalling. Nature. 2014; 509(7499):240-+. doi: 10.1038/nature13133. PubMed PMID: WOS:000335454300042.

50. Song F F, Hu Y J, Wang Y Q, Smith D E, Jiang H D. Functional Characterization of Human Peptide/Histidine Transporter 1 in Stably Transfected MDCK Cells. Molecular Pharmaceutics. 2018; 15(2):385-93. doi: 10.1021/acs.molpharmaceut.7b00728. PubMed PMID: WOS:000424730900005.

51. Martinez Molledo M, Quistgaard E M, Flayhan A, Pieprzyk J, Low C. Multispecific Substrate Recognition in a Proton-Dependent Oligopeptide Transporter. Structure. 2018; 26(3):467-76 e4. Epub 2018 Feb. 13. doi: 10.1016/j.str.2018.01.005. PubMed PMID: 29429879; PMCID: PMC5845931.

52. Rutz M, Metzger J, Gellert T, Luppa P, Lipford G B, Wagner H, Bauer S. Toll-like receptor 9 binds single-stranded CpG-DNA in a sequence- and pH-dependent manner. European Journal of Immunology. 2004; 34(9): 2541-50. doi: 10.1002/eji.200425218. PubMed PMID: WOS:000223810400020.

53. Ewald S E, Engel A, Lee J, Wang M, Bogyo M, Barton G M. Nucleic acid recognition by Toll-like receptors is coupled to stepwise processing by cathepsins and asparagine endopeptidase. J Exp Med. 2011; 208(4):643-51. Epub 2011 Mar. 16. doi: 10.1084/jem.20100682. PubMed PMID: 21402738; PMCID: PMC3135342.

54. Majer O, Liu B, Barton G M. Nucleic acid-sensing TLRs: trafficking and regulation. Current Opinion in Immunology. 2017; 44:26-33. doi: 10.1016/j.coi.2016.10.003. PubMed PMID: WOS: 000403403800006.

55. Onji M, Kanno A, Saitoh S I, Fukui R, Motoi Y. Shibata T, Matsumoto F, Lamichhane A, Sato S, Kiyono H, Yamamoto K, Miyake K. An essential role for the N-terminal fragment of Toll-like receptor 9 in DNA sensing. Nature Communications. 2013; 4. doi: ARTN 1949 10.1038/ncomms2949. PubMed PMID: WOS: 000323624100017.

56. Sinha S S, Cameron J, Brooks J C, Leifer C A. Complex Negative Regulation of TLR9 by Multiple Proteolytic Cleavage Events. Journal of Immunology. 2016; 197(4): 1343-52. doi: 10.4049/jimmunol.1502357. PubMed PMID: WOS:000384999100033.

57. Rutz M, Metzger J. Gellert T. Luppa P, Lipford G B, Wagner H, Bauer S. Toll-like receptor 9 binds single-stranded CpG-DNA in a sequence- and pH-dependent manner. Eur J Immunol. 2004; 34(9):2541-50. Epub 2004 Aug. 13. doi: 10.1002/eji.200425218. PubMed PMID: 15307186.

58. Yi A K, Tuetken R, Redford T, Waldschmidt M, Kirsch J, Krieg A M. CpG motifs in bacterial DNA activate leukocytes through the pH-dependent generation of reactive oxygen species. J Immunol. 1998; 160(10):4755-61. Epub 1998 May 20. PubMed PMID: 9590221.

59. Brasel K, De Smedt T. Smith J L, Maliszewski C R. Generation of murine dendritic cells from flt3-ligand-supplemented bone marrow cultures. Blood. 2000; 96(9): 3029-39. Epub 2000 Oct. 26. PubMed PMID: 11049981.

60. Teijaro J R, Studer S, Leaf N, Kiosses W B, Nguyen N, Matsuki K, Negishi H, Taniguchi T, Oldstone M B, Rosen H. S1PR1-mediated IFNAR1 degradation modulates plasmacytoid dendritic cell interferon-alpha autoamplification. Proc Natl Acad Sci USA. 2016; 113(5):1351 6.

Epub 2016 Jan. 21. doi: 10.1073/pnas.1525356113. PubMed PMID: 26787880; PMCID: PMC4747766.

61. Ewald S E, Engel A, Lee J. Wang M Q, Bogyo M, Barton G M. Nucleic acid recognition by Toll-like receptors is coupled to stepwise processing by cathepsins and asparagine endopeptidase. Journal of Experimental Medicine. 2011; 208(4):643-51. doi: 10.1084/jem.20100682. PubMed PMID: WOS:000289404800002.
62. Kleifeld O, Doucet A, auf dem Keller U, Prudova A, Schilling O, Kainthan R K, Starr A E, Foster L J, Kizhakkedathu J N, Overall C M. Isotopic labeling of terminal amines in complex samples identifies protein N-termini and protease cleavage products. Nat Biotechnol. 2010; 28(3):281-8. Epub 2010 Mar. 9. doi: 10.1038/nbt.1611. PubMed PMID: 20208520.
63. Klein T. Fung S Y, Renner F, Blank M A, Dufour A, Kang S, Bolger-Munro M. Scurll J M, Priatel J J, Schweigler P, Melkko S, Gold M R, Viner R I, Regnier C H, Turvey S E, Overall C M. The paracaspase MALT1 cleaves HOIL1 reducing linear ubiquitination by LUBAC to dampen lymphocyte N F-kappaB signalling. Nat Commun. 2015; 6:8777. Epub 2015 Nov. 4. doi: 10.1038/ncomms9777. PubMed PMID: 26525107; PMCID: PMC4659944.
64. Wyant G A, Abu-Remaileh M, Wolfson R L, Chen W W, Freinkman E, Danai L V, Heiden M G V, Sabatini D M. mTORC1 Activator SLC38A9 Is Required to Efflux Essential Amino Acids from Lysosomes and Use Protein as a Nutrient. Cell. 2017; 171(3):642-+. doi: 10.1016/j.cell.2017.09.046. PubMed PMID: WOS: 000413263300014.
65. Rebsamen M, Pochini L, Stasyk T, de Araujo M E G, Galluccio M, Kandasamy R K, Snijder B, Fauster A, Rudashevskaya E L, Bruckner M, Scorzoni S, Filipek P A, Huber K V M, Bigenzahn J W, Heinz L X, Kraft C, Bennett K L, Indiveri C, Huber L A, Superti-Furga G. SLC38A9 is a component of the lysosomal amino acid sensing machinery that controls mTORC1. Nature. 2015; 519(7544):477-+. doi: 10.1038/nature14107. PubMed PMID: WOS:000351602800057.
66. Mattera R, Boehm M, Chaudhuri R, Prabhu Y, Bonifacino J S. Conservation and diversification of dileucine signal recognition by adaptor protein (A P) complex variants. J Biol Chem. 2011; 286(3):2022-30. Epub 2010 Nov. 26. doi: 10.1074/jbc.M110.197178. PubMed PMID: 21097499; PMCID: PMC3023499.
67. Dell'Angelica E C. AP-3-dependent trafficking and disease: the first decade. Curr Opin Cell Biol. 2009; 21(4):552-9. Epub 2009 Jun. 6. doi: 10.1016/j.ceb.2009.04.014. PubMed PMID: 19497727.
68. Lyons J A, Parker J L, Solcan N, Brinth A, Li D, Shah S T, Caffrey M, Newstead S. Structural basis for polyspecificity in the POT family of proton-coupled oligopeptide transporters. EMBO Rep. 2014; 15(8):886-93. Epub 2014 Jun. 12. doi: 10.15252/embr.201338403. PubMed PMID: 24916388; PMCID: PMC4149780.
69. Szychowski J, Mandavi A, Hodas J J, Bagert J D, Ngo J T, Landgraf P, Dieterich D C, Schuman E M, Tirrell D A. Cleavable biotin probes for labeling of biomolecules via azide-alkyne cycloaddition. J Am Chem Soc. 2010: 132(51):18351-60. Epub 2010 Dec. 15. doi: 10.1021/ja1083909. PubMed PMID: 21141861; PMCID: PMC3016050.
70. Minhas G S, Newstead S. Structural basis for prodrug recognition by the SLC15 family of proton-coupled peptide transporters. Proc Natl Acad Sci USA. 2019; 116(3): 804-9. Epub 2019 Jan. 4. doi: 10.1073/pnas.1813715116. PubMed PMID: 30602453; PMCID: PMC6338836.
71. Kobayashi T, Shimabukuro-Demoto S, Yoshida-Sugitani R, Furuyama-Tanaka K, Karyu H, Sugiura Y, Shimizu Y, Hosaka T, Goto M, Kato N, Okamura T, Suematsu M, Yokoyama S. Toyama-Sorimachi N. The histidine transporter SLC15A4 coordinates mTOR-dependent inflammatory responses and pathogenic antibody production. Immunity. 2014; 41(3):375-88. Epub 2014 Sep. 23. doi: 10.1016/j.immuni.2014.08.011. PubMed PMID: 25238095.
72. Ogasawara D, Ichu T A, Vartabedian V F, Benthuysen J, Jing H, Reed A, Ulanovskaya O A, Hulce J J, Roberts A, Brown S, Rosen H, Teijaro J R, Cravatt B F. Selective blockade of the lyso-PS lipase ABHD12 stimulates immune responses in vivo. Nat Chem Biol. 2018; 14(12): 1099-108. Epub 2018 Nov. 14. doi: 10.1038/s41589-018-0155-8. PubMed PMID: 30420694; PMCID: PMC6263940.
73. Zaro B W, Vinogradova E V, Lazar D C, Blewett M M, Suciu R M, Takaya J. Studer S, de la Torre J C, Casanova J L, Cravatt B F, Teijaro J R. Dimethyl Fumarate Disrupts Human Innate immune Signaling by Targeting the IRAK4-MyD88 Complex. J Immunol. 2019; 202(9): 2737-46. Epub 2019 Mar. 20. doi: 10.4049/jimmunol.1801627. PubMed PMID: 30885957; PMCID: PMC6478521.
74. Manzanero S. Generation of mouse bone marrow-derived macrophages. Methods Mol Biol. 2012; 844:177-81. Epub 2012 Jan. 21. doi: 10.1007/978-1-61779-527-5_12. PubMed PMID: 22262442.
75. Parker C G, Kuttruff C A, Galmozzi A, Jorgensen L, Yeh C H, Hermanson D J, Wang Y J, Artola M, McKerrall S J, Josyln C M, Norremark B, Dunstl G, Felding J, Saez E, Baran P S, Cravatt B F. Chemical Proteomics Identifies SLC25A20 as a Functional Target of the Ingenol Class of Actinic Keratosis Drugs. Acs Central Science. 2017; 3(12):1276-85. doi: 10.1021/acscentsci.7b00420. PubMed PMID: WOS:000418706200009.
76. Schonhoft J D, Monteiro C, Plate L, Eisele Y S, Kelly J M, Boland D, Parker C G, Cravatt B F, Teruya S, Helmke S, Maurer M, Berk J, Sekijima Y, Novais M, Coelho T, Powers E T, Kelly J W. Peptide probes detect misfolded transthyretin oligomers in plasma of hereditary amyloidosis patients. Science Translational Medicine. 2017; 9(407). doi: ARTN eaam7621 10.1126/scitranslmed.aam7621. PubMed PMID: WOS: 000410560500004.
77. Galmozzi A, Kok B P, Kim A S, Montenegro-Burke J R, Lee J Y, Spreafico R, Mosure S, Albert V. Cintron-Colon R, Godio C, Webb W R, Conti B, Solt L A, Kojetin D, Parker C G, Peluso J J, Pru J K, Siuzdak G, Cravatt B F, Saez E. PGRMC2 is an intracellular haem chaperone critical for adipocyte function. Nature. 2019:576(7785): 138-+. doi: 10.1038/s41586-019-1774 2. PubMed PMID: WOS:000501599200054.
78. Maeda T, Murata K, Fukushima T, Sugahara K, Tsuruda K, Anami M, Onimaru Y, Tsukasaki K, Tomonaga M, Moriuchi R, Hasegawa H, Yamada Y, Kamihira S. A novel plasmacytoid dendritic cell line, CAL-1, established from a patient with blastic natural killer cell lymphoma. Int J Hematol. 2005; 81(2):148-54. Epub 2005 Mar. 16. doi: 10.1532/ijh97.04116. PubMed PMID: 15765784.
79. Andrews B S, Eisenberg R A, Theofilopoulos A N, Izui S, Wilson C B, McConahey P J, Murphy E D, Roths J B, Dixon F J. Spontaneous murine lupus-like syndromes. Clinical and immunopathological manifestations in several strains. J Exp Med. 1978; 148(5):1198-215. Epub 1978 Nov. 1. PubMed PMID: 309911.

80. Liao X, Li S, Settlage R E, Sun S, Ren J, Reihl A M, Zhang H, Karyala S V, Reilly C M, Ahmed S A, Luo X M. Cutting Edge: Plasmacytoid Dendritic Cells in Late-Stage Lupus Mice Defective in Producing IFN-alpha. J Immunol. 2015; 195(10):4578-82. Epub 2015 Oct. 9. doi: 10.4049/jimmunol.1501157. PubMed PMID: 26447229.

81. Teijaro J R, Walsh K B, Rice S. Rosen H, Oldstone M B. Mapping the innate signaling cascade essential for cytokine storm during influenza virus infection. Proc Natl Acad Sci USA. 2014; 111(10):3799-804. Epub 2014 Feb. 28. doi: 10.1073/pnas.1400593111. PubMed PMID: 24572573; PMCID: PMC3956176.

82. Teijaro J R, Walsh K B, Cahalan S, Fremgen D M, Roberts E, Scott F, Martinborough E, Peach R, Oldstone M B, Rosen H. Endothelial cells are central orchestrators of cytokine amplification during influenza virus infection. Cell. 2011; 146(6):980-91. Epub 2011 Sep. 20. doi: 10.1016/j.cell.2011.08.015. PubMed PMID: 21925319; PMCID: PMC3176439.

We claim:

1. A compound which is of formula (I) or (II):

(I)

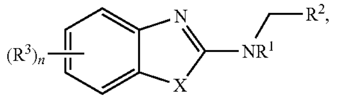

(II)

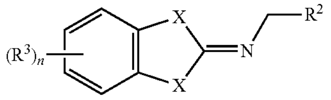

or is a pharmaceutically acceptable salt thereof, wherein:

X is $NR^4$;

$R^1$ is H or —C(O)—$C_{1-10}$alkyl;

$R^2$ is heterocyclyl or substituted aryl;

$R^3$ is halogen, —$CHF_2$, or $CF_3$;

$R^4$ is —C(O)—$C_{3-10}$alkyl, —C(O)—$C_{3-10}$cycloalkyl, —$S(O)_2$—$C_{1-10}$alkyl, or

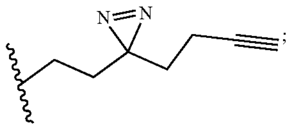 [SMILES: *CCC1(CCC#C)N=N1]

and n is 0, 1, 2, 3, or 4.

2. The compound of claim 1, which compound is a compound of Formula (I).

3. The compound of claim 1, which compound is a compound of Formula (II).

4. The compound of any one of claims 1-3, wherein $R^1$ is H.

5. The compound of any one of claims 1-3, wherein $R^1$ is —C(O)—$C_{1-10}$alkyl.

6. The compound of any one of claims 1-3, wherein $R^1$ is —C(O)—$C_3H_7$.

7. The compound of any one of claims 1-3, wherein $R^2$ is unsubstituted heterocyclyl.

8. The compound of any one of claims 1-3, wherein $R^2$ is substituted heterocyclyl.

9. The compound of claim 1, wherein the heterocyclyl is monocyclic.

10. The compound of claim 1, wherein the heterocyclyl is bicyclic.

11. The compound of claim 1, wherein the heterocyclyl is tricyclic.

12. The compound of claim 1, wherein the heterocyclyl is aromatic.

13. The compound of claim 1, wherein the heterocyclyl is non-aromatic.

14. The compound of any one of claims 1-3, wherein $R^2$ is selected from the group consisting of:

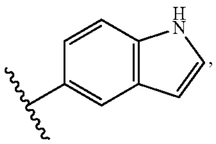
,
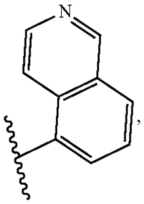
,
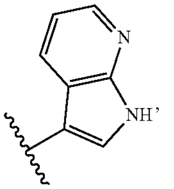
,
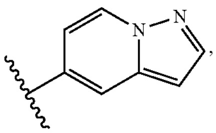
,
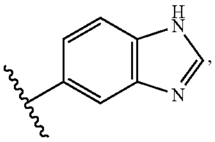
, and
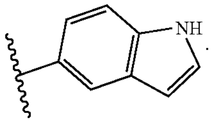
.

15. The compound of any one of claims 1-3, wherein $R^2$ is:

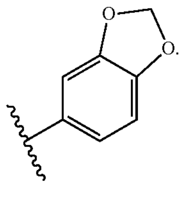 [SMILES: *c1ccc2c(c1)OCO2]

16. The compound of any one of claims 1-3, wherein $R^2$ is:

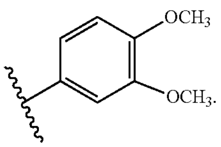 [SMILES: *c1ccc(OC)c(OC)c1]

17. The compound of any one of claims 1-3, wherein $R^2$ is

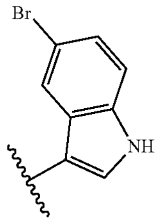 or 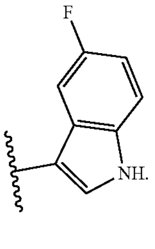

18. A compound of formula (I)

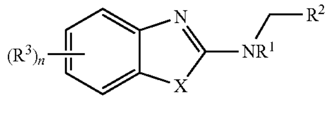
(I)

or a pharmaceutically acceptable salt thereof, wherein:

X is $NR^4$ or S;

$R^1$ is H or —C(O)—$C_{1-10}$alkyl;

$R^2$ is

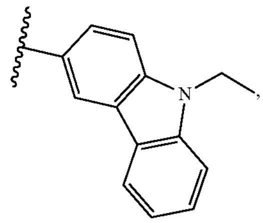, or 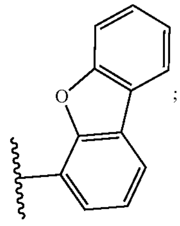;

$R^3$ is halogen;

$R^4$ is H, —$C_{1-10}$alkyl, —C(O)—$C_{1-10}$alkyl, —C(O)—$C_{3-10}$cycloalkyl, —$S(O)_2$—$C_{1-10}$alkyl, or

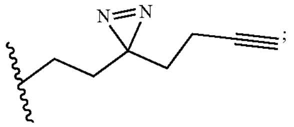 [SMILES: *CCC1(CCC#C)N=N1];

and n is 0, 1, 2, 3, or 4.

19. The compound of any one of claims 1-3, wherein $R^2$ is selected from the group consisting of

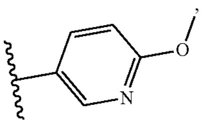, 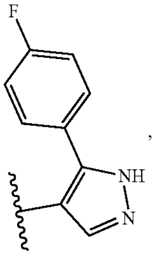,

-continued

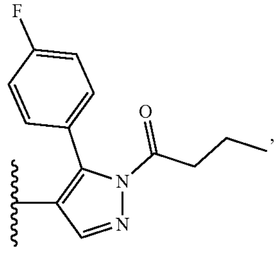, and 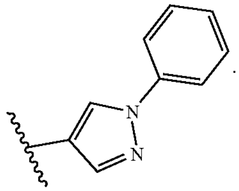.

20. The compound of any one of claims 1-3, wherein $R^3$ is F.

21. The compound of any one of claims 1-3, wherein $R^3$ is Cl.

22. The compound of any one of claims 1-3, wherein $R^3$ is Br.

23. The compound of any one of claims 1-3, wherein is $R^3$ is —$CHF_2$.

24. The compound of any one of claims 1-3, wherein is $R^3$ is —$CF_3$.

25. The compound of claim 18, wherein $R^4$ is —C(O)—$C_{1-10}$alkyl.

26. The compound of claim 25, wherein $R^4$ is

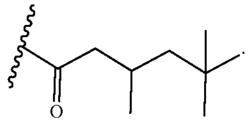.

27. The compound of claim 25, wherein $R^4$ is —C(O)—$C_3H_7$.

28. The compound of any one of claims 1-3, wherein $R^4$ is —C(O)—$C_{3-10}$cycloalkyl.

29. The compound of any one of claims 1-3, wherein $R^4$ is —C(O)-cyclopropyl.

30. The compound of any one of claims 1-3, wherein $R^4$ is —C(O)-cyclohexyl.

31. The compound of any one of claims 1-3, wherein $R^4$ is —$S(O)_2$—$C_{1-10}$alkyl.

32. The compound of any one of claims 1-3, wherein $R^4$ is —$S(O)_2$—$C_3H_7$.

33. The compound of any one of claims 1-3, wherein $R^4$ is

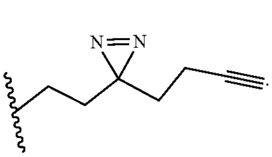.

34. The compound of any one of claims 1-3, wherein n is 0.

35. The compound of any one of claims 1-3, wherein n is 1.

36. The compound of any one of claims 1-3, wherein n is 2.

37. The compound of any one of claims 1-3, wherein n is 3.

38. The compound of any one of claims 1-3, wherein n is 4.

39. A compound, which compound is:

1-(2-(((1H-indol-5-yl)methyl)amino)-1H-benzo[d]imidazol-1-yl)butan-1-one;

N-((1H-indol-5-yl)methyl)-N-(benzo[d]thiazol-2-yl)butyramide;

N-((5-bromo-1H-indol-3-yl)methyl)-1H-benzo[d]imidazol-2-amine;

1-(2-(((5-bromo-1H-indol-3-yl)methyl)amino)-1H-benzo[d]imidazol-1-yl)butan-1-one;

1-(2-((isoquinolin-5-ylmethyl)amino)-1H-benzo[d]imidazol-1-yl)butan-1-one;

1-(2-(((1H-pyrrolo[2,3-b]pyridin-3-yl)methyl)amino)-1H-benzo[d]imidazol-1-yl)butan-1-one;

1-(2-((pyrazolo[1,5-a]pyridin-5-ylmethyl)amino)-1H-benzo[d]imidazol-1-yl)butan-1-one;

1-(2-((3,4-dimethoxybenzyl)amino)-1H-benzo[d]imidazol-1-yl)butan-1-one;

1-(2-(((1-benzyl-1H-indol-5-yl)methyl)amino)-1H-benzo[d]imidazol-1-yl)butan-1-one;

1-(2-(((1H-benzo[d]imidazol-5-yl)methyl)amino)-1H-benzo[d]imidazol-1-yl)butan-1-one;

(2-(((1H-indol-5-yl)methyl)amino)-1H-benzo[d]imidazol-1-yl)(cyclopropyl)methanone;

N-((1H-indol-5-yl)methyl)-1-(propylsulfonyl)-1H-benzo[d]imidazol-2-amine;

1-(2-(((1H-indol-5-yl)methyl)amino)-1H-benzo[d]imidazol-1-yl)-3,5,5-trimethylhexan-1-one;

1-(2-(((1H-indol-5-yl)methyl)amino)-1H-benzo[d]imidazol-1-yl)-3-cyclopentylpropan-1-one;

(2-(((1H-indol-5-yl)methyl)amino)-1H-benzo[d]imidazol-1-yl)(cyclohexyl)methanone;

1-(2-(((1H-indol-5-yl)methyl)amino)-1H-benzo[d]imidazol-1-yl)-3-(3-(but-3-yn-1-yl)-3H-diazirin-3-yl)propan-1-one;

1-(2-(((6-methoxypyridin-3-yl)methyl)amino)-1H-benzo[d]imidazol-1-yl)butan-1-one;

1-(2-(((5-fluoro-1H-indol-3-yl)methyl)amino)-1H-benzo[d]imidazol-1-yl)butan-1-one;

1-(2-(((5-fluoro-1H-indol-3-yl)methyl)amino)-1H-benzo[d]imidazol-1-yl)butan-1-one;

N-((1H-indol-5-yl)methyl)-N-(2-oxo-1,2,3,4-tetrahydroquinolin-3-yl)butyramide;

1-(2-((dibenzo[b,d]furan-4-ylmethyl)amino)-1H-benzo[d]imidazol-1-yl)butan-1-one;

1-(2-(((5-(4-fluorophenyl)-1H-pyrazol-4-yl)methyl)amino)-1H-benzo[d]imidazol-1-yl)butan-1-one;

1-(4-(((1-butyryl-1H-benzo[d]imidazol-2-yl)amino)methyl)-5-(4-fluorophenyl)-1H-pyrazol-1-yl)butan-1-one;

N-((1H-indol-5-yl)methyl)-N-(2,3-dihydro-1H-inden-2-yl)butyramide;

N-((1H-benzo[d]imidazol-2-yl)methyl)-N-((1H-indol-5-yl)methyl)butyramide;

1-(2-(((1H-indol-5-yl)methyl)amino)-5-fluoro-1H-benzo[d]imidazol-1-yl)butan-1-one;

N-((9-ethyl-9H-carbazol-3-yl)methyl)-1H-benzo[d]imidazol-2-amine;

1-(2-(((9-ethyl-9H-carbazol-3-yl)methyl)amino)-1H-benzo[d]imidazol-1-yl)butan-1-one;

1-(2-(((1-phenyl-1H-pyrazol-4-yl)methyl)amino)-1H-benzo[d]imidazol-1-yl)butan-1-one;

N-((5-bromo-1H-indol-3-yl)methyl)-1-methyl-1H-benzo[d]imidazol-2-amine;

N-((1H-indol-5-yl)methyl)-1-methyl-1H-benzo[d]imidazol-2-amine;

N-((9-ethyl-9H-carbazol-3-yl)methyl)-1-methyl-1H-benzo[d]imidazol-2-amine;

N-((9-ethyl-9H-carbazol-3-yl)methyl)-N-(1-methyl-1H-benzo[d]imidazol-2-yl)butyramide;

3-(3-(but-3-yn-1-yl)-3H-diazirin-3-yl)-N-((9-ethyl-9H-carbazol-3-yl)methyl)-N-(1-methyl-1H-benzo[d]imidazol-2-yl)propenamide;

N-((5-bromo-1H-indol-3-yl)methyl)-3-(3-(but-3-yn-1-yl)-3H-diazirin-3-yl)-N-(1-methyl-1H-benzo[d]imidazol-2-yl)propenamide;

1-(2-(3-(but-3-yn-1-yl)-3H-diazirin-3-yl)ethyl)-N-((9-ethyl-9H-carbazol-3-yl)methyl)-1H-benzo[d]imidazol-2-amine;

N-((1,6,7,8-tetrahydrocyclopenta[g]indol-3-yl)methyl)-1H-benzo[d]imidazol-2-amine;

1-(2-(((1,6,7,8-tetrahydrocyclopenta[g]indol-3-yl)methyl)amino)-1H-benzo[d]imidazol-1-yl)butan-1-one;

3-(((1H-benzo[d]imidazol-2-yl)amino)methyl)-1H-indole-6-carbonitrile;

N-((5-chloro-1H-indol-3-yl)methyl)-1H-benzo[d]imidazol-2-amine;

9-ethyl-6-(((1-methyl-1H-benzo[d]imidazol-2-yl)amino)methyl)-9H-carbazole-3-carbonitrile;

N-((9-ethyl-3,3-dimethyl-2,3,4,9-tetrahydro-1H-carbazol-6-yl)methyl)-1-methyl-1H-benzo[d]imidazol-2-amine;

N-((9-ethyl-3,3-dimethyl-2,3,4,9-tetrahydro-1H-carbazol-6-yl)methyl)-1H-benzo[d]imidazol-2-amine;

1-butyl-N-((9-ethyl-3,3-dimethyl-2,3,4,9-tetrahydro-1H-carbazol-6-yl)methyl)-1H-benzo[d]imidazol-2-amine;

1-butyl-N-((9-ethyl-9H-carbazol-3-yl)methyl)-1H-benzo[d]imidazol-2-amine;

N-((1H-indol-5-yl)methyl)-1-butyl-1H-benzo[d]imidazol-2-amine;

1-butyl-N-(dibenzo[b,d]furan-4-ylmethyl)-1H-benzo[d]imidazol-2-amine;

1-butyl-N-((6-methoxypyridin-3-yl)methyl)-1H-benzo[d]imidazol-2-amine;

N-(benzo[d][1,3]dioxol-5-ylmethyl)-1-butyl-1H-benzo[d]imidazol-2-amine;

N-((5-bromo-1H-indol-3-yl)methyl)-1-butyl-1H-benzo[d]imidazol-2-amine;

N-((9-ethyl-3-(trifluoromethyl)-2,3,4,9-tetrahydro-1H-carbazol-6-yl)methyl)-1-methyl-1H-benzo[d]imidazol-2-amine;

N-((9-ethyl-3-(trifluoromethyl)-2,3,4,9-tetrahydro-1H-carbazol-6-yl)methyl)-1H-benzo[d]imidazol-2-amine;

1-butyl-N-((9-ethyl-3-(trifluoromethyl)-2,3,4,9-tetrahydro-1H-carbazol-6-yl)methyl)-1H-benzo[d]imidazol-2-amine;

(R)-1-(1H-benzo[d]imidazol-2-yl)-N-((9-ethyl-9H-carbazol-3-yl)methyl)ethan-1-amine;

Methyl 3-(((1H-benzo[d]imidazol-2-yl)amino)methyl)-1H-indole-5-carboxylate;

3-(((1H-benzo[d]imidazol-2-yl)amino)methyl)-1H-indole-5-carboxylic acid;

N-((1H-benzo[g]indol-3-yl)methyl)-1H-benzo[d]imidazol-2-amine;

N-((1H-benzo[g]indol-3-yl)methyl)-1-methyl-1H-benzo[d]imidazol-2-amine;

N-((9-ethyl-9H-carbazol-3-yl)methyl)quinolin-3-amine;

1-(2-(3-(but-3-yn-1-yl)-3H-diazirin-3-yl)ethyl)-N-(3,4-dimethoxybenzyl)-1H benzo[d]imidazol-2-amine;

N-((7-ethyl-7H-benzo[c]carbazol-10-yl)methyl)-1H-benzo[d]imidazol-2-amine;

N-((7-ethyl-7H-benzo[c]carbazol-10-yl)methyl)-1-methyl-1H-benzo[d]imidazol-2-amine;

N-((9-(4-(tert-butyl)phenyl)-9H-carbazol-3-yl)methyl)-1-methyl-1H-benzo[d]imidazol-2-amine N-((6-(3,5-dimethylisoxazol-4-yl)-9-ethyl-9H-carbazol-3-yl)methyl)-1H-benzo[d]imidazol-2-amine N-((6-(3,5-dimethylisoxazol-4-yl)-9-ethyl-9H-carbazol-3-yl)methyl)-1-methyl-1H-benzo[d]imidazol-2-amine N-((6-bromo-9-ethyl-9H-carbazol-3-yl)methyl)-1-methyl-1H-benzo[d]imidazol-2-amine;

N-((6-(benzo[d][,3]dioxol-5-yl)-9-ethyl-9H-carbazol-3-yl)methyl)-1-methyl-1H-benzo[d]imidazol-2-amine;

3-(9-ethyl-6-(((i-methyl-1H-benzo[d]imidazol-2-yl)amino)methyl)-9H-carbazol-3-yl)phenol;

N-((9-ethyl-6-methoxy-9H-carbazol-3-yl)methyl)-1-methyl-1H-benzo[d]imidazol-2-amine;

N-((5-methoxy-1H-indol-3-yl)methyl)-1-methyl-1H-benzo[d]imidazol-2-amine;

N-((9-ethyl-6-(4-methylpentyl)-9H-carbazol-3-yl)methyl)-1-methyl-1H-benzo[d]imidazol-2-amine 1-(2-(3-(but-3-yn-1-yl)-3H-diazirin-3-yl)ethyl)-N-((1-phenyl-1H-pyrazol-4-yl)methyl)-1H-benzo[d]imidazol-2-amine;

1-(2-((benzo[d][,3]dioxol-5-ylmethyl)amino)-1H-benzo[d]imidazol-1-yl)butan-1-one;

or a pharmaceutically acceptable salt thereof.

40. A pharmaceutical composition comprising a compound of claim 1, 18, or 39, and a pharmaceutically acceptable carrier.

* * * * *